US007378275B2

(12) United States Patent
McCall et al.

(10) Patent No.: US 7,378,275 B2
(45) Date of Patent: May 27, 2008

(54) CANINE IL-13 RECEPTOR ALPHA-1 SUBUNIT NUCLEIC ACID MOLECULES

(75) Inventors: Catherine A. McCall, Boulder, CO (US); Liang Tang, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 640 days.

(21) Appl. No.: 10/753,159

(22) Filed: Jan. 7, 2004

(65) Prior Publication Data

US 2004/0142372 A1 Jul. 22, 2004

Related U.S. Application Data

(62) Division of application No. 09/828,995, filed on Apr. 9, 2001, now Pat. No. 6,703,360.

(60) Provisional application No. 60/195,874, filed on Apr. 7, 2000, provisional application No. 60/195,659, filed on Apr. 7, 2000.

(51) Int. Cl.
*C07H 21/04* (2006.01)
*C12N 15/19* (2006.01)
*C07K 14/54* (2006.01)
*C07K 19/00* (2006.01)

(52) U.S. Cl. .............. 435/325; 435/69.1; 435/69.7; 435/320.1; 536/23.5; 536/24.5; 530/350; 530/387.3

(58) Field of Classification Search ............... None
See application file for complete search history.

(56) References Cited

U.S. PATENT DOCUMENTS

| | | | |
|---|---|---|---|
| 5,593,861 A | 1/1997 | Maeda et al. | |
| 5,596,072 A | 1/1997 | Culpepper et al. | |
| 5,614,191 A | 3/1997 | Puri et al. | |
| 5,622,842 A | 4/1997 | Hollis et al. | |
| 5,629,415 A | 5/1997 | Hollis et al. | |
| 5,652,123 A | 7/1997 | Caput et al. | |
| 5,696,234 A | 12/1997 | Zurawski et al. | |
| 5,710,023 A | 1/1998 | Collins et al. | |
| 5,783,181 A | 7/1998 | Browne et al. | |
| 5,830,453 A | 11/1998 | Badr et al. | |
| 5,852,183 A | 12/1998 | Maeda et al. | |
| 5,858,347 A | 1/1999 | Bauer et al. | |
| 5,919,456 A | 7/1999 | Puri et al. | |
| 5,935,824 A * | 8/1999 | Sgarlato | 435/69.7 |
| 2002/0137139 A1* | 9/2002 | Byatt et al. | 435/69.1 |

FOREIGN PATENT DOCUMENTS

| | | |
|---|---|---|
| JP | 4-40894 | 2/1992 |
| WO | WO 97/20926 | 6/1997 |
| WO | WO 97/31946 | 9/1997 |
| WO | WO 98/08957 | 3/1998 |
| WO | WO 98/10638 | 3/1998 |

OTHER PUBLICATIONS

J.A. Wells, "Additivity of mutational effects in proteins", 1990, Biochemistry 29:8509-8517.*
J.T. Ngo et al., Computational complexitiycomplexity, protein structure prediction, and the Levinthal Paradox, Chapter 14 in The protein folding problem and tertiary structure prediction, K. Merz, Jr. Ed., Birkhauser, Boston, 1994. pp. 492-495.*
P. Bork, "Powers and pitfalls in sequence analysis: The 70% hurdle", Genome Research 10:398-400, 2000.*
J. Skolnick et al., "From genes to protein structure and function: novel applications of computational approaches in the genomic era", Trends in Biotech 18(1):34-39, 2000.*
T. Doerks et al., "Protein annotation: detective work for function prediction", Trends in Genetics, 4(g):248-250, Jun. 1998.*
T.F. Smith et al., The challenges of genome sequence annotation or "The devil is in the details", Nature Biotechnology 15:1222-1223, 1997.*
S.E. Brenner, "Errors in genome annotation", Trends in Genetics 15(4) 132-133, 1999.*
P. Bork, "Go hunting in sequence databases but watch out for the traps", Trends in Genetics 12(10):425-426, 1996.bv.*
Ashkenazi et al., *Current Opinion in Immunology*, 1997, vol. 9, pp. 195-200.
Capon et al., *Nature*, 1989, vol. 337, pp. 525-531.
Day et al., *Research in Veterinary Science*, 1996, vol. 61, pp. 136-142.
Day et al., *Research in Veterinary Science*, 1995, vol. 58, pp. 82-89.
Hayden et al., *Current Opinion in Immunology*, 1997, vol. 9, pp. 201-212.
Johnson et al., *The Journal of Immunology*, 1967, vol. 98, No. 5, pp. 935-940.
Mazza et al., *Research in Veterinary Science*, 1994, vol. 57, pp. 133-139.
Mazza et al., *Journal of Immunological Methods*, 1993, vol. 161, pp. 193-203.

(Continued)

*Primary Examiner*—Lorraine Spector

(57) ABSTRACT

The invention relates to canine immunoglobulin G (IgG) and canine interleukin-13 receptors (IL-13R) as well as fusion proteins containing canine IgG and/or canine IL-13R. In particular, the present invention discloses nucleic acid molecules encoding canine IgG, including species-specific regions of the heavy chain of canine IgG, and canine IL-13R alpha chain (IL-13Rα) proteins, particularly canine interleuken receptor alpha 1 (IL-13Rα1) and canine interleuken receptor alpha 2 (IL-13Rα2) proteins. Also included are canine IgG and IL-13Rα proteins, antibodies having selectivity for such proteins, inhibitors of such proteins and/or nucleic acid molecules, cells transformed with said nucleic acid molecules, assays employing such cells, nucleic acids molecules, proteins, antibodies and/or inhibitors, and therapeutic compositions comprising said nucleic acids molecules, proteins, antibodies and/or inhibitors. Also included are kits containing said molecules or chimera thereof, including their use to evaluate and regulate an immune response in an animal.

20 Claims, No Drawings

OTHER PUBLICATIONS

Schur, Peter H. MD, *Annals of Allergy*, 1987, vol. 58, pp. 89-101.
Avery, et al., Sequence Submission, 1998, Accession No. AF067449.
Avery, et al., Sequence Submission, 1998, Accession No. AF067450.
Avery, et al., Sequence Submission, 1998, Accession No. AF067451.
Avery, et al., Sequence Submission, 1998, Accession No. AF067452.
Avery, et al., Sequence Submission, 1998, Accession No. AF067453.
Avery, et al., Sequence Submission, 1998, Accession No. AF079118.
Avery, et al., Sequence Submission, 1998, Accession No. AF079119.
Avery, et al., Sequence Submission, 1998, Accession No. AF079120.
Avery, et al., Sequence Submission, 1998, Accession No. AF079121.
Avery, et al., Sequence Submission, 1998, Accession No. AF079122.
Avery, et al., Sequence Submission, 1998, Accession No. AF079123.
Redpath, et al., 1998, *Human Immunology*, vol. 59, pp. 720-727.
DeBoer, et al., 1993, *Veterinary Immunology and Immunopathology*, vol. 37, No. 3-4, pp. 183-199.
Callard, et al., 1996, *Immunology Today*, vol. 17, No. 3, pp. 108-110 (XP002010895).
Tang, et al., 2001, *Journal of Allergy and Clinical Immunology*, vol. 107, No. 2, abstract, p. S91 (XP001030691).

* cited by examiner

SEQUENCE LISTING

<160> NUMBER OF SEQ ID NOS: 104

<210> SEQ ID NO 1
<211> LENGTH: 51
<212> TYPE: DNA
<213> ORGANISM: Canis familiaris
<220> FEATURE:
<221> NAME/KEY: CDS
<222> LOCATION: (1)..(51)
<223> OTHER INFORMATION:

<400> SEQUENCE: 1

```
ttc aat gaa tgc aga tgc act gat aca ccc cca tgc cca gtc cct gaa    48
Phe Asn Glu Cys Arg Cys Thr Asp Thr Pro Pro Cys Pro Val Pro Glu
1               5                   10                  15 cct                                                                51
Pro
```

<210> SEQ ID NO 2
<211> LENGTH: 17
<212> TYPE: PRT
<213> ORGANISM: Canis familiaris

<400> SEQUENCE: 2

```
Phe Asn Glu Cys Arg Cys Thr Asp Thr Pro Pro Cys Pro Val Pro Glu
1               5                   10                  15

Pro
```

<210> SEQ ID NO 3
<211> LENGTH: 51
<212> TYPE: DNA
<213> ORGANISM: Canis familiaris

<400> SEQUENCE: 3
aggttcaggg actgggcatg ggggtgtatc agtgcatctg cattcattga a            51

<210> SEQ ID NO 4
<211> LENGTH: 1654
<212> TYPE: DNA
<213> ORGANISM: Canis familiaris
<220> FEATURE:
<221> NAME/KEY: CDS
<222> LOCATION: (70)..(1473)
<223> OTHER INFORMATION:

<400> SEQUENCE: 4

```
ggcacgagcc agcccccagg atccccaggt gaccccattc agtgctcagg acacaacaca    60 gacaccacc atg gag tct gtg ttc tgc tgg gtt ttc ctt gtc gtt att tta   111
           Met Glu Ser Val Phe Cys Trp Val Phe Leu Val Val Ile Leu
               1               5                   10 aaa ggt gtc cag ggt gag gtg cag ttg gtg gag tct ggg gga gac ctg    159
Lys Gly Val Gln Gly Glu Val Gln Leu Val Glu Ser Gly Gly Asp Leu
15                  20                  25                  30 gtg aag cct ggg ggg tcc ctg aga ctc tcc tgt gtg gcc tct gga ttc    207
Val Lys Pro Gly Gly Ser Leu Arg Leu Ser Cys Val Ala Ser Gly Phe
                35                  40                  45 acc ttc agt tcg tac tac atg cat tgg atc cgc cag gct cca ggg aag    255
Thr Phe Ser Ser Tyr Tyr Met His Trp Ile Arg Gln Ala Pro Gly Lys
            50                  55                  60 ggg ctt cag cgg gtc gca cat att aga ggt gat gga agg act aca cac    303
Gly Leu Gln Arg Val Ala His Ile Arg Gly Asp Gly Arg Thr Thr His
        65                  70                  75
```

| | | |
|---|---|---|
| tac gca gac gct atg aag ggc cga ttc acc atc tcc aga gac aac gcc<br>Tyr Ala Asp Ala Met Lys Gly Arg Phe Thr Ile Ser Arg Asp Asn Ala<br>80                       85                            90 | | 351 |
| aag aac acg ctg tat ctg cag atg aat agc ctg aca gtc gaa gac acg<br>Lys Asn Thr Leu Tyr Leu Gln Met Asn Ser Leu Thr Val Glu Asp Thr<br>95                      100                   105                  110 | | 399 |
| gct att tat tac tgt gta aag gac ata tac tat ggg gtc ggg gac tat<br>Ala Ile Tyr Tyr Cys Val Lys Asp Ile Tyr Tyr Gly Val Gly Asp Tyr<br>                    115                   120                  125 | | 447 |
| tgg ggc cag gga acc ctg gtc acc gtc tca gcc tcc acc acg gcc<br>Trp Gly Gln Gly Thr Leu Val Thr Val Ser Ser Ala Ser Thr Thr Ala<br>      130                   135                  140 | | 495 |
| ccc tcg gtt ttc cca ctg gcc ccc agc tgc ggg tcc act tcc ggc tcc<br>Pro Ser Val Phe Pro Leu Ala Pro Ser Cys Gly Ser Thr Ser Gly Ser<br>              145                   150                  155 | | 543 |
| acg gtg gcc ctg gcc tgc ctg gtg tca ggc tac ttc ccc gag cct gta<br>Thr Val Ala Leu Ala Cys Leu Val Ser Gly Tyr Phe Pro Glu Pro Val<br>160                       165                   170 | | 591 |
| act gtg tcc tgg aat tcc ggc tcc ttg acc agc ggt gtg cac acc ttc<br>Thr Val Ser Trp Asn Ser Gly Ser Leu Thr Ser Gly Val His Thr Phe<br>175                    180                  185                  190 | | 639 |
| ccg tcc gtc ctg cag tcc tca ggg ctt cac tcc ctc agc agc atg gtg<br>Pro Ser Val Leu Gln Ser Ser Gly Leu His Ser Leu Ser Ser Met Val<br>                    195                   200                  205 | | 687 |
| aca gtg ccc tcc agc agg tgg ccc agc gag acc ttc acc tgc aac gtg<br>Thr Val Pro Ser Ser Arg Trp Pro Ser Glu Thr Phe Thr Cys Asn Val<br>              210                   215                  220 | | 735 |
| gtc cac cca gcc agc aac act aaa gta gac aag cca gtg ttc aat gaa<br>Val His Pro Ala Ser Asn Thr Lys Val Asp Lys Pro Val Phe Asn Glu<br>225                       230                   235 | | 783 |
| tgc aga tgc act gat aca ccc cca tgc cca gtc cct gaa cct ctg gga<br>Cys Arg Cys Thr Asp Thr Pro Pro Cys Pro Val Pro Glu Pro Leu Gly<br>240                       245                   250 | | 831 |
| ggg cct tcg gtc ctc atc ttt ccc ccg aaa ccc aag gac atc ctc agg<br>Gly Pro Ser Val Leu Ile Phe Pro Pro Lys Pro Lys Asp Ile Leu Arg<br>255                    260                  265                  270 | | 879 |
| att acc cga aca ccc gag gtc acc tgt gtg gtg tta gat ctg ggc cgt<br>Ile Thr Arg Thr Pro Glu Val Thr Cys Val Val Leu Asp Leu Gly Arg<br>                    275                   280                  285 | | 927 |
| gag gac cct gag gtc cag atc agc tgg ttc gtg gat ggt aag gag gtg<br>Glu Asp Pro Glu Val Gln Ile Ser Trp Phe Val Asp Gly Lys Glu Val<br>              290                   295                  300 | | 975 |
| cac aca gcc aag acc cag tct cgt gag cag cag ttc aac ggc acc tac<br>His Thr Ala Lys Thr Gln Ser Arg Glu Gln Gln Phe Asn Gly Thr Tyr<br>305                       310                   315 | | 1023 |
| cgt gtg gtc agc gtc ctc ccc att gag cac cag gac tgg ctc aca ggg<br>Arg Val Val Ser Val Leu Pro Ile Glu His Gln Asp Trp Leu Thr Gly<br>320                       325                   330 | | 1071 |
| aag gag ttc aag tgc aga gtc aac cac ata gac ctc ccg tct ccc atc<br>Lys Glu Phe Lys Cys Arg Val Asn His Ile Asp Leu Pro Ser Pro Ile<br>335                    340                  345                  350 | | 1119 |
| gag agg acc atc tct aag gcc aga ggg agg gcc cat aag ccc agt gtg<br>Glu Arg Thr Ile Ser Lys Ala Arg Gly Arg Ala His Lys Pro Ser Val<br>                    355                   360                  365 | | 1167 |
| tat gtc ctg ccg cca tcc cca aag gag ttg tca tcc agt gac aca gtc<br>Tyr Val Leu Pro Pro Ser Pro Lys Glu Leu Ser Ser Ser Asp Thr Val<br>              370                   375                  380 | | 1215 |
| agc atc acc tgc ctg ata aaa gac ttc tac cca cct gac att gat gtg<br>Ser Ile Thr Cys Leu Ile Lys Asp Phe Tyr Pro Pro Asp Ile Asp Val | | 1263 |

-continued

```
                  385                 390                 395
gag tgg cag agc aat gga cag cag gag ccc gag agg aag cac cgc atg   1311
Glu Trp Gln Ser Asn Gly Gln Gln Glu Pro Glu Arg Lys His Arg Met
        400                 405                 410 acc ccg ccc cag ctg gac gag gac ggg tcc tac ttc ctg tac agc aag   1359
Thr Pro Pro Gln Leu Asp Glu Asp Gly Ser Tyr Phe Leu Tyr Ser Lys
415                 420                 425                 430 ctc tct gtg gac aag agc cgc tgg cag cag gga gac ccc ttc aca tgt   1407
Leu Ser Val Asp Lys Ser Arg Trp Gln Gln Gly Asp Pro Phe Thr Cys
                435                 440                 445 gcg gtg atg cat gaa act cta cag aac cac tac aca gat cta tcc ctc   1455
Ala Val Met His Glu Thr Leu Gln Asn His Tyr Thr Asp Leu Ser Leu
            450                 455                 460 tcc cat tct ccg ggt aaa tgagcaacac gcccggcacc cagcaagccc          1503
Ser His Ser Pro Gly Lys
        465 cccaccttg gctctcagga tccctgagg acacctgagc cctgtccct gtgtacataa    1563 ccctgggtag gcacccatca tgaaataaag cacccagcac tgccctgggc cctgcaaaaa 1623 aaaaaaaaaa aaaaaaaaaa aaaaaaaaaa a                                1654

<210> SEQ ID NO 5
<211> LENGTH: 468
<212> TYPE: PRT
<213> ORGANISM: Canis familiaris

<400> SEQUENCE: 5

Met Glu Ser Val Phe Cys Trp Val Phe Leu Val Val Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Ser Tyr Tyr Met His Trp Ile Arg Gln Ala Pro Gly Lys Gly Leu
    50                  55                  60

Gln Arg Val Ala His Ile Arg Gly Asp Gly Arg Thr Thr His Tyr Ala
65                  70                  75                  80

Asp Ala Met Lys Gly Arg Phe Thr Ile Ser Arg Asp Asn Ala Lys Asn
                85                  90                  95

Thr Leu Tyr Leu Gln Met Asn Ser Leu Thr Val Glu Asp Thr Ala Ile
            100                 105                 110

Tyr Tyr Cys Val Lys Asp Ile Tyr Tyr Gly Val Gly Asp Tyr Trp Gly
        115                 120                 125

Gln Gly Thr Leu Val Thr Val Ser Ser Ala Ser Thr Thr Ala Pro Ser
    130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
                165                 170                 175

Ser Trp Asn Ser Gly Ser Leu Thr Ser Gly Val His Thr Phe Pro Ser
            180                 185                 190

Val Leu Gln Ser Ser Gly Leu His Ser Leu Ser Ser Met Val Thr Val
        195                 200                 205

Pro Ser Ser Arg Trp Pro Ser Glu Thr Phe Thr Cys Asn Val Val His
    210                 215                 220

Pro Ala Ser Asn Thr Lys Val Asp Lys Pro Val Phe Asn Glu Cys Arg
```

```
                225                 230                 235                 240
Cys Thr Asp Thr Pro Pro Cys Pro Val Pro Glu Pro Leu Gly Gly Pro
                    245                 250                 255
Ser Val Leu Ile Phe Pro Pro Lys Pro Lys Asp Ile Leu Arg Ile Thr
                260                 265                 270
Arg Thr Pro Glu Val Thr Cys Val Val Leu Asp Leu Gly Arg Glu Asp
            275                 280                 285
Pro Glu Val Gln Ile Ser Trp Phe Val Asp Gly Lys Glu Val His Thr
        290                 295                 300
Ala Lys Thr Gln Ser Arg Glu Gln Gln Phe Asn Gly Thr Tyr Arg Val
305                 310                 315                 320
Val Ser Val Leu Pro Ile Glu His Gln Asp Trp Leu Thr Gly Lys Glu
                325                 330                 335
Phe Lys Cys Arg Val Asn His Ile Asp Leu Pro Ser Pro Ile Glu Arg
                340                 345                 350
Thr Ile Ser Lys Ala Arg Gly Arg Ala His Lys Pro Ser Val Tyr Val
            355                 360                 365
Leu Pro Pro Ser Pro Lys Glu Leu Ser Ser Ser Asp Thr Val Ser Ile
        370                 375                 380
Thr Cys Leu Ile Lys Asp Phe Tyr Pro Pro Asp Ile Asp Val Glu Trp
385                 390                 395                 400
Gln Ser Asn Gly Gln Gln Glu Pro Glu Arg Lys His Arg Met Thr Pro
                405                 410                 415
Pro Gln Leu Asp Glu Asp Gly Ser Tyr Phe Leu Tyr Ser Lys Leu Ser
                420                 425                 430
Val Asp Lys Ser Arg Trp Gln Gln Gly Asp Pro Phe Thr Cys Ala Val
            435                 440                 445
Met His Glu Thr Leu Gln Asn His Tyr Thr Asp Leu Ser Leu Ser His
        450                 455                 460
Ser Pro Gly Lys
465

<210> SEQ ID NO 6
<211> LENGTH: 1654
<212> TYPE: DNA
<213> ORGANISM: Canis familiaris

<400> SEQUENCE: 6
tttttttttt tttttttttt tttttttttt tttttttgcag ggcccagggc agtgctgggt     60
gctttatttc atgatgggtg cctacccagg gttatgtaca cagggacagg ggctcaggtg    120
tcctcagggg atcctgagag ccaagggtgg ggggcttgct gggtgccggg cgtgttgctc    180
atttacccgg agaatgggag agggatagat ctgtgtagtg gttctgtaga gtttcatgca    240
tcaccgcaca tgtgaagggg tctccctgct gccagcggct cttgtccaca gagagcttgc    300
tgtacaggaa gtaggacccg tcctcgtcca gctggggcgg ggtcatgcgg tgcttcctct    360
cgggctcctg ctgtccattg ctctgccact ccacatcaat gtcaggtggg tagaagtctt    420
ttatcaggca ggtgatgctg actgtgtcac tggatgacaa ctccttgggg atggcggca    480
ggacatacac actgggctta tgggccctcc ctctggcctt agagatggtc ctctcgatgg    540
gagacgggag gtctatgtgg ttgactctgc acttgaactc cttccctgtg agccagtcct    600
ggtgctcaat ggggaggacg ctgaccacac ggtaggtgcc gttgaactgc tgctcacgag    660
actgggtctt ggctgtgtgc acctccttac catccacgaa ccagctgatc tgcacctcag    720
```

-continued

```
ggtcctcacg gcccagatct aacaccacac aggtgacctc gggtgttcgg gtaatcctga      780
ggatgtcctt gggtttcggg ggaaagatga ggaccgaagg ccctcccaga ggttcaggga      840
ctgggcatgg gggtgtatca gtgcatctgc attcattgaa cactggcttg tctactttag      900
tgttgctggc tgggtggacc acgttgcagg tgaaggtctc gctgggccac ctgctggagg      960
gcactgtcac catgctgctg agggagtgaa gccctgagga ctgcaggacg gacgggaagg     1020
tgtgcacacc gctggtcaag gagccggaat tccaggacag agttacaggc tcggggaagt     1080
agcctgacac caggcaggcc agggccaccg tggagccgga gtggacccg cagctggggg      1140 ccagtgggaa aaccgagggg gccgtggtgg aggctgagga cggtgacc agggttccct       1200 ggccccaata gtccccgacc ccatagtata tgtcctttac acagtaataa atagccgtgt     1260
cttcgactgt caggctattc atctgcagat acagcgtgtt cttggcgttg tctctggaga     1320
tggtgaatcg gcccttcata gcgtctgcgt agtgtgtagt ccttccatca cctctaatat     1380
gtgcgacccg ctgaagcccc ttccctggag cctggcggat ccaatgcatg tagtacgaac     1440
tgaaggtgaa tccagaggcc acacaggaga gtctcaggga ccccccaggc ttcaccaggt     1500
ctcccccaga ctccaccaac tgcacctcac cctggacacc ttttaaaata acgacaagga    1560
aaacccagca gaacacagac tccatggtgg tgtctgtgtt gtgtcctgag cactgaatgg     1620
ggtcacctgg ggatcctggg ggctggctcg tgcc                                1654
```

```
<210> SEQ ID NO 7
<211> LENGTH: 51
<212> TYPE: DNA
<213> ORGANISM: Canis familiaris
<220> FEATURE:
<221> NAME/KEY: CDS
<222> LOCATION: (1)..(51)
<223> OTHER INFORMATION:

<400> SEQUENCE: 7 ccc aaa gag tcc acc tgc aag tgt ata tcc cca tgc cca gtc cct gaa       48
Pro Lys Glu Ser Thr Cys Lys Cys Ile Ser Pro Cys Pro Val Pro Glu
1               5                  10                  15 tca                                                                   51
Ser

<210> SEQ ID NO 8
<211> LENGTH: 17
<212> TYPE: PRT
<213> ORGANISM: Canis familiaris

<400> SEQUENCE: 8

Pro Lys Glu Ser Thr Cys Lys Cys Ile Ser Pro Cys Pro Val Pro Glu
1               5                  10                  15

Ser

<210> SEQ ID NO 9
<211> LENGTH: 51
<212> TYPE: DNA
<213> ORGANISM: Canis familiaris

<400> SEQUENCE: 9
tgattcaggg actgggcatg gggatataca cttgcaggtg gactctttgg g              51

<210> SEQ ID NO 10
<211> LENGTH: 1460
<212> TYPE: DNA
<213> ORGANISM: Canis familiaris
```

-continued

```
<220> FEATURE:
<221> NAME/KEY: CDS
<222> LOCATION: (48)..(1457)
<223> OTHER INFORMATION:

<400> SEQUENCE: 10
ccaggtgacc ccattcagtg ctcaggacac aacacagaca aaccacc atg gag tct        56
                                                   Met Glu Ser
                                                   1 gtg ctc tgc tgg gtt ttc ctt gtc tct att tta aaa ggt gtc cag ggt       104
Val Leu Cys Trp Val Phe Leu Val Ser Ile Leu Lys Gly Val Gln Gly
    5              10                  15 gag gtg caa ctg gtg gag tct ggg gga gac ctg gtg aag cct ggg ggg       152
Glu Val Gln Leu Val Glu Ser Gly Gly Asp Leu Val Lys Pro Gly Gly
20                  25                  30                  35 tcc ttg aga ctg tcc tgt gtg gcc tct gga ttc acc ttc agt gac tat       200
Ser Leu Arg Leu Ser Cys Val Ala Ser Gly Phe Thr Phe Ser Asp Tyr
                40                  45                  50 ggc atg agt tgg gtc cgt cag tct cca ggg aag ggg ctg cag tgg gtc       248
Gly Met Ser Trp Val Arg Gln Ser Pro Gly Lys Gly Leu Gln Trp Val
            55                  60                  65 gca gct gtt agc aat cgt gga gat act tac tac gca gac gct gtg aag       296
Ala Ala Val Ser Asn Arg Gly Asp Thr Tyr Tyr Ala Asp Ala Val Lys
        70                  75                  80 ggc cga ttc acc atc tcc aga gac aac gcc aag aac acg ctg tat ctc       344
Gly Arg Phe Thr Ile Ser Arg Asp Asn Ala Lys Asn Thr Leu Tyr Leu
    85                  90                  95 cag atg agc agc ctg aaa gcc gag gac acg gca atc tat cac tgt gtg       392
Gln Met Ser Ser Leu Lys Ala Glu Asp Thr Ala Ile Tyr His Cys Val
100                 105                 110                 115 acg gga gta tgg ccg cga cat tat tat ggt atg gac cac tgg ggc aat       440
Thr Gly Val Trp Pro Arg His Tyr Tyr Gly Met Asp His Trp Gly Asn
                120                 125                 130 ggc acc tca ctc ttc gtg tcc tca gcc tcc acc acg gcc ccc tcg gtt       488
Gly Thr Ser Leu Phe Val Ser Ser Ala Ser Thr Thr Ala Pro Ser Val
            135                 140                 145 ttc cca ctg gcc ccc agc tgc ggg tcc act tcc ggc tcc acg gtg gcc       536
Phe Pro Leu Ala Pro Ser Cys Gly Ser Thr Ser Gly Ser Thr Val Ala
        150                 155                 160 ctg gcc tgc ctg gtg tca ggc tac ttc ccc gag cct gta act gtg tcc       584
Leu Ala Cys Leu Val Ser Gly Tyr Phe Pro Glu Pro Val Thr Val Ser
    165                 170                 175 tgg aat tcc ggc tcc ttg acc agc ggt gtg cac acc ttc ccg tcc gtc       632
Trp Asn Ser Gly Ser Leu Thr Ser Gly Val His Thr Phe Pro Ser Val
180                 185                 190                 195 ctg cag tcc tca ggg ctc tac tcc ctc agc agc acg gtg aca gtg ccc       680
Leu Gln Ser Ser Gly Leu Tyr Ser Leu Ser Ser Thr Val Thr Val Pro
                200                 205                 210 tcc agc agg tgg ccc agc gag acc ttc acc tgc aac gtg gtc cac ccg       728
Ser Ser Arg Trp Pro Ser Glu Thr Phe Thr Cys Asn Val Val His Pro
            215                 220                 225 gcc agc aac act aaa gta gac aag cca gtg ccc aaa gag tcc acc tgc       776
Ala Ser Asn Thr Lys Val Asp Lys Pro Val Pro Lys Glu Ser Thr Cys
        230                 235                 240 aag tgt ata tcc cca tgc cca gtc cct gaa tca ctg gga ggg cct tcg       824
Lys Cys Ile Ser Pro Cys Pro Val Pro Glu Ser Leu Gly Gly Pro Ser
    245                 250                 255 gtc ttc atc ttt ccc ccg aaa ccc aag gac atc ctc agg att acc cga       872
Val Phe Ile Phe Pro Pro Lys Pro Lys Asp Ile Leu Arg Ile Thr Arg
260                 265                 270                 275
```

```
aca ccc gag atc acc tgt gtg gtg tta gat ctg ggc cgt gag gac cct    920
Thr Pro Glu Ile Thr Cys Val Val Leu Asp Leu Gly Arg Glu Asp Pro
            280                 285                 290 gag gtg cag atc agc tgg ttc gtg gat ggt aag gag gtg cac aca gcc    968
Glu Val Gln Ile Ser Trp Phe Val Asp Gly Lys Glu Val His Thr Ala
        295                 300                 305 aag acg cag cct cgt gag cag cag ttc aac agc acc tac cgt gtg gtc   1016
Lys Thr Gln Pro Arg Glu Gln Gln Phe Asn Ser Thr Tyr Arg Val Val
    310                 315                 320 agc gtc ctc ccc att gag cac cag gac tgg ctc acc gga aag gag ttc   1064
Ser Val Leu Pro Ile Glu His Gln Asp Trp Leu Thr Gly Lys Glu Phe
325                 330                 335 aag tgc aga gtc aac cac ata ggc ctc ccg tcc ccc atc gag agg act   1112
Lys Cys Arg Val Asn His Ile Gly Leu Pro Ser Pro Ile Glu Arg Thr
340                 345                 350                 355 atc tcc aaa gcc aga ggg caa gcc cat cag ccc agt gtg tat gtc ctg   1160
Ile Ser Lys Ala Arg Gly Gln Ala His Gln Pro Ser Val Tyr Val Leu
                360                 365                 370 cca cca tcc cca aag gag ttg tca tcc agt gac acg gtc acc ctg acc   1208
Pro Pro Ser Pro Lys Glu Leu Ser Ser Ser Asp Thr Val Thr Leu Thr
            375                 380                 385 tgc ctg atc aaa gac ttc ttc cca cct gag att gat gtg gag tgg cag   1256
Cys Leu Ile Lys Asp Phe Phe Pro Pro Glu Ile Asp Val Glu Trp Gln
        390                 395                 400 agc aat gga cag ccg gag ccc gag agc aag tac cac acg act gcg ccc   1304
Ser Asn Gly Gln Pro Glu Pro Glu Ser Lys Tyr His Thr Thr Ala Pro
    405                 410                 415 cag ctg gac gag gac ggg tcc tac ttc ctg tac agc aag ctc tct gtg   1352
Gln Leu Asp Glu Asp Gly Ser Tyr Phe Leu Tyr Ser Lys Leu Ser Val
420                 425                 430                 435 gac aag agc cgc tgg cag cag gga gac acc ttc aca tgt gcg gtg atg   1400
Asp Lys Ser Arg Trp Gln Gln Gly Asp Thr Phe Thr Cys Ala Val Met
                440                 445                 450 cat gaa gct cta cag aac cac tac aca gat cta tcc ctc tcc cat tct   1448
His Glu Ala Leu Gln Asn His Tyr Thr Asp Leu Ser Leu Ser His Ser
            455                 460                 465 ccg ggt aaa tga                                                    1460
Pro Gly Lys
    470
```

<210> SEQ ID NO 11
<211> LENGTH: 470
<212> TYPE: PRT
<213> ORGANISM: Canis familiaris

<400> SEQUENCE: 11

```
Met Glu Ser Val Leu Cys Trp Val Phe Leu Val Ser Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Asp Tyr Gly Met Ser Trp Val Arg Gln Ser Pro Gly Lys Gly Leu
    50                  55                  60

Gln Trp Val Ala Ala Val Ser Asn Arg Gly Asp Thr Tyr Tyr Ala Asp
65                  70                  75                  80

Ala Val Lys Gly Arg Phe Thr Ile Ser Arg Asp Asn Ala Lys Asn Thr
                85                  90                  95

Leu Tyr Leu Gln Met Ser Ser Leu Lys Ala Glu Asp Thr Ala Ile Tyr
```

```
                100             105             110
His Cys Val Thr Gly Val Trp Pro Arg His Tyr Tyr Gly Met Asp His
            115                 120                 125

Trp Gly Asn Gly Thr Ser Leu Phe Val Ser Ser Ala Ser Thr Thr Ala
        130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
            180                 185                 190

Pro Ser Val Leu Gln Ser Ser Gly Leu Tyr Ser Leu Ser Ser Thr Val
        195                 200                 205

Thr Val Pro Ser Ser Arg Trp Pro Ser Glu Thr Phe Thr Cys Asn Val
210                 215                 220

Val His Pro Ala Ser Asn Thr Lys Val Asp Lys Pro Val Pro Lys Glu
225                 230                 235                 240

Ser Thr Cys Lys Cys Ile Ser Pro Cys Pro Val Pro Glu Ser Leu Gly
                245                 250                 255

Gly Pro Ser Val Phe Ile Phe Pro Pro Lys Pro Lys Asp Ile Leu Arg
            260                 265                 270

Ile Thr Arg Thr Pro Glu Ile Thr Cys Val Val Leu Asp Leu Gly Arg
        275                 280                 285

Glu Asp Pro Glu Val Gln Ile Ser Trp Phe Val Asp Gly Lys Glu Val
    290                 295                 300

His Thr Ala Lys Thr Gln Pro Arg Glu Gln Gln Phe Asn Ser Thr Tyr
305                 310                 315                 320

Arg Val Val Ser Val Leu Pro Ile Glu His Gln Asp Trp Leu Thr Gly
                325                 330                 335

Lys Glu Phe Lys Cys Arg Val Asn His Ile Gly Leu Pro Ser Pro Ile
            340                 345                 350

Glu Arg Thr Ile Ser Lys Ala Arg Gly Gln Ala His Gln Pro Ser Val
        355                 360                 365

Tyr Val Leu Pro Pro Ser Pro Lys Glu Leu Ser Ser Ser Asp Thr Val
    370                 375                 380

Thr Leu Thr Cys Leu Ile Lys Asp Phe Phe Pro Pro Glu Ile Asp Val
385                 390                 395                 400

Glu Trp Gln Ser Asn Gly Gln Pro Glu Pro Glu Ser Lys Tyr His Thr
                405                 410                 415

Thr Ala Pro Gln Leu Asp Glu Asp Gly Ser Tyr Phe Leu Tyr Ser Lys
            420                 425                 430

Leu Ser Val Asp Lys Ser Arg Trp Gln Gln Gly Asp Thr Phe Thr Cys
        435                 440                 445

Ala Val Met His Glu Ala Leu Gln Asn His Tyr Thr Asp Leu Ser Leu
    450                 455                 460

Ser His Ser Pro Gly Lys
465                 470

<210> SEQ ID NO 12
<211> LENGTH: 1460
<212> TYPE: DNA
<213> ORGANISM: Canis familiaris

<400> SEQUENCE: 12
```

```
tcatttaccc ggagaatggg agagggatag atctgtgtag tggttctgta gagcttcatg      60
catcaccgca catgtgaagg tgtctccctg ctgccagcgg ctcttgtcca cagagagctt     120
gctgtacagg aagtaggacc cgtcctcgtc cagctgggc gcagtcgtgt ggtacttgct      180
ctcgggctcc ggctgtccat tgctctgcca ctccacatca atctcaggtg gaagaagtc     240 tttgatcagg caggtcaggg tgaccgtgtc actggatgac aactcctttg gggatggtgg    300
caggacatac acactgggct gatgggcttg ccctctggct ttggagatag tcctctcgat    360
gggggacggg aggcctatgt ggttgactct gcacttgaac tcctttccgg tgagccagtc    420
ctggtgctca atggggagga cgctgaccac acggtaggtg ctgttgaact gctgctcacg    480
aggctgcgtc ttggctgtgt gcacctcctt accatccacg aaccagctga tctgcacctc    540
agggtcctca cggcccagat ctaacaccac acaggtgatc tcgggtgttc gggtaatcct    600
gaggatgtcc ttgggtttcg ggggaaagat gaagaccgaa ggccctccca gtgattcagg    660
gactgggcat ggggatatac acttgcaggt ggactctttg ggcactggct tgtctacttt    720
agtgttgctg gccgggtgga ccacgttgca ggtgaaggtc tcgctgggcc acctgctgga    780
gggcactgtc accgtgctgc tgagggagta gagccctgag gactgcagga cggacgggaa    840
ggtgtgcaca ccgctggtca aggagccgga attccaggac acagttacag gctcggggaa    900
gtagcctgac accaggcagg ccaggccac cgtggagccg gaagtggacc cgcagctggg    960
ggccagtggg aaaaccgagg gggccgtggt ggaggctgag gacacgaaga gtgaggtgcc   1020
attgccccag tggtccatac cataataatg tcgcggccat actcccgtca cacagtgata   1080
gattgccgtg tcctcggctt tcaggctgct catctggaga tacagcgtgt tcttggcgtt   1140
gtctctggag atggtgaatc ggcccttcac agcgtctgcg tagtaagtat ctccacgatt   1200
gctaacagct gcgacccact gcagccctt ccctggagac tgacggaccc aactcatgcc    1260
atagtcactg aaggtgaatc cagaggccac acaggacagt ctcaaggacc ccccaggctt   1320
caccaggtct cccccagact ccaccagttg cacctcaccc tggacacctt ttaaaataga   1380
gacaaggaaa acccagcaga gcacagactc catggtggtt tgtctgtgtt gtgtcctgag   1440
cactgaatgg ggtcacctgg                                               1460

<210> SEQ ID NO 13
<211> LENGTH: 60
<212> TYPE: DNA
<213> ORGANISM: Canis familiaris
<220> FEATURE:
<221> NAME/KEY: CDS
<222> LOCATION: (1)..(60)
<223> OTHER INFORMATION:

<400> SEQUENCE: 13 gcc aaa gaa tgc gag tgc aag tgt aac tgt aac aac tgc cca tgc cca      48
Ala Lys Glu Cys Glu Cys Lys Cys Asn Cys Asn Asn Cys Pro Cys Pro
1               5                   10                  15 ggt tgt ggc ctg                                                      60
Gly Cys Gly Leu
            20

<210> SEQ ID NO 14
<211> LENGTH: 20
<212> TYPE: PRT
<213> ORGANISM: Canis familiaris

<400> SEQUENCE: 14

Ala Lys Glu Cys Glu Cys Lys Cys Asn Cys Asn Asn Cys Pro Cys Pro
```

-continued

```
1               5                   10                  15

Gly Cys Gly Leu
        20

<210> SEQ ID NO 15
<211> LENGTH: 60
<212> TYPE: DNA
<213> ORGANISM: Canis familiaris

<400> SEQUENCE: 15
caggccacaa cctgggcatg ggcagttgtt acagttacac ttgcactcgc attctttggc    60

<210> SEQ ID NO 16
<211> LENGTH: 1456
<212> TYPE: DNA
<213> ORGANISM: Canis familiaris
<220> FEATURE:
<221> NAME/KEY: CDS
<222> LOCATION: (32)..(1453)
<223> OTHER INFORMATION:
<220> FEATURE:
<221> NAME/KEY: misc_feature
<222> LOCATION: (27)..(27)
<223> OTHER INFORMATION: At nucleotide 27, n = unknown

<400> SEQUENCE: 16
aagtgctcag gcacaacaca gacaaancac c atg gag tct gtg ctc tac tgg       52
                                   Met Glu Ser Val Leu Tyr Trp
                                   1               5 gtt ttc ctt gtc gct att tta aag ggt gtc cag ggt gac gtg cag ctg     100
Val Phe Leu Val Ala Ile Leu Lys Gly Val Gln Gly Asp Val Gln Leu
        10                  15                  20 gtg gag tct ggg gga gac ctg gtg aag cct ggg ggg tcc ttg aga ctg     148
Val Glu Ser Gly Gly Asp Leu Val Lys Pro Gly Gly Ser Leu Arg Leu
    25                  30                  35 tcc tgt gtg gcc tct gga ttc acc ttt agt agc tgt gcc atg agc tgg     196
Ser Cys Val Ala Ser Gly Phe Thr Phe Ser Ser Cys Ala Met Ser Trp
40                  45                  50                  55 gtc cgt cag tct cca ggg aag ggg cct cag tgg gtc gca act att cgg     244
Val Arg Gln Ser Pro Gly Lys Gly Pro Gln Trp Val Ala Thr Ile Arg
                60                  65                  70 tat gat gga agt gat ata tac tac gca gac gct gtg aag ggc cga ttc     292
Tyr Asp Gly Ser Asp Ile Tyr Tyr Ala Asp Ala Val Lys Gly Arg Phe
            75                  80                  85 agc atc tcc aga gac aac gcc aag aac acg gtg tat ctg cag atg aac     340
Ser Ile Ser Arg Asp Asn Ala Lys Asn Thr Val Tyr Leu Gln Met Asn
        90                  95                 100 agc ctg aga gcc gag gac acg gcc gtg tat tat tgt gcg aag gcc ccc     388
Ser Leu Arg Ala Glu Asp Thr Ala Val Tyr Tyr Cys Ala Lys Ala Pro
    105                 110                 115 ccc tac gat agt tac cac tat ggt atg gac tat tgg ggt cct ggc act     436
Pro Tyr Asp Ser Tyr His Tyr Gly Met Asp Tyr Trp Gly Pro Gly Thr
120                 125                 130                 135 tcc ctc ttc gtg tcg tca gcc tcc acc acg gcc ccc tcg gtt ttc cca     484
Ser Leu Phe Val Ser Ser Ala Ser Thr Thr Ala Pro Ser Val Phe Pro
                140                 145                 150 ctg gcc ccc agc tgt ggg tcc caa tcc ggc tcc acg gtg gcc ctg gcc     532
Leu Ala Pro Ser Cys Gly Ser Gln Ser Gly Ser Thr Val Ala Leu Ala
            155                 160                 165 tgc ctg gtg tca ggc tac atc ccc gag cct gta act gtg tcc tgg aat     580
Cys Leu Val Ser Gly Tyr Ile Pro Glu Pro Val Thr Val Ser Trp Asn
        170                 175                 180
```

```
tcc gtc tcc ttg acc agc ggt gtg cac acc ttc ccg tcc gtc ctg cag      628
Ser Val Ser Leu Thr Ser Gly Val His Thr Phe Pro Ser Val Leu Gln
    185                 190                 195 tcc tca ggg ctc tac tcc ctc agc agc atg gtg aca gtg ccc tcc agc      676
Ser Ser Gly Leu Tyr Ser Leu Ser Ser Met Val Thr Val Pro Ser Ser
200                 205                 210                 215 agg tgg ccc agc gag acc ttc acc tgc aat gtg gcc cac ccg gcc acc      724
Arg Trp Pro Ser Glu Thr Phe Thr Cys Asn Val Ala His Pro Ala Thr
                220                 225                 230 aac act aaa gta gac aag cca gtg gcc aaa gaa tgc gag tgc aag tgt      772
Asn Thr Lys Val Asp Lys Pro Val Ala Lys Glu Cys Glu Cys Lys Cys
            235                 240                 245 aac tgt aac aac tgc cca tgc cca ggt tgt ggc ctg ctg gga ggg cct      820
Asn Cys Asn Asn Cys Pro Cys Pro Gly Cys Gly Leu Leu Gly Gly Pro
        250                 255                 260 tcg gtc ttc atc ttt ccc cca aaa ccc aag gac atc ctc gtg act gcc      868
Ser Val Phe Ile Phe Pro Pro Lys Pro Lys Asp Ile Leu Val Thr Ala
265                 270                 275 cgg aca ccc aca gtc act tgt gtg gtg gtg gat ctg gac cca gaa aac      916
Arg Thr Pro Thr Val Thr Cys Val Val Val Asp Leu Asp Pro Glu Asn
280                 285                 290                 295 cct gag gtg cag atc agc tgg ttc gtg gat agt aag cag gtg caa aca      964
Pro Glu Val Gln Ile Ser Trp Phe Val Asp Ser Lys Gln Val Gln Thr
                300                 305                 310 gcc aac acg cag cct cgt gag gag cag tcc aat ggc acc tac cgt gtg     1012
Ala Asn Thr Gln Pro Arg Glu Glu Gln Ser Asn Gly Thr Tyr Arg Val
            315                 320                 325 gtc agt gtc ctc ccc att ggg cac cag gac tgg ctt tca ggg aag cag     1060
Val Ser Val Leu Pro Ile Gly His Gln Asp Trp Leu Ser Gly Lys Gln
        330                 335                 340 ttc aag tgc aaa gtc aac aac aaa gcc ctc cca tcc ccc att gag gag     1108
Phe Lys Cys Lys Val Asn Asn Lys Ala Leu Pro Ser Pro Ile Glu Glu
345                 350                 355 atc atc tcc aag acc cca ggg cag gcc cat cag cct aat gtg tat gtc     1156
Ile Ile Ser Lys Thr Pro Gly Gln Ala His Gln Pro Asn Val Tyr Val
360                 365                 370                 375 ctg ccg cca tcg cgg gat gag atg agc aag aat acg gtc acc ctg acc     1204
Leu Pro Pro Ser Arg Asp Glu Met Ser Lys Asn Thr Val Thr Leu Thr
                380                 385                 390 tgt ctg gtc aaa gac ttc ttc cca cct gag att gat gtg gag tgg cag     1252
Cys Leu Val Lys Asp Phe Phe Pro Pro Glu Ile Asp Val Glu Trp Gln
            395                 400                 405 agc aat gga cag cag gag cct gag agc aag tac cgc atg acc ccg ccc     1300
Ser Asn Gly Gln Gln Glu Pro Glu Ser Lys Tyr Arg Met Thr Pro Pro
        410                 415                 420 cag ctg gat gaa gat ggg tcc tac ttc cta tac agc aag ctc tcc gtg     1348
Gln Leu Asp Glu Asp Gly Ser Tyr Phe Leu Tyr Ser Lys Leu Ser Val
425                 430                 435 gac aag agc cgc tgg cag cgg gga gac acc ttc ata tgt gcg gtg atg     1396
Asp Lys Ser Arg Trp Gln Arg Gly Asp Thr Phe Ile Cys Ala Val Met
440                 445                 450                 455 cat gaa gct cta cac aac cac tac aca cag ata tcc ctc tcc cat tct     1444
His Glu Ala Leu His Asn His Tyr Thr Gln Ile Ser Leu Ser His Ser
                460                 465                 470 ccg ggt aaa tga                                                      1456
Pro Gly Lys

<210> SEQ ID NO 17
<211> LENGTH: 474
<212> TYPE: PRT
```

<213> ORGANISM: Canis familiaris

<400> SEQUENCE: 17

```
Met Glu Ser Val Leu Tyr Trp Val Phe Leu Val Ala Ile Leu Lys Gly
1               5                   10                  15
Val Gln Gly Asp Val Gln Leu Val Glu Ser Gly Gly Asp Leu Val Lys
            20                  25                  30
Pro Gly Gly Ser Leu Arg Leu Ser Cys Val Ala Ser Gly Phe Thr Phe
        35                  40                  45
Ser Ser Cys Ala Met Ser Trp Val Arg Gln Ser Pro Gly Lys Gly Pro
    50                  55                  60
Gln Trp Val Ala Thr Ile Arg Tyr Asp Gly Ser Asp Ile Tyr Tyr Ala
65                  70                  75                  80
Asp Ala Val Lys Gly Arg Phe Ser Ile Ser Arg Asp Asn Ala Lys Asn
                85                  90                  95
Thr Val Tyr Leu Gln Met Asn Ser Leu Arg Ala Glu Asp Thr Ala Val
            100                 105                 110
Tyr Tyr Cys Ala Lys Ala Pro Pro Tyr Asp Ser Tyr His Tyr Gly Met
        115                 120                 125
Asp Tyr Trp Gly Pro Gly Thr Ser Leu Phe Val Ser Ser Ala Ser Thr
    130                 135                 140
Thr Ala Pro Ser Val Phe Pro Leu Ala Pro Ser Cys Gly Ser Gln Ser
145                 150                 155                 160
Gly Ser Thr Val Ala Leu Ala Cys Leu Val Ser Gly Tyr Ile Pro Glu
                165                 170                 175
Pro Val Thr Val Ser Trp Asn Ser Val Ser Leu Thr Ser Gly Val His
            180                 185                 190
Thr Phe Pro Ser Val Leu Gln Ser Ser Gly Leu Tyr Ser Leu Ser Ser
        195                 200                 205
Met Val Thr Val Pro Ser Ser Arg Trp Pro Ser Glu Thr Phe Thr Cys
    210                 215                 220
Asn Val Ala His Pro Ala Thr Asn Thr Lys Val Asp Lys Pro Val Ala
225                 230                 235                 240
Lys Glu Cys Glu Cys Lys Cys Asn Cys Asn Asn Cys Pro Cys Pro Gly
                245                 250                 255
Cys Gly Leu Leu Gly Gly Pro Ser Val Phe Ile Phe Pro Pro Lys Pro
            260                 265                 270
Lys Asp Ile Leu Val Thr Ala Arg Thr Pro Thr Val Thr Cys Val Val
        275                 280                 285
Val Asp Leu Asp Pro Glu Asn Pro Glu Val Gln Ile Ser Trp Phe Val
    290                 295                 300
Asp Ser Lys Gln Val Gln Thr Ala Asn Thr Gln Pro Arg Glu Glu Gln
305                 310                 315                 320
Ser Asn Gly Thr Tyr Arg Val Val Ser Val Leu Pro Ile Gly His Gln
                325                 330                 335
Asp Trp Leu Ser Gly Lys Gln Phe Lys Cys Lys Val Asn Asn Lys Ala
            340                 345                 350
Leu Pro Ser Pro Ile Glu Glu Ile Ile Ser Lys Thr Pro Gly Gln Ala
        355                 360                 365
His Gln Pro Asn Val Tyr Val Leu Pro Pro Ser Arg Asp Glu Met Ser
    370                 375                 380
Lys Asn Thr Val Thr Leu Thr Cys Leu Val Lys Asp Phe Phe Pro Pro
385                 390                 395                 400
```

```
Glu Ile Asp Val Glu Trp Gln Ser Asn Gly Gln Gln Glu Pro Glu Ser
                405                 410                 415

Lys Tyr Arg Met Thr Pro Pro Gln Leu Asp Glu Asp Gly Ser Tyr Phe
                420                 425                 430

Leu Tyr Ser Lys Leu Ser Val Asp Lys Ser Arg Trp Gln Arg Gly Asp
            435                 440                 445

Thr Phe Ile Cys Ala Val Met His Glu Ala Leu His Asn His Tyr Thr
        450                 455                 460

Gln Ile Ser Leu Ser His Ser Pro Gly Lys
465                 470

<210> SEQ ID NO 18
<211> LENGTH: 1456
<212> TYPE: DNA
<213> ORGANISM: Canis familiaris
<220> FEATURE:
<221> NAME/KEY: misc_feature
<222> LOCATION: (1430)..(1430)
<223> OTHER INFORMATION: At nucleotide 1430, n = unknown

<400> SEQUENCE: 18
tcatttaccc ggagaatggg agagggatat ctgtgtgtag tggttgtgta gagcttcatg      60
catcaccgca catatgaagg tgtctccccg ctgccagcgg ctcttgtcca cggagagctt     120
gctgtatagg aagtaggacc catcttcatc cagctggggc ggggtcatgc ggtacttgct     180
ctcaggctcc tgctgtccat tgctctgcca ctccacatca atctcaggtg ggaagaagtc     240
tttgaccaga caggtcaggg tgaccgtatt cttgctcatc tcatcccgcg atggcggcag     300
gacatacaca ttaggctgat gggcctgccc tggggtcttg gagatgatct cctcaatggg     360
ggatgggagg gctttgttgt tgactttgca cttgaactgc ttccctgaaa gccagtcctg     420
gtgcccaatg ggaggacac tgaccacacg gtaggtgcca ttggactgct cctcacgagg      480
ctgcgtgttg gctgtttgca cctgcttact atccacgaac cagctgatct gcacctcagg     540
gttttctggg tccagatcca ccaccacaca agtgactgtg ggtgtccggg cagtcacgag     600
gatgtccttg ggttttgggg gaaagatgaa gaccgaaggc cctcccagca ggccacaacc     660
tgggcatggg cagttgttac agttacactt gcactcgcat tctttggcca ctggcttgtc     720
tactttagtt ttggtggccg ggtgggccac attgcaggtg aaggtctcgc tgggccacct     780
gctggagggc actgtcacca tgctgctgag ggagtagagc cctgaggact gcaggacgga     840
cgggaaggtg tgcacaccgc tggtcaagga gacggaattc caggacacag ttacaggctc     900
ggggatgtag cctgacacca ggcaggccag ggccaccgtg gagccggatt gggacccaca     960 gctggggcc agtgggaaaa ccgagggggc cgtggtggag gctgacgaca cgaagaggga    1020
agtgccagga ccccaatagt ccataccata gtggtaacta tcgtagggg gggccttcgc    1080 acaataatac acgccgtgt cctcggctct caggctgttc atctgcagat acaccgtgtt    1140
cttggcgttg tctctggaga tgctgaatcg gcccttcaca gcgtctgcgt agtatatatc    1200
acttccatca taccgaatag ttgcgaccca ctgaggcccc ttccctggag actgacggac    1260
ccagctcatg gcacagctac taaaggtgaa tccagaggcc acacaggaca gtctcaagga    1320 cccccaggc ttcaccaggt ctcccccaga ctccaccagc tgcacgtcac cctgacacac     1380
ctttaaaata gcgacaagga aaacccagta gagcacagac tccatggtgn tttgtctgtg    1440
ttgtgcctga gcactt                                                    1456

<210> SEQ ID NO 19
```

```
<211> LENGTH: 1453
<212> TYPE: DNA
<213> ORGANISM: Canis familiaris
<220> FEATURE:
<221> NAME/KEY: CDS
<222> LOCATION: (32)..(1450)
<223> OTHER INFORMATION:

<400> SEQUENCE: 19
```

| | | | | | | | | | | | | | | | | |
|---|---|---|---|---|---|---|---|---|---|---|---|---|---|---|---|---|
| agtgctcagg | acaccacaca | gacaaatcac | c atg gag tct gtg ctc ttc tgg | | | | | | | | | | | | | 52 |
| | | | Met Glu Ser Val Leu Phe Trp | | | | | | | | | | | | | |
| | | | 1 | | | 5 | | | | | | | | | | |

| gtt | ttc | ctt | gtc | act | att | tta | aaa | ggt | gtc | cag | ggt | gag | gta | cgt | ttg | 100 |
|---|---|---|---|---|---|---|---|---|---|---|---|---|---|---|---|---|
| Val | Phe | Leu | Val | Thr | Ile | Leu | Lys | Gly | Val | Gln | Gly | Glu | Val | Arg | Leu | |
| | | 10 | | | | | 15 | | | | | 20 | | | | |

| gtg | gag | tct | gga | gga | acc | ctg | gtg | aag | cct | ggg | ggg | tcc | ctg | aaa | ctc | 148 |
|---|---|---|---|---|---|---|---|---|---|---|---|---|---|---|---|---|
| Val | Glu | Ser | Gly | Gly | Thr | Leu | Val | Lys | Pro | Gly | Gly | Ser | Leu | Lys | Leu | |
| | 25 | | | | | 30 | | | | | 35 | | | | | |

| tct | tgt | gtg | gcc | tct | gga | ttc | acc | ttc | aga | aga | tac | tcc | atg | gac | tgg | 196 |
|---|---|---|---|---|---|---|---|---|---|---|---|---|---|---|---|---|
| Ser | Cys | Val | Ala | Ser | Gly | Phe | Thr | Phe | Arg | Arg | Tyr | Ser | Met | Asp | Trp | |
| 40 | | | | | 45 | | | | | 50 | | | | | 55 | |

| gtc | cgc | cag | gct | cca | ggc | aag | agc | ctg | cag | tgg | gtc | gcc | ggg | att | aac | 244 |
|---|---|---|---|---|---|---|---|---|---|---|---|---|---|---|---|---|
| Val | Arg | Gln | Ala | Pro | Gly | Lys | Ser | Leu | Gln | Trp | Val | Ala | Gly | Ile | Asn | |
| | | | | 60 | | | | | 65 | | | | | 70 | | |

| ggt | gat | ggc | aca | gga | aca | tcc | tat | tca | cag | act | gtg | aag | ggc | cga | ttc | 292 |
|---|---|---|---|---|---|---|---|---|---|---|---|---|---|---|---|---|
| Gly | Asp | Gly | Thr | Gly | Thr | Ser | Tyr | Ser | Gln | Thr | Val | Lys | Gly | Arg | Phe | |
| | | | 75 | | | | | 80 | | | | | 85 | | | |

| acc | atc | tcc | aga | gac | aac | gcc | aag | aac | acc | ctc | tat | ctg | cag | ata | aac | 340 |
|---|---|---|---|---|---|---|---|---|---|---|---|---|---|---|---|---|
| Thr | Ile | Ser | Arg | Asp | Asn | Ala | Lys | Asn | Thr | Leu | Tyr | Leu | Gln | Ile | Asn | |
| | | 90 | | | | | 95 | | | | | 100 | | | | |

| agc | ctg | aga | gcc | gaa | gac | tct | gct | gtg | tat | tat | tgt | gcc | aag | agc | tgg | 388 |
|---|---|---|---|---|---|---|---|---|---|---|---|---|---|---|---|---|
| Ser | Leu | Arg | Ala | Glu | Asp | Ser | Ala | Val | Tyr | Tyr | Cys | Ala | Lys | Ser | Trp | |
| | 105 | | | | | 110 | | | | | 115 | | | | | |

| tct | cgt | aat | ggg | gat | ctt | gac | tac | tgg | ggc | cag | gga | acc | ctg | gtc | acc | 436 |
|---|---|---|---|---|---|---|---|---|---|---|---|---|---|---|---|---|
| Ser | Arg | Asn | Gly | Asp | Leu | Asp | Tyr | Trp | Gly | Gln | Gly | Thr | Leu | Val | Thr | |
| 120 | | | | | 125 | | | | | 130 | | | | | 135 | |

| gtc | tcc | tca | gcc | tcc | acc | acg | gcc | ccc | tcg | gtt | ttc | cca | ctg | gcc | ccc | 484 |
|---|---|---|---|---|---|---|---|---|---|---|---|---|---|---|---|---|
| Val | Ser | Ser | Ala | Ser | Thr | Thr | Ala | Pro | Ser | Val | Phe | Pro | Leu | Ala | Pro | |
| | | | | 140 | | | | | 145 | | | | | 150 | | |

| agc | tgc | ggg | tcc | act | tcc | ggc | tcc | acg | gtg | gcc | ctg | gcc | tgc | ctg | gtg | 532 |
|---|---|---|---|---|---|---|---|---|---|---|---|---|---|---|---|---|
| Ser | Cys | Gly | Ser | Thr | Ser | Gly | Ser | Thr | Val | Ala | Leu | Ala | Cys | Leu | Val | |
| | | | 155 | | | | | 160 | | | | | 165 | | | |

| tca | ggc | tac | ttc | ccc | gag | cct | gta | act | gtg | tcc | tgg | aat | tcc | ggc | tcc | 580 |
|---|---|---|---|---|---|---|---|---|---|---|---|---|---|---|---|---|
| Ser | Gly | Tyr | Phe | Pro | Glu | Pro | Val | Thr | Val | Ser | Trp | Asn | Ser | Gly | Ser | |
| | | 170 | | | | | 175 | | | | | 180 | | | | |

| ttg | acc | agc | ggt | gtg | cac | acc | ttc | ccg | tcc | gtc | ctg | cag | tcc | tca | ggg | 628 |
|---|---|---|---|---|---|---|---|---|---|---|---|---|---|---|---|---|
| Leu | Thr | Ser | Gly | Val | His | Thr | Phe | Pro | Ser | Val | Leu | Gln | Ser | Ser | Gly | |
| | 185 | | | | | 190 | | | | | 195 | | | | | |

| ctc | tac | tcc | ctc | agc | agc | atg | gtg | aca | gtg | ccc | tcc | agc | agg | tgg | ccc | 676 |
|---|---|---|---|---|---|---|---|---|---|---|---|---|---|---|---|---|
| Leu | Tyr | Ser | Leu | Ser | Ser | Met | Val | Thr | Val | Pro | Ser | Ser | Arg | Trp | Pro | |
| 200 | | | | | 205 | | | | | 210 | | | | | 215 | |

| agc | gag | acc | ttc | acc | tgc | aac | gtg | gcc | cac | ccg | gcc | agc | aaa | act | aaa | 724 |
|---|---|---|---|---|---|---|---|---|---|---|---|---|---|---|---|---|
| Ser | Glu | Thr | Phe | Thr | Cys | Asn | Val | Ala | His | Pro | Ala | Ser | Lys | Thr | Lys | |
| | | | | 220 | | | | | 225 | | | | | 230 | | |

| gta | gac | aag | cca | gtg | ccc | aaa | aga | gaa | aat | gga | aga | gtt | cct | cgc | cca | 772 |
|---|---|---|---|---|---|---|---|---|---|---|---|---|---|---|---|---|
| Val | Asp | Lys | Pro | Val | Pro | Lys | Arg | Glu | Asn | Gly | Arg | Val | Pro | Arg | Pro | |
| | | | 235 | | | | | 240 | | | | | 245 | | | |

| cct | gat | tgt | ccc | aaa | tgc | cca | gcc | cct | gaa | atg | ctg | gga | ggg | cct | tcg | 820 |
|---|---|---|---|---|---|---|---|---|---|---|---|---|---|---|---|---|
| Pro | Asp | Cys | Pro | Lys | Cys | Pro | Ala | Pro | Glu | Met | Leu | Gly | Gly | Pro | Ser | |
| | | 250 | | | | | 255 | | | | | 260 | | | | |

| gtc | ttc | atc | ttt | ccc | ccg | aaa | ccc | aag | gac | acc | ctc | ttg | att | gcc | cga | 868 |

```

Val Phe Ile Phe Pro Pro Lys Pro Lys Asp Thr Leu Leu Ile Ala Arg
    265                 270                 275 aca cct gag gtc aca tgt gtg gtg gtg gat ctg gac cca gaa gac cct         916
Thr Pro Glu Val Thr Cys Val Val Val Asp Leu Asp Pro Glu Asp Pro
280                 285                 290                 295 gag gtg cag atc agc tgg ttc gtg gac ggt aag cag atg caa aca gcc         964
Glu Val Gln Ile Ser Trp Phe Val Asp Gly Lys Gln Met Gln Thr Ala
            300                 305                 310 aag act cag cct cgt gag gag cag ttc aat ggc acc tac cgt gtg gtc        1012
Lys Thr Gln Pro Arg Glu Glu Gln Phe Asn Gly Thr Tyr Arg Val Val
        315                 320                 325 agt gtc ctc ccc att ggg cac cag gac tgg ctc aag ggg aag cag ttc        1060
Ser Val Leu Pro Ile Gly His Gln Asp Trp Leu Lys Gly Lys Gln Phe
    330                 335                 340 acg tgc aaa gtc aac aac aaa gcc ctc cca tcc ccg atc gag agg acc        1108
Thr Cys Lys Val Asn Asn Lys Ala Leu Pro Ser Pro Ile Glu Arg Thr
345                 350                 355 atc tcc aag gcc aga ggg caa gcc cat cag ccc agt gtg tat gtc ctg        1156
Ile Ser Lys Ala Arg Gly Gln Ala His Gln Pro Ser Val Tyr Val Leu
360                 365                 370                 375 ccg cca tcc cgg gag gag ttg agc aag aac aca gtc agc ttg aca tgc        1204
Pro Pro Ser Arg Glu Glu Leu Ser Lys Asn Thr Val Ser Leu Thr Cys
            380                 385                 390 ctg atc aaa gac ttc ttc cca cct gac att gat gtg gag tgg cag agc        1252
Leu Ile Lys Asp Phe Phe Pro Pro Asp Ile Asp Val Glu Trp Gln Ser
        395                 400                 405 aat gga cag cag gag cct gag agc aag tac cgc acg acc ccg ccc cag        1300
Asn Gly Gln Gln Glu Pro Glu Ser Lys Tyr Arg Thr Thr Pro Pro Gln
    410                 415                 420 ctg gac gag gac ggg tcc tac ttc ctg tac agc aag ctc tct gtg gac        1348
Leu Asp Glu Asp Gly Ser Tyr Phe Leu Tyr Ser Lys Leu Ser Val Asp
425                 430                 435 aag agc cgc tgg cag cgg gga gac acc ttc ata tgt gcg gtg atg cat        1396
Lys Ser Arg Trp Gln Arg Gly Asp Thr Phe Ile Cys Ala Val Met His
440                 445                 450                 455 gaa gct cta cac aac cac tac aca cag gaa tcc ctc tcc cat tct ccg        1444
Glu Ala Leu His Asn His Tyr Thr Gln Glu Ser Leu Ser His Ser Pro
            460                 465                 470 ggt aaa tga                                                             1453
Gly Lys <210> SEQ ID NO 20
<211> LENGTH: 473
<212> TYPE: PRT
<213> ORGANISM: Canis familiaris

<400> SEQUENCE: 20

Met Glu Ser Val Leu Phe Trp Val Phe Leu Val Thr Ile Leu Lys Gly
1               5                   10                  15

Val Gln Gly Glu Val Arg Leu Val Glu Ser Gly Gly Thr Leu Val Lys
            20                  25                  30

Pro Gly Gly Ser Leu Lys Leu Ser Cys Val Ala Ser Gly Phe Thr Phe
        35                  40                  45

Arg Arg Tyr Ser Met Asp Trp Val Arg Gln Ala Pro Gly Lys Ser Leu
    50                  55                  60

Gln Trp Val Ala Gly Ile Asn Gly Asp Gly Thr Gly Thr Ser Tyr Ser
65                  70                  75                  80

Gln Thr Val Lys Gly Arg Phe Thr Ile Ser Arg Asp Asn Ala Lys Asn
                85                  90                  95
```

Thr Leu Tyr Leu Gln Ile Asn Ser Leu Arg Ala Glu Asp Ser Ala Val
            100                 105                 110

Tyr Tyr Cys Ala Lys Ser Trp Ser Arg Asn Gly Asp Leu Asp Tyr Trp
            115                 120                 125

Gly Gln Gly Thr Leu Val Thr Val Ser Ser Ala Ser Thr Thr Ala Pro
        130                 135                 140

Ser Val Phe Pro Leu Ala Pro Ser Cys Gly Ser Thr Ser Gly Ser Thr
145                 150                 155                 160

Val Ala Leu Ala Cys Leu Val Ser Gly Tyr Phe Pro Glu Pro Val Thr
                165                 170                 175

Val Ser Trp Asn Ser Gly Ser Leu Thr Ser Gly Val His Thr Phe Pro
            180                 185                 190

Ser Val Leu Gln Ser Ser Gly Leu Tyr Ser Leu Ser Ser Met Val Thr
        195                 200                 205

Val Pro Ser Ser Arg Trp Pro Ser Glu Thr Phe Thr Cys Asn Val Ala
    210                 215                 220

His Pro Ala Ser Lys Thr Lys Val Asp Lys Pro Val Pro Lys Arg Glu
225                 230                 235                 240

Asn Gly Arg Val Pro Arg Pro Pro Asp Cys Pro Lys Cys Pro Ala Pro
                245                 250                 255

Glu Met Leu Gly Gly Pro Ser Val Phe Ile Phe Pro Pro Lys Pro Lys
            260                 265                 270

Asp Thr Leu Leu Ile Ala Arg Thr Pro Glu Val Thr Cys Val Val Val
        275                 280                 285

Asp Leu Asp Pro Glu Asp Pro Glu Val Gln Ile Ser Trp Phe Val Asp
    290                 295                 300

Gly Lys Gln Met Gln Thr Ala Lys Thr Gln Pro Arg Glu Glu Gln Phe
305                 310                 315                 320

Asn Gly Thr Tyr Arg Val Val Ser Val Leu Pro Ile Gly His Gln Asp
                325                 330                 335

Trp Leu Lys Gly Lys Gln Phe Thr Cys Lys Val Asn Asn Lys Ala Leu
            340                 345                 350

Pro Ser Pro Ile Glu Arg Thr Ile Ser Lys Ala Arg Gly Gln Ala His
        355                 360                 365

Gln Pro Ser Val Tyr Val Leu Pro Pro Ser Arg Glu Glu Leu Ser Lys
    370                 375                 380

Asn Thr Val Ser Leu Thr Cys Leu Ile Lys Asp Phe Phe Pro Pro Asp
385                 390                 395                 400

Ile Asp Val Glu Trp Gln Ser Asn Gly Gln Gln Glu Pro Glu Ser Lys
                405                 410                 415

Tyr Arg Thr Thr Pro Pro Gln Leu Asp Glu Asp Gly Ser Tyr Phe Leu
            420                 425                 430

Tyr Ser Lys Leu Ser Val Asp Lys Ser Arg Trp Gln Arg Gly Asp Thr
        435                 440                 445

Phe Ile Cys Ala Val Met His Glu Ala Leu His Asn His Tyr Thr Gln
    450                 455                 460

Glu Ser Leu Ser His Ser Pro Gly Lys
465                 470

<210> SEQ ID NO 21
<211> LENGTH: 1453
<212> TYPE: DNA
<213> ORGANISM: Canis familiaris

```
<400> SEQUENCE: 21
tcatttaccc ggagaatggg agagggattc ctgtgtgtag tggttgtgta gagcttcatg      60
catcaccgca catatgaagg tgtctccccg ctgccagcgg ctcttgtcca cagagagctt     120
gctgtacagg aagtaggacc cgtcctcgtc cagctggggc ggggtcgtgc ggtacttgct     180
ctcaggctcc tgctgtccat tgctctgcca ctccacatca atgtcaggtg gaagaagtc      240 tttgatcagg catgtcaagc tgactgtgtt cttgctcaac cctcccggg atggcggcag      300 gacatacaca ctgggctgat gggcttgccc tctggccttg gagatggtcc tctcgatcgg     360
ggatgggagg gctttgttgt tgactttgca cgtgaactgc ttccccttga ccagtcctg     420 gtgcccaatg gggaggacac tgaccacacg gtaggtgcca ttgaactgct cctcacgagg     480
ctgagtcttg gctgtttgca tctgcttacc gtccacgaac cagctgatct gcacctcagg     540
gtcttctggg tccagatcca ccaccacaca tgtgacctca ggtgttcggg caatcaagag     600
ggtgtccttg ggtttcgggg gaaagatgaa gaccgaaggc cctcccagca tttcaggggc     660
tgggcatttg ggacaatcag gtgggcgagg aactcttcca tttttctcttt tgggcactgg    720 cttgtctact ttagttttgc tggccgggtg ggccacgttg caggtgaagg tctcgctggg    780
ccacctgctg gagggcactg tcaccatgct gctgagggag tagagccctg aggactgcag    840
gacgacggag aaggtgtgca caccgctggt caaggagccg gaattccagg acacagttac     900
aggctcgggg aagtagcctg acaccaggca ggccagggcc accgtggagc cggaagtgga    960
cccgcagctg ggggccagtg ggaaaaccga ggggccgtg gtggaggctg aggagacggt    1020
gaccagggtt ccctggcccc agtagtcaag atccccatta cgagaccagc tcttggcaca   1080
ataatacaca gcagagtctt cggctctcag gctgtttatc tgcagataga gggtgttctt    1140
ggcgttgtct ctggagatgg tgaatcggcc cttcacagtc tgtgaatagg atgttcctgt   1200
gccatcaccg ttaatcccgg cgacccactg caggctcttg cctggagcct ggcggaccca   1260
gtccatggag tatcttctga aggtgaatcc agaggccaca caagagagtt tcagggaccc   1320
cccaggcttc accagggttc ctccagactc caccaaacgt acctcaccct ggacaccttt    1380
taaaatagtg acaaggaaaa cccagaagag cacagactcc atggtgattt gtctgtgtgg   1440
tgtcctgagc act                                                       1453

<210> SEQ ID NO 22
<211> LENGTH: 66
<212> TYPE: DNA
<213> ORGANISM: Canis familiaris
<220> FEATURE:
<221> NAME/KEY: CDS
<222> LOCATION: (1)..(66)
<223> OTHER INFORMATION:

<400> SEQUENCE: 22 ccc aaa aga gaa aat gga aga gtt cct cgc cca cct gat tgt ccc aaa      48
Pro Lys Arg Glu Asn Gly Arg Val Pro Arg Pro Pro Asp Cys Pro Lys
1               5                   10                  15 tgc cca gcc cct gaa atg                                              66
Cys Pro Ala Pro Glu Met
            20

<210> SEQ ID NO 23
<211> LENGTH: 22
<212> TYPE: PRT
<213> ORGANISM: Canis familiaris

<400> SEQUENCE: 23
```

```
Pro Lys Arg Glu Asn Gly Arg Val Pro Arg Pro Pro Asp Cys Pro Lys
1               5                   10                  15

Cys Pro Ala Pro Glu Met
            20

<210> SEQ ID NO 24
<211> LENGTH: 66
<212> TYPE: DNA
<213> ORGANISM: Canis familiaris

<400> SEQUENCE: 24
catttcaggg gctgggcatt tgggacaatc aggtgggcga ggaactcttc cattttctct    60
tttggg                                                              66

<210> SEQ ID NO 25
<211> LENGTH: 938
<212> TYPE: DNA
<213> ORGANISM: Canis familiaris
<220> FEATURE:
<221> NAME/KEY: CDS
<222> LOCATION: (37)..(753)
<223> OTHER INFORMATION:
<220> FEATURE:
<221> NAME/KEY: misc_feature
<222> LOCATION: (475)..(475)
<223> OTHER INFORMATION: At nucleotide 475, n = unknown At amino acid
                        residue 147, Xaa = Pro, Ser, Ala or Thr
<220> FEATURE:
<221> NAME/KEY: misc_feature
<222> LOCATION: (479)..(479)
<223> OTHER INFORMATION: At nucleotide 479, y = c or t; At amino acid
                        residue 148, Xaa = Ser or Phe
<220> FEATURE:
<221> NAME/KEY: misc_feature
<222> LOCATION: (482)..(482)
<223> OTHER INFORMATION: At nucleotide 482, y = c or t; At amino acid
                        residue 149, Xaa = Ser or Phe
<220> FEATURE:
<221> NAME/KEY: misc_feature
<222> LOCATION: (542)..(542)
<223> OTHER INFORMATION: At nucleotide 542, r = a or g; At amino acid
                        residue 169, Xaa = Asn or Ser

<400> SEQUENCE: 25
ggcacgaggg tccccagaag gcaggatcaa tcagtg atg tcc tcc gac atg gcc     54
                                        Met Ser Ser Asp Met Ala
                                        1               5 tgg tcc cct ctc ctc ctc aca ctc ctc gct cac tgc aca ggg tcc tgg   102
Trp Ser Pro Leu Leu Leu Thr Leu Leu Ala His Cys Thr Gly Ser Trp
            10                  15                  20 gcc cag gct gtg ttg aat cag ccg gcc tca gta tct ggg gcc ctg ggc   150
Ala Gln Ala Val Leu Asn Gln Pro Ala Ser Val Ser Gly Ala Leu Gly
        25                  30                  35 cag aag gtc acc atc tcc tgc tct gga gac acg aat gac att gat ata   198
Gln Lys Val Thr Ile Ser Cys Ser Gly Asp Thr Asn Asp Ile Asp Ile
40                  45                  50 ttc ggt gtg aac tgg tac caa caa ctc cca gga aag gcc cct aca gtc   246
Phe Gly Val Asn Trp Tyr Gln Gln Leu Pro Gly Lys Ala Pro Thr Val
55                  60                  65                  70 ctc gtg gac agt gat ggg gat cga ccc tca ggg gtc cct gac aga ttt   294
Leu Val Asp Ser Asp Gly Asp Arg Pro Ser Gly Val Pro Asp Arg Phe
                75                  80                  85 tct ggc tcc agt tct ggc aac tca ggc acc ctg acc atc act ggg ctc   342
Ser Gly Ser Ser Ser Gly Asn Ser Gly Thr Leu Thr Ile Thr Gly Leu
        90                  95                  100
```

```
cag gct gag gac gag gct gat tat tac tgt cag tct gtt gat tcc acg      390
Gln Ala Glu Asp Glu Ala Asp Tyr Tyr Cys Gln Ser Val Asp Ser Thr
            105                 110                 115 ctt ggt gtt tac gtg ttc ggc tca gga acc caa ctg act gtc ctt ggt      438
Leu Gly Val Tyr Val Phe Gly Ser Gly Thr Gln Leu Thr Val Leu Gly
    120                 125                 130 cag ccc aag gcc tcc ccc tcg gtc aca ctc ttc ccg ncc tyc tyt gag      486
Gln Pro Lys Ala Ser Pro Ser Val Thr Leu Phe Pro Xaa Xaa Xaa Glu
135                 140                 145                 150 gag ctc ggc gcc aac aag gcc acc ctg gtg tgc ctc atc agc gac ttc      534
Glu Leu Gly Ala Asn Lys Ala Thr Leu Val Cys Leu Ile Ser Asp Phe
                155                 160                 165 tac ccc arc ggc gtg acg gtg gcc tgg aag gca gac ggc agc ccc gtc      582
Tyr Pro Xaa Gly Val Thr Val Ala Trp Lys Ala Asp Gly Ser Pro Val
            170                 175                 180 acc cag ggc gtg gag acc acc aag ccc tcc aag cag agc aac aac aag      630
Thr Gln Gly Val Glu Thr Thr Lys Pro Ser Lys Gln Ser Asn Asn Lys
    185                 190                 195 tac gcg gcc agc agc tac ctg agc ctg acg cct gac aag tgg aaa tct      678
Tyr Ala Ala Ser Ser Tyr Leu Ser Leu Thr Pro Asp Lys Trp Lys Ser
200                 205                 210 cac agc agc ttc agc tgc ctg gtc acg cat gag ggg agc ccc gtg gaa      726
His Ser Ser Phe Ser Cys Leu Val Thr His Glu Gly Ser Pro Val Glu
215                 220                 225                 230 aaa aag gtg gcc ccc gca aag tgc tct taggttccg atgccccccg              773
Lys Lys Val Ala Pro Ala Lys Cys Ser
                235 cccaccaaag ggggctcaaa gcctcaggac ctccaggagg atcttgcctc ccatctgggt     833 catcccagcc attcccctta aacccaggca acattcaata aagtgttctt tcttcaatca     893 gaaaaaaaaa aaaaaaaaaa aaaaaaaaaa aaaaaaaaaa aaaaa                     938

<210> SEQ ID NO 26
<211> LENGTH: 239
<212> TYPE: PRT
<213> ORGANISM: Canis familiaris
<220> FEATURE:
<221> NAME/KEY: misc_feature
<222> LOCATION: (147)..(147)
<223> OTHER INFORMATION: The 'Xaa' at location 147 stands for Thr, Ala,
      Pro, or Ser.
<220> FEATURE:
<221> NAME/KEY: misc_feature
<222> LOCATION: (148)..(148)
<223> OTHER INFORMATION: The 'Xaa' at location 148 stands for Ser, or
      Phe.
<220> FEATURE:
<221> NAME/KEY: misc_feature
<222> LOCATION: (149)..(149)
<223> OTHER INFORMATION: The 'Xaa' at location 149 stands for Ser, or
      Phe.
<220> FEATURE:
<221> NAME/KEY: misc_feature
<222> LOCATION: (169)..(169)
<223> OTHER INFORMATION: The 'Xaa' at location 169 stands for Ser, or
      Asn.

<400> SEQUENCE: 26

Met Ser Ser Asp Met Ala Trp Ser Pro Leu Leu Leu Thr Leu Leu Ala
1               5                   10                  15

His Cys Thr Gly Ser Trp Ala Gln Ala Val Leu Asn Gln Pro Ala Ser
            20                  25                  30

Val Ser Gly Ala Leu Gly Gln Lys Val Thr Ile Ser Cys Ser Gly Asp
        35                  40                  45
```

```
Thr Asn Asp Ile Asp Ile Phe Gly Val Asn Trp Tyr Gln Gln Leu Pro
 50                  55                  60
Gly Lys Ala Pro Thr Val Leu Val Asp Ser Asp Gly Asp Arg Pro Ser
 65                  70                  75                  80
Gly Val Pro Asp Arg Phe Ser Gly Ser Ser Ser Gly Asn Ser Gly Thr
                 85                  90                  95
Leu Thr Ile Thr Gly Leu Gln Ala Glu Asp Glu Ala Asp Tyr Tyr Cys
                100                 105                 110
Gln Ser Val Asp Ser Thr Leu Gly Val Tyr Val Phe Gly Ser Gly Thr
                115                 120                 125
Gln Leu Thr Val Leu Gly Gln Pro Lys Ala Ser Pro Ser Val Thr Leu
130                 135                 140
Phe Pro Xaa Xaa Xaa Glu Glu Leu Gly Ala Asn Lys Ala Thr Leu Val
145                 150                 155                 160
Cys Leu Ile Ser Asp Phe Tyr Pro Xaa Gly Val Thr Val Ala Trp Lys
                165                 170                 175
Ala Asp Gly Ser Pro Val Thr Gln Gly Val Glu Thr Thr Lys Pro Ser
                180                 185                 190
Lys Gln Ser Asn Asn Lys Tyr Ala Ala Ser Ser Tyr Leu Ser Leu Thr
                195                 200                 205
Pro Asp Lys Trp Lys Ser His Ser Ser Phe Ser Cys Leu Val Thr His
210                 215                 220
Glu Gly Ser Pro Val Glu Lys Lys Val Ala Pro Ala Lys Cys Ser
225                 230                 235

<210> SEQ ID NO 27
<211> LENGTH: 938
<212> TYPE: DNA
<213> ORGANISM: Canis familiaris
<220> FEATURE:
<221> NAME/KEY: misc_feature
<222> LOCATION: (464)..(464)
<223> OTHER INFORMATION: At nucleotide 464, n = unknown

<400> SEQUENCE: 27
tttttttttt tttttttttt tttttttttt tttttttttt ttttctgatt gaagaaagaa      60
cactttattg aatgttgcct gggtttaagg ggaatggctg ggatgaccca gatgggaggc     120
aagatcctcc tggaggtcct gaggctttga gccccctttg gtgggcgggg ggcatcggga     180
acctaagagc actttgcggg ggccaccttt ttttccacgg ggctcccctc atgcgtgacc     240
aggcagctga agctgctgtg agatttccac ttgtcaggcg tcaggctcag gtagctgctg     300
gccgcgtact tgttgttgct ctgcttggag ggcttggtgg tctccacgcc ctgggtgacg     360
gggctgccgt ctgccttcca ggccaccgtc acgccgytgg ggtagaagtc gctgatgagg     420
cacaccaggg tggccttgtt ggcgccgagc tcctcaragr aggncgggaa gagtgtgacc     480
gagggggagg ccttgggctg accaaggaca gtcagttggg ttcctgagcc gaacacgtaa     540
acaccaagcg tggaatcaac agactgacag taataatcag cctcgtcctc agcctggagc     600
ccagtgatgg tcagggtgcc tgagttgcca gaactggagc cagaaaatct gtcagggacc     660
cctgagggtc gatccccatc actgtccacg aggactgtag gggccttttcc tgggagttgt     720 tggtaccagt tcacaccgaa tatatcaatg tcattcgtgt ctccagagca ggagatggtg     780
accttctggc ccagggcccc agatactgag gccggctgat tcaacacagc ctgggcccag     840
gaccctgtgc agtgagcgag gagtgtgagg aggagagggg accaggccat gtcggaggac     900
atcactgatt gatcctgcct tctggggacc ctcgtgcc                            938
```

<210> SEQ ID NO 28
<211> LENGTH: 578
<212> TYPE: DNA
<213> ORGANISM: Canis familiaris
<220> FEATURE:
<221> NAME/KEY: CDS
<222> LOCATION: (1)..(423)
<223> OTHER INFORMATION:
<220> FEATURE:
<221> NAME/KEY: misc_feature
<222> LOCATION: (471)..(471)
<223> OTHER INFORMATION: At nucleotide 471, n = unknown
<220> FEATURE:
<221> NAME/KEY: misc_feature
<222> LOCATION: (481)..(481)
<223> OTHER INFORMATION: At nucleotide 481, n = unknown
<220> FEATURE:
<221> NAME/KEY: misc_feature
<222> LOCATION: (522)..(522)
<223> OTHER INFORMATION: At nucleotide 522, n = unknown
<220> FEATURE:
<221> NAME/KEY: misc_feature
<222> LOCATION: (549)..(549)
<223> OTHER INFORMATION: At nucleotide 549, n = unknown

<400> SEQUENCE: 28

```
cat caa gat tgg ttt aat ggt aag gag ttc aaa tgt aga gtc aac cac        48
His Gln Asp Trp Phe Asn Gly Lys Glu Phe Lys Cys Arg Val Asn His
1               5                  10                  15 ata gac ctc ccg tct ccc atc gag agg acc atc tct aag gcc aga ggg        96
Ile Asp Leu Pro Ser Pro Ile Glu Arg Thr Ile Ser Lys Ala Arg Gly
             20                  25                  30 agg gcc cat aag ccc agt gtg tat gtc ctg ccg cca tcc cca aag gag       144
Arg Ala His Lys Pro Ser Val Tyr Val Leu Pro Pro Ser Pro Lys Glu
         35                  40                  45 ttg tca tcc agt gac aca gtc agc atc acc tgc ctg ata aaa gac ttc       192
Leu Ser Ser Ser Asp Thr Val Ser Ile Thr Cys Leu Ile Lys Asp Phe
     50                  55                  60 tac cca cct gac att gat gtg gag tgg cag agc aat gga cag cag gag       240
Tyr Pro Pro Asp Ile Asp Val Glu Trp Gln Ser Asn Gly Gln Gln Glu
65                  70                  75                  80 cct gag agc aag tac cgc acg acc ccg ccc cag ctg gac gag gac ggg       288
Pro Glu Ser Lys Tyr Arg Thr Thr Pro Pro Gln Leu Asp Glu Asp Gly
                 85                  90                  95 tcc tac ttc ctg tac agc aag ctc tct gtg gac aag agc cgc tgg cag       336
Ser Tyr Phe Leu Tyr Ser Lys Leu Ser Val Asp Lys Ser Arg Trp Gln
            100                 105                 110 cgg gga gac acc ttc ata tgt gcg gtg atg cat gaa gct cta cac aac       384
Arg Gly Asp Thr Phe Ile Cys Ala Val Met His Glu Ala Leu His Asn
        115                 120                 125 cac tac aca cag aaa tcc ctc tcc cat tct ccg ggt aaa tgagcaacac        433
His Tyr Thr Gln Lys Ser Leu Ser His Ser Pro Gly Lys
    130                 135                 140 gcccggcacc cagcaagccc cccacccttg gctctcanga tccctganga cacctgagcc    493
cctgtccctg tgtacataac cctgggtang cacccatcat gaaataaagc acccancact    553
gccctgggcc cttgcaaaaa aaaaa                                          578
```

<210> SEQ ID NO 29
<211> LENGTH: 141
<212> TYPE: PRT
<213> ORGANISM: Canis familiaris

<400> SEQUENCE: 29

His Gln Asp Trp Phe Asn Gly Lys Glu Phe Lys Cys Arg Val Asn His
1               5                   10                  15

Ile Asp Leu Pro Ser Pro Ile Glu Arg Thr Ile Ser Lys Ala Arg Gly
            20                  25                  30

Arg Ala His Lys Pro Ser Val Tyr Val Leu Pro Pro Ser Pro Lys Glu
            35                  40                  45

Leu Ser Ser Ser Asp Thr Val Ser Ile Thr Cys Leu Ile Lys Asp Phe
50                  55                  60

Tyr Pro Pro Asp Ile Asp Val Glu Trp Gln Ser Asn Gly Gln Gln Glu
65                  70                  75                  80

Pro Glu Ser Lys Tyr Arg Thr Thr Pro Pro Gln Leu Asp Glu Asp Gly
            85                  90                  95

Ser Tyr Phe Leu Tyr Ser Lys Leu Ser Val Asp Lys Ser Arg Trp Gln
            100                 105                 110

Arg Gly Asp Thr Phe Ile Cys Ala Val Met His Glu Ala Leu His Asn
            115                 120                 125

His Tyr Thr Gln Lys Ser Leu Ser His Ser Pro Gly Lys
            130                 135                 140

<210> SEQ ID NO 30
<211> LENGTH: 578
<212> TYPE: DNA
<213> ORGANISM: Canis familiaris
<220> FEATURE:
<221> NAME/KEY: misc_feature
<222> LOCATION: (30)..(30)
<223> OTHER INFORMATION: At nucleotide 30, n = unknown
<220> FEATURE:
<221> NAME/KEY: misc_feature
<222> LOCATION: (57)..(57)
<223> OTHER INFORMATION: At nucleotide 57, n = unknown
<220> FEATURE:
<221> NAME/KEY: misc_feature
<222> LOCATION: (98)..(98)
<223> OTHER INFORMATION: At nucleotide 98, n = unknown
<220> FEATURE:
<221> NAME/KEY: misc_feature
<222> LOCATION: (108)..(108)
<223> OTHER INFORMATION: At nucleotide 108, n = unknown

<400> SEQUENCE: 30
tttttttttt gcaagggccc agggcagtgn tgggtgcttt atttcatgat gggtgcntac      60
ccagggttat gtacacaggg acaggggctc aggtgtcntc aggatcntg agagccaagg     120 gtgggggct tgctgggtgc cgggcgtgtt gctcatttac ccggagaatg ggagagggat     180
ttctgtgtgt agtggttgtg tagagcttca tgcatcaccg cacatatgaa ggtgtctccc     240
cgctgccagc ggctcttgtc cacagagagc ttgctgtaca ggaagtagga cccgtcctcg     300
tccagctggg gcggggtcgt gcggtacttg ctctcaggct cctgctgtcc attgctctgc     360
cactccacat caatgtcagg tgggtagaag tcttttatca ggcaggtgat gctgactgtg     420
tcactggatg acaactcctt tggggatggc ggcaggacat acacactggg cttatgggcc     480
ctccctctgg ccttagagat ggtcctctcg atgggagacg ggaggtctat gtggttgact     540
ctacatttga actccttacc attaaaccaa tcttgatg                             578

<210> SEQ ID NO 31
<211> LENGTH: 1364
<212> TYPE: DNA
<213> ORGANISM: Canis familiaris
<220> FEATURE:
<221> NAME/KEY: CDS
<222> LOCATION: (59)..(1183)

<223> OTHER INFORMATION:

<400> SEQUENCE: 31

```
ggcacgaggc cgattcacca tttccagaga caatgtcgag aacacgctgt atctgcag            58 atg aac agc ctg aga gct gag gat acg gcc ctg tat tac tgt aca agt          106
Met Asn Ser Leu Arg Ala Glu Asp Thr Ala Leu Tyr Tyr Cys Thr Ser
1               5                   10                  15 ggg tta tgg atc aac tgg tac ggt ccg aat ttt gac tcc tgg ggc cag          154
Gly Leu Trp Ile Asn Trp Tyr Gly Pro Asn Phe Asp Ser Trp Gly Gln
            20                  25                  30 gga acc ctg gtc acc gtc tcc tca gcc tcc acc acg gcc ccc tcg gtt          202
Gly Thr Leu Val Thr Val Ser Ser Ala Ser Thr Thr Ala Pro Ser Val
        35                  40                  45 ttc cca ctg gcc ccc agc tgc ggg tcc act tcc ggc tcc acg gtg gcc          250
Phe Pro Leu Ala Pro Ser Cys Gly Ser Thr Ser Gly Ser Thr Val Ala
    50                  55                  60 ctg gcc tgc ctg gtg tca ggc tac ttc ccc gag cct gta act gtg tcc          298
Leu Ala Cys Leu Val Ser Gly Tyr Phe Pro Glu Pro Val Thr Val Ser
65                  70                  75                  80 tgg aat tcc ggc tcc ttg acc agc ggt gtg cac acc ttc ccg tcc gtc          346
Trp Asn Ser Gly Ser Leu Thr Ser Gly Val His Thr Phe Pro Ser Val
                85                  90                  95 ctg cag tcc tca ggg ctc tac tcc ctc agc agc atg gtg aca gtg ccc          394
Leu Gln Ser Ser Gly Leu Tyr Ser Leu Ser Ser Met Val Thr Val Pro
            100                 105                 110 tcc agc agg tgg ccc agc gag acc ttc acc tgc aac gtg gcc cac ccg          442
Ser Ser Arg Trp Pro Ser Glu Thr Phe Thr Cys Asn Val Ala His Pro
        115                 120                 125 gcc agc aaa act aaa gta gac aag cca gtg ccc aaa aga gaa aat gga          490
Ala Ser Lys Thr Lys Val Asp Lys Pro Val Pro Lys Arg Glu Asn Gly
    130                 135                 140 aga gtt cct cgc cca cct gat tgt ccc aaa tgc cca acc cct gaa atg          538
Arg Val Pro Arg Pro Pro Asp Cys Pro Lys Cys Pro Thr Pro Glu Met
145                 150                 155                 160 ctg gga ggg cct tcg gtc ttc atc ttt ccc ccg aaa ccc aag gac acc          586
Leu Gly Gly Pro Ser Val Phe Ile Phe Pro Pro Lys Pro Lys Asp Thr
                165                 170                 175 ctc ttg att gcc cga aca cct gag gtc aca tgt gtg gtg gtg gat ctg          634
Leu Leu Ile Ala Arg Thr Pro Glu Val Thr Cys Val Val Val Asp Leu
            180                 185                 190 gac cca gaa gac cct gag gtg cag atc agc tgg ttc gtg gac ggt aag          682
Asp Pro Glu Asp Pro Glu Val Gln Ile Ser Trp Phe Val Asp Gly Lys
        195                 200                 205 cag atg caa aca gcc aag act cag cct cgt gag gag cag ttc aat ggc          730
Gln Met Gln Thr Ala Lys Thr Gln Pro Arg Glu Glu Gln Phe Asn Gly
    210                 215                 220 acc tac cgt gtg gtc agt gtc ctc ccc att ggg cac cag gac tgg ctc          778
Thr Tyr Arg Val Val Ser Val Leu Pro Ile Gly His Gln Asp Trp Leu
225                 230                 235                 240 aag ggg aag cag ttc acg tgc aaa gtc aac aac aaa gcc ctc cca tcc          826
Lys Gly Lys Gln Phe Thr Cys Lys Val Asn Asn Lys Ala Leu Pro Ser
                245                 250                 255 cca atc gag agg acc atc tcc aag gcc aga ggg cag gcc cat caa ccc          874
Pro Ile Glu Arg Thr Ile Ser Lys Ala Arg Gly Gln Ala His Gln Pro
            260                 265                 270 agt gtg tat gtc ctg ccg cca tcc cgg gag gag ttg agc aag aac aca          922
Ser Val Tyr Val Leu Pro Pro Ser Arg Glu Glu Leu Ser Lys Asn Thr
        275                 280                 285 gtc agc ttg aca tgc ctg atc aaa gac ttc ttc cca cct gac att gat          970
Val Ser Leu Thr Cys Leu Ile Lys Asp Phe Phe Pro Pro Asp Ile Asp
```

```
Val Ser Leu Thr Cys Leu Ile Lys Asp Phe Phe Pro Pro Asp Ile Asp
    290                 295                 300 gtg gag tgg cag agc aat gga cag cag gag cct gag agc aag tac cgc    1018
Val Glu Trp Gln Ser Asn Gly Gln Gln Glu Pro Glu Ser Lys Tyr Arg
305                 310                 315                 320 acg acc ccg ccc cag ctg gac gag gac ggg tcc tac ttc ctg tac agc    1066
Thr Thr Pro Pro Gln Leu Asp Glu Asp Gly Ser Tyr Phe Leu Tyr Ser
                325                 330                 335 aag ctc tct gtg gac aag agc cgc tgg cag cgg gga gac acc ttc ata    1114
Lys Leu Ser Val Asp Lys Ser Arg Trp Gln Arg Gly Asp Thr Phe Ile
            340                 345                 350 tgt gcg gtg atg cat gaa gct tta cac aac cac tac aca cag aaa tcc    1162
Cys Ala Val Met His Glu Ala Leu His Asn His Tyr Thr Gln Lys Ser
        355                 360                 365 ctc tcc cat tct ccg ggt aaa tgagcaacac gcccggcacc cagcaagccc       1213
Leu Ser His Ser Pro Gly Lys
    370                 375 cccacccttg ctttcagga tcccatgagg atgcctgagc cccatccct gtgtacataa    1273 ccccgggtag gcacctggca tgaaataaag cacccagtac tgccctggaa aaaaaaaaa   1333 aaaaaaaaaa aaaaaaaaaa aaaaaaaaaa a                                 1364

<210> SEQ ID NO 32
<211> LENGTH: 375
<212> TYPE: PRT
<213> ORGANISM: Canis familiaris

<400> SEQUENCE: 32

Met Asn Ser Leu Arg Ala Glu Asp Thr Ala Leu Tyr Tyr Cys Thr Ser
1               5                   10                  15

Gly Leu Trp Ile Asn Trp Tyr Gly Pro Asn Phe Asp Ser Trp Gly Gln
            20                  25                  30

Gly Thr Leu Val Thr Val Ser Ser Ala Ser Thr Thr Ala Pro Ser Val
        35                  40                  45

Phe Pro Leu Ala Pro Ser Cys Gly Ser Thr Ser Gly Ser Thr Val Ala
    50                  55                  60

Leu Ala Cys Leu Val Ser Gly Tyr Phe Pro Glu Pro Val Thr Val Ser
65                  70                  75                  80

Trp Asn Ser Gly Ser Leu Thr Ser Gly Val His Thr Phe Pro Ser Val
                85                  90                  95

Leu Gln Ser Ser Gly Leu Tyr Ser Leu Ser Ser Met Val Thr Val Pro
            100                 105                 110

Ser Ser Arg Trp Pro Ser Glu Thr Phe Thr Cys Asn Val Ala His Pro
        115                 120                 125

Ala Ser Lys Thr Lys Val Asp Lys Pro Val Pro Lys Arg Glu Asn Gly
    130                 135                 140

Arg Val Pro Arg Pro Pro Asp Cys Pro Lys Cys Pro Thr Pro Glu Met
145                 150                 155                 160

Leu Gly Gly Pro Ser Val Phe Ile Phe Pro Pro Lys Pro Lys Asp Thr
                165                 170                 175

Leu Leu Ile Ala Arg Thr Pro Glu Val Thr Cys Val Val Val Asp Leu
            180                 185                 190

Asp Pro Glu Asp Pro Glu Val Gln Ile Ser Trp Phe Val Asp Gly Lys
        195                 200                 205

Gln Met Gln Thr Ala Lys Thr Gln Pro Arg Glu Glu Gln Phe Asn Gly
    210                 215                 220
```

```
Thr Tyr Arg Val Val Ser Val Leu Pro Ile Gly His Gln Asp Trp Leu
225                 230                 235                 240

Lys Gly Lys Gln Phe Thr Cys Lys Val Asn Asn Lys Ala Leu Pro Ser
            245                 250                 255

Pro Ile Glu Arg Thr Ile Ser Lys Ala Arg Gly Gln Ala His Gln Pro
        260                 265                 270

Ser Val Tyr Val Leu Pro Pro Ser Arg Glu Glu Leu Ser Lys Asn Thr
    275                 280                 285

Val Ser Leu Thr Cys Leu Ile Lys Asp Phe Phe Pro Pro Asp Ile Asp
290                 295                 300

Val Glu Trp Gln Ser Asn Gly Gln Gln Glu Pro Glu Ser Lys Tyr Arg
305                 310                 315                 320

Thr Thr Pro Pro Gln Leu Asp Glu Asp Gly Ser Tyr Phe Leu Tyr Ser
            325                 330                 335

Lys Leu Ser Val Asp Lys Ser Arg Trp Gln Arg Gly Asp Thr Phe Ile
        340                 345                 350

Cys Ala Val Met His Glu Ala Leu His Asn His Tyr Thr Gln Lys Ser
    355                 360                 365

Leu Ser His Ser Pro Gly Lys
    370                 375

<210> SEQ ID NO 33
<211> LENGTH: 1364
<212> TYPE: DNA
<213> ORGANISM: Canis familiaris

<400> SEQUENCE: 33
tttttttttt tttttttttt tttttttttt tttttttttt tttccagggc agtactgggt     60
gctttatttc atgccaggtg cctacccggg gttatgtaca cagggatggg ggctcaggca    120
tcctcatggg atcctgaaag ccaagggtgg ggggcttgct gggtgccggg cgtgttgctc    180
atttacccgg agaatgggag agggatttct gtgtgtagtg gttgtgtaaa gcttcatgca    240
tcaccgcaca tatgaaggtg tctccccgct gccagcggct cttgtccaca gagagcttgc    300
tgtacaggaa gtaggacccg tcctcgtcca gctgggcgg ggtcgtgcgg tacttgctct    360
caggctcctg ctgtccattg ctctgccact ccacatcaat gtcaggtggg aagaagtctt    420
tgatcaggca tgtcaagctg actgtgttct tgctcaactc ctcccgggat ggcggcagga    480
catacacact gggttgatgg gcctgccctc tggccttgga gatggtcctc tcgattgggg    540
atgggagggc tttgttgttg actttgcacg tgaactgctt ccccttgagc cagtcctggt    600
gcccaatggg gaggacactg accacacggt aggtgccatt gaactgctcc tcacgaggct    660
gagtcttggc tgtttgcatc tgcttaccgt ccacgaacca gctgatctgc acctcagggt    720
cttctgggtc cagatccacc accacacatg tgacctcagg tgttcgggca atcaagaggg    780
tgtccttggg tttcggggga agatgaaga ccgaaggccc tcccagcatt tcaggggttg    840
ggcatttggg acaatcaggt gggcgaggaa ctcttccatt ttctcttttg ggcactggct    900
tgtctacttt agttttgctg gccgggtggg ccacgttgca ggtgaaggtc tcgctgggcc    960
acctgctgga gggcactgtc accatgctgc tgagggagta gagccctgag gactgcagga   1020
cggacgggaa ggtgtgcaca ccgctggtca aggagccgga attccaggac acagttacag   1080
gctcggggaa gtagcctgac accaggcagg ccagggccac cgtggagccg aagtggacc   1140
cgcagctggg ggccagtggg aaaaccgagg gggccgtggt ggaggctgag gagacggtga   1200
ccagggttcc ctggccccag gagtcaaaat tcggaccgta ccagttgatc cataacccac   1260
```

```
ttgtacagta atacagggcc gtatcctcag ctctcaggct gttcatctgc agatacagcg    1320
tgttctcgac attgtctctg gaaatggtga atcggcctcg tgcc                    1364

<210> SEQ ID NO 34
<211> LENGTH: 1168
<212> TYPE: DNA
<213> ORGANISM: Canis familiaris
<220> FEATURE:
<221> NAME/KEY: CDS
<222> LOCATION: (48)..(1166)
<223> OTHER INFORMATION:

<400> SEQUENCE: 34
ccaggtgacc ccattcagtg ctcaggacac aacacagaca aaccacc atg gag tct       56
                                                   Met Glu Ser
                                                   1 gtg ctc tgc tgg gtt ttc ctt gtc tct att tta aaa ggt gtc cag ggt      104
Val Leu Cys Trp Val Phe Leu Val Ser Ile Leu Lys Gly Val Gln Gly
     5                  10                  15 gag gtg caa ctg gtg gag tct ggg gga gac ctg gtg aag cct ggg ggg      152
Glu Val Gln Leu Val Glu Ser Gly Gly Asp Leu Val Lys Pro Gly Gly
 20                  25                  30                  35 tcc ttg aga ctg tcc tgt gtg gcc tct gga ttc acc ttc agt gac tat      200
Ser Leu Arg Leu Ser Cys Val Ala Ser Gly Phe Thr Phe Ser Asp Tyr
                 40                  45                  50 ggc atg agt tgg gtc cgt cag tct cca ggg aag ggg ctg cag tgg gtc      248
Gly Met Ser Trp Val Arg Gln Ser Pro Gly Lys Gly Leu Gln Trp Val
             55                  60                  65 gca gct gtt agc aat cgt gga gat act tac tac gca gac gct gtg aag      296
Ala Ala Val Ser Asn Arg Gly Asp Thr Tyr Tyr Ala Asp Ala Val Lys
         70                  75                  80 ggc cga ttc acc atc tcc aga gac aac gcc aag aac acg ctg tat ctc      344
Gly Arg Phe Thr Ile Ser Arg Asp Asn Ala Lys Asn Thr Leu Tyr Leu
     85                  90                  95 cag atg agc agc ctg aaa gcc gag gac acg gca atc tat cac tgt gtg      392
Gln Met Ser Ser Leu Lys Ala Glu Asp Thr Ala Ile Tyr His Cys Val
100                 105                 110                 115 acg gga gta tgg ccg cga cat tat tat ggt atg gac cac tgg ggc aat      440
Thr Gly Val Trp Pro Arg His Tyr Tyr Gly Met Asp His Trp Gly Asn
                120                 125                 130 ggc acc tca ctc ttc gtg tcc tca gcc tcc acc acg gcc ccc tcg gtt      488
Gly Thr Ser Leu Phe Val Ser Ser Ala Ser Thr Thr Ala Pro Ser Val
            135                 140                 145 ttc cca ctg gcc ccc agc tgc ggg tcc act tcc ggc tcc acg gtg gcc      536
Phe Pro Leu Ala Pro Ser Cys Gly Ser Thr Ser Gly Ser Thr Val Ala
        150                 155                 160 ctg gcc tgc ctg gtg tca ggc tac ttc ccc gag cct gta act gtg tcc      584
Leu Ala Cys Leu Val Ser Gly Tyr Phe Pro Glu Pro Val Thr Val Ser
    165                 170                 175 tgg aat tcc ggc tcc ttg acc agc ggt gtg cac acc ttc ccg tcc gtc      632
Trp Asn Ser Gly Ser Leu Thr Ser Gly Val His Thr Phe Pro Ser Val
180                 185                 190                 195 ctg cag tcc tca ggg ctc tac tcc ctc agc agc acg gtg aca gtg ccc      680
Leu Gln Ser Ser Gly Leu Tyr Ser Leu Ser Ser Thr Val Thr Val Pro
                200                 205                 210 tcc agc agg tgg ccc agc gag acc ttc acc tgc aac gtg gtc cac ccg      728
Ser Ser Arg Trp Pro Ser Glu Thr Phe Thr Cys Asn Val Val His Pro
            215                 220                 225 gcc agc aac act aaa gta gac aag cca gtg ccc aaa gag tcc acc tgc      776
Ala Ser Asn Thr Lys Val Asp Lys Pro Val Pro Lys Glu Ser Thr Cys
```

-continued

```
                230                 235                 240
aag tgt ata tcc cca tgc cca gtc cct gaa tca ctg gga ggg cct tcg    824
Lys Cys Ile Ser Pro Cys Pro Val Pro Glu Ser Leu Gly Gly Pro Ser
    245                 250                 255 gtc ttc atc ttt ccc ccg aaa ccc aag gac atc ctc agg att acc cga    872
Val Phe Ile Phe Pro Pro Lys Pro Lys Asp Ile Leu Arg Ile Thr Arg
260                 265                 270                 275 aca ccc gag atc acc tgt gtg gtg tta gat ctg ggc cgt gag gac cct    920
Thr Pro Glu Ile Thr Cys Val Val Leu Asp Leu Gly Arg Glu Asp Pro
                280                 285                 290 gag gtg cag atc agc tgg ttc gtg gat ggt aag gag gtg cac aca gcc    968
Glu Val Gln Ile Ser Trp Phe Val Asp Gly Lys Glu Val His Thr Ala
            295                 300                 305 aag acg cag cct cgt gag cag cag ttc aac agc acc tac cgt gtg gtc   1016
Lys Thr Gln Pro Arg Glu Gln Gln Phe Asn Ser Thr Tyr Arg Val Val
        310                 315                 320 agc gtc ctc ccc att gag cac cag gac tgg ctc acc gga aag gag ttc   1064
Ser Val Leu Pro Ile Glu His Gln Asp Trp Leu Thr Gly Lys Glu Phe
    325                 330                 335 aag tgc aga gtc aac cac ata ggc ccc ccg tcc ccc atc gag agg act   1112
Lys Cys Arg Val Asn His Ile Gly Pro Pro Ser Pro Ile Glu Arg Thr
340                 345                 350                 355 atc tcc aaa gcc aga ggg caa gcc cat cag ccc agt gtg tat gtc ctg   1160
Ile Ser Lys Ala Arg Gly Gln Ala His Gln Pro Ser Val Tyr Val Leu
                360                 365                 370 ccg cca tc                                                        1168
Pro Pro
```

<210> SEQ ID NO 35
<211> LENGTH: 373
<212> TYPE: PRT
<213> ORGANISM: Canis familiaris

<400> SEQUENCE: 35

```
Met Glu Ser Val Leu Cys Trp Val Phe Leu Val Ser Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Asp Tyr Gly Met Ser Trp Val Arg Gln Ser Pro Gly Lys Gly Leu
    50                  55                  60

Gln Trp Val Ala Ala Val Ser Asn Arg Gly Asp Thr Tyr Tyr Ala Asp
65                  70                  75                  80

Ala Val Lys Gly Arg Phe Thr Ile Ser Arg Asp Asn Ala Lys Asn Thr
                85                  90                  95

Leu Tyr Leu Gln Met Ser Ser Leu Lys Ala Glu Asp Thr Ala Ile Tyr
            100                 105                 110

His Cys Val Thr Gly Val Trp Pro Arg His Tyr Tyr Gly Met Asp His
        115                 120                 125

Trp Gly Asn Gly Thr Ser Leu Phe Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
```

```
                180                 185                 190
Pro Ser Val Leu Gln Ser Ser Gly Leu Tyr Ser Leu Ser Ser Thr Val
        195                 200                 205
Thr Val Pro Ser Ser Arg Trp Pro Ser Glu Thr Phe Thr Cys Asn Val
    210                 215                 220
Val His Pro Ala Ser Asn Thr Lys Val Asp Lys Pro Val Pro Lys Glu
225                 230                 235                 240
Ser Thr Cys Lys Cys Ile Ser Pro Cys Pro Val Pro Glu Ser Leu Gly
            245                 250                 255
Gly Pro Ser Val Phe Ile Phe Pro Pro Lys Pro Lys Asp Ile Leu Arg
        260                 265                 270
Ile Thr Arg Thr Pro Glu Ile Thr Cys Val Val Leu Asp Leu Gly Arg
    275                 280                 285
Glu Asp Pro Glu Val Gln Ile Ser Trp Phe Val Asp Gly Lys Glu Val
290                 295                 300
His Thr Ala Lys Thr Gln Pro Arg Glu Gln Gln Phe Asn Ser Thr Tyr
305                 310                 315                 320
Arg Val Val Ser Val Leu Pro Ile Glu His Gln Asp Trp Leu Thr Gly
            325                 330                 335
Lys Glu Phe Lys Cys Arg Val Asn His Ile Gly Pro Pro Ser Pro Ile
        340                 345                 350
Glu Arg Thr Ile Ser Lys Ala Arg Gly Gln Ala His Gln Pro Ser Val
    355                 360                 365
Tyr Val Leu Pro Pro
    370

<210> SEQ ID NO 36
<211> LENGTH: 1168
<212> TYPE: DNA
<213> ORGANISM: Canis familiaris

<400> SEQUENCE: 36
gatggcggca ggacatacac actgggctga tgggcttgcc ctctggcttt ggagatagtc    60
ctctcgatgg gggacggggg gcctatgtgg ttgactctgc acttgaactc ctttccggtg   120
agccagtcct ggtgctcaat ggggaggacg ctgaccacac ggtaggtgct gttgaactgc   180
tgctcacgag gctgcgtctt ggctgtgtgc acctccttac catccacgaa ccagctgatc   240
tgcacctcag gtcctcacg gcccagatct aacaccacac aggtgatctc gggtgttcgg   300
gtaatcctga ggatgtcctt gggtttcggg ggaaagatga agaccgaagg ccctcccagt   360
gattcaggga ctgggcatgg ggatatacac ttgcaggtgg actctttggg cactggcttg   420
tctactttag tgttgctggc cgggtggacc acgttgcagg tgaaggtctc gctgggccac   480
ctgctggagg gcactgtcac cgtgctgctg agggagtaga gccctgagga ctgcaggacg   540
gacgggaagg tgtgcacacc gctggtcaag agccggaat tccaggacac agttacaggc   600
tcggggaagt agcctgacac caggcaggcc agggccaccg tggagccgga agtggacccg   660
cagctggggg ccagtgggaa aaccgagggg gccgtggtgg aggctgagga cacgaagagt   720
gaggtgccat tgccccagtg gtccatacca taataatgtc gcggccatac tcccgtcaca   780
cagtgataga ttgccgtgtc ctcggctttc aggctgctca tctggagata cagcgtgttc   840
ttggcgttgt ctctggagat ggtgaatcgg cccttcacag cgtctgcgta gtaagtatct   900
ccacgattgc taacagctgc gacccactgc agccccttcc ctggagactg acggacccaa   960
ctcatgccat agtcactgaa ggtgaatcca gaggccacac aggacagtct caaggacccc  1020
```

```
ccaggcttca ccaggtctcc cccagactcc accagttgca cctcaccctg gacaccttttt    1080 aaaatagaga caaggaaaac ccagcagagc acagactcca tggtggtttg tctgtgttgt    1140
gtcctgagca ctgaatgggg tcacctgg                                       1168
```

<210> SEQ ID NO 37
<211> LENGTH: 1059
<212> TYPE: DNA
<213> ORGANISM: Canis familiaris
<220> FEATURE:
<221> NAME/KEY: CDS
<222> LOCATION: (1)..(1056)
<223> OTHER INFORMATION:

<400> SEQUENCE: 37

```
tgg ccg cga cat tat tat ggt atg gac cac tgg ggc aat ggc acc tca      48
Trp Pro Arg His Tyr Tyr Gly Met Asp His Trp Gly Asn Gly Thr Ser
 1               5                  10                  15 ctc ttc gtg tcc tca gcc tcc acc acg gcc ccc tcg gtt ttc cca ctg      96
Leu Phe Val Ser Ser Ala Ser Thr Thr Ala Pro Ser Val Phe Pro Leu
             20                  25                  30 gcc ccc agc tgc ggg tcc act tcc ggc tcc acg gtg gcc ctg gcc tgc     144
Ala Pro Ser Cys Gly Ser Thr Ser Gly Ser Thr Val Ala Leu Ala Cys
         35                  40                  45 ctg gtg tca ggc tac ttc ccc gag cct gta act gtg tcc tgg aat tcc     192
Leu Val Ser Gly Tyr Phe Pro Glu Pro Val Thr Val Ser Trp Asn Ser
     50                  55                  60 gac tcc ttg acc agc ggt gtg cac acc ttc ccg tcc gtc ctg cag tcc     240
Asp Ser Leu Thr Ser Gly Val His Thr Phe Pro Ser Val Leu Gln Ser
 65                  70                  75                  80 tca ggg ctc tac tcc ctc agc agc acg gtg aca gtg ccc tcc agc agg     288
Ser Gly Leu Tyr Ser Leu Ser Ser Thr Val Thr Val Pro Ser Ser Arg
                 85                  90                  95 tgg ccc agc gag acc ttc acc tgc aac gtg gtc cac ccg gcc agc aac     336
Trp Pro Ser Glu Thr Phe Thr Cys Asn Val Val His Pro Ala Ser Asn
            100                 105                 110 act aaa gta gac aag cca gtg ccc aaa gag tcc acc tgc aag tgt ata     384
Thr Lys Val Asp Lys Pro Val Pro Lys Glu Ser Thr Cys Lys Cys Ile
        115                 120                 125 tcc cca tgc cca gtc cct gaa tca ctg gga ggg cct tcg gtc ttc atc     432
Ser Pro Cys Pro Val Pro Glu Ser Leu Gly Gly Pro Ser Val Phe Ile
    130                 135                 140 ttt ccc ccg aaa ccc aag gac atc ctc agg att acc cga aca ccc gag     480
Phe Pro Pro Lys Pro Lys Asp Ile Leu Arg Ile Thr Arg Thr Pro Glu
145                 150                 155                 160 atc acc tgt gtg gtg tta gat ctg ggc cgt gag gac cct gag gtg cag     528
Ile Thr Cys Val Val Leu Asp Leu Gly Arg Glu Asp Pro Glu Val Gln
                165                 170                 175 atc agc tgg ttc gtg gat ggt aag gag gtg cac aca gcc aag acg cag     576
Ile Ser Trp Phe Val Asp Gly Lys Glu Val His Thr Ala Lys Thr Gln
            180                 185                 190 cct cgt gag cag cag ttc aac agc acc tac cgt gtg gtc agc gtc ctc     624
Pro Arg Glu Gln Gln Phe Asn Ser Thr Tyr Arg Val Val Ser Val Leu
        195                 200                 205 ccc att gag cac cag gac tgg ctc acc gga aag gag ttc aag tgc aga     672
Pro Ile Glu His Gln Asp Trp Leu Thr Gly Lys Glu Phe Lys Cys Arg
    210                 215                 220 gtc aac cac ata ggc ctc ccg tcc ccc atc gag agg act atc tcc aaa     720
Val Asn His Ile Gly Leu Pro Ser Pro Ile Glu Arg Thr Ile Ser Lys
225                 230                 235                 240
```

```
gcc aga ggg caa gcc cat cag ccc agt gtg tat gtc ctg cca cca tcc       768
Ala Arg Gly Gln Ala His Gln Pro Ser Val Tyr Val Leu Pro Pro Ser
            245                 250                 255 cca aag gag ttg tca tcc agt gac acg gtc acc ctg acc tgc ctg atc       816
Pro Lys Glu Leu Ser Ser Ser Asp Thr Val Thr Leu Thr Cys Leu Ile
        260                 265                 270 aaa gac ttc ttc cca cct gag att gat gtg gag tgg cag agc aat gga       864
Lys Asp Phe Phe Pro Pro Glu Ile Asp Val Glu Trp Gln Ser Asn Gly
    275                 280                 285 cag ccg gag ccc gag agc aag tac cac acg act gcg ccc cag ctg gac       912
Gln Pro Glu Pro Glu Ser Lys Tyr His Thr Thr Ala Pro Gln Leu Asp
290                 295                 300 gag gac ggg tcc tac ttc ctg tac agc aag ctc tct gtg gac aag agc       960
Glu Asp Gly Ser Tyr Phe Leu Tyr Ser Lys Leu Ser Val Asp Lys Ser
305                 310                 315                 320 cgc tgg cag cag gga gac ccc ttc aca tgt gcg gtg atg cat gaa gct      1008
Arg Trp Gln Gln Gly Asp Pro Phe Thr Cys Ala Val Met His Glu Ala
                325                 330                 335 cta cag aac cac tac aca gat cta tcc ctc tcc cat tct ccg ggt aaa      1056
Leu Gln Asn His Tyr Thr Asp Leu Ser Leu Ser His Ser Pro Gly Lys
            340                 345                 350 tga                                                                   1059
```

<210> SEQ ID NO 38
<211> LENGTH: 352
<212> TYPE: PRT
<213> ORGANISM: Canis familiaris

<400> SEQUENCE: 38

```
Trp Pro Arg His Tyr Tyr Gly Met Asp His Trp Gly Asn Gly Thr Ser
1               5                   10                  15

Leu Phe Val Ser Ser Ala Ser Thr Thr Ala Pro Ser Val Phe Pro Leu
            20                  25                  30

Ala Pro Ser Cys Gly Ser Thr Ser Gly Ser Thr Val Ala Leu Ala Cys
        35                  40                  45

Leu Val Ser Gly Tyr Phe Pro Glu Pro Val Thr Val Ser Trp Asn Ser
    50                  55                  60

Asp Ser Leu Thr Ser Gly Val His Thr Phe Pro Ser Val Leu Gln Ser
65                  70                  75                  80

Ser Gly Leu Tyr Ser Leu Ser Ser Thr Val Thr Val Pro Ser Ser Arg
                85                  90                  95

Trp Pro Ser Glu Thr Phe Thr Cys Asn Val Val His Pro Ala Ser Asn
            100                 105                 110

Thr Lys Val Asp Lys Pro Val Pro Lys Glu Ser Thr Cys Lys Cys Ile
        115                 120                 125

Ser Pro Cys Pro Val Pro Glu Ser Leu Gly Gly Pro Ser Val Phe Ile
    130                 135                 140

Phe Pro Pro Lys Pro Lys Asp Ile Leu Arg Ile Thr Arg Thr Pro Glu
145                 150                 155                 160

Ile Thr Cys Val Val Leu Asp Leu Gly Arg Glu Asp Pro Glu Val Gln
                165                 170                 175

Ile Ser Trp Phe Val Asp Gly Lys Glu Val His Thr Ala Lys Thr Gln
            180                 185                 190

Pro Arg Glu Gln Gln Phe Asn Ser Thr Tyr Arg Val Val Ser Val Leu
        195                 200                 205

Pro Ile Glu His Gln Asp Trp Leu Thr Gly Lys Glu Phe Lys Cys Arg
    210                 215                 220
```

Val Asn His Ile Gly Leu Pro Ser Pro Ile Glu Arg Thr Ile Ser Lys
225                 230                 235                 240

Ala Arg Gly Gln Ala His Gln Pro Ser Val Tyr Val Leu Pro Pro Ser
            245                 250                 255

Pro Lys Glu Leu Ser Ser Ser Asp Thr Val Thr Leu Thr Cys Leu Ile
            260                 265                 270

Lys Asp Phe Phe Pro Pro Glu Ile Asp Val Glu Trp Gln Ser Asn Gly
            275                 280                 285

Gln Pro Glu Pro Glu Ser Lys Tyr His Thr Thr Ala Pro Gln Leu Asp
            290                 295                 300

Glu Asp Gly Ser Tyr Phe Leu Tyr Ser Lys Leu Ser Val Asp Lys Ser
305                 310                 315                 320

Arg Trp Gln Gln Gly Asp Pro Phe Thr Cys Ala Val Met His Glu Ala
                325                 330                 335

Leu Gln Asn His Tyr Thr Asp Leu Ser Leu Ser His Ser Pro Gly Lys
            340                 345                 350

<210> SEQ ID NO 39
<211> LENGTH: 1059
<212> TYPE: DNA
<213> ORGANISM: Canis familiaris

<400> SEQUENCE: 39
tcatttaccc ggagaatggg agagggatag atctgtgtag tggttctgta gagcttcatg     60
catcaccgca catgtgaagg ggtctccctg ctgccagcgg ctcttgtcca cagagagctt    120
gctgtacagg aagtaggacc cgtcctcgtc cagctggggc gcagtcgtgt ggtacttgct    180
ctcgggctcc ggctgtccat tgctctgcca ctccacatca atctcaggtg gaagaagtc    240 tttgatcagg caggtcaggg tgaccgtgtc actggatgac aactcctttg gggatggtgg    300
caggacatac acactgggct gatgggcttg ccctctggct ttggagatag tcctctcgat    360
gggggacggg aggcctatgt ggttgactct gcacttgaac tcctttccgg tgagccagtc    420
ctggtgctca atggggagga cgctgaccac acggtaggtg ctgttgaact gctgctcacg    480
aggctgcgtc ttggctgtgt gcacctcctt accatccacg aaccagctga tctgcacctc    540
agggtcctca cggcccagat ctaacaccac acaggtgatc tcgggtgttc gggtaatcct    600
gaggatgtcc ttgggtttcg ggggaaagat gaagaccgaa ggccctccca gtgattcagg    660
gactgggcat ggggatatac acttgcaggt ggactctttg ggcactggct tgtctacttt    720
agtgttgctg gccgggtgga ccacgttgca ggtgaaggtc tcgctgggcc acctgctgga    780
gggcactgtc accgtgctgc tgagggagta gagccctgag gactgcagga cggacgggaa    840
ggtgtgcaca ccgctggtca aggagtcgga attccaggac acagttacag gctcggggaa    900
gtagcctgac accaggcagg ccagggccac cgtggagccg aagtggacc cgcagctggg    960 ggccagtggg aaaaccgagg gggccgtggt ggaggctgag gacacgaaga gtgaggtgcc   1020
attgccccag tggtccatac cataataatg tcgcggcca                         1059

<210> SEQ ID NO 40
<211> LENGTH: 36
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (15)..(15)

<223> OTHER INFORMATION: At nucleotide 15, n = unknown
<220> FEATURE:
<221> NAME/KEY: misc_feature
<222> LOCATION: (21)..(21)
<223> OTHER INFORMATION: At nucleotide 21, n = unknown

<400> SEQUENCE: 40
caycargayt ggytnaaygg naargartty aartgy                    36

<210> SEQ ID NO 41
<211> LENGTH: 28
<212> TYPE: DNA
<213> ORGANISM: Artificial sequence
<220> FEATURE:
<223> OTHER INFORMATION: Synthetic Primer

<400> SEQUENCE: 41
gccctccagc aggtggccca gcgagacc                             28

<210> SEQ ID NO 42
<211> LENGTH: 23
<212> TYPE: DNA
<213> ORGANISM: Artificial sequence
<220> FEATURE:
<223> OTHER INFORMATION: Synthetic Primer

<400> SEQUENCE: 42
ggggatggcg gcaggacata cac                                  23

<210> SEQ ID NO 43
<211> LENGTH: 23
<212> TYPE: DNA
<213> ORGANISM: Artificial sequence
<220> FEATURE:
<223> OTHER INFORMATION: Synthetic Primer

<400> SEQUENCE: 43
tttacccgga gaatgggaga ggg                                  23

<210> SEQ ID NO 44
<211> LENGTH: 28
<212> TYPE: DNA
<213> ORGANISM: Artificial sequence
<220> FEATURE:
<223> OTHER INFORMATION: Synthetic Primer

<400> SEQUENCE: 44
ggtctgcgtg ggccacctgc tggagggc                             28

<210> SEQ ID NO 45
<211> LENGTH: 28
<212> TYPE: DNA
<213> ORGANISM: Artificial sequence
<220> FEATURE:
<223> OTHER INFORMATION: Synthetic Primer

<400> SEQUENCE: 45
gggtgggggg cttgctgggt gccgggcg                             28

<210> SEQ ID NO 46
<211> LENGTH: 30
<212> TYPE: DNA
<213> ORGANISM: Artificial sequence
<220> FEATURE:
<223> OTHER INFORMATION: Synthetic Primer

<400> SEQUENCE: 46

```
<210> SEQ ID NO 47
<211> LENGTH: 26
<212> TYPE: DNA
<213> ORGANISM: Artificial sequence
<220> FEATURE:
<223> OTHER INFORMATION: Synthetic Primer

<400> SEQUENCE: 47
ctgtgtgacg ggagtatggc cgcgac                                         26

<210> SEQ ID NO 48
<211> LENGTH: 483
<212> TYPE: DNA
<213> ORGANISM: Canis familiaris
<220> FEATURE:
<221> NAME/KEY: misc_feature
<222> LOCATION: (470)..(470)
<223> OTHER INFORMATION: At nucleotide 470, n = unknown

<400> SEQUENCE: 48
cttatttgga catggaaccc cccagagggc gccagcccga attgcacctt acggtatttt     60
agtcattttg acaacaaaca ggataagaaa attgctcctg aaactcatcg ttcaaaagaa    120
gtacccctga atgagaggat ttgtctgcaa gtggggtccc agtgcagcac caatgaaagt    180
gacaatccta gcattttggt ggaaaagtgc accccaccac ctgaaggtgg tcctgagtcg    240
gctgtgactg agctacaatg tgtttggcac aacctgagct acatgaagtg tacttggctt    300
cctggaagga atacaagccc tgacaccaac tatactctct actattggca cagcagcctg    360
ggaaaaattc ttcaatgcga agacatctat agagaaggtc aacacattgg ttgttccttt    420
gctctgacta atttgaagga ttccagtttt gaacaacaca gtgtccagan gatggtcaag    480
gtt                                                                 483

<210> SEQ ID NO 49
<211> LENGTH: 1547
<212> TYPE: DNA
<213> ORGANISM: Canis familiaris
<220> FEATURE:
<221> NAME/KEY: CDS
<222> LOCATION: (1)..(1215)
<223> OTHER INFORMATION:

<400> SEQUENCE: 49 ggc ggg gtc gcc gca ccc acc gaa act cag cca cct gtg acg aat ttg      48
Gly Gly Val Ala Ala Pro Thr Glu Thr Gln Pro Pro Val Thr Asn Leu
1               5                   10                  15 agt gtt tct gtt gaa aac ctc tgc acg gtc ata tgg aca tgg aac cct      96
Ser Val Ser Val Glu Asn Leu Cys Thr Val Ile Trp Thr Trp Asn Pro
            20                  25                  30 ccc gag gga gcc agc ccg aat tgc acc tta cgg tat ttt agt cat ttt     144
Pro Glu Gly Ala Ser Pro Asn Cys Thr Leu Arg Tyr Phe Ser His Phe
        35                  40                  45 gac aac aaa cag gat aag aaa att gct cct gaa act cat cgt tca aaa     192
Asp Asn Lys Gln Asp Lys Lys Ile Ala Pro Glu Thr His Arg Ser Lys
    50                  55                  60 gaa gta ccc ctg aat gag agg att tgt ctg caa gtg ggg tcc cag tgc     240
Glu Val Pro Leu Asn Glu Arg Ile Cys Leu Gln Val Gly Ser Gln Cys
65                  70                  75                  80 agc acc aat gaa agt gac aat cct agc att ttg gtg gaa aag tgc acc     288
Ser Thr Asn Glu Ser Asp Asn Pro Ser Ile Leu Val Glu Lys Cys Thr
```

-continued

|  |  |  |  |  |  |  |  |  |  |  |  |  |  |  |  |
|---|---|---|---|---|---|---|---|---|---|---|---|---|---|---|---|
| cca | cca | cct | gaa | ggt | gat | cct | gag | tcg | gct | gtg | act | gag | cta | caa | tgt | 336 |
| Pro | Pro | Pro | Glu<br>100 | Gly | Asp | Pro | Glu | Ser<br>105 | Ala | Val | Thr | Glu | Leu<br>110 | Gln | Cys |

| gtt | tgg | cac | aac | ctg | agc | tac | atg | aag | tgt | act | tgg | ctt | cct | gga | agg | 384 |
| Val | Trp | His<br>115 | Asn | Leu | Ser | Tyr | Met<br>120 | Lys | Cys | Thr | Trp | Leu<br>125 | Pro | Gly | Arg |

| aat | aca | agc | cct | gac | acc | aac | tat | act | ctc | tac | tat | tgg | cac | agc | agc | 432 |
| Asn | Thr | Ser | Pro<br>130 | Asp | Thr | Asn | Tyr | Thr<br>135 | Leu | Tyr | Tyr | Trp | His<br>140 | Ser | Ser |

| ctg | gga | aaa | att | ctt | caa | tgc | gaa | gac | atc | tat | aga | gaa | ggt | caa | cac | 480 |
| Leu<br>145 | Gly | Lys | Ile | Leu | Gln<br>150 | Cys | Glu | Asp | Ile | Tyr<br>155 | Arg | Glu | Gly | Gln | His<br>160 |

| att | ggt | tgt | tcc | ttt | gct | ctg | act | aat | ttg | aag | gat | tcc | agt | ttt | gaa | 528 |
| Ile | Gly | Cys | Ser | Phe<br>165 | Ala | Leu | Thr | Asn | Leu<br>170 | Lys | Asp | Ser | Ser | Phe<br>175 | Glu |

| caa | cac | agt | gtc | caa | ata | atg | gtc | aag | gat | aat | gca | aga | aaa | att | aga | 576 |
| Gln | His | Ser | Val<br>180 | Gln | Ile | Met | Val | Lys<br>185 | Asp | Asn | Ala | Arg | Lys<br>190 | Ile | Arg |

| ccg | tcc | ttc | aat | ata | gtg | cct | tta | act | tct | cat | gtg | aaa | cct | gat | ccc | 624 |
| Pro | Ser | Phe | Asn<br>195 | Ile | Val | Pro | Leu | Thr<br>200 | Ser | His | Val | Lys | Pro<br>205 | Asp | Pro |

| ccc | cat | att | aag | cgt | ctc | ttc | ttc | caa | aat | ggt | aac | ttg | tat | gtg | caa | 672 |
| Pro | His | Ile<br>210 | Lys | Arg | Leu | Phe | Phe<br>215 | Gln | Asn | Gly | Asn | Leu<br>220 | Tyr | Val | Gln |

| tgg | aag | aat | cca | caa | aat | ttt | tat | agc | aga | tgc | tta | tct | tac | caa | gta | 720 |
| Trp<br>225 | Lys | Asn | Pro | Gln | Asn<br>230 | Phe | Tyr | Ser | Arg | Cys<br>235 | Leu | Ser | Tyr | Gln | Val<br>240 |

| gaa | gtc | aat | aac | agc | cag | act | gag | acg | aat | gat | ata | ttc | tac | gtt | gaa | 768 |
| Glu | Val | Asn | Asn | Ser<br>245 | Gln | Thr | Glu | Thr | Asn<br>250 | Asp | Ile | Phe | Tyr | Val<br>255 | Glu |

| gaa | gcc | aaa | tgt | cag | aat | tca | gaa | ttt | gag | gga | aac | ctg | gag | ggt | aca | 816 |
| Glu | Ala | Lys | Cys<br>260 | Gln | Asn | Ser | Glu | Phe<br>265 | Glu | Gly | Asn | Leu | Glu<br>270 | Gly | Thr |

| att | tgt | ttc | atg | gtc | ccc | ggc | gtt | ctt | cct | gat | act | ttg | aac | aca | gtc | 864 |
| Ile | Cys | Phe | Met<br>275 | Val | Pro | Gly | Val | Leu<br>280 | Pro | Asp | Thr | Leu | Asn<br>285 | Thr | Val |

| aga | ata | aga | gtc | aga | aca | aat | aag | tta | tgc | tat | gag | gat | gac | aaa | ctc | 912 |
| Arg | Ile | Arg<br>290 | Val | Arg | Thr | Asn | Lys<br>295 | Leu | Cys | Tyr | Glu | Asp<br>300 | Asp | Lys | Leu |

| tgg | agt | aat | tgg | agt | caa | gcg | atg | agt | ata | ggt | gag | aat | acc | gac | ccc | 960 |
| Trp<br>305 | Ser | Asn | Trp | Ser | Gln<br>310 | Ala | Met | Ser | Ile | Gly<br>315 | Glu | Asn | Thr | Asp | Pro<br>320 |

| acg | ttc | tat | ata | acc | atg | ttg | ctc | gcc | act | caa | gtc | atc | gtt | gca | ggt | 1008 |
| Thr | Phe | Tyr | Ile | Thr<br>325 | Met | Leu | Leu | Ala | Thr<br>330 | Gln | Val | Ile | Val | Ala<br>335 | Gly |

| gcc | atc | ata | atc | ctt | ctg | ctt | tat | ctc | aaa | agg | ctc | aag | atc | att | ata | 1056 |
| Ala | Ile | Ile | Ile<br>340 | Leu | Leu | Leu | Tyr | Leu<br>345 | Lys | Arg | Leu | Lys | Ile<br>350 | Ile | Ile |

| ttc | cct | cca | att | cct | gat | cct | ggc | aag | att | ttt | aaa | gaa | atg | ttt | gga | 1104 |
| Phe | Pro | Pro | Ile<br>355 | Pro | Asp | Pro | Gly | Lys<br>360 | Ile | Phe | Lys | Glu | Met<br>365 | Phe | Gly |

| gac | cag | aat | gat | gat | acg | ctg | cac | tgg | agg | aag | tac | gac | atc | tat | gag | 1152 |
| Asp | Gln | Asn | Asp<br>370 | Asp | Thr | Leu | His | Trp<br>375 | Arg | Lys | Tyr | Asp | Ile<br>380 | Tyr | Glu |

| aag | caa | aca | aaa | gaa | gaa | acg | gac | tca | gta | gtg | ctg | att | gaa | aac | ctg | 1200 |
| Lys<br>385 | Gln | Thr | Lys | Glu | Glu<br>390 | Thr | Asp | Ser | Val | Val<br>395 | Leu | Ile | Glu | Asn | Leu<br>400 |

| aag aaa gcc tct cag taatggggat aacttatttt agccttcagc atgaccttgt | 1255 |

```
Lys Lys Ala Ser Gln
            405 aaagattcat ccccacgttc tcgggaagct tcaaggtcaa gcatcttggg aaaggacatt    1315 acagtttcta cagcatggtg tacctgggca tctccgacta cttcttcaac acagcagggc    1375 ttgtgtacca agaggcaggg gccttaaaca tgaccatcac ggacgacatg ataccaaaga    1435 aatccaaatt ccgactgaca accgattttt tggggaccct catacccaa gtggccgaga    1495 tgttccccaa catgacggtt caattcaacg tctgggcctc ctccccgccg ca            1547

<210> SEQ ID NO 50
<211> LENGTH: 405
<212> TYPE: PRT
<213> ORGANISM: Canis familiaris

<400> SEQUENCE: 50

Gly Gly Val Ala Ala Pro Thr Glu Thr Gln Pro Pro Val Thr Asn Leu
1               5                   10                  15

Ser Val Ser Val Glu Asn Leu Cys Thr Val Ile Trp Thr Trp Asn Pro
                20                  25                  30

Pro Glu Gly Ala Ser Pro Asn Cys Thr Leu Arg Tyr Phe Ser His Phe
            35                  40                  45

Asp Asn Lys Gln Asp Lys Lys Ile Ala Pro Glu Thr His Arg Ser Lys
        50                  55                  60

Glu Val Pro Leu Asn Glu Arg Ile Cys Leu Gln Val Gly Ser Gln Cys
65                  70                  75                  80

Ser Thr Asn Glu Ser Asp Asn Pro Ser Ile Leu Val Glu Lys Cys Thr
                85                  90                  95

Pro Pro Pro Glu Gly Asp Pro Ser Ala Val Thr Glu Leu Gln Cys
            100                 105                 110

Val Trp His Asn Leu Ser Tyr Met Lys Cys Thr Trp Leu Pro Gly Arg
            115                 120                 125

Asn Thr Ser Pro Asp Thr Asn Tyr Thr Leu Tyr Tyr Trp His Ser Ser
        130                 135                 140

Leu Gly Lys Ile Leu Gln Cys Glu Asp Ile Tyr Arg Glu Gly Gln His
145                 150                 155                 160

Ile Gly Cys Ser Phe Ala Leu Thr Asn Leu Lys Asp Ser Ser Phe Glu
                165                 170                 175

Gln His Ser Val Gln Ile Met Val Lys Asp Asn Ala Arg Lys Ile Arg
            180                 185                 190

Pro Ser Phe Asn Ile Val Pro Leu Thr Ser His Val Lys Pro Asp Pro
        195                 200                 205

Pro His Ile Lys Arg Leu Phe Phe Gln Asn Gly Asn Leu Tyr Val Gln
    210                 215                 220

Trp Lys Asn Pro Gln Asn Phe Tyr Ser Arg Cys Leu Ser Tyr Gln Val
225                 230                 235                 240

Glu Val Asn Asn Ser Gln Thr Glu Thr Asn Asp Ile Phe Tyr Val Glu
                245                 250                 255

Glu Ala Lys Cys Gln Asn Ser Glu Phe Glu Gly Asn Leu Glu Gly Thr
            260                 265                 270

Ile Cys Phe Met Val Pro Gly Val Leu Pro Asp Thr Leu Asn Thr Val
        275                 280                 285

Arg Ile Arg Val Arg Thr Asn Lys Leu Cys Tyr Glu Asp Asp Lys Leu
    290                 295                 300

Trp Ser Asn Trp Ser Gln Ala Met Ser Ile Gly Glu Asn Thr Asp Pro
```

|     |     |     |     |     |     |     |     |     |     |     |     |     |
| --- | --- | --- | --- | --- | --- | --- | --- | --- | --- | --- | --- | --- |
| 305 |     |     |     | 310 |     |     |     | 315 |     |     |     | 320 |
| Thr | Phe | Tyr | Ile | Thr | Met | Leu | Leu | Ala | Thr | Gln | Val | Ile | Val | Ala | Gly |
|     |     |     |     | 325 |     |     |     |     | 330 |     |     |     |     | 335 |     |
| Ala | Ile | Ile | Ile | Leu | Leu | Leu | Tyr | Leu | Lys | Arg | Leu | Lys | Ile | Ile | Ile |
|     |     |     | 340 |     |     |     |     | 345 |     |     |     |     | 350 |     |     |
| Phe | Pro | Pro | Ile | Pro | Asp | Pro | Gly | Lys | Ile | Phe | Lys | Glu | Met | Phe | Gly |
|     |     |     | 355 |     |     |     |     | 360 |     |     |     |     | 365 |     |     |
| Asp | Gln | Asn | Asp | Asp | Thr | Leu | His | Trp | Arg | Lys | Tyr | Asp | Ile | Tyr | Glu |
|     |     |     | 370 |     |     |     |     | 375 |     |     |     |     | 380 |     |     |
| Lys | Gln | Thr | Lys | Glu | Glu | Thr | Asp | Ser | Val | Val | Leu | Ile | Glu | Asn | Leu |
| 385 |     |     |     |     | 390 |     |     |     |     | 395 |     |     |     |     | 400 |
| Lys | Lys | Ala | Ser | Gln |
|     |     |     |     | 405 |

<210> SEQ ID NO 51
<211> LENGTH: 1547
<212> TYPE: DNA
<213> ORGANISM: Canis familiaris

<400> SEQUENCE: 51

```
tgcggcgggg aggaggccca gacgttgaat tgaaccgtca tgttggggaa catctcggcc      60
acttggggta tgagggtccc caaaaaatcg gttgtcagtc ggaatttgga tttctttggt     120
atcatgtcgt ccgtgatggt catgtttaag gcccctgcct cttggtacac aagccctgct     180
gtgttgaaga agtagtcgga gatgcccagg tacaccatgc tgtagaaact gtaatgtcct     240
ttcccaagat gcttgacctt gaagcttccc gagaacgtgg ggatgaatct ttacaaggtc     300
atgctgaagg ctaaaataag ttatccccat tactgagagg ctttcttcag gttttcaatc     360
agcactactg agtccgtttc ttcttttgtt tgcttctcat agatgtcgta cttcctccag     420
tgcagcgtat catcattctg gtctccaaac atttctttaa aaatcttgcc aggatcagga     480
attggaggga atataatgat cttgagcctt tgagataaa gcagaaggat tatgatggca     540
cctgcaacga tgacttgagt ggcgagcaac atggttatat agaacgtggg gtcggtattc     600
tcacctatac tcatcgcttg actccaatta ctccagagtt tgtcatcctc atagcataac     660
ttatttgttc tgactcttat tctgactgtg ttcaaagtat caggaagaac gccggggacc     720
atgaaacaaa ttgtaccctc caggtttccc tcaaattctg aattctgaca tttggcttct     780
tcaacgtaga atatatcatt cgtctcagtc tggctgttat tgacttctac ttggtaagat     840
aagcatctgc tataaaaatt tgtggattc ttccattgca catacaagtt accattttgg     900
aagaagagac gcttaatatg ggggggatca ggtttcacat gagaagttaa aggcactata     960
ttgaaggacg tctaattttt tcttgcatta tccttgacca ttatttggac actgtgttgt    1020
tcaaaactgg aatccttcaa attagtcaga gcaaggaac aaccaatgtg ttgaccttct    1080
ctatagatgt cttcgcattg aagaattttt cccaggctgc tgtgccaata gtagagagta    1140
tagttggtgt cagggcttgt attccttcca ggaagccaag tacacttcat gtagctcagg    1200
ttgtgccaaa cacattgtag ctcagtcaca gccgactcag gatcaccttc aggtggtggg    1260
gtgcactttt ccaccaaaat gctaggattg tcactttcat tggtgctgca ctgggacccc    1320
acttgcagac aaatcctctc attcaggggt acttcttttg aacgatgagt ttcaggagca    1380
atttttcttat cctgtttgtt gtcaaaatga ctaaaatacc gtaaggtgca attcgggctg    1440
gctccctcgg gagggttcca tgtccatatg accgtgcaga ggttttcaac agaaacactc    1500
aaattcgtca caggtggctg agtttcggtg ggtgcggcga ccccgcc               1547
```

<210> SEQ ID NO 52
<211> LENGTH: 1215
<212> TYPE: DNA
<213> ORGANISM: Canis familiaris

<400> SEQUENCE: 52

| | |
|---|---|
| ggcggggtcg ccgcacccac cgaaactcag ccacctgtga cgaatttgag tgtttctgtt | 60 |
| gaaaacctct gcacggtcat atggacatgg aaccctcccg agggagccag cccgaattgc | 120 |
| accttacggt attttagtca ttttgacaac aaacaggata agaaaattgc tcctgaaact | 180 |
| catcgttcaa aagaagtacc cctgaatgag aggatttgtc tgcaagtggg gtcccagtgc | 240 |
| agcaccaatg aaagtgacaa tcctagcatt ttggtggaaa agtgcacccc accacctgaa | 300 |
| ggtgatcctg agtcggctgt gactgagcta caatgtgttt ggcacaacct gagctacatg | 360 |
| aagtgtactt ggcttcctgg aaggaataca agccctgaca ccaactatac tctctactat | 420 |
| tggcacagca gcctgggaaa aattcttcaa tgcgaagaca tctatagaga aggtcaacac | 480 |
| attggttgtt cctttgctct gactaatttg aaggattcca gttttgaaca acacagtgtc | 540 |
| caaataatgg tcaaggataa tgcaagaaaa attagaccgt ccttcaatat agtgccttta | 600 |
| acttctcatg tgaaacctga tccccccccat attaagcgtc tcttcttcca aaatggtaac | 660 |
| ttgtatgtgc aatggaagaa tccacaaaat ttttatagca gatgcttatc ttaccaagta | 720 |
| gaagtcaata acagccagac tgagacgaat gatatattct acgttgaaga agccaaatgt | 780 |
| cagaattcag aatttgaggg aaacctggag ggtacaattt gtttcatggt ccccggcgtt | 840 |
| cttcctgata cttttgaacac agtcagaata agagtcagaa caaataagtt atgctatgag | 900 |
| gatgacaaac tctggagtaa ttggagtcaa gcgatgagta taggtgagaa taccgacccc | 960 |
| acgttctata taaccatgtt gctcgccact caagtcatcg ttgcaggtgc catcataatc | 1020 |
| cttctgcttt atctcaaaag gctcaagatc attatattcc ctccaattcc tgatcctggc | 1080 |
| aagattttta agaaatgtt tggagaccag aatgatgata cgctgcactg gaggaagtac | 1140 |
| gacatctatg agaagcaaac aaaagaagaa acggactcag tagtgctgat tgaaaacctg | 1200 |
| aagaaagcct ctcag | 1215 |

<210> SEQ ID NO 53
<211> LENGTH: 1215
<212> TYPE: DNA
<213> ORGANISM: Canis familiaris

<400> SEQUENCE: 53

| | |
|---|---|
| ctgagaggct ttcttcaggt tttcaatcag cactactgag tccgtttctt cttttgtttg | 60 |
| cttctcatag atgtcgtact tcctccagtg cagcgtatca tcattctggt ctccaaacat | 120 |
| ttctttaaaa atcttgccag gatcaggaat tggagggaat ataatgatct tgagccttt | 180 |
| gagataaagc agaaggatta tgatggcacc tgcaacgatg acttgagtgg cgagcaacat | 240 |
| ggttatatag aacgtggggt cggtattctc acctatactc atcgcttgac tccaattact | 300 |
| ccagagtttg tcatcctcat agcataactt atttgttctg actcttattc tgactgtgtt | 360 |
| caaagtatca ggaagaacgc cggggaccat gaaacaaatt gtaccctcca ggtttccctc | 420 |
| aaattctgaa ttctgacatt tggcttcttc aacgtagaat atatcattcg tctcagtctg | 480 |
| gctgttattg acttctactt ggtaagataa gcatctgcta aaaaatttt gtggattctt | 540 |
| ccattgcaca tacaagttac cattttggaa gaagagacgc ttaatatggg ggggatcagg | 600 |

-continued

```
tttcacatga gaagttaaag gcactatatt gaaggacggt ctaattttc ttgcattatc    660 cttgaccatt atttggacac tgtgttgttc aaaactggaa tccttcaaat tagtcagagc    720
aaaggaacaa ccaatgtgtt gaccttctct atagatgtct tcgcattgaa gaattttttcc   780 caggctgctg tgccaatagt agagagtata gttggtgtca gggcttgtat tccttccagg    840
aagccaagta cacttcatgt agctcaggtt gtgccaaaca cattgtagct cagtcacagc    900
cgactcagga tcaccttcag gtggtggggt gcacttttcc accaaaatgc taggattgtc    960
actttcattg gtgctgcact gggaccccac ttgcagacaa atcctctcat tcagggtac    1020 ttcttttgaa cgatgagttt caggagcaat tttcttatcc tgtttgttgt caaaatgact   1080
aaaataccgt aaggtgcaat tcgggctggc tccctcggga gggttccatg tccatatgac   1140
cgtgcagagg ttttcaacag aaacactcaa attcgtcaca ggtggctgag tttcggtggg   1200
tgcggcgacc ccgcc                                                    1215
```

<210> SEQ ID NO 54
<211> LENGTH: 620
<212> TYPE: DNA
<213> ORGANISM: Canis familiaris
<220> FEATURE:
<221> NAME/KEY: CDS
<222> LOCATION: (184)..(618)
<223> OTHER INFORMATION:

<400> SEQUENCE: 54

```
ggcacgaggc tgagtttgtg tgcttgatta tcagacagga agggaagtct tagagattct     60
aattaatgtc tccaaactgg agaagagaaa aaaagagga cctgtgataa ttgcctatga    120
taattcattt cttgagaaac catattattg agtggaaact tcaaagtatt gaatcttgga   180 gga atg gct ttc att cat ttg gat gtc gga ttc ctc tat acc ctg ctt      228
    Met Ala Phe Ile His Leu Asp Val Gly Phe Leu Tyr Thr Leu Leu
    1               5                   10                  15 gtt tgc aca gca ttt ggc tct atg ctt tca aat gct gag ata aaa gtt      276
Val Cys Thr Ala Phe Gly Ser Met Leu Ser Asn Ala Glu Ile Lys Val
                20                  25                  30 aat cct cct cag gat ttt gag ata gtg gac cct gga tat tta ggt tat      324
Asn Pro Pro Gln Asp Phe Glu Ile Val Asp Pro Gly Tyr Leu Gly Tyr
            35                  40                  45 ctc tct ttg caa tgg caa cct cca tta ttt ccg gat aat ttt aag gaa      372
Leu Ser Leu Gln Trp Gln Pro Pro Leu Phe Pro Asp Asn Phe Lys Glu
        50                  55                  60 tgc aca ata gaa tat gaa tta aaa tac cga aac att gat agt gaa aac      420
Cys Thr Ile Glu Tyr Glu Leu Lys Tyr Arg Asn Ile Asp Ser Glu Asn
65                  70                  75 tgg aag acc atc att acc aag aat cta cat tac aaa gat ggg ttt gat      468
Trp Lys Thr Ile Ile Thr Lys Asn Leu His Tyr Lys Asp Gly Phe Asp
80                  85                  90                  95 ctt aac aaa ggt att gaa gca aag ata aac aca ctt ctg cca gca caa      516
Leu Asn Lys Gly Ile Glu Ala Lys Ile Asn Thr Leu Leu Pro Ala Gln
                100                 105                 110 tgc aca aat gga tca gaa gtt aga agt tca tgg gca gaa act act tat      564
Cys Thr Asn Gly Ser Glu Val Arg Ser Ser Trp Ala Glu Thr Thr Tyr
            115                 120                 125 tgg aca tca cca caa gga aat cgg gaa act aaa att caa gat atg gac      612
Trp Thr Ser Pro Gln Gly Asn Arg Glu Thr Lys Ile Gln Asp Met Asp
        130                 135                 140 tgt gta ta                                                          620
Cys Val
    145
```

<210> SEQ ID NO 55
<211> LENGTH: 145
<212> TYPE: PRT
<213> ORGANISM: Canis familiaris

<400> SEQUENCE: 55

```
Met Ala Phe Ile His Leu Asp Val Gly Phe Leu Tyr Thr Leu Leu Val
1               5                   10                  15

Cys Thr Ala Phe Gly Ser Met Leu Ser Asn Ala Glu Ile Lys Val Asn
            20                  25                  30

Pro Pro Gln Asp Phe Glu Ile Val Asp Pro Gly Tyr Leu Gly Tyr Leu
        35                  40                  45

Ser Leu Gln Trp Gln Pro Pro Leu Phe Pro Asp Asn Phe Lys Glu Cys
    50                  55                  60

Thr Ile Glu Tyr Glu Leu Lys Tyr Arg Asn Ile Asp Ser Glu Asn Trp
65                  70                  75                  80

Lys Thr Ile Ile Thr Lys Asn Leu His Tyr Lys Asp Gly Phe Asp Leu
                85                  90                  95

Asn Lys Gly Ile Glu Ala Lys Ile Asn Thr Leu Leu Pro Ala Gln Cys
            100                 105                 110

Thr Asn Gly Ser Glu Val Arg Ser Ser Trp Ala Glu Thr Thr Tyr Trp
        115                 120                 125

Thr Ser Pro Gln Gly Asn Arg Glu Thr Lys Ile Gln Asp Met Asp Cys
    130                 135                 140

Val
145
```

<210> SEQ ID NO 56
<211> LENGTH: 620
<212> TYPE: DNA
<213> ORGANISM: Canis familiaris

<400> SEQUENCE: 56

```
tatacacagt ccatatcttg aattttagtt tcccgatttc cttgtggtga tgtccaataa      60
gtagtttctg cccatgaact tctaacttct gatccatttg tgcattgtgc tggcagaagt     120
gtgtttatct ttgcttcaat acctttgtta agatcaaacc catctttgta atgtagattc     180
ttggtaatga tggtcttcca gttttcacta tcaatgtttc ggtattttaa ttcatattct     240
attgtgcatt ccttaaaatt atccggaaat aatggaggtt gccattgcaa agagagataa     300
cctaaatatc cagggtccac tatctcaaaa tcctgaggag gattaacttt tatctcagca     360
tttgaaagca tagagccaaa tgctgtgcaa acaagcaggg tatagaggaa tccgacatcc     420
aaatgaatga aagccattcc tccaagattc aatactttga agtttccact caataatatg     480
gtttctcaag aaatgaatta tcataggcaa ttatcacagg tcctcttttt tttctcttct     540
ccagtttgga gacattaatt agaatctcta agacttccct tcctgtctga taatcaagca     600
cacaaactca gcctcgtgcc                                                 620
```

<210> SEQ ID NO 57
<211> LENGTH: 878
<212> TYPE: DNA
<213> ORGANISM: Canis familiaris
<220> FEATURE:
<221> NAME/KEY: CDS
<222> LOCATION: (1)..(765)
<223> OTHER INFORMATION:
<220> FEATURE:

<221> NAME/KEY: misc_feature
<222> LOCATION: (862)..(862)
<223> OTHER INFORMATION: At nucleotide 862, n = unknown

<400> SEQUENCE: 57

| | | | | | | | | | | | | | | | | |
|---|---|---|---|---|---|---|---|---|---|---|---|---|---|---|---|---|
| caa | gga | aat | cgg | gaa | act | aaa | att | caa | gat | atg | gac | tgt | gta | tat | tac | 48 |
| Gln | Gly | Asn | Arg | Glu | Thr | Lys | Ile | Gln | Asp | Met | Asp | Cys | Val | Tyr | Tyr | |
| 1 | | | | 5 | | | | | 10 | | | | | 15 | | |
| aac | tgg | caa | tat | tta | gtc | tgc | tct | tgg | aaa | cct | ggc | atg | ggt | gtc | cat | 96 |
| Asn | Trp | Gln | Tyr | Leu | Val | Cys | Ser | Trp | Lys | Pro | Gly | Met | Gly | Val | His | |
| | | | 20 | | | | | 25 | | | | | 30 | | | |
| ttt | gat | acc | aat | tac | cag | ttg | ttt | tac | tgg | tat | gag | ggc | ttg | gac | cat | 144 |
| Phe | Asp | Thr | Asn | Tyr | Gln | Leu | Phe | Tyr | Trp | Tyr | Glu | Gly | Leu | Asp | His | |
| | | | | 35 | | | | | 40 | | | | | 45 | | |
| tca | gca | gag | tgt | act | gat | tac | atc | aag | gtt | aat | gga | aaa | aat | atg | gga | 192 |
| Ser | Ala | Glu | Cys | Thr | Asp | Tyr | Ile | Lys | Val | Asn | Gly | Lys | Asn | Met | Gly | |
| 50 | | | | | 55 | | | | | 60 | | | | | | |
| tgc | agg | ttt | ccc | tat | ttg | gag | tca | tca | gac | tat | aaa | gat | ttc | tac | atc | 240 |
| Cys | Arg | Phe | Pro | Tyr | Leu | Glu | Ser | Ser | Asp | Tyr | Lys | Asp | Phe | Tyr | Ile | |
| 65 | | | | | 70 | | | | | 75 | | | | | 80 | |
| tgt | gtt | aat | ggg | tca | tca | gaa | tcc | cag | cct | atc | aga | ccc | agc | tat | ttt | 288 |
| Cys | Val | Asn | Gly | Ser | Ser | Glu | Ser | Gln | Pro | Ile | Arg | Pro | Ser | Tyr | Phe | |
| | | | | 85 | | | | | 90 | | | | | 95 | | |
| att | ttt | cag | ctt | caa | aat | ata | gtt | aaa | cct | atg | cca | cca | gac | tac | ctt | 336 |
| Ile | Phe | Gln | Leu | Gln | Asn | Ile | Val | Lys | Pro | Met | Pro | Pro | Asp | Tyr | Leu | |
| | | | | 100 | | | | | 105 | | | | | 110 | | |
| agt | ctt | act | gtg | aag | aat | tca | gag | gaa | att | aac | ctg | aaa | tgg | aac | atg | 384 |
| Ser | Leu | Thr | Val | Lys | Asn | Ser | Glu | Glu | Ile | Asn | Leu | Lys | Trp | Asn | Met | |
| | | | 115 | | | | | 120 | | | | | 125 | | | |
| cct | aaa | gga | ccc | att | cca | gcc | aaa | tgt | ttc | att | tat | gaa | att | gaa | ttc | 432 |
| Pro | Lys | Gly | Pro | Ile | Pro | Ala | Lys | Cys | Phe | Ile | Tyr | Glu | Ile | Glu | Phe | |
| | | 130 | | | | | 135 | | | | | 140 | | | | |
| aca | gag | gat | ggt | act | act | tgg | gtg | act | acc | aca | gtt | gag | aat | gag | ata | 480 |
| Thr | Glu | Asp | Gly | Thr | Thr | Trp | Val | Thr | Thr | Thr | Val | Glu | Asn | Glu | Ile | |
| 145 | | | | | 150 | | | | | 155 | | | | | 160 | |
| caa | atc | aca | aga | aca | tca | aat | gaa | agc | caa | aaa | tta | tgc | ttt | ttg | gta | 528 |
| Gln | Ile | Thr | Arg | Thr | Ser | Asn | Glu | Ser | Gln | Lys | Leu | Cys | Phe | Leu | Val | |
| | | | | 165 | | | | | 170 | | | | | 175 | | |
| aga | agt | aaa | gtg | aat | att | tat | tgc | tca | gat | gat | gga | atc | tgg | agt | gag | 576 |
| Arg | Ser | Lys | Val | Asn | Ile | Tyr | Cys | Ser | Asp | Asp | Gly | Ile | Trp | Ser | Glu | |
| | | | 180 | | | | | 185 | | | | | 190 | | | |
| tgg | agt | gat | gaa | caa | tgc | tgg | aaa | ggt | gac | ata | tgg | aag | gaa | acc | tta | 624 |
| Trp | Ser | Asp | Glu | Gln | Cys | Trp | Lys | Gly | Asp | Ile | Trp | Lys | Glu | Thr | Leu | |
| | | 195 | | | | | 200 | | | | | 205 | | | | |
| gta | ttt | ttc | ttg | ata | cca | ttt | gct | ttt | gtc | tca | ata | ttt | gtt | ttg | gta | 672 |
| Val | Phe | Phe | Leu | Ile | Pro | Phe | Ala | Phe | Val | Ser | Ile | Phe | Val | Leu | Val | |
| 210 | | | | | 215 | | | | | 220 | | | | | | |
| ata | act | tgc | ctg | ctt | ttg | tat | aag | caa | agg | gct | tta | ctg | aaa | acg | atc | 720 |
| Ile | Thr | Cys | Leu | Leu | Leu | Tyr | Lys | Gln | Arg | Ala | Leu | Leu | Lys | Thr | Ile | |
| 225 | | | | | 230 | | | | | 235 | | | | | 240 | |
| ttt | cat | aca | aaa | aaa | gaa | gtc | ttt | tct | cat | caa | gac | aca | ttc | tgt | | 765 |
| Phe | His | Thr | Lys | Lys | Glu | Val | Phe | Ser | His | Gln | Asp | Thr | Phe | Cys | | |
| | | | | 245 | | | | | 250 | | | | | 255 | | | tgactcagta actttcagtc ttatggccag atgttaaata tgagtcttat taaactgaag    825 cttttcctca aatattgaat aaatcttatt ttaaangaa aaaaaaaaaa aaa          878

<210> SEQ ID NO 58
<211> LENGTH: 255
<212> TYPE: PRT
<213> ORGANISM: Canis familiaris

<400> SEQUENCE: 58

| | | | | | | | | | | | | | | |
|---|---|---|---|---|---|---|---|---|---|---|---|---|---|---|
| Gln | Gly | Asn | Arg | Glu | Thr | Lys | Ile | Gln | Asp | Met | Asp | Cys | Val | Tyr | Tyr |
| 1 | | | | 5 | | | | | 10 | | | | | 15 | |
| Asn | Trp | Gln | Tyr | Leu | Val | Cys | Ser | Trp | Lys | Pro | Gly | Met | Gly | Val | His |
| | | | 20 | | | | | 25 | | | | | 30 | | |
| Phe | Asp | Thr | Asn | Tyr | Gln | Leu | Phe | Tyr | Trp | Tyr | Glu | Gly | Leu | Asp | His |
| | | 35 | | | | | 40 | | | | | 45 | | | |
| Ser | Ala | Glu | Cys | Thr | Asp | Tyr | Ile | Lys | Val | Asn | Gly | Lys | Asn | Met | Gly |
| 50 | | | | | 55 | | | | | 60 | | | | | |
| Cys | Arg | Phe | Pro | Tyr | Leu | Glu | Ser | Ser | Asp | Tyr | Lys | Asp | Phe | Tyr | Ile |
| 65 | | | | | 70 | | | | | 75 | | | | | 80 |
| Cys | Val | Asn | Gly | Ser | Ser | Glu | Ser | Gln | Pro | Ile | Arg | Pro | Ser | Tyr | Phe |
| | | | | 85 | | | | | 90 | | | | | 95 | |
| Ile | Phe | Gln | Leu | Gln | Asn | Ile | Val | Lys | Pro | Met | Pro | Pro | Asp | Tyr | Leu |
| | | | 100 | | | | | 105 | | | | | 110 | | |
| Ser | Leu | Thr | Val | Lys | Asn | Ser | Glu | Glu | Ile | Asn | Leu | Lys | Trp | Asn | Met |
| | | 115 | | | | | 120 | | | | | 125 | | | |
| Pro | Lys | Gly | Pro | Ile | Pro | Ala | Lys | Cys | Phe | Ile | Tyr | Glu | Ile | Glu | Phe |
| | 130 | | | | | 135 | | | | | 140 | | | | |
| Thr | Glu | Asp | Gly | Thr | Thr | Trp | Val | Thr | Thr | Val | Glu | Asn | Glu | Ile |
| 145 | | | | | 150 | | | | | 155 | | | | | 160 |
| Gln | Ile | Thr | Arg | Thr | Ser | Asn | Glu | Ser | Gln | Lys | Leu | Cys | Phe | Leu | Val |
| | | | 165 | | | | | 170 | | | | | 175 | | |
| Arg | Ser | Lys | Val | Asn | Ile | Tyr | Cys | Ser | Asp | Asp | Gly | Ile | Trp | Ser | Glu |
| | | | 180 | | | | | 185 | | | | | 190 | | |
| Trp | Ser | Asp | Glu | Gln | Cys | Trp | Lys | Gly | Asp | Ile | Trp | Lys | Glu | Thr | Leu |
| | | 195 | | | | | 200 | | | | | 205 | | | |
| Val | Phe | Phe | Leu | Ile | Pro | Phe | Ala | Phe | Val | Ser | Ile | Phe | Val | Leu | Val |
| | 210 | | | | | 215 | | | | | 220 | | | | |
| Ile | Thr | Cys | Leu | Leu | Leu | Tyr | Lys | Gln | Arg | Ala | Leu | Leu | Lys | Thr | Ile |
| 225 | | | | | 230 | | | | | 235 | | | | | 240 |
| Phe | His | Thr | Lys | Lys | Glu | Val | Phe | Ser | His | Gln | Asp | Thr | Phe | Cys |
| | | | | 245 | | | | | 250 | | | | | 255 |

<210> SEQ ID NO 59
<211> LENGTH: 878
<212> TYPE: DNA
<213> ORGANISM: Canis familiaris
<220> FEATURE:
<221> NAME/KEY: misc_feature
<222> LOCATION: (17)..(17)
<223> OTHER INFORMATION: At nucleotide 17, n = unknown

<400> SEQUENCE: 59

```
ttttttttt tttttcnttt taaaataaga tttattcaat atttgaggaa aagcttcagt      60
ttaataagac tcatatttaa catctggcca taagactgaa agttactgag tcaacagaat   120
gtgtcttgat gagaaaagac ttctttttt gtatgaaaga tcgttttcag taaagcctt    180
tgcttataca aaagcaggca agttattacc aaaacaaata ttgagacaaa agcaaatggt   240
atcaagaaaa atactaaggt ttccttccat atgtcacctt ccagcattg ttcatcactc    300
cactcactcc agattccatc atctgagcaa taaatattca ctttacttct taccaaaaag  360
cataatttt ggctttcatt tgatgttctt gtgatttgta tctcattctc aactgtggta   420
gtcacccaag tagtaccatc ctctgtgaat tcaatttcat aaatgaaaca tttggctgga  480
```

-continued

```
atgggtcctt taggcatgtt ccatttcagg ttaatttcct ctgaattctt cacagtaaga    540
ctaaggtagt ctggtggcat aggtttaact atattttgaa gctgaaaaat aaaatagctg    600
ggtctgatag gctgggattc tgatgaccca ttaacacaga tgtagaaatc tttatagtct    660
gatgactcca aatagggaaa cctgcatccc atattttttc cattaacctt gatgtaatca    720
gtacactctg ctgaatggtc caagccctca taccagtaaa acaactggta attggtatca    780
aaatggacac ccatgccagg tttccaagag cagactaaat attgccagtt gtaatataca    840
cagtccatat cttgaatttt agtttcccga tttccttg                            878
```

<210> SEQ ID NO 60
<211> LENGTH: 1454
<212> TYPE: DNA
<213> ORGANISM: Canis familiaris
<220> FEATURE:
<221> NAME/KEY: CDS
<222> LOCATION: (184)..(1341)
<223> OTHER INFORMATION:
<220> FEATURE:
<221> NAME/KEY: misc_feature
<222> LOCATION: (1438)..(1438)
<223> OTHER INFORMATION: At nucleotide 1438, n = unknown

<400> SEQUENCE: 60

```
ggcacgaggc tgagtttgtg tgcttgatta tcagacagga agggaagtct tagagattct     60
aattaatgtc tccaaactgg agaagagaaa aaaagagga cctgtgataa ttgcctatga    120
taattcattt cttgagaaac catattattg agtggaaact tcaaagtatt gaatcttgga    180 gga atg gct ttc att cat ttg gat gtc gga ttc ctc tat acc ctg ctt    228
    Met Ala Phe Ile His Leu Asp Val Gly Phe Leu Tyr Thr Leu Leu
    1               5                   10                  15 gtt tgc aca gca ttt ggc tct atg ctt tca aat gct gag ata aaa gtt    276
Val Cys Thr Ala Phe Gly Ser Met Leu Ser Asn Ala Glu Ile Lys Val
            20                  25                  30 aat cct cct cag gat ttt gag ata gtg gac cct gga tat tta ggt tat    324
Asn Pro Pro Gln Asp Phe Glu Ile Val Asp Pro Gly Tyr Leu Gly Tyr
        35                  40                  45 ctc tct ttg caa tgg caa cct cca tta ttt ccg gat aat ttt aag gaa    372
Leu Ser Leu Gln Trp Gln Pro Pro Leu Phe Pro Asp Asn Phe Lys Glu
    50                  55                  60 tgc aca ata gaa tat gaa tta aaa tac cga aac att gat agt gaa aac    420
Cys Thr Ile Glu Tyr Glu Leu Lys Tyr Arg Asn Ile Asp Ser Glu Asn
65                  70                  75 tgg aag acc atc att acc aag aat cta cat tac aaa gat ggg ttt gat    468
Trp Lys Thr Ile Ile Thr Lys Asn Leu His Tyr Lys Asp Gly Phe Asp
80                  85                  90                  95 ctt aac aaa ggt att gaa gca aag ata aac aca ctt ctg cca gca caa    516
Leu Asn Lys Gly Ile Glu Ala Lys Ile Asn Thr Leu Leu Pro Ala Gln
                100                 105                 110 tgc aca aat gga tca gaa gtt aga agt tca tgg gca gaa act act tat    564
Cys Thr Asn Gly Ser Glu Val Arg Ser Ser Trp Ala Glu Thr Thr Tyr
            115                 120                 125 tgg aca tca cca caa gga aat cgg gaa act aaa att caa gat atg gac    612
Trp Thr Ser Pro Gln Gly Asn Arg Glu Thr Lys Ile Gln Asp Met Asp
        130                 135                 140 tgt gta tat tac aac tgg caa tat tta gtc tgc tct tgg aaa cct ggc    660
Cys Val Tyr Tyr Asn Trp Gln Tyr Leu Val Cys Ser Trp Lys Pro Gly
    145                 150                 155 atg ggt gtc cat ttt gat acc aat tac cag ttg ttt tac tgg tat gag    708
Met Gly Val His Phe Asp Thr Asn Tyr Gln Leu Phe Tyr Trp Tyr Glu
160                 165                 170                 175
```

```
ggc ttg gac cat tca gca gag tgt act gat tac atc aag gtt aat gga      756
Gly Leu Asp His Ser Ala Glu Cys Thr Asp Tyr Ile Lys Val Asn Gly
            180                 185                 190 aaa aat atg gga tgc agg ttt ccc tat ttg gag tca tca gac tat aaa      804
Lys Asn Met Gly Cys Arg Phe Pro Tyr Leu Glu Ser Ser Asp Tyr Lys
        195                 200                 205 gat ttc tac atc tgt gtt aat ggg tca tca gaa tcc cag cct atc aga      852
Asp Phe Tyr Ile Cys Val Asn Gly Ser Ser Glu Ser Gln Pro Ile Arg
        210                 215                 220 ccc agc tat ttt att ttt cag ctt caa aat ata gtt aaa cct atg cca      900
Pro Ser Tyr Phe Ile Phe Gln Leu Gln Asn Ile Val Lys Pro Met Pro
    225                 230                 235 cca gac tac ctt agt ctt act gtg aag aat tca gag gaa att aac ctg      948
Pro Asp Tyr Leu Ser Leu Thr Val Lys Asn Ser Glu Glu Ile Asn Leu
240                 245                 250                 255 aaa tgg aac atg cct aaa gga ccc att cca gcc aaa tgt ttc att tat      996
Lys Trp Asn Met Pro Lys Gly Pro Ile Pro Ala Lys Cys Phe Ile Tyr
                260                 265                 270 gaa att gaa ttc aca gag gat ggt act act tgg gtg act acc aca gtt     1044
Glu Ile Glu Phe Thr Glu Asp Gly Thr Thr Trp Val Thr Thr Thr Val
            275                 280                 285 gag aat gag ata caa atc aca aga aca tca aat gaa agc caa aaa tta     1092
Glu Asn Glu Ile Gln Ile Thr Arg Thr Ser Asn Glu Ser Gln Lys Leu
        290                 295                 300 tgc ttt ttg gta aga agt aaa gtg aat att tat tgc tca gat gat gga     1140
Cys Phe Leu Val Arg Ser Lys Val Asn Ile Tyr Cys Ser Asp Asp Gly
305                 310                 315 atc tgg agt gag tgg agt gat gaa caa tgc tgg aaa ggt gac ata tgg     1188
Ile Trp Ser Glu Trp Ser Asp Glu Gln Cys Trp Lys Gly Asp Ile Trp
320                 325                 330                 335 aag gaa acc tta gta ttt ttc ttg ata cca ttt gct ttt gtc tca ata     1236
Lys Glu Thr Leu Val Phe Phe Leu Ile Pro Phe Ala Phe Val Ser Ile
                340                 345                 350 ttt gtt ttg gta ata act tgc ctg ctt ttg tat aag caa agg gct tta     1284
Phe Val Leu Val Ile Thr Cys Leu Leu Leu Tyr Lys Gln Arg Ala Leu
            355                 360                 365 ctg aaa acg atc ttt cat aca aaa aaa gaa gtc ttt tct cat caa gac     1332
Leu Lys Thr Ile Phe His Thr Lys Lys Glu Val Phe Ser His Gln Asp
        370                 375                 380 aca ttc tgt tgactcagta actttcagtc ttatggccag atgttaaata             1381
Thr Phe Cys
    385 tgagtcttat taaactgaag cttttcctca aatattgaat aaatcttatt ttaaaangaa   1441 aaaaaaaaaa aaa                                                      1454

<210> SEQ ID NO 61
<211> LENGTH: 386
<212> TYPE: PRT
<213> ORGANISM: Canis familiaris

<400> SEQUENCE: 61

Met Ala Phe Ile His Leu Asp Val Gly Phe Leu Tyr Thr Leu Leu Val
1               5                   10                  15

Cys Thr Ala Phe Gly Ser Met Leu Ser Asn Ala Glu Ile Lys Val Asn
            20                  25                  30

Pro Pro Gln Asp Phe Glu Ile Val Asp Pro Gly Tyr Leu Gly Tyr Leu
        35                  40                  45

Ser Leu Gln Trp Gln Pro Pro Leu Phe Pro Asp Asn Phe Lys Glu Cys
```

| | | | | | | | | | | |
|---|---|---|---|---|---|---|---|---|---|---|
| | | 50 | | | 55 | | | 60 | | |

Thr Ile Glu Tyr Glu Leu Lys Tyr Arg Asn Ile Asp Ser Glu Asn Trp
65                  70                  75                  80

Lys Thr Ile Ile Thr Lys Asn Leu His Tyr Lys Asp Gly Phe Asp Leu
                85                  90                  95

Asn Lys Gly Ile Glu Ala Lys Ile Asn Thr Leu Leu Pro Ala Gln Cys
            100                 105                 110

Thr Asn Gly Ser Glu Val Arg Ser Ser Trp Ala Glu Thr Thr Tyr Trp
        115                 120                 125

Thr Ser Pro Gln Gly Asn Arg Glu Thr Lys Ile Gln Asp Met Asp Cys
    130                 135                 140

Val Tyr Tyr Asn Trp Gln Tyr Leu Val Cys Ser Trp Lys Pro Gly Met
145                 150                 155                 160

Gly Val His Phe Asp Thr Asn Tyr Gln Leu Phe Tyr Trp Tyr Glu Gly
                165                 170                 175

Leu Asp His Ser Ala Glu Cys Thr Asp Tyr Ile Lys Val Asn Gly Lys
            180                 185                 190

Asn Met Gly Cys Arg Phe Pro Tyr Leu Glu Ser Ser Asp Tyr Lys Asp
        195                 200                 205

Phe Tyr Ile Cys Val Asn Gly Ser Ser Glu Ser Gln Pro Ile Arg Pro
    210                 215                 220

Ser Tyr Phe Ile Phe Gln Leu Gln Asn Ile Val Lys Pro Met Pro Pro
225                 230                 235                 240

Asp Tyr Leu Ser Leu Thr Val Lys Asn Ser Glu Glu Ile Asn Leu Lys
                245                 250                 255

Trp Asn Met Pro Lys Gly Pro Ile Pro Ala Lys Cys Phe Ile Tyr Glu
            260                 265                 270

Ile Glu Phe Thr Glu Asp Gly Thr Thr Trp Val Thr Thr Val Glu
        275                 280                 285

Asn Glu Ile Gln Ile Thr Arg Thr Ser Asn Glu Ser Gln Lys Leu Cys
    290                 295                 300

Phe Leu Val Arg Ser Lys Val Asn Ile Tyr Cys Ser Asp Asp Gly Ile
305                 310                 315                 320

Trp Ser Glu Trp Ser Asp Glu Gln Cys Trp Lys Gly Asp Ile Trp Lys
                325                 330                 335

Glu Thr Leu Val Phe Phe Leu Ile Pro Phe Ala Phe Val Ser Ile Phe
            340                 345                 350

Val Leu Val Ile Thr Cys Leu Leu Leu Tyr Lys Gln Arg Ala Leu Leu
        355                 360                 365

Lys Thr Ile Phe His Thr Lys Lys Glu Val Phe Ser His Gln Asp Thr
    370                 375                 380

Phe Cys
385

<210> SEQ ID NO 62
<211> LENGTH: 1454
<212> TYPE: DNA
<213> ORGANISM: Canis familiaris
<220> FEATURE:
<221> NAME/KEY: misc_feature
<222> LOCATION: (17)..(17)
<223> OTHER INFORMATION: At nucleotide 17, n = unknown

<400> SEQUENCE: 62
tttttttttt ttttcnttt taaaataaga tttattcaat atttgaggaa aagcttcagt    60

-continued

```
ttaataagac tcatatttaa catctggcca taagactgaa agttactgag tcaacagaat    120
gtgtcttgat gagaaaagac ttctttttt gtatgaaaga tcgttttcag taaagccctt    180
tgcttataca aaagcaggca agttattacc aaaacaaata ttgagacaaa agcaaatggt    240
atcaagaaaa atactaaggt ttccttccat atgtcacctt tccagcattg ttcatcactc    300
cactcactcc agattccatc atctgagcaa taaatattca ctttacttct taccaaaaag    360
cataattttt ggctttcatt tgatgttctt gtgatttgta tctcattctc aactgtggta    420
gtcacccaag tagtaccatc ctctgtgaat tcaatttcat aaatgaaaca tttggctgga    480
atgggtcctt taggcatgtt ccatttcagg ttaatttcct ctgaattctt cacagtaaga    540
ctaaggtagt ctggtggcat aggtttaact atattttgaa gctgaaaaat aaaatagctg    600
ggtctgatag gctgggattc tgatgaccca ttaacacaga tgtagaaatc tttatagtct    660
gatgactcca aatagggaaa cctgcatccc atatttttc cattaacctt gatgtaatca    720
gtacactctg ctgaatggtc caagccctca taccagtaaa acaactggta attggtatca    780
aaatggacac ccatgccagg tttccaagag cagactaaat attgccagtt gtaatataca    840
cagtccatat cttgaatttt agtttcccga tttccttgtg gtgatgtcca ataagtagtt    900
tctgcccatg aacttctaac ttctgatcca tttgtgcatt gtgctggcag aagtgtgttt    960
atctttgctt caatacccttt gttaagatca aacccatctt tgtaatgtag attcttggta   1020
atgatggtct tccagttttc actatcaatg tttcggtatt ttaattcata ttctattgtg   1080
cattccttaa aattatccgg aaataatgga ggttgccatt gcaaagagag ataacctaaa   1140
tatccagggt ccactatctc aaaatcctga ggaggattaa cttttatctc agcatttgaa   1200
agcatagagc caaatgctgt gcaaacaagc agggtataga ggaatccgac atccaaatga   1260
atgaaagcca ttcctccaag attcaatact ttgaagtttc cactcaataa tatggtttct   1320
caagaaatga attatcatag gcaattatca caggtcctct tttttttctc ttctccagtt   1380
tggagacatt aattagaatc tctaagactt cccttcctgt ctgataatca agcacacaaa   1440
ctcagcctcg tgcc                                                      1454
```

<210> SEQ ID NO 63
<211> LENGTH: 1158
<212> TYPE: DNA
<213> ORGANISM: Canis familiaris

<400> SEQUENCE: 63

```
atggctttca ttcatttgga tgtcggattc ctctataccc tgcttgtttg cacagcattt     60
ggctctatgc tttcaaatgc tgagataaaa gttaatcctc ctcaggattt tgagatagtg    120
gaccctggat atttaggtta tctctctttg caatggcaac ctccattatt tccggataat    180
tttaaggaat gcacaataga atatgaatta aaataccgaa acattgatag tgaaaactgg    240
aagaccatca ttaccaagaa tctacattac aaagatgggt ttgatcttaa caaaggtatt    300
gaagcaaaga taaacacact tctgccagca caatgcacaa atggatcaga agttagaagt    360
tcatgggcag aaaactactta ttggacatca ccacaaggaa atcgggaaac taaaattcaa    420
gatatggact gtgtatatta caactggcaa tatttagtct gctcttggaa acctggcatg    480
ggtgtccatt tgataccaa ttaccagttg ttttactggt atgagggctt ggaccattca    540
gcagagtgta ctgattacat caaggttaat ggaaaaaata tgggatgcag gtttccctat    600
ttggagtcat cagactataa agatttctac atctgtgtta atgggtcatc agaatcccag    660
cctatcagac ccagctattt tatttttcag cttcaaaata tagttaaacc tatgccacca    720
```

```
gactaccctta gtcttactgt gaagaattca gaggaaatta acctgaaatg gaacatgcct      780
aaaggaccca ttccagccaa atgtttcatt tatgaaattg aattcacaga ggatggtact      840
acttgggtga ctaccacagt tgagaatgag atacaaatca caagaacatc aaatgaaagc      900
caaaaattat gcttttttggt aagaagtaaa gtgaatattt attgctcaga tgatggaatc      960
tggagtgagt ggagtgatga acaatgctgg aaaggtgaca tatggaagga aaccttagta     1020
tttttcttga taccatttgc ttttgtctca atatttgttt tggtaataac ttgcctgctt     1080
ttgtataagc aaagggcttt actgaaaacg atctttcata caaaaaaga agtctttttct     1140 catcaagaca cattctgt                                                    1158

<210> SEQ ID NO 64
<211> LENGTH: 1158
<212> TYPE: DNA
<213> ORGANISM: Canis familiaris

<400> SEQUENCE: 64
acagaatgtg tcttgatgag aaaagacttc ttttttttgta tgaaagatcg ttttcagtaa      60 agcccttttgc ttatacaaaa gcaggcaagt tattaccaaa acaaatattg agacaaaagc    120
aaatggtatc aagaaaaata ctaaggtttc cttccatatg tcacctttcc agcattgttc    180
atcactccac tcactccaga ttccatcatc tgagcaataa atattcactt tacttcttac    240
caaaaagcat aattttttggc tttcatttga tgttcttgtg atttgtatct cattctcaac    300
tgtggtagtc acccaagtag taccatcctc tgtgaattca atttcataaa tgaaacattt    360
ggctggaatg ggtcctttag gcatgttcca tttcaggtta atttcctctg aattcttcac    420
agtaagacta aggtagtctg gtggcatagg tttaactata ttttgaagct gaaaaataaa    480
atagctgggt ctgataggct gggattctga tgacccatta acacagatgt agaaatcttt    540
atagtctgat gactccaaat agggaaacct gcatcccata ttttttccat taaccttgat    600
gtaatcagta cactctgctg aatggtccaa gccctcatac cagtaaaaca actggtaatt    660
ggtatcaaaa tggacaccca tgccaggttt ccaagagcag actaaatatt gccagttgta    720
atatacacag tccatatctt gaattttagt ttcccgattt ccttgtggtg atgtccaata    780
agtagtttct gcccatgaac ttctaacttc tgatccattt gtgcattgtg ctggcagaag    840
tgtgtttatc tttgcttcaa tacctttgtt aagatcaaac ccatctttgt aatgtagatt    900
cttggtaatg atggtcttcc agttttcact atcaatgttt cggtatttta attcatattc    960
tattgtgcat tccttaaaat tatccggaaa taatggaggt tgccattgca agagagata    1020 acctaaatat ccagggtcca ctatctcaaa atcctgagga ggattaactt ttatctcagc    1080
atttgaaagc atagagccaa atgctgtgca acaagcagg gtatagagga atccgacatc    1140
caaatgaatg aaagccat                                                  1158

<210> SEQ ID NO 65
<211> LENGTH: 1095
<212> TYPE: DNA
<213> ORGANISM: Canis familiaris
<220> FEATURE:
<221> NAME/KEY: CDS
<222> LOCATION: (1)..(1095)
<223> OTHER INFORMATION:

<400> SEQUENCE: 65 tct atg ctt tca aat gct gag ata aaa gtt aat cct cct cag gat ttt       48
Ser Met Leu Ser Asn Ala Glu Ile Lys Val Asn Pro Pro Gln Asp Phe
```

```
                                                         -continued 1             5                 10                15 gag ata gtg gac cct gga tat tta ggt tat ctc tct ttg caa tgg caa       96
Glu Ile Val Asp Pro Gly Tyr Leu Gly Tyr Leu Ser Leu Gln Trp Gln
            20                  25              30 cct cca tta ttt ccg gat aat ttt aag gaa tgc aca ata gaa tat gaa      144
Pro Pro Leu Phe Pro Asp Asn Phe Lys Glu Cys Thr Ile Glu Tyr Glu
        35                  40                  45 tta aaa tac cga aac att gat agt gaa aac tgg aag acc atc att acc      192
Leu Lys Tyr Arg Asn Ile Asp Ser Glu Asn Trp Lys Thr Ile Ile Thr
    50                  55                  60 aag aat cta cat tac aaa gat ggg ttt gat ctt aac aaa ggt att gaa      240
Lys Asn Leu His Tyr Lys Asp Gly Phe Asp Leu Asn Lys Gly Ile Glu
65                  70                  75                  80 gca aag ata aac aca ctt ctg cca gca caa tgc aca aat gga tca gaa      288
Ala Lys Ile Asn Thr Leu Leu Pro Ala Gln Cys Thr Asn Gly Ser Glu
                85                  90                  95 gtt aga agt tca tgg gca gaa act act tat tgg aca tca cca caa gga      336
Val Arg Ser Ser Trp Ala Glu Thr Thr Tyr Trp Thr Ser Pro Gln Gly
            100                 105                 110 aat cgg gaa act aaa att caa gat atg gac tgt gta tat tac aac tgg      384
Asn Arg Glu Thr Lys Ile Gln Asp Met Asp Cys Val Tyr Tyr Asn Trp
        115                 120                 125 caa tat tta gtc tgc tct tgg aaa cct ggc atg ggt gtc cat ttt gat      432
Gln Tyr Leu Val Cys Ser Trp Lys Pro Gly Met Gly Val His Phe Asp
    130                 135                 140 acc aat tac cag ttg ttt tac tgg tat gag ggc ttg gac cat tca gca      480
Thr Asn Tyr Gln Leu Phe Tyr Trp Tyr Glu Gly Leu Asp His Ser Ala
145                 150                 155                 160 gag tgt act gat tac atc aag gtt aat gga aaa aat atg gga tgc agg      528
Glu Cys Thr Asp Tyr Ile Lys Val Asn Gly Lys Asn Met Gly Cys Arg
                165                 170                 175 ttt ccc tat ttg gag tca tca gac tat aaa gat ttc tac atc tgt gtt      576
Phe Pro Tyr Leu Glu Ser Ser Asp Tyr Lys Asp Phe Tyr Ile Cys Val
            180                 185                 190 aat ggg tca tca gaa tcc cag cct atc aga ccc agc tat ttt att ttt      624
Asn Gly Ser Ser Glu Ser Gln Pro Ile Arg Pro Ser Tyr Phe Ile Phe
        195                 200                 205 cag ctt caa aat ata gtt aaa cct atg cca cca gac tac ctt agt ctt      672
Gln Leu Gln Asn Ile Val Lys Pro Met Pro Pro Asp Tyr Leu Ser Leu
    210                 215                 220 act gtg aag aat tca gag gaa att aac ctg aaa tgg aac atg cct aaa      720
Thr Val Lys Asn Ser Glu Glu Ile Asn Leu Lys Trp Asn Met Pro Lys
225                 230                 235                 240 gga ccc att cca gcc aaa tgt ttc att tat gaa att gaa ttc aca gag      768
Gly Pro Ile Pro Ala Lys Cys Phe Ile Tyr Glu Ile Glu Phe Thr Glu
                245                 250                 255 gat ggt act act tgg gtg act acc aca gtt gag aat gag ata caa atc      816
Asp Gly Thr Thr Trp Val Thr Thr Thr Val Glu Asn Glu Ile Gln Ile
            260                 265                 270 aca aga aca tca aat gaa agc caa aaa tta tgc ttt ttg gta aga agt      864
Thr Arg Thr Ser Asn Glu Ser Gln Lys Leu Cys Phe Leu Val Arg Ser
        275                 280                 285 aaa gtg aat att tat tgc tca gat gat gga atc tgg agt gag tgg agt      912
Lys Val Asn Ile Tyr Cys Ser Asp Asp Gly Ile Trp Ser Glu Trp Ser
    290                 295                 300 gat gaa caa tgc tgg aaa ggt gac ata tgg aag gaa acc tta gta ttt      960
Asp Glu Gln Cys Trp Lys Gly Asp Ile Trp Lys Glu Thr Leu Val Phe
305                 310                 315                 320 ttc ttg ata cca ttt gct ttt gtc tca ata ttt gtt ttg gta ata act     1008
```

```
Phe Leu Ile Pro Phe Ala Phe Val Ser Ile Phe Val Leu Val Ile Thr
                325                 330                 335 tgc ctg ctt ttg tat aag caa agg gct tta ctg aaa acg atc ttt cat    1056
Cys Leu Leu Leu Tyr Lys Gln Arg Ala Leu Leu Lys Thr Ile Phe His
                340                 345                 350 aca aaa aaa gaa gtc ttt tct cat caa gac aca ttc tgt                1095
Thr Lys Lys Glu Val Phe Ser His Gln Asp Thr Phe Cys
                355                 360                 365

<210> SEQ ID NO 66
<211> LENGTH: 365
<212> TYPE: PRT
<213> ORGANISM: Canis familiaris

<400> SEQUENCE: 66

Ser Met Leu Ser Asn Ala Glu Ile Lys Val Asn Pro Gln Asp Phe
1               5                   10                  15

Glu Ile Val Asp Pro Gly Tyr Leu Gly Tyr Leu Ser Leu Gln Trp Gln
                20                  25                  30

Pro Pro Leu Phe Pro Asp Asn Phe Lys Glu Cys Thr Ile Glu Tyr Glu
            35                  40                  45

Leu Lys Tyr Arg Asn Ile Asp Ser Glu Asn Trp Lys Thr Ile Ile Thr
        50                  55                  60

Lys Asn Leu His Tyr Lys Asp Gly Phe Asp Leu Asn Lys Gly Ile Glu
65                  70                  75                  80

Ala Lys Ile Asn Thr Leu Leu Pro Ala Gln Cys Thr Asn Gly Ser Glu
                85                  90                  95

Val Arg Ser Ser Trp Ala Glu Thr Thr Tyr Trp Thr Ser Pro Gln Gly
                100                 105                 110

Asn Arg Glu Thr Lys Ile Gln Asp Met Asp Cys Val Tyr Tyr Asn Trp
            115                 120                 125

Gln Tyr Leu Val Cys Ser Trp Lys Pro Gly Met Gly Val His Phe Asp
        130                 135                 140

Thr Asn Tyr Gln Leu Phe Tyr Trp Tyr Glu Gly Leu Asp His Ser Ala
145                 150                 155                 160

Glu Cys Thr Asp Tyr Ile Lys Val Asn Gly Lys Asn Met Gly Cys Arg
                165                 170                 175

Phe Pro Tyr Leu Glu Ser Ser Asp Tyr Lys Asp Phe Tyr Ile Cys Val
                180                 185                 190

Asn Gly Ser Ser Glu Ser Gln Pro Ile Arg Pro Ser Tyr Phe Ile Phe
            195                 200                 205

Gln Leu Gln Asn Ile Val Lys Pro Met Pro Pro Asp Tyr Leu Ser Leu
        210                 215                 220

Thr Val Lys Asn Ser Glu Glu Ile Asn Leu Lys Trp Asn Met Pro Lys
225                 230                 235                 240

Gly Pro Ile Pro Ala Lys Cys Phe Ile Tyr Glu Ile Glu Phe Thr Glu
                245                 250                 255

Asp Gly Thr Thr Trp Val Thr Thr Val Glu Asn Glu Ile Gln Ile
                260                 265                 270

Thr Arg Thr Ser Asn Glu Ser Gln Lys Leu Cys Phe Leu Val Arg Ser
        275                 280                 285

Lys Val Asn Ile Tyr Cys Ser Asp Asp Gly Ile Trp Ser Glu Trp Ser
        290                 295                 300

Asp Glu Gln Cys Trp Lys Gly Asp Ile Trp Lys Glu Thr Leu Val Phe
305                 310                 315                 320
```

```
Phe Leu Ile Pro Phe Ala Phe Val Ser Ile Phe Val Leu Val Ile Thr
            325                 330                 335

Cys Leu Leu Leu Tyr Lys Gln Arg Ala Leu Leu Lys Thr Ile Phe His
        340                 345                 350

Thr Lys Lys Glu Val Phe Ser His Gln Asp Thr Phe Cys
    355                 360                 365

<210> SEQ ID NO 67
<211> LENGTH: 1095
<212> TYPE: DNA
<213> ORGANISM: Canis familiaris

<400> SEQUENCE: 67
acagaatgtg tcttgatgag aaaagacttc ttttttgta tgaaagatcg ttttcagtaa      60 agcccttgc ttatacaaaa gcaggcaagt tattaccaaa acaaatattg agacaaaagc    120
aaatggtatc aagaaaaata ctaaggtttc cttccatatg tcacctttcc agcattgttc    180
atcactccac tcactccaga ttccatcatc tgagcaataa atattcactt tacttcttac    240
caaaaagcat aatttttggc tttcatttga tgttcttgtg atttgtatct cattctcaac    300
tgtggtagtc acccaagtag taccatcctc tgtgaattca atttcataaa tgaaacattt    360
ggctggaatg ggtcctttag gcatgttcca tttcaggtta atttcctctg aattcttcac    420
agtaagacta aggtagtctg gtggcatagg tttaactata ttttgaagct gaaaaataaa    480
atagctgggt ctgataggct gggattctga tgacccatta acacagatgt agaaatcttt    540
atagtctgat gactccaaat agggaaacct gcatcccata ttttttccat taaccttgat    600
gtaatcagta cactctgctg aatggtccaa gccctcatac cagtaaaaca actggtaatt    660
ggtatcaaaa tggacaccca tgccaggttt ccaagagcag actaaatatt gccagttgta    720
atatacacag tccatatctt gaattttagt ttcccgattt ccttgtggtg atgtccaata    780
agtagtttct gcccatgaac ttctaacttc tgatccattt gtgcattgtg ctggcagaag    840
tgtgtttatc tttgcttcaa tacctttgtt aagatcaaac ccatctttgt aatgtagatt    900
cttggtaatg atggtcttcc agttttcact atcaatgttt cggtatttta attcatattc    960
tattgtgcat tccttaaaat tatccggaaa taatggaggt tgccattgca aagagagata   1020 acctaaaatat ccagggtcca ctatctcaaa atcctgagga ggattaactt ttatctcagc   1080
atttgaaagc ataga                                                    1095

<210> SEQ ID NO 68
<211> LENGTH: 954
<212> TYPE: DNA
<213> ORGANISM: Canis familiaris
<220> FEATURE:
<221> NAME/KEY: CDS
<222> LOCATION: (1)..(954)
<223> OTHER INFORMATION:

<400> SEQUENCE: 68 atg tct atg ctt tca aat gct gag ata aaa gtt aat cct cct cag gat     48
Met Ser Met Leu Ser Asn Ala Glu Ile Lys Val Asn Pro Pro Gln Asp
 1               5                  10                  15 ttt gag ata gtg gac cct gga tat tta ggt tat ctc tct ttg caa tgg     96
Phe Glu Ile Val Asp Pro Gly Tyr Leu Gly Tyr Leu Ser Leu Gln Trp
                20                  25                  30 caa cct cca tta ttt ccg gat aat ttt aag gaa tgc aca ata gaa tat    144
Gln Pro Pro Leu Phe Pro Asp Asn Phe Lys Glu Cys Thr Ile Glu Tyr
            35                  40                  45
```

```
gaa tta aaa tac cga aac att gat agt gaa aac tgg aag acc atc att    192
Glu Leu Lys Tyr Arg Asn Ile Asp Ser Glu Asn Trp Lys Thr Ile Ile
     50                  55                  60 acc aag aat cta cat tac aaa gat ggg ttt gat ctt aac aaa ggt att    240
Thr Lys Asn Leu His Tyr Lys Asp Gly Phe Asp Leu Asn Lys Gly Ile
 65                  70                  75                  80 gaa gca aag ata aac aca ctt ctg cca gca caa tgc aca aat gga tca    288
Glu Ala Lys Ile Asn Thr Leu Leu Pro Ala Gln Cys Thr Asn Gly Ser
                 85                  90                  95 gaa gtt aga agt tca tgg gca gaa act act tat tgg aca tca cca caa    336
Glu Val Arg Ser Ser Trp Ala Glu Thr Thr Tyr Trp Thr Ser Pro Gln
            100                 105                 110 gga aat cgg gaa act aaa att caa gat atg gac tgt gta tat tac aac    384
Gly Asn Arg Glu Thr Lys Ile Gln Asp Met Asp Cys Val Tyr Tyr Asn
        115                 120                 125 tgg caa tat tta gtc tgc tct tgg aaa cct ggc atg ggt gtc cat ttt    432
Trp Gln Tyr Leu Val Cys Ser Trp Lys Pro Gly Met Gly Val His Phe
    130                 135                 140 gat acc aat tac cag ttg ttt tac tgg tat gag ggc ttg gac cat tca    480
Asp Thr Asn Tyr Gln Leu Phe Tyr Trp Tyr Glu Gly Leu Asp His Ser
145                 150                 155                 160 gca gag tgt act gat tac atc aag gtt aat gga aaa aat atg gga tgc    528
Ala Glu Cys Thr Asp Tyr Ile Lys Val Asn Gly Lys Asn Met Gly Cys
                165                 170                 175 agg ttt ccc tat ttg gag tca tca gac tat aaa gat ttc tac atc tgt    576
Arg Phe Pro Tyr Leu Glu Ser Ser Asp Tyr Lys Asp Phe Tyr Ile Cys
            180                 185                 190 gtt aat ggg tca tca gaa tcc cag cct atc aga ccc agc tat ttt att    624
Val Asn Gly Ser Ser Glu Ser Gln Pro Ile Arg Pro Ser Tyr Phe Ile
        195                 200                 205 ttt cag ctt caa aat ata gtt aaa cct atg cca cca gac tac ctt agt    672
Phe Gln Leu Gln Asn Ile Val Lys Pro Met Pro Pro Asp Tyr Leu Ser
    210                 215                 220 ctt act gtg aag aat tca gag gaa att aac ctg aaa tgg aac atg cct    720
Leu Thr Val Lys Asn Ser Glu Glu Ile Asn Leu Lys Trp Asn Met Pro
225                 230                 235                 240 aaa gga ccc att cca gcc aaa tgt ttc att tat gaa att gaa ttc aca    768
Lys Gly Pro Ile Pro Ala Lys Cys Phe Ile Tyr Glu Ile Glu Phe Thr
                245                 250                 255 gag gat ggt act act tgg gtg act acc aca gtt gag aat gag ata caa    816
Glu Asp Gly Thr Thr Trp Val Thr Thr Thr Val Glu Asn Glu Ile Gln
            260                 265                 270 atc aca aga aca tca aat gaa agc caa aaa tta tgc ttt ttg gta aga    864
Ile Thr Arg Thr Ser Asn Glu Ser Gln Lys Leu Cys Phe Leu Val Arg
        275                 280                 285 agt aaa gtg aat att tat tgc tca gat gat gga atc tgg agt gag tgg    912
Ser Lys Val Asn Ile Tyr Cys Ser Asp Asp Gly Ile Trp Ser Glu Trp
    290                 295                 300 agt gat gaa caa tgc tgg aaa ggt gat atc tgg aag gaa acc            954
Ser Asp Glu Gln Cys Trp Lys Gly Asp Ile Trp Lys Glu Thr
305                 310                 315

<210> SEQ ID NO 69
<211> LENGTH: 318
<212> TYPE: PRT
<213> ORGANISM: Canis familiaris

<400> SEQUENCE: 69

Met Ser Met Leu Ser Asn Ala Glu Ile Lys Val Asn Pro Pro Gln Asp
1               5                   10                  15
```

Phe Glu Ile Val Asp Pro Gly Tyr Leu Gly Tyr Leu Ser Leu Gln Trp
              20                  25                  30

Gln Pro Pro Leu Phe Pro Asp Asn Phe Lys Glu Cys Thr Ile Glu Tyr
         35                  40                  45

Glu Leu Lys Tyr Arg Asn Ile Asp Ser Glu Asn Trp Lys Thr Ile Ile
     50                  55                  60

Thr Lys Asn Leu His Tyr Lys Asp Gly Phe Asp Leu Asn Lys Gly Ile
65                  70                  75                  80

Glu Ala Lys Ile Asn Thr Leu Leu Pro Ala Gln Cys Thr Asn Gly Ser
                 85                  90                  95

Glu Val Arg Ser Ser Trp Ala Glu Thr Thr Tyr Trp Thr Ser Pro Gln
            100                 105                 110

Gly Asn Arg Glu Thr Lys Ile Gln Asp Met Asp Cys Val Tyr Tyr Asn
        115                 120                 125

Trp Gln Tyr Leu Val Cys Ser Trp Lys Pro Gly Met Gly Val His Phe
    130                 135                 140

Asp Thr Asn Tyr Gln Leu Phe Tyr Trp Tyr Glu Gly Leu Asp His Ser
145                 150                 155                 160

Ala Glu Cys Thr Asp Tyr Ile Lys Val Asn Gly Lys Asn Met Gly Cys
                165                 170                 175

Arg Phe Pro Tyr Leu Glu Ser Ser Asp Tyr Lys Asp Phe Tyr Ile Cys
            180                 185                 190

Val Asn Gly Ser Ser Glu Ser Gln Pro Ile Arg Pro Ser Tyr Phe Ile
        195                 200                 205

Phe Gln Leu Gln Asn Ile Val Lys Pro Met Pro Pro Asp Tyr Leu Ser
    210                 215                 220

Leu Thr Val Lys Asn Ser Glu Glu Ile Asn Leu Lys Trp Asn Met Pro
225                 230                 235                 240

Lys Gly Pro Ile Pro Ala Lys Cys Phe Ile Tyr Glu Ile Glu Phe Thr
                245                 250                 255

Glu Asp Gly Thr Thr Trp Val Thr Thr Val Glu Asn Glu Ile Gln
            260                 265                 270

Ile Thr Arg Thr Ser Asn Glu Ser Gln Lys Leu Cys Phe Leu Val Arg
        275                 280                 285

Ser Lys Val Asn Ile Tyr Cys Ser Asp Asp Gly Ile Trp Ser Glu Trp
    290                 295                 300

Ser Asp Glu Gln Cys Trp Lys Gly Asp Ile Trp Lys Glu Thr
305                 310                 315

<210> SEQ ID NO 70
<211> LENGTH: 954
<212> TYPE: DNA
<213> ORGANISM: Canis familiaris

<400> SEQUENCE: 70
ggtttccttc agatatcac ctttccagca ttgttcatca ctccactcac tccagattcc     60
atcatctgag caataaatat tcactttact tcttaccaaa aagcataatt tttggctttc    120
atttgatgtt cttgtgattt gtatctcatt ctcaactgtg gtagtcaccc aagtagtacc    180
atcctctgtg aattcaattt cataaatgaa acatttggct ggaatgggtc ctttaggcat    240
gttccatttc aggttaattt cctctgaatt cttcacagta agactaaggt agtctggtgg    300
cataggttta actatatttt gaagctgaaa aataaaatag ctgggtctga taggctggga    360
ttctgatgac ccattaacac agatgtagaa atctttatag tctgatgact ccaaataggg    420

-continued

```
aaacctgcat cccatatttt ttccattaac cttgatgtaa tcagtacact ctgctgaatg      480
gtccaagccc tcataccagt aaaacaactg gtaattggta tcaaaatgga cacccatgcc      540
aggtttccaa gagcagacta atattgcca gttgtaatat acacagtcca tatcttgaat      600
tttagtttcc cgatttcctt gtggtgatgt ccaataagta gtttctgccc atgaacttct      660
aacttctgat ccatttgtgc attgtgctgg cagaagtgtg tttatctttg cttcaatacc      720
tttgttaaga tcaaacccat cttttgtaatg tagattcttg gtaatgatgg tcttccagtt     780
ttcactatca atgtttcggt attttaattc atattctatt gtgcattcct taaaattatc      840
cggaaataat ggaggttgcc attgcaaaga gagataacct aaatatccag ggtccactat      900
ctcaaaatcc tgaggaggat taacttttat ctcagcattt gaaagcatag acat            954
```

<210> SEQ ID NO 71
<211> LENGTH: 1686
<212> TYPE: DNA
<213> ORGANISM: Canis familiaris
<220> FEATURE:
<221> NAME/KEY: CDS
<222> LOCATION: (1)..(1683)
<223> OTHER INFORMATION:

<400> SEQUENCE: 71

| | | | | | | | | | | | | | | | | |
|---|---|---|---|---|---|---|---|---|---|---|---|---|---|---|---|---|
| atg | tct | atg | ctt | tca | aat | gct | gag | ata | aaa | gtt | aat | cct | cct | cag | gat | 48 |
| Met | Ser | Met | Leu | Ser | Asn | Ala | Glu | Ile | Lys | Val | Asn | Pro | Pro | Gln | Asp | |
| 1 | | | | 5 | | | | | 10 | | | | | 15 | | |

| ttt | gag | ata | gtg | gac | cct | gga | tat | tta | ggt | tat | ctc | tct | ttg | caa | tgg | 96 |
|---|---|---|---|---|---|---|---|---|---|---|---|---|---|---|---|---|
| Phe | Glu | Ile | Val | Asp | Pro | Gly | Tyr | Leu | Gly | Tyr | Leu | Ser | Leu | Gln | Trp | |
| | | | 20 | | | | | 25 | | | | | 30 | | | |

| caa | cct | cca | tta | ttt | ccg | gat | aat | ttt | aag | gaa | tgc | aca | ata | gaa | tat | 144 |
|---|---|---|---|---|---|---|---|---|---|---|---|---|---|---|---|---|
| Gln | Pro | Pro | Leu | Phe | Pro | Asp | Asn | Phe | Lys | Glu | Cys | Thr | Ile | Glu | Tyr | |
| | | 35 | | | | | 40 | | | | | 45 | | | | |

| gaa | tta | aaa | tac | cga | aac | att | gat | agt | gaa | aac | tgg | aag | acc | atc | att | 192 |
|---|---|---|---|---|---|---|---|---|---|---|---|---|---|---|---|---|
| Glu | Leu | Lys | Tyr | Arg | Asn | Ile | Asp | Ser | Glu | Asn | Trp | Lys | Thr | Ile | Ile | |
| 50 | | | | | 55 | | | | | 60 | | | | | | |

| acc | aag | aat | cta | cat | tac | aaa | gat | ggg | ttt | gat | ctt | aac | aaa | ggt | att | 240 |
|---|---|---|---|---|---|---|---|---|---|---|---|---|---|---|---|---|
| Thr | Lys | Asn | Leu | His | Tyr | Lys | Asp | Gly | Phe | Asp | Leu | Asn | Lys | Gly | Ile | |
| 65 | | | | 70 | | | | | 75 | | | | | 80 | | |

| gaa | gca | aag | ata | aac | aca | ctt | ctg | cca | gca | caa | tgc | aca | aat | gga | tca | 288 |
|---|---|---|---|---|---|---|---|---|---|---|---|---|---|---|---|---|
| Glu | Ala | Lys | Ile | Asn | Thr | Leu | Leu | Pro | Ala | Gln | Cys | Thr | Asn | Gly | Ser | |
| | | | | 85 | | | | | 90 | | | | | 95 | | |

| gaa | gtt | aga | agt | tca | tgg | gca | gaa | act | act | tat | tgg | aca | tca | cca | caa | 336 |
|---|---|---|---|---|---|---|---|---|---|---|---|---|---|---|---|---|
| Glu | Val | Arg | Ser | Ser | Trp | Ala | Glu | Thr | Thr | Tyr | Trp | Thr | Ser | Pro | Gln | |
| | | | 100 | | | | | 105 | | | | | 110 | | | |

| gga | aat | cgg | gaa | act | aaa | att | caa | gat | atg | gac | tgt | gta | tat | tac | aac | 384 |
|---|---|---|---|---|---|---|---|---|---|---|---|---|---|---|---|---|
| Gly | Asn | Arg | Glu | Thr | Lys | Ile | Gln | Asp | Met | Asp | Cys | Val | Tyr | Tyr | Asn | |
| | | 115 | | | | | 120 | | | | | 125 | | | | |

| tgg | caa | tat | tta | gtc | tgc | tct | tgg | aaa | cct | ggc | atg | ggt | gtc | cat | ttt | 432 |
|---|---|---|---|---|---|---|---|---|---|---|---|---|---|---|---|---|
| Trp | Gln | Tyr | Leu | Val | Cys | Ser | Trp | Lys | Pro | Gly | Met | Gly | Val | His | Phe | |
| | 130 | | | | | 135 | | | | | 140 | | | | | |

| gat | acc | aat | tac | cag | ttg | ttt | tac | tgg | tat | gag | ggc | ttg | gac | cat | tca | 480 |
|---|---|---|---|---|---|---|---|---|---|---|---|---|---|---|---|---|
| Asp | Thr | Asn | Tyr | Gln | Leu | Phe | Tyr | Trp | Tyr | Glu | Gly | Leu | Asp | His | Ser | |
| 145 | | | | | 150 | | | | | 155 | | | | | 160 | |

| gca | gag | tgt | act | gat | tac | atc | aag | gtt | aat | gga | aaa | aat | atg | gga | tgc | 528 |
|---|---|---|---|---|---|---|---|---|---|---|---|---|---|---|---|---|
| Ala | Glu | Cys | Thr | Asp | Tyr | Ile | Lys | Val | Asn | Gly | Lys | Asn | Met | Gly | Cys | |
| | | | | 165 | | | | | 170 | | | | | 175 | | |

| agg | ttt | ccc | tat | ttg | gag | tca | tca | gac | tat | aaa | gat | ttc | tac | atc | tgt | 576 |
|---|---|---|---|---|---|---|---|---|---|---|---|---|---|---|---|---|
| Arg | Phe | Pro | Tyr | Leu | Glu | Ser | Ser | Asp | Tyr | Lys | Asp | Phe | Tyr | Ile | Cys | |
| | | | 180 | | | | | 185 | | | | | 190 | | | |

| gtt | aat | ggg | tca | tca | gaa | tcc | cag | cct | atc | aga | ccc | agc | tat | ttt | att | 624 |
|---|---|---|---|---|---|---|---|---|---|---|---|---|---|---|---|---|

-continued

```
                Val Asn Gly Ser Ser Glu Ser Gln Pro Ile Arg Pro Ser Tyr Phe Ile
                        195                 200                 205 ttt cag ctt caa aat ata gtt aaa cct atg cca cca gac tac ctt agt          672
Phe Gln Leu Gln Asn Ile Val Lys Pro Met Pro Pro Asp Tyr Leu Ser
    210                 215                 220 ctt act gtg aag aat tca gag gaa att aac ctg aaa tgg aac atg cct          720
Leu Thr Val Lys Asn Ser Glu Glu Ile Asn Leu Lys Trp Asn Met Pro
225                 230                 235                 240 aaa gga ccc att cca gcc aaa tgt ttc att tat gaa att gaa ttc aca          768
Lys Gly Pro Ile Pro Ala Lys Cys Phe Ile Tyr Glu Ile Glu Phe Thr
                245                 250                 255 gag gat ggt act act tgg gtg act acc aca gtt gag aat gag ata caa          816
Glu Asp Gly Thr Thr Trp Val Thr Thr Thr Val Glu Asn Glu Ile Gln
            260                 265                 270 atc aca aga aca tca aat gaa agc caa aaa tta tgc ttt ttg gta aga          864
Ile Thr Arg Thr Ser Asn Glu Ser Gln Lys Leu Cys Phe Leu Val Arg
        275                 280                 285 agt aaa gtg aat att tat tgc tca gat gat gga atc tgg agt gag tgg          912
Ser Lys Val Asn Ile Tyr Cys Ser Asp Asp Gly Ile Trp Ser Glu Trp
    290                 295                 300 agt gat gaa caa tgc tgg aaa ggt gat atc tgg aag gaa acc gga tcc          960
Ser Asp Glu Gln Cys Trp Lys Gly Asp Ile Trp Lys Glu Thr Gly Ser
305                 310                 315                 320 aac act aaa gta gac aag cca gtg ttc aat gaa tgc aga tgc act gat         1008
Asn Thr Lys Val Asp Lys Pro Val Phe Asn Glu Cys Arg Cys Thr Asp
                325                 330                 335 aca ccc cca tgc cca gtc cct gaa cct ctg gga ggg cct tcg gtc ctc         1056
Thr Pro Pro Cys Pro Val Pro Glu Pro Leu Gly Gly Pro Ser Val Leu
            340                 345                 350 atc ttt ccc ccg aaa ccc aag gac atc ctc agg att acc cga aca ccc         1104
Ile Phe Pro Pro Lys Pro Lys Asp Ile Leu Arg Ile Thr Arg Thr Pro
        355                 360                 365 gag gtc acc tgt gtg gtg tta gat ctg ggc cgt gag gac cct gag gtg         1152
Glu Val Thr Cys Val Val Leu Asp Leu Gly Arg Glu Asp Pro Glu Val
    370                 375                 380 cag atc agc tgg ttc gtg gat ggt aag gag gtg cac aca gcc aag acc         1200
Gln Ile Ser Trp Phe Val Asp Gly Lys Glu Val His Thr Ala Lys Thr
385                 390                 395                 400 cag tct cgt gag cag cag ttc aac ggc acc tac cgt gtg gtc agc gtc         1248
Gln Ser Arg Glu Gln Gln Phe Asn Gly Thr Tyr Arg Val Val Ser Val
                405                 410                 415 ctc ccc att gag cac cag gac tgg ctc aca ggg aag gag ttc aag tgc         1296
Leu Pro Ile Glu His Gln Asp Trp Leu Thr Gly Lys Glu Phe Lys Cys
            420                 425                 430 aga gtc aac cac ata gac ctc ccg tct ccc atc gag agg acc atc tct         1344
Arg Val Asn His Ile Asp Leu Pro Ser Pro Ile Glu Arg Thr Ile Ser
        435                 440                 445 aag gcc aga ggg agg gcc cat aag ccc agt gtg tat gtc ctg ccg cca         1392
Lys Ala Arg Gly Arg Ala His Lys Pro Ser Val Tyr Val Leu Pro Pro
    450                 455                 460 tcc cca aag gag ttg tca tcc agt gac aca gtc agc atc acc tgc ctg         1440
Ser Pro Lys Glu Leu Ser Ser Ser Asp Thr Val Ser Ile Thr Cys Leu
465                 470                 475                 480 ata aaa gac ttc tac cca cct gac att gat gtg gag tgg cag agc aat         1488
Ile Lys Asp Phe Tyr Pro Pro Asp Ile Asp Val Glu Trp Gln Ser Asn
                485                 490                 495 gga cag cag gag ccc gag agg aag cac cgc atg acc ccg ccc cag ctg         1536
Gly Gln Gln Glu Pro Glu Arg Lys His Arg Met Thr Pro Pro Gln Leu
            500                 505                 510
```

-continued

```
gac gag gac ggg tcc tac ttc ctg tac agc aag ctc tct gtg gac aag      1584
Asp Glu Asp Gly Ser Tyr Phe Leu Tyr Ser Lys Leu Ser Val Asp Lys
        515                 520                 525 agc cgc tgg cag cag gga gac ccc ttc aca tgt gcg gtg atg cat gaa      1632
Ser Arg Trp Gln Gln Gly Asp Pro Phe Thr Cys Ala Val Met His Glu
    530                 535                 540 act cta cag aac cac tac aca gat cta tcc ctc tcc cat tct ccg ggt      1680
Thr Leu Gln Asn His Tyr Thr Asp Leu Ser Leu Ser His Ser Pro Gly
545                 550                 555                 560 aaa tga                                                              1686
Lys

<210> SEQ ID NO 72
<211> LENGTH: 561
<212> TYPE: PRT
<213> ORGANISM: Canis familiaris

<400> SEQUENCE: 72

Met Ser Met Leu Ser Asn Ala Glu Ile Lys Val Asn Pro Pro Gln Asp
1               5                   10                  15

Phe Glu Ile Val Asp Pro Gly Tyr Leu Gly Tyr Leu Ser Leu Gln Trp
            20                  25                  30

Gln Pro Pro Leu Phe Pro Asp Asn Phe Lys Glu Cys Thr Ile Glu Tyr
        35                  40                  45

Glu Leu Lys Tyr Arg Asn Ile Asp Ser Glu Asn Trp Lys Thr Ile Ile
    50                  55                  60

Thr Lys Asn Leu His Tyr Lys Asp Gly Phe Asp Leu Asn Lys Gly Ile
65                  70                  75                  80

Glu Ala Lys Ile Asn Thr Leu Leu Pro Ala Gln Cys Thr Asn Gly Ser
                85                  90                  95

Glu Val Arg Ser Ser Trp Ala Glu Thr Thr Tyr Trp Thr Ser Pro Gln
            100                 105                 110

Gly Asn Arg Glu Thr Lys Ile Gln Asp Met Asp Cys Val Tyr Tyr Asn
        115                 120                 125

Trp Gln Tyr Leu Val Cys Ser Trp Lys Pro Gly Met Gly Val His Phe
    130                 135                 140

Asp Thr Asn Tyr Gln Leu Phe Tyr Trp Tyr Glu Gly Leu Asp His Ser
145                 150                 155                 160

Ala Glu Cys Thr Asp Tyr Ile Lys Val Asn Gly Lys Asn Met Gly Cys
                165                 170                 175

Arg Phe Pro Tyr Leu Glu Ser Ser Asp Tyr Lys Asp Phe Tyr Ile Cys
            180                 185                 190

Val Asn Gly Ser Ser Glu Ser Gln Pro Ile Arg Pro Ser Tyr Phe Ile
        195                 200                 205

Phe Gln Leu Gln Asn Ile Val Lys Pro Met Pro Pro Asp Tyr Leu Ser
    210                 215                 220

Leu Thr Val Lys Asn Ser Glu Glu Ile Asn Leu Lys Trp Asn Met Pro
225                 230                 235                 240

Lys Gly Pro Ile Pro Ala Lys Cys Phe Ile Tyr Glu Ile Glu Phe Thr
                245                 250                 255

Glu Asp Gly Thr Thr Trp Val Thr Thr Thr Val Glu Asn Glu Ile Gln
            260                 265                 270

Ile Thr Arg Thr Ser Asn Glu Ser Gln Lys Leu Cys Phe Leu Val Arg
        275                 280                 285

Ser Lys Val Asn Ile Tyr Cys Ser Asp Asp Gly Ile Trp Ser Glu Trp
    290                 295                 300
```

```
Ser Asp Glu Gln Cys Trp Lys Gly Asp Ile Trp Lys Glu Thr Gly Ser
305                 310                 315                 320

Asn Thr Lys Val Asp Lys Pro Val Phe Asn Glu Cys Arg Cys Thr Asp
                325                 330                 335

Thr Pro Pro Cys Pro Val Pro Glu Pro Leu Gly Gly Pro Ser Val Leu
            340                 345                 350

Ile Phe Pro Pro Lys Pro Lys Asp Ile Leu Arg Ile Thr Arg Thr Pro
        355                 360                 365

Glu Val Thr Cys Val Val Leu Asp Leu Gly Arg Glu Asp Pro Glu Val
    370                 375                 380

Gln Ile Ser Trp Phe Val Asp Gly Lys Glu Val His Thr Ala Lys Thr
385                 390                 395                 400

Gln Ser Arg Glu Gln Gln Phe Asn Gly Thr Tyr Arg Val Val Ser Val
                405                 410                 415

Leu Pro Ile Glu His Gln Asp Trp Leu Thr Gly Lys Glu Phe Lys Cys
            420                 425                 430

Arg Val Asn His Ile Asp Leu Pro Ser Pro Ile Glu Arg Thr Ile Ser
        435                 440                 445

Lys Ala Arg Gly Arg Ala His Lys Pro Ser Val Tyr Val Leu Pro Pro
    450                 455                 460

Ser Pro Lys Glu Leu Ser Ser Ser Asp Thr Val Ser Ile Thr Cys Leu
465                 470                 475                 480

Ile Lys Asp Phe Tyr Pro Pro Asp Ile Asp Val Glu Trp Gln Ser Asn
                485                 490                 495

Gly Gln Gln Glu Pro Glu Arg Lys His Arg Met Thr Pro Pro Gln Leu
            500                 505                 510

Asp Glu Asp Gly Ser Tyr Phe Leu Tyr Ser Lys Leu Ser Val Asp Lys
        515                 520                 525

Ser Arg Trp Gln Gln Gly Asp Pro Phe Thr Cys Ala Val Met His Glu
    530                 535                 540

Thr Leu Gln Asn His Tyr Thr Asp Leu Ser Leu Ser His Ser Pro Gly
545                 550                 555                 560

Lys

<210> SEQ ID NO 73
<211> LENGTH: 1686
<212> TYPE: DNA
<213> ORGANISM: Canis familiaris

<400> SEQUENCE: 73
tcatttaccc ggagaatggg agagggatag atctgtgtag tggttctgta gagtttcatg     60
catcaccgca catgtgaagg ggtctccctg ctgccagcgg ctcttgtcca cagagagctt    120
gctgtacagg aagtaggacc cgtcctcgtc cagctgggc gggtcatgc ggtgcttcct     180
ctcgggctcc tgctgtccat tgctctgcca ctccacatca atgtcaggtg ggtagaagtc    240
ttttatcagg caggtgatgc tgactgtgtc actggatgac aactcctttg gggatggcgg    300
caggacatac acactgggct tatgggccct ccctctggcc ttagagatgg tcctctcgat    360
gggagacggg aggtctatgt ggttgactct gcacttgaac tccttccctg tgagccagtc    420
ctggtgctca atggggagga cgctgaccac acggtaggtg ccgttgaact gctgctcacg    480
agactgggtc ttggctgtgt gcacctcctt accatccacg aaccagctga tctgcacctc    540
agggtcctca cggcccagat ctaacaccac acaggtgacc tcgggtgttc gggtaatcct    600
```

-continued

```
gaggatgtcc ttgggtttcg ggggaaagat gaggaccgaa ggccctccca gaggttcagg      660
gactgggcat gggggtgtat cagtgcatct gcattcattg aacactggct tgtctacttt      720
agtgttggat ccggtttcct tccagatatc acctttccag cattgttcat cactccactc      780
actccagatt ccatcatctg agcaataaat attcacttta cttcttacca aaaagcataa      840 ttttggctt tcatttgatg ttcttgtgat ttgtatctca ttctcaactg tggtagtcac      900
ccaagtagta ccatcctctg tgaattcaat ttcataaatg aaacatttgg ctggaatggg      960
tcctttaggc atgttccatt tcaggttaat ttcctctgaa ttcttcacag taagactaag     1020
gtagtctggt ggcataggtt taactatatt ttgaagctga aaaataaaat agctgggtct     1080
gataggctgg gattctgatg acccattaac acagatgtag aaatctttat agtctgatga     1140
ctccaaatag ggaaacctgc atcccatatt ttttccatta accttgatgt aatcagtaca     1200
ctctgctgaa tggtccaagc cctcatacca gtaaaacaac tggtaattgg tatcaaaatg     1260
gacacccatg ccaggtttcc aagagcagac taaatattgc cagttgtaat atacacagtc     1320
catatcttga attttagttt cccgatttcc ttgtggtgat gtccaataag tagtttctgc     1380
ccatgaactt ctaacttctg atccattgt gcattgtgct ggcagaagtg tgtttatctt     1440
tgcttcaata cctttgttaa gatcaaaccc atctttgtaa tgtagattct tggtaatgat     1500
ggtcttccag ttttcactat caatgtttcg gtattttaat tcatattcta ttgtgcattc     1560
cttaaaatta tccggaaata atggaggttg ccattgcaaa gagagataac ctaaatatcc     1620
agggtccact atctcaaaat cctgaggagg attaactttt atctcagcat ttgaaagcat     1680
agacat                                                               1686
```

```
<210> SEQ ID NO 74
<211> LENGTH: 1698
<212> TYPE: DNA
<213> ORGANISM: Canis familiaris
<220> FEATURE:
<221> NAME/KEY: CDS
<222> LOCATION: (1)..(1695)
<223> OTHER INFORMATION:

<400> SEQUENCE: 74
```

```
atg tct atg ctt tca aat gct gag ata aaa gtt aat cct cct cag gat      48
Met Ser Met Leu Ser Asn Ala Glu Ile Lys Val Asn Pro Pro Gln Asp
1               5                   10                  15 ttt gag ata gtg gac cct gga tat tta ggt tat ctc tct ttg caa tgg      96
Phe Glu Ile Val Asp Pro Gly Tyr Leu Gly Tyr Leu Ser Leu Gln Trp
            20                  25                  30 caa cct cca tta ttt ccg gat aat ttt aag gaa tgc aca ata gaa tat    144
Gln Pro Pro Leu Phe Pro Asp Asn Phe Lys Glu Cys Thr Ile Glu Tyr
        35                  40                  45 gaa tta aaa tac cga aac att gat agt gaa aac tgg aag acc atc att    192
Glu Leu Lys Tyr Arg Asn Ile Asp Ser Glu Asn Trp Lys Thr Ile Ile
    50                  55                  60 acc aag aat cta cat tac aaa gat ggg ttt gat ctt aac aaa ggt att    240
Thr Lys Asn Leu His Tyr Lys Asp Gly Phe Asp Leu Asn Lys Gly Ile
65                  70                  75                  80 gaa gca aag ata aac aca ctt ctg cca gca caa tgc aca aat gga tca    288
Glu Ala Lys Ile Asn Thr Leu Leu Pro Ala Gln Cys Thr Asn Gly Ser
                85                  90                  95 gaa gtt aga agt tca tgg gca gaa act act tat tgg aca tca cca caa    336
Glu Val Arg Ser Ser Trp Ala Glu Thr Thr Tyr Trp Thr Ser Pro Gln
            100                 105                 110 gga aat cgg gaa act aaa att caa gat atg gac tgt gta tat tac aac    384
```

```
                Gly Asn Arg Glu Thr Lys Ile Gln Asp Met Asp Cys Val Tyr Tyr Asn
                            115                 120                 125 tgg caa tat tta gtc tgc tct tgg aaa cct ggc atg ggt gtc cat ttt            432
Trp Gln Tyr Leu Val Cys Ser Trp Lys Pro Gly Met Gly Val His Phe
    130                 135                 140 gat acc aat tac cag ttg ttt tac tgg tat gag ggc ttg gac cat tca            480
Asp Thr Asn Tyr Gln Leu Phe Tyr Trp Tyr Glu Gly Leu Asp His Ser
145                 150                 155                 160 gca gag tgt act gat tac atc aag gtt aat gga aaa aat atg gga tgc            528
Ala Glu Cys Thr Asp Tyr Ile Lys Val Asn Gly Lys Asn Met Gly Cys
                165                 170                 175 agg ttt ccc tat ttg gag tca tca gac tat aaa gat ttc tac atc tgt            576
Arg Phe Pro Tyr Leu Glu Ser Ser Asp Tyr Lys Asp Phe Tyr Ile Cys
                180                 185                 190 gtt aat ggg tca tca gaa tcc cag cct atc aga ccc agc tat ttt att            624
Val Asn Gly Ser Ser Glu Ser Gln Pro Ile Arg Pro Ser Tyr Phe Ile
                195                 200                 205 ttt cag ctt caa aat ata gtt aaa cct atg cca cca gac tac ctt agt            672
Phe Gln Leu Gln Asn Ile Val Lys Pro Met Pro Pro Asp Tyr Leu Ser
    210                 215                 220 ctt act gtg aag aat tca gag gaa att aac ctg aaa tgg aac atg cct            720
Leu Thr Val Lys Asn Ser Glu Glu Ile Asn Leu Lys Trp Asn Met Pro
225                 230                 235                 240 aaa gga ccc att cca gcc aaa tgt ttc att tat gaa att gaa ttc aca            768
Lys Gly Pro Ile Pro Ala Lys Cys Phe Ile Tyr Glu Ile Glu Phe Thr
                245                 250                 255 gag gat ggt act act tgg gtg act acc aca gtt gag aat gag ata caa            816
Glu Asp Gly Thr Thr Trp Val Thr Thr Thr Val Glu Asn Glu Ile Gln
                260                 265                 270 atc aca aga aca tca aat gaa agc caa aaa tta tgc ttt ttg gta aga            864
Ile Thr Arg Thr Ser Asn Glu Ser Gln Lys Leu Cys Phe Leu Val Arg
                275                 280                 285 agt aaa gtg aat att tat tgc tca gat gat gga atc tgg agt gag tgg            912
Ser Lys Val Asn Ile Tyr Cys Ser Asp Asp Gly Ile Trp Ser Glu Trp
    290                 295                 300 agt gat gaa caa tgc tgg aaa ggt gat atc tgg aag gaa acc gga tcc            960
Ser Asp Glu Gln Cys Trp Lys Gly Asp Ile Trp Lys Glu Thr Gly Ser
305                 310                 315                 320 aac act aaa gta gac aag cca gtg ccc aaa aga gaa aat gga aga gtt           1008
Asn Thr Lys Val Asp Lys Pro Val Pro Lys Arg Glu Asn Gly Arg Val
                325                 330                 335 cct cgc cca cct gat tgt ccc aaa tgc cca gcc cct gaa atg ctg gga           1056
Pro Arg Pro Pro Asp Cys Pro Lys Cys Pro Ala Pro Glu Met Leu Gly
                340                 345                 350 ggg cct tcg gtc ttc atc ttt ccc ccg aaa ccc aag gac acc ctc ttg           1104
Gly Pro Ser Val Phe Ile Phe Pro Pro Lys Pro Lys Asp Thr Leu Leu
                355                 360                 365 att gcc cga aca cct gag gtc aca tgt gtg gtg gtg gat ctg gac cca           1152
Ile Ala Arg Thr Pro Glu Val Thr Cys Val Val Val Asp Leu Asp Pro
                370                 375                 380 gaa gac cct gag gtg cag atc agc tgg ttc gtg gac ggt aag cag atg           1200
Glu Asp Pro Glu Val Gln Ile Ser Trp Phe Val Asp Gly Lys Gln Met
385                 390                 395                 400 caa aca gcc aag act cag cct cgt gag gag cag ttc aat ggc acc tac           1248
Gln Thr Ala Lys Thr Gln Pro Arg Glu Glu Gln Phe Asn Gly Thr Tyr
                405                 410                 415 cgt gtg gtc agt gtc ctc ccc att ggg cac cag gac tgg ctc aag ggg           1296
Arg Val Val Ser Val Leu Pro Ile Gly His Gln Asp Trp Leu Lys Gly
                420                 425                 430
```

-continued

```
aag cag ttc acg tgc aaa gtc aac aac aaa gcc ctc cca tcc ccg atc    1344
Lys Gln Phe Thr Cys Lys Val Asn Asn Lys Ala Leu Pro Ser Pro Ile
            435                 440                 445 gag agg acc atc tcc aag gcc aga ggg caa gcc cat cag ccc agt gtg    1392
Glu Arg Thr Ile Ser Lys Ala Arg Gly Gln Ala His Gln Pro Ser Val
    450                 455                 460 tat gtc ctg ccg cca tcc cgg gag gag ttg agc aag aac aca gtc agc    1440
Tyr Val Leu Pro Pro Ser Arg Glu Glu Leu Ser Lys Asn Thr Val Ser
465                 470                 475                 480 ttg aca tgc ctg atc aaa gac ttc ttc cca cct gac att gat gtg gag    1488
Leu Thr Cys Leu Ile Lys Asp Phe Phe Pro Pro Asp Ile Asp Val Glu
                485                 490                 495 tgg cag agc aat gga cag cag gag cct gag agc aag tac cgc acg acc    1536
Trp Gln Ser Asn Gly Gln Gln Glu Pro Glu Ser Lys Tyr Arg Thr Thr
            500                 505                 510 ccg ccc cag ctg gac gag gac ggg tcc tac ttc ctg tac agc aag ctc    1584
Pro Pro Gln Leu Asp Glu Asp Gly Ser Tyr Phe Leu Tyr Ser Lys Leu
        515                 520                 525 tct gtg gac aag agc cgc tgg cag cgg gga gac acc ttc ata tgt gcg    1632
Ser Val Asp Lys Ser Arg Trp Gln Arg Gly Asp Thr Phe Ile Cys Ala
    530                 535                 540 gtg atg cat gaa gct cta cac aac cac tac aca cag gaa tcc ctc tcc    1680
Val Met His Glu Ala Leu His Asn His Tyr Thr Gln Glu Ser Leu Ser
545                 550                 555                 560 cat tct ccg ggt aaa tga                                             1698
His Ser Pro Gly Lys
                565

<210> SEQ ID NO 75
<211> LENGTH: 565
<212> TYPE: PRT
<213> ORGANISM: Canis familiaris

<400> SEQUENCE: 75

Met Ser Met Leu Ser Asn Ala Glu Ile Lys Val Asn Pro Pro Gln Asp
1               5                   10                  15

Phe Glu Ile Val Asp Pro Gly Tyr Leu Gly Tyr Leu Ser Leu Gln Trp
            20                  25                  30

Gln Pro Pro Leu Phe Pro Asp Asn Phe Lys Glu Cys Thr Ile Glu Tyr
        35                  40                  45

Glu Leu Lys Tyr Arg Asn Ile Asp Ser Glu Asn Trp Lys Thr Ile Ile
    50                  55                  60

Thr Lys Asn Leu His Tyr Lys Asp Gly Phe Asp Leu Asn Lys Gly Ile
65                  70                  75                  80

Glu Ala Lys Ile Asn Thr Leu Leu Pro Ala Gln Cys Thr Asn Gly Ser
                85                  90                  95

Glu Val Arg Ser Ser Trp Ala Glu Thr Thr Tyr Trp Thr Ser Pro Gln
            100                 105                 110

Gly Asn Arg Glu Thr Lys Ile Gln Asp Met Asp Cys Val Tyr Tyr Asn
        115                 120                 125

Trp Gln Tyr Leu Val Cys Ser Trp Lys Pro Gly Met Gly Val His Phe
    130                 135                 140

Asp Thr Asn Tyr Gln Leu Phe Tyr Trp Tyr Glu Gly Leu Asp His Ser
145                 150                 155                 160

Ala Glu Cys Thr Asp Tyr Ile Lys Val Asn Gly Lys Asn Met Gly Cys
                165                 170                 175

Arg Phe Pro Tyr Leu Glu Ser Ser Asp Tyr Lys Asp Phe Tyr Ile Cys
            180                 185                 190
```

-continued

Val Asn Gly Ser Ser Glu Ser Gln Pro Ile Arg Pro Ser Tyr Phe Ile
        195                 200                 205

Phe Gln Leu Gln Asn Ile Val Lys Pro Met Pro Pro Asp Tyr Leu Ser
    210                 215                 220

Leu Thr Val Lys Asn Ser Glu Glu Ile Asn Leu Lys Trp Asn Met Pro
225                 230                 235                 240

Lys Gly Pro Ile Pro Ala Lys Cys Phe Ile Tyr Glu Ile Glu Phe Thr
                245                 250                 255

Glu Asp Gly Thr Thr Trp Val Thr Thr Thr Val Glu Asn Glu Ile Gln
            260                 265                 270

Ile Thr Arg Thr Ser Asn Glu Ser Gln Lys Leu Cys Phe Leu Val Arg
        275                 280                 285

Ser Lys Val Asn Ile Tyr Cys Ser Asp Asp Gly Ile Trp Ser Glu Trp
    290                 295                 300

Ser Asp Glu Gln Cys Trp Lys Gly Asp Ile Trp Lys Glu Thr Gly Ser
305                 310                 315                 320

Asn Thr Lys Val Asp Lys Pro Val Pro Lys Arg Glu Asn Gly Arg Val
                325                 330                 335

Pro Arg Pro Pro Asp Cys Pro Lys Cys Pro Ala Pro Glu Met Leu Gly
            340                 345                 350

Gly Pro Ser Val Phe Ile Phe Pro Pro Lys Pro Lys Asp Thr Leu Leu
        355                 360                 365

Ile Ala Arg Thr Pro Glu Val Thr Cys Val Val Val Asp Leu Asp Pro
    370                 375                 380

Glu Asp Pro Glu Val Gln Ile Ser Trp Phe Val Asp Gly Lys Gln Met
385                 390                 395                 400

Gln Thr Ala Lys Thr Gln Pro Arg Glu Glu Gln Phe Asn Gly Thr Tyr
                405                 410                 415

Arg Val Val Ser Val Leu Pro Ile Gly His Gln Asp Trp Leu Lys Gly
            420                 425                 430

Lys Gln Phe Thr Cys Lys Val Asn Asn Lys Ala Leu Pro Ser Pro Ile
        435                 440                 445

Glu Arg Thr Ile Ser Lys Ala Arg Gly Gln Ala His Gln Pro Ser Val
    450                 455                 460

Tyr Val Leu Pro Pro Ser Arg Glu Glu Leu Ser Lys Asn Thr Val Ser
465                 470                 475                 480

Leu Thr Cys Leu Ile Lys Asp Phe Phe Pro Pro Asp Ile Asp Val Glu
                485                 490                 495

Trp Gln Ser Asn Gly Gln Gln Glu Pro Glu Ser Lys Tyr Arg Thr Thr
            500                 505                 510

Pro Pro Gln Leu Asp Glu Asp Gly Ser Tyr Phe Leu Tyr Ser Lys Leu
        515                 520                 525

Ser Val Asp Lys Ser Arg Trp Gln Arg Gly Asp Thr Phe Ile Cys Ala
    530                 535                 540

Val Met His Glu Ala Leu His Asn His Tyr Thr Gln Glu Ser Leu Ser
545                 550                 555                 560

His Ser Pro Gly Lys
                565

<210> SEQ ID NO 76
<211> LENGTH: 1698
<212> TYPE: DNA
<213> ORGANISM: Canis familiaris

```
<400> SEQUENCE: 76
tcatttaccc ggagaatggg agagggattc ctgtgtgtag tggttgtgta gagcttcatg      60
catcaccgca catatgaagg tgtctccccg ctgccagcgg ctcttgtcca cagagagctt     120
gctgtacagg aagtaggacc cgtcctcgtc cagctggggc ggggtcgtgc ggtacttgct     180
ctcaggctcc tgctgtccat tgctctgcca ctccacatca atgtcaggtg ggaagaagtc     240
tttgatcagg catgtcaagc tgactgtgtt cttgctcaac tcctcccggg atggcggcag     300
gacatacaca ctgggctgat gggcttgccc tctggccttg gagatggtcc tctcgatcgg     360
ggatgggagg gctttgttgt tgactttgca cgtgaactgc ttcccttga gccagtcctg      420
gtgcccaatg ggaggacac tgaccacacg taggtgcca ttgaactgct cctcacgagg       480
ctgagtcttg gctgtttgca tctgcttacc gtccacgaac cagctgatct gcacctcagg    540
gtcttctggg tccagatcca ccaccacaca tgtgacctca ggtgttcggg caatcaagag     600
ggtgtccttg ggtttcgggg aaagatgaa accgaaggc cctcccagca tttcaggggc       660
tgggcatttg ggacaatcag gtgggcgagg aactcttcca ttttctcttt tgggcactgg    720
cttgtctact ttagtgttgg atccggtttc cttccagata tcacctttcc agcattgttc    780
atcactccac tcactccaga ttccatcatc tgagcaataa atattcactt tacttcttac    840
caaaaagcat aattttggc tttcatttga tgttcttgtg atttgtatct cattctcaac     900
tgtggtagtc acccaagtag taccatcctc tgtgaattca atttcataaa tgaaacattt    960
ggctggaatg ggtcctttag gcatgttcca tttcaggtta atttcctctg aattcttcac   1020
agtaagacta aggtagtctg gtggcatagg tttaactata ttttgaagct gaaaaataaa   1080
atagctgggt ctgataggct gggattctga tgacccatta acacagatgt agaaatcttt   1140
atagtctgat gactccaaat agggaaacct gcatcccata ttttttccat taaccttgat   1200
gtaatcagta cactctgctg aatggtccaa gccctcatac cagtaaaaca actggtaatt   1260
ggtatcaaaa tggacaccca tgccaggttt ccaagagcag actaaatatt gccagttgta   1320
atatacacag tccatatctt gaattttagt ttcccgattt ccttgtggtg atgtccaata   1380
agtagtttct gcccatgaac ttctaacttc tgatccattt gtgcattgtg ctggcagaag   1440
tgtgtttatc tttgcttcaa tacctttgtt aagatcaaac ccatctttgt aatgtagatt   1500
cttggtaatg atggtcttcc agttttcact atcaatgttt cggtatttta attcatattc   1560
tattgtgcat tccttaaaat tatccggaaa taatggaggt tgccattgca aagagagata   1620
acctaaatat ccagggtcca ctatctcaaa atcctgagga ggattaactt ttatctcagc   1680
atttgaaagc atagacat                                                  1698

<210> SEQ ID NO 77
<211> LENGTH: 1692
<212> TYPE: DNA
<213> ORGANISM: Canis familiaris
<220> FEATURE:
<221> NAME/KEY: CDS
<222> LOCATION: (1)..(1689)
<223> OTHER INFORMATION:

<400> SEQUENCE: 77 atg tct atg ctt tca aat gct gag ata aaa gtt aat cct cct cag gat      48
Met Ser Met Leu Ser Asn Ala Glu Ile Lys Val Asn Pro Pro Gln Asp
1               5                   10                  15 ttt gag ata gtg gac cct gga tat tta ggt tat ctc tct ttg caa tgg      96
Phe Glu Ile Val Asp Pro Gly Tyr Leu Gly Tyr Leu Ser Leu Gln Trp
            20                  25                  30
```

-continued

```
caa cct cca tta ttt ccg gat aat ttt aag gaa tgc aca ata gaa tat      144
Gln Pro Pro Leu Phe Pro Asp Asn Phe Lys Glu Cys Thr Ile Glu Tyr
         35                  40                  45 gaa tta aaa tac cga aac att gat agt gaa aac tgg aag acc atc att      192
Glu Leu Lys Tyr Arg Asn Ile Asp Ser Glu Asn Trp Lys Thr Ile Ile
 50                  55                  60 acc aag aat cta cat tac aaa gat ggg ttt gat ctt aac aaa ggt att      240
Thr Lys Asn Leu His Tyr Lys Asp Gly Phe Asp Leu Asn Lys Gly Ile
 65                  70                  75                  80 gaa gca aag ata aac aca ctt ctg cca gca caa tgc aca aat gga tca      288
Glu Ala Lys Ile Asn Thr Leu Leu Pro Ala Gln Cys Thr Asn Gly Ser
                 85                  90                  95 gaa gtt aga agt tca tgg gca gaa act act tat tgg aca tca cca caa      336
Glu Val Arg Ser Ser Trp Ala Glu Thr Thr Tyr Trp Thr Ser Pro Gln
                100                 105                 110 gga aat cgg gaa act aaa att caa gat atg gac tgt gta tat tac aac      384
Gly Asn Arg Glu Thr Lys Ile Gln Asp Met Asp Cys Val Tyr Tyr Asn
            115                 120                 125 tgg caa tat tta gtc tgc tct tgg aaa cct ggc atg ggt gtc cat ttt      432
Trp Gln Tyr Leu Val Cys Ser Trp Lys Pro Gly Met Gly Val His Phe
130                 135                 140 gat acc aat tac cag ttg ttt tac tgg tat gag ggc ttg gac cat tca      480
Asp Thr Asn Tyr Gln Leu Phe Tyr Trp Tyr Glu Gly Leu Asp His Ser
145                 150                 155                 160 gca gag tgt act gat tac atc aag gtt aat gga aaa aat atg gga tgc      528
Ala Glu Cys Thr Asp Tyr Ile Lys Val Asn Gly Lys Asn Met Gly Cys
                165                 170                 175 agg ttt ccc tat ttg gag tca tca gac tat aaa gat ttc tac atc tgt      576
Arg Phe Pro Tyr Leu Glu Ser Ser Asp Tyr Lys Asp Phe Tyr Ile Cys
            180                 185                 190 gtt aat ggg tca tca gaa tcc cag cct atc aga ccc agc tat ttt att      624
Val Asn Gly Ser Ser Glu Ser Gln Pro Ile Arg Pro Ser Tyr Phe Ile
        195                 200                 205 ttt cag ctt caa aat ata gtt aaa cct atg cca cca gac tac ctt agt      672
Phe Gln Leu Gln Asn Ile Val Lys Pro Met Pro Pro Asp Tyr Leu Ser
    210                 215                 220 ctt act gtg aag aat tca gag gaa att aac ctg aaa tgg aac atg cct      720
Leu Thr Val Lys Asn Ser Glu Glu Ile Asn Leu Lys Trp Asn Met Pro
225                 230                 235                 240 aaa gga ccc att cca gcc aaa tgt ttc att tat gaa att gaa ttc aca      768
Lys Gly Pro Ile Pro Ala Lys Cys Phe Ile Tyr Glu Ile Glu Phe Thr
                245                 250                 255 gag gat ggt act act tgg gtg act acc aca gtt gag aat gag ata caa      816
Glu Asp Gly Thr Thr Trp Val Thr Thr Thr Val Glu Asn Glu Ile Gln
            260                 265                 270 atc aca aga aca tca aat gaa agc caa aaa tta tgc ttt ttg gta aga      864
Ile Thr Arg Thr Ser Asn Glu Ser Gln Lys Leu Cys Phe Leu Val Arg
        275                 280                 285 agt aaa gtg aat att tat tgc tca gat gat gga atc tgg agt gag tgg      912
Ser Lys Val Asn Ile Tyr Cys Ser Asp Asp Gly Ile Trp Ser Glu Trp
    290                 295                 300 agt gat gaa caa tgc tgg aaa ggt gat atc tgg aag gaa acc gga tcc      960
Ser Asp Glu Gln Cys Trp Lys Gly Asp Ile Trp Lys Glu Thr Gly Ser
305                 310                 315                 320 aac act aaa gta gac aag cca gtg gcc aaa gaa tgc gag tgc aag tgt     1008
Asn Thr Lys Val Asp Lys Pro Val Ala Lys Glu Cys Glu Cys Lys Cys
                325                 330                 335 aac tgt aac aac tgc cca tgc cca ggt tgt ggc ctg ctg gga ggg cct     1056
Asn Cys Asn Asn Cys Pro Cys Pro Gly Cys Gly Leu Leu Gly Gly Pro
```

```
                340                 345                 350
tcg gtc ttc atc ttt ccc cca aaa ccc aag gac atc ctc gtg act gcc      1104
Ser Val Phe Ile Phe Pro Pro Lys Pro Lys Asp Ile Leu Val Thr Ala
        355                 360                 365 cgg aca ccc aca gtc act tgt gtg gtg gtg gat ctg gac cca gaa aac      1152
Arg Thr Pro Thr Val Thr Cys Val Val Val Asp Leu Asp Pro Glu Asn
370                 375                 380 cct gag gtg cag atc agc tgg ttc gtg gat agt aag cag gtg caa aca      1200
Pro Glu Val Gln Ile Ser Trp Phe Val Asp Ser Lys Gln Val Gln Thr
385                 390                 395                 400 gcc aac acg cag cct cgt gag gag cag tcc aat ggc acc tac cgt gtg      1248
Ala Asn Thr Gln Pro Arg Glu Glu Gln Ser Asn Gly Thr Tyr Arg Val
            405                 410                 415 gtc agt gtc ctc ccc att ggg cac cag gac tgg ctt tca ggg aag cag      1296
Val Ser Val Leu Pro Ile Gly His Gln Asp Trp Leu Ser Gly Lys Gln
            420                 425                 430 ttc aag tgc aaa gtc aac aac aaa gcc ctc cca tcc ccc att gag gag      1344
Phe Lys Cys Lys Val Asn Asn Lys Ala Leu Pro Ser Pro Ile Glu Glu
            435                 440                 445 atc atc tcc aag acc cca ggg cag gcc cat cag cct aat gtg tat gtc      1392
Ile Ile Ser Lys Thr Pro Gly Gln Ala His Gln Pro Asn Val Tyr Val
    450                 455                 460 ctg ccg cca tcg cgg gat gag atg agc aag aat acg gtc acc ctg acc      1440
Leu Pro Pro Ser Arg Asp Glu Met Ser Lys Asn Thr Val Thr Leu Thr
465                 470                 475                 480 tgt ctg gtc aaa gac ttc ttc cca cct gag att gat gtg gag tgg cag      1488
Cys Leu Val Lys Asp Phe Phe Pro Pro Glu Ile Asp Val Glu Trp Gln
                485                 490                 495 agc aat gga cag cag gag cct gag agc aag tac cgc atg acc ccg ccc      1536
Ser Asn Gly Gln Gln Glu Pro Glu Ser Lys Tyr Arg Met Thr Pro Pro
            500                 505                 510 cag ctg gat gaa gat ggg tcc tac ttc cta tac agc aag ctc tcc gtg      1584
Gln Leu Asp Glu Asp Gly Ser Tyr Phe Leu Tyr Ser Lys Leu Ser Val
            515                 520                 525 gac aag agc cgc tgg cag cgg gga gac acc ttc ata tgt gcg gtg atg      1632
Asp Lys Ser Arg Trp Gln Arg Gly Asp Thr Phe Ile Cys Ala Val Met
530                 535                 540 cat gaa gct cta cac aac cac tac aca cag ata tcc ctc tcc cat tct      1680
His Glu Ala Leu His Asn His Tyr Thr Gln Ile Ser Leu Ser His Ser
545                 550                 555                 560 ccg ggt aaa tga                                                       1692
Pro Gly Lys <210> SEQ ID NO 78
<211> LENGTH: 563
<212> TYPE: PRT
<213> ORGANISM: Canis familiaris

<400> SEQUENCE: 78

Met Ser Met Leu Ser Asn Ala Glu Ile Lys Val Asn Pro Pro Gln Asp
1               5                   10                  15

Phe Glu Ile Val Asp Pro Gly Tyr Leu Gly Tyr Leu Ser Leu Gln Trp
                20                  25                  30

Gln Pro Pro Leu Phe Pro Asp Asn Phe Lys Glu Cys Thr Ile Glu Tyr
            35                  40                  45

Glu Leu Lys Tyr Arg Asn Ile Asp Ser Glu Asn Trp Lys Thr Ile Ile
        50                  55                  60

Thr Lys Asn Leu His Tyr Lys Asp Gly Phe Asp Leu Asn Lys Gly Ile
65                  70                  75                  80
```

-continued

```
Glu Ala Lys Ile Asn Thr Leu Leu Pro Ala Gln Cys Thr Asn Gly Ser
             85                  90                  95
Glu Val Arg Ser Ser Trp Ala Glu Thr Thr Tyr Trp Thr Ser Pro Gln
         100                 105                 110
Gly Asn Arg Glu Thr Lys Ile Gln Asp Met Asp Cys Val Tyr Tyr Asn
         115                 120                 125
Trp Gln Tyr Leu Val Cys Ser Trp Lys Pro Gly Met Gly Val His Phe
         130                 135                 140
Asp Thr Asn Tyr Gln Leu Phe Tyr Trp Tyr Glu Gly Leu Asp His Ser
145                 150                 155                 160
Ala Glu Cys Thr Asp Tyr Ile Lys Val Asn Gly Lys Asn Met Gly Cys
                 165                 170                 175
Arg Phe Pro Tyr Leu Glu Ser Ser Asp Tyr Lys Asp Phe Tyr Ile Cys
             180                 185                 190
Val Asn Gly Ser Ser Glu Ser Gln Pro Ile Arg Pro Ser Tyr Phe Ile
         195                 200                 205
Phe Gln Leu Gln Asn Ile Val Lys Pro Met Pro Pro Asp Tyr Leu Ser
         210                 215                 220
Leu Thr Val Lys Asn Ser Glu Glu Ile Asn Leu Lys Trp Asn Met Pro
225                 230                 235                 240
Lys Gly Pro Ile Pro Ala Lys Cys Phe Ile Tyr Glu Ile Glu Phe Thr
                 245                 250                 255
Glu Asp Gly Thr Thr Trp Val Thr Thr Thr Val Glu Asn Glu Ile Gln
             260                 265                 270
Ile Thr Arg Thr Ser Asn Glu Ser Gln Lys Leu Cys Phe Leu Val Arg
         275                 280                 285
Ser Lys Val Asn Ile Tyr Cys Ser Asp Asp Gly Ile Trp Ser Glu Trp
         290                 295                 300
Ser Asp Glu Gln Cys Trp Lys Gly Asp Ile Trp Lys Glu Thr Gly Ser
305                 310                 315                 320
Asn Thr Lys Val Asp Lys Pro Val Ala Lys Glu Cys Glu Cys Lys Cys
                 325                 330                 335
Asn Cys Asn Asn Cys Pro Cys Pro Gly Cys Gly Leu Leu Gly Gly Pro
             340                 345                 350
Ser Val Phe Ile Phe Pro Pro Lys Pro Lys Asp Ile Leu Val Thr Ala
         355                 360                 365
Arg Thr Pro Thr Val Thr Cys Val Val Val Asp Leu Asp Pro Glu Asn
         370                 375                 380
Pro Glu Val Gln Ile Ser Trp Phe Val Asp Ser Lys Gln Val Gln Thr
385                 390                 395                 400
Ala Asn Thr Gln Pro Arg Glu Glu Gln Ser Asn Gly Thr Tyr Arg Val
                 405                 410                 415
Val Ser Val Leu Pro Ile Gly His Gln Asp Trp Leu Ser Gly Lys Gln
             420                 425                 430
Phe Lys Cys Lys Val Asn Asn Lys Ala Leu Pro Ser Pro Ile Glu Glu
         435                 440                 445
Ile Ile Ser Lys Thr Pro Gly Gln Ala His Gln Pro Asn Val Tyr Val
         450                 455                 460
Leu Pro Pro Ser Arg Asp Glu Met Ser Lys Asn Thr Val Thr Leu Thr
465                 470                 475                 480
Cys Leu Val Lys Asp Phe Phe Pro Pro Glu Ile Asp Val Glu Trp Gln
                 485                 490                 495
```

```
Ser Asn Gly Gln Gln Glu Pro Glu Ser Lys Tyr Arg Met Thr Pro Pro
            500                 505                 510
Gln Leu Asp Glu Asp Gly Ser Tyr Phe Leu Tyr Ser Lys Leu Ser Val
            515                 520                 525
Asp Lys Ser Arg Trp Gln Arg Gly Asp Thr Phe Ile Cys Ala Val Met
        530                 535                 540
His Glu Ala Leu His Asn His Tyr Thr Gln Ile Ser Leu Ser His Ser
545                 550                 555                 560
Pro Gly Lys
```

<210> SEQ ID NO 79
<211> LENGTH: 1692
<212> TYPE: DNA
<213> ORGANISM: Canis familiaris

<400> SEQUENCE: 79

```
tcatttaccc ggagaatggg agagggatat ctgtgtgtag tggttgtgta gagcttcatg    60
catcaccgca catatgaagg tgtctccccg ctgccagcgg ctcttgtcca cggagagctt   120
gctgtatagg aagtaggacc catcttcatc cagctgggc gggtcatgc ggtacttgct    180
ctcaggctcc tgctgtccat tgctctgcca ctccacatca atctcaggtg ggaagaagtc   240
tttgaccaga caggtcaggg tgaccgtatt cttgctcatc tcatcccgcg atggcggcag   300
gacatacaca ttaggctgat gggcctgccc tggggtcttg gagatgatct cctcaatggg   360
ggatgggagg gctttgttgt tgactttgca cttgaactgc ttccctgaaa gccagtcctg   420
gtgcccaatg gggaggacac tgaccacacg gtaggtgcca ttggactgct cctcacgagg   480
ctgcgtgttg gctgtttgca cctgcttact atccacgaac cagctgatct gcacctcagg   540
gttttctggg tccagatcca ccaccacaca agtgactgtg ggtgtccggg cagtcacgag   600
gatgtccttg ggttttgggg gaaagatgaa gaccgaaggc cctcccagca ggccacaacc   660
tgggcatggg cagttgttac agttacactt gcactcgcat tctttggcca ctggcttgtc   720
tactttagtg tttggatccgg tttccttcca gatatcacct ttccagcatt gttcatcact   780
ccactcactc cagattccat catctgagca ataaatattc actttacttc ttaccaaaaa   840
gcataatttt tggctttcat ttgatgttct tgtgatttgt atctcattct caactgtggt   900
agtcacccaa gtagtaccat cctctgtgaa ttcaattcca taaatgaaac atttggctgg   960
aatgggtcct ttaggcatgt tccatttcag gttaatttcc tctgaattct tcacagtaag  1020
actaaggtag tctggtggca taggtttaac tatattttga agctgaaaaa taaaatagct  1080
gggtctgata ggctgggatt ctgatgaccc attaacacag atgtagaaat ctttatagtc  1140
tgatgactcc aaataggaa acctgcatcc catattttt ccattaacct tgatgtaatc  1200
agtacactct gctgaatggt ccaagccctc ataccagtaa acaactggt aattggtatc  1260
aaaatggaca cccatgccag gtttccaaga gcagactaaa tattgccagt tgtaatatac  1320
acagtccata tcttgaattt tagtttcccg atttccttgt ggtgatgtcc aataagtagt  1380
ttctgcccat gaacttctaa cttctgatcc atttgtgcat tgtgctggca gaagtgtgtt  1440
tatctttgct tcaataccctt tgttaagatc aaacccatct tgtaatgta gattcttggt  1500
aatgatggtc ttccagtttt cactatcaat gtttcggtat tttaattcat attctattgt  1560
gcattcctta aaattatccg gaaataatgg aggttgccat tgcaaagaga gataacctaa  1620
atatccaggg tccactatct caaaatcctg aggaggatta cttttatct cagcatttga  1680
aagcatagac at                                                     1692
```

```
<210> SEQ ID NO 80
<211> LENGTH: 1686
<212> TYPE: DNA
<213> ORGANISM: Canis familiaris
<220> FEATURE:
<221> NAME/KEY: CDS
<222> LOCATION: (1)..(1683)
<223> OTHER INFORMATION:

<400> SEQUENCE: 80 atg tct atg ctt tca aat gct gag ata aaa gtt aat cct cct cag gat       48
Met Ser Met Leu Ser Asn Ala Glu Ile Lys Val Asn Pro Pro Gln Asp
1               5                  10                  15 ttt gag ata gtg gac cct gga tat tta ggt tat ctc tct ttg caa tgg       96
Phe Glu Ile Val Asp Pro Gly Tyr Leu Gly Tyr Leu Ser Leu Gln Trp
            20                  25                  30 caa cct cca tta ttt ccg gat aat ttt aag gaa tgc aca ata gaa tat      144
Gln Pro Pro Leu Phe Pro Asp Asn Phe Lys Glu Cys Thr Ile Glu Tyr
        35                  40                  45 gaa tta aaa tac cga aac att gat agt gaa aac tgg aag acc atc att      192
Glu Leu Lys Tyr Arg Asn Ile Asp Ser Glu Asn Trp Lys Thr Ile Ile
 50                  55                  60 acc aag aat cta cat tac aaa gat ggg ttt gat ctt aac aaa ggt att      240
Thr Lys Asn Leu His Tyr Lys Asp Gly Phe Asp Leu Asn Lys Gly Ile
65                  70                  75                  80 gaa gca aag ata aac aca ctt ctg cca gca caa tgc aca aat gga tca      288
Glu Ala Lys Ile Asn Thr Leu Leu Pro Ala Gln Cys Thr Asn Gly Ser
                85                  90                  95 gaa gtt aga agt tca tgg gca gaa act act tat tgg aca tca cca caa      336
Glu Val Arg Ser Ser Trp Ala Glu Thr Thr Tyr Trp Thr Ser Pro Gln
            100                 105                 110 gga aat cgg gaa act aaa att caa gat atg gac tgt gta tat tac aac      384
Gly Asn Arg Glu Thr Lys Ile Gln Asp Met Asp Cys Val Tyr Tyr Asn
        115                 120                 125 tgg caa tat tta gtc tgc tct tgg aaa cct ggc atg ggt gtc cat ttt      432
Trp Gln Tyr Leu Val Cys Ser Trp Lys Pro Gly Met Gly Val His Phe
130                 135                 140 gat acc aat tac cag ttg ttt tac tgg tat gag ggc ttg gac cat tca      480
Asp Thr Asn Tyr Gln Leu Phe Tyr Trp Tyr Glu Gly Leu Asp His Ser
145                 150                 155                 160 gca gag tgt act gat tac atc aag gtt aat gga aaa aat atg gga tgc      528
Ala Glu Cys Thr Asp Tyr Ile Lys Val Asn Gly Lys Asn Met Gly Cys
                165                 170                 175 agg ttt ccc tat ttg gag tca tca gac tat aaa gat ttc tac atc tgt      576
Arg Phe Pro Tyr Leu Glu Ser Ser Asp Tyr Lys Asp Phe Tyr Ile Cys
            180                 185                 190 gtt aat ggg tca tca gaa tcc cag cct atc aga ccc agc tat ttt att      624
Val Asn Gly Ser Ser Glu Ser Gln Pro Ile Arg Pro Ser Tyr Phe Ile
        195                 200                 205 ttt cag ctt caa aat ata gtt aaa cct atg cca cca gac tac ctt agt      672
Phe Gln Leu Gln Asn Ile Val Lys Pro Met Pro Pro Asp Tyr Leu Ser
210                 215                 220 ctt act gtg aag aat tca gag gaa att aac ctg aaa tgg aac atg cct      720
Leu Thr Val Lys Asn Ser Glu Glu Ile Asn Leu Lys Trp Asn Met Pro
225                 230                 235                 240 aaa gga ccc att cca gcc aaa tgt ttc att tat gaa att gaa ttc aca      768
Lys Gly Pro Ile Pro Ala Lys Cys Phe Ile Tyr Glu Ile Glu Phe Thr
                245                 250                 255 gag gat ggt act act tgg gtg act acc aca gtt gag aat gag ata caa      816
Glu Asp Gly Thr Thr Trp Val Thr Thr Thr Val Glu Asn Glu Ile Gln
```

-continued

```
                 260                 265                 270
atc aca aga aca tca aat gaa agc caa aaa tta tgc ttt ttg gta aga      864
Ile Thr Arg Thr Ser Asn Glu Ser Gln Lys Leu Cys Phe Leu Val Arg
            275                 280                 285 agt aaa gtg aat att tat tgc tca gat gat gga atc tgg agt gag tgg      912
Ser Lys Val Asn Ile Tyr Cys Ser Asp Asp Gly Ile Trp Ser Glu Trp
        290                 295                 300 agt gat gaa caa tgc tgg aaa ggt gat atc tgg aag gaa acc gga tcc      960
Ser Asp Glu Gln Cys Trp Lys Gly Asp Ile Trp Lys Glu Thr Gly Ser
305                 310                 315                 320 aac act aaa gta gac aag cca gtg ccc aaa gag tcc acc tgc aag tgt     1008
Asn Thr Lys Val Asp Lys Pro Val Pro Lys Glu Ser Thr Cys Lys Cys
                325                 330                 335 ata tcc cca tgc cca gtc cct gaa tca ctg gga ggg cct tcg gtc ttc     1056
Ile Ser Pro Cys Pro Val Pro Glu Ser Leu Gly Gly Pro Ser Val Phe
            340                 345                 350 atc ttt ccc ccg aaa ccc aag gac atc ctc agg att acc cga aca ccc     1104
Ile Phe Pro Pro Lys Pro Lys Asp Ile Leu Arg Ile Thr Arg Thr Pro
        355                 360                 365 gag atc acc tgt gtg gtg tta gat ctg ggc cgt gag gac cct gag gtg     1152
Glu Ile Thr Cys Val Val Leu Asp Leu Gly Arg Glu Asp Pro Glu Val
370                 375                 380 cag atc agc tgg ttc gtg gat ggt aag gag gtg cac aca gcc aag acg     1200
Gln Ile Ser Trp Phe Val Asp Gly Lys Glu Val His Thr Ala Lys Thr
385                 390                 395                 400 cag cct cgt gag cag cag ttc aac agc acc tac cgt gtg gtc agc gtc     1248
Gln Pro Arg Glu Gln Gln Phe Asn Ser Thr Tyr Arg Val Val Ser Val
                405                 410                 415 ctc ccc att gag cac cag gac tgg ctc acc gga aag gag ttc aag tgc     1296
Leu Pro Ile Glu His Gln Asp Trp Leu Thr Gly Lys Glu Phe Lys Cys
            420                 425                 430 aga gtc aac cac ata ggc ctc ccg tcc ccc atc gag agg act atc tcc     1344
Arg Val Asn His Ile Gly Leu Pro Ser Pro Ile Glu Arg Thr Ile Ser
        435                 440                 445 aaa gcc aga ggg caa gcc cat cag ccc agt gtg tat gtc ctg cca cca     1392
Lys Ala Arg Gly Gln Ala His Gln Pro Ser Val Tyr Val Leu Pro Pro
450                 455                 460 tcc cca aag gag ttg tca tcc agt gac acg gtc acc ctg acc tgc ctg     1440
Ser Pro Lys Glu Leu Ser Ser Ser Asp Thr Val Thr Leu Thr Cys Leu
465                 470                 475                 480 atc aaa gac ttc ttc cca cct gag att gat gtg gag tgg cag agc aat     1488
Ile Lys Asp Phe Phe Pro Pro Glu Ile Asp Val Glu Trp Gln Ser Asn
                485                 490                 495 gga cag ccg gag ccc gag agc aag tac cac acg act gcg ccc cag ctg     1536
Gly Gln Pro Glu Pro Glu Ser Lys Tyr His Thr Thr Ala Pro Gln Leu
            500                 505                 510 gac gag gac ggg tcc tac ttc ctg tac agc aag ctc tct gtg gac aag     1584
Asp Glu Asp Gly Ser Tyr Phe Leu Tyr Ser Lys Leu Ser Val Asp Lys
        515                 520                 525 agc cgc tgg cag cag gga gac acc ttc aca tgt gcg gtg atg cat gaa     1632
Ser Arg Trp Gln Gln Gly Asp Thr Phe Thr Cys Ala Val Met His Glu
530                 535                 540 gct cta cag aac cac tac aca gat cta tcc ctc tcc cat tct ccg ggt     1680
Ala Leu Gln Asn His Tyr Thr Asp Leu Ser Leu Ser His Ser Pro Gly
545                 550                 555                 560 aaa tga                                                              1686
Lys
```

<210> SEQ ID NO 81

```
<211> LENGTH: 561
<212> TYPE: PRT
<213> ORGANISM: Canis familiaris

<400> SEQUENCE: 81

Met Ser Met Leu Ser Asn Ala Glu Ile Lys Val Asn Pro Pro Gln Asp
1               5                   10                  15

Phe Glu Ile Val Asp Pro Gly Tyr Leu Gly Tyr Leu Ser Leu Gln Trp
            20                  25                  30

Gln Pro Pro Leu Phe Pro Asp Asn Phe Lys Glu Cys Thr Ile Glu Tyr
        35                  40                  45

Glu Leu Lys Tyr Arg Asn Ile Asp Ser Glu Asn Trp Lys Thr Ile Ile
    50                  55                  60

Thr Lys Asn Leu His Tyr Lys Asp Gly Phe Asp Leu Asn Lys Gly Ile
65                  70                  75                  80

Glu Ala Lys Ile Asn Thr Leu Leu Pro Ala Gln Cys Thr Asn Gly Ser
                85                  90                  95

Glu Val Arg Ser Ser Trp Ala Glu Thr Thr Tyr Trp Thr Ser Pro Gln
            100                 105                 110

Gly Asn Arg Glu Thr Lys Ile Gln Asp Met Asp Cys Val Tyr Tyr Asn
        115                 120                 125

Trp Gln Tyr Leu Val Cys Ser Trp Lys Pro Gly Met Gly Val His Phe
    130                 135                 140

Asp Thr Asn Tyr Gln Leu Phe Tyr Trp Tyr Glu Gly Leu Asp His Ser
145                 150                 155                 160

Ala Glu Cys Thr Asp Tyr Ile Lys Val Asn Gly Lys Asn Met Gly Cys
                165                 170                 175

Arg Phe Pro Tyr Leu Glu Ser Ser Asp Tyr Lys Asp Phe Tyr Ile Cys
            180                 185                 190

Val Asn Gly Ser Ser Glu Ser Gln Pro Ile Arg Pro Ser Tyr Phe Ile
        195                 200                 205

Phe Gln Leu Gln Asn Ile Val Lys Pro Met Pro Pro Asp Tyr Leu Ser
    210                 215                 220

Leu Thr Val Lys Asn Ser Glu Glu Ile Asn Leu Lys Trp Asn Met Pro
225                 230                 235                 240

Lys Gly Pro Ile Pro Ala Lys Cys Phe Ile Tyr Glu Ile Glu Phe Thr
                245                 250                 255

Glu Asp Gly Thr Thr Trp Val Thr Thr Thr Val Glu Asn Glu Ile Gln
            260                 265                 270

Ile Thr Arg Thr Ser Asn Glu Ser Gln Lys Leu Cys Phe Leu Val Arg
        275                 280                 285

Ser Lys Val Asn Ile Tyr Cys Ser Asp Asp Gly Ile Trp Ser Glu Trp
    290                 295                 300

Ser Asp Glu Gln Cys Trp Lys Gly Asp Ile Trp Lys Glu Thr Gly Ser
305                 310                 315                 320

Asn Thr Lys Val Asp Lys Pro Val Pro Lys Glu Ser Thr Cys Lys Cys
                325                 330                 335

Ile Ser Pro Cys Pro Val Pro Glu Ser Leu Gly Gly Pro Ser Val Phe
            340                 345                 350

Ile Phe Pro Pro Lys Pro Lys Asp Ile Leu Arg Ile Thr Arg Thr Pro
        355                 360                 365

Glu Ile Thr Cys Val Val Leu Asp Leu Gly Arg Glu Asp Pro Glu Val
    370                 375                 380

Gln Ile Ser Trp Phe Val Asp Gly Lys Glu Val His Thr Ala Lys Thr
```

```
385                 390                 395                 400
Gln Pro Arg Glu Gln Gln Phe Asn Ser Thr Tyr Arg Val Val Ser Val
                405                 410                 415
Leu Pro Ile Glu His Gln Asp Trp Leu Thr Gly Lys Glu Phe Lys Cys
            420                 425                 430
Arg Val Asn His Ile Gly Leu Pro Ser Pro Ile Glu Arg Thr Ile Ser
            435                 440                 445
Lys Ala Arg Gly Gln Ala His Gln Pro Ser Val Tyr Val Leu Pro Pro
        450                 455                 460
Ser Pro Lys Glu Leu Ser Ser Ser Asp Thr Val Thr Leu Thr Cys Leu
465                 470                 475                 480
Ile Lys Asp Phe Phe Pro Pro Glu Ile Asp Val Glu Trp Gln Ser Asn
                485                 490                 495
Gly Gln Pro Glu Pro Glu Ser Lys Tyr His Thr Thr Ala Pro Gln Leu
            500                 505                 510
Asp Glu Asp Gly Ser Tyr Phe Leu Tyr Ser Lys Leu Ser Val Asp Lys
            515                 520                 525
Ser Arg Trp Gln Gln Gly Asp Thr Phe Thr Cys Ala Val Met His Glu
        530                 535                 540
Ala Leu Gln Asn His Tyr Thr Asp Leu Ser Leu Ser His Ser Pro Gly
545                 550                 555                 560
Lys

<210> SEQ ID NO 82
<211> LENGTH: 1686
<212> TYPE: DNA
<213> ORGANISM: Canis familiaris

<400> SEQUENCE: 82
tcatttaccc ggagaatggg agagggatag atctgtgtag tggttctgta gagcttcatg      60
catcaccgca catgtgaagg tgtctccctg ctgccagcgg ctcttgtcca cagagagctt     120
gctgtacagg aagtaggacc cgtcctcgtc cagctggggc gcagtcgtgt ggtacttgct     180
ctcgggctcc ggctgtccat tgctctgcca ctccacatca atctcaggtg gaagaagtc     240
tttgatcagg caggtcaggg tgaccgtgtc actggatgac aactcctttg gggatggtgg     300
caggacatac acactgggct gatgggcttg ccctctggct ttggagatag tcctctcgat     360
gggggacggg aggcctatgt ggttgactct gcacttgaac tcctttccgg tgagccagtc     420
ctggtgctca atggggagga cgctgaccac acggtaggtg ctgttgaact gctgctcacg     480
aggctgcgtc ttggctgtgt gcacctcctt accatccacg aaccagctga tctgcacctc     540
agggtcctca cggcccagat ctaacaccac acaggtgatc tcgggtgttc gggtaatcct     600
gaggatgtcc ttgggtttcg ggggaaagat gaagaccgaa ggccctccca gtgattcagg     660
gactgggcat gggatatac acttgcaggt ggactctttg ggcactggct tgtctacttt      720
agtgttggat ccggtttcct tccagatatc acctttccag cattgttcat cactccactc     780
actccagatt ccatcatctg agcaataaat attcacttta cttcttacca aaaagcataa     840
ttttggcttt tcatttgatg ttcttgtgat ttgtatctca ttctcaactg tggtagtcac     900
ccaagtagta ccatcctctg tgaattcaat ttcataaatg aaacatttgg ctggaatggg     960
tcctttaggc atgttccatt tcaggttaat ttcctctgaa ttcttcacag taagactaag    1020
gtagtctggt ggcataggtt taactatatt ttgaagctga aaaataaaat agctgggtct    1080
gataggctgg gattctgatg acccattaac acagatgtag aaatctttat agtctgatga    1140
```

```
ctccaaatag ggaaacctgc atcccatatt ttttccatta accttgatgt aatcagtaca    1200
ctctgctgaa tggtccaagc cctcatacca gtaaaacaac tggtaattgg tatcaaaatg    1260
gacacccatg ccaggtttcc aagagcagac taaatattgc cagttgtaat atacacagtc    1320
catatcttga attttagttt cccgatttcc ttgtggtgat gtccaataag tagtttctgc    1380
ccatgaactt ctaacttctg atccatttgt gcattgtgct ggcagaagtg tgtttatctt    1440
tgcttcaata cctttgttaa gatcaaaccc atctttgtaa tgtagattct tggtaatgat    1500
ggtcttccag ttttcactat caatgtttcg gtattttaat tcatattcta ttgtgcattc    1560
cttaaaatta tccggaaata atggaggttg ccattgcaaa gagagataac ctaaatatcc    1620
agggtccact atctcaaaat cctgaggagg attaactttt atctcagcat ttgaaagcat    1680
agacat                                                                1686
```

<210> SEQ ID NO 83
<211> LENGTH: 29
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (9)..(9)
<223> OTHER INFORMATION: At nucleotide 9, n = unknown
<220> FEATURE:
<221> NAME/KEY: misc_feature
<222> LOCATION: (18)..(18)
<223> OTHER INFORMATION: At nucleotide 18, n = unknown
<220> FEATURE:
<221> NAME/KEY: misc_feature
<222> LOCATION: (21)..(21)
<223> OTHER INFORMATION: At nucleotide 21, n = unknown
<220> FEATURE:
<221> NAME/KEY: misc_feature
<222> LOCATION: (27)..(27)
<223> OTHER INFORMATION: At nucleotide 27, n = unknown

<400> SEQUENCE: 83
athtggacnt ggaayccncc ngarggngc                                        29

<210> SEQ ID NO 84
<211> LENGTH: 35
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (6)..(6)
<223> OTHER INFORMATION: At nucleotide 6, n = unknown
<220> FEATURE:
<221> NAME/KEY: misc_feature
<222> LOCATION: (9)..(9)
<223> OTHER INFORMATION: At nucleotide 9, n = unknown
<220> FEATURE:
<221> NAME/KEY: misc_feature
<222> LOCATION: (21)..(21)
<223> OTHER INFORMATION: At nucleotide 21, n = unknown
<220> FEATURE:
<221> NAME/KEY: misc_feature
<222> LOCATION: (33)..(33)
<223> OTHER INFORMATION: At nucleotide 33, n = unknown

<400> SEQUENCE: 84
atyttnccng crttrtcytt naccatdaty tgnac                                 35

<210> SEQ ID NO 85

```
<211> LENGTH: 35
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (12)..(12)
<223> OTHER INFORMATION: At nucleotide 12, n = unknown
<220> FEATURE:
<221> NAME/KEY: misc_feature
<222> LOCATION: (18)..(18)
<223> OTHER INFORMATION: At nucleotide 18, n = unknown
<220> FEATURE:
<221> NAME/KEY: misc_feature
<222> LOCATION: (21)..(21)
<223> OTHER INFORMATION: At nucleotide 21, n = unknown

<400> SEQUENCE: 85
garathaarg tnaayccncc ncargaytty garat                               35

<210> SEQ ID NO 86
<211> LENGTH: 36
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (12)..(12)
<223> OTHER INFORMATION: At nucleotide 12, n = unknown
<220> FEATURE:
<221> NAME/KEY: misc_feature
<222> LOCATION: (22)..(22)
<223> OTHER INFORMATION: At nucleotide 22, n = unknown
<220> FEATURE:
<221> NAME/KEY: misc_feature
<222> LOCATION: (31)..(31)
<223> OTHER INFORMATION: At nucleotide 31, n = unknown

<400> SEQUENCE: 86
tayaargayg gnttctgayy tnaayaargg nathga                             36

<210> SEQ ID NO 87
<211> LENGTH: 45
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (7)..(7)
<223> OTHER INFORMATION: At nucleotide 7, n = unknown
<220> FEATURE:
<221> NAME/KEY: misc_feature
<222> LOCATION: (16)..(16)
<223> OTHER INFORMATION: At nucleotide 16, n = unknown
<220> FEATURE:
<221> NAME/KEY: misc_feature
<222> LOCATION: (25)..(25)
<223> OTHER INFORMATION: At nucleotide 25, n = unknown
<220> FEATURE:
<221> NAME/KEY: misc_feature
<222> LOCATION: (40)..(40)
<223> OTHER INFORMATION: At nucleotide 40, n = unknown

<400> SEQUENCE: 87
ccaytcnswc cadatnccrt crtcngcrca rtadatrttn acytt                   45

<210> SEQ ID NO 88
<211> LENGTH: 23
<212> TYPE: DNA
<213> ORGANISM: Artificial sequence
```

```
<220> FEATURE:
<223> OTHER INFORMATION: Synthetic Primer
<220> FEATURE:
<221> NAME/KEY: misc_feature
<222> LOCATION: (9)..(9)
<223> OTHER INFORMATION: At nucleotide 9, n = unknown
<220> FEATURE:
<221> NAME/KEY: misc_feature
<222> LOCATION: (12)..(12)
<223> OTHER INFORMATION: At nucleotide 12, n = unknown

<400> SEQUENCE: 88
gcrtgrtcna rnccytcrta cca                                            23

<210> SEQ ID NO 89
<211> LENGTH: 53
<212> TYPE: DNA
<213> ORGANISM: Artificial sequence
<220> FEATURE:
<223> OTHER INFORMATION: Synthetic Primer

<400> SEQUENCE: 89
agcggatccc tctatgcttt caaatgctga gataaaagtt aatcctcctc agg           53

<210> SEQ ID NO 90
<211> LENGTH: 25
<212> TYPE: DNA
<213> ORGANISM: Artificial sequence
<220> FEATURE:
<223> OTHER INFORMATION: Synthetic Primer

<400> SEQUENCE: 90
tggacatcac cacaaggaaa tcggg                                          25

<210> SEQ ID NO 91
<211> LENGTH: 51
<212> TYPE: DNA
<213> ORGANISM: Artificial sequence
<220> FEATURE:
<223> OTHER INFORMATION: Synthetic Primer

<400> SEQUENCE: 91
gcacatatgt ctatgctttc aaatgctgaa taaagttaa tcctcctcag g              51

<210> SEQ ID NO 92
<211> LENGTH: 36
<212> TYPE: DNA
<213> ORGANISM: Artificial sequence
<220> FEATURE:
<223> OTHER INFORMATION: Synthetic Primer

<400> SEQUENCE: 92
aaaggatccg gtttccttcc agatatcatt tccagc                              36

<210> SEQ ID NO 93
<211> LENGTH: 31
<212> TYPE: DNA
<213> ORGANISM: Artificial sequence
<220> FEATURE:
<223> OTHER INFORMATION: Synthetic Primer

<400> SEQUENCE: 93
ccgggatcca acactaaagt agacaagcgt g                                   31

<210> SEQ ID NO 94
<211> LENGTH: 33
<212> TYPE: DNA
```

```
<213> ORGANISM: Artificial sequence
<220> FEATURE:
<223> OTHER INFORMATION: Synthetic Primer

<400> SEQUENCE: 94
gcgctcgagt catttacccg gagaatggga ggg                                    33

<210> SEQ ID NO 95
<211> LENGTH: 1525
<212> TYPE: DNA
<213> ORGANISM: Canis familiaris

<400> SEQUENCE: 95
gaattcggca cgagggagag gaggagggaa agatagaaag agagagagaa agattgcttg        60
ctacccctga acagtgacct ctctcaagac agtgctttgc tcttcacgta taaggaagga      120
aaacagtaga gattcaattt agtgtctaat gtggaaagga ggacaaagag gtcttgtgat      180
aactgcctgt gataatacat ttcttgagaa accatattat tgagtagagc tttcagcaca      240
ctaaatcctg gagaaatggc ttttgtgcat atcagatgct tgtgtttcat tcttctttgt      300
acaataactg gctattcttt ggagataaaa gttaatcctc ctcaggattt tgaaatattg      360
gatcctggat tacttggtta tctctatttg caatggaaac ctcctgtggt tatagaaaaa      420
tttaagggct gtacactaga atatgagtta aaataccgaa atgttgatag cgacagctgg      480
aagactataa ttactaggaa tctaatttac aaggatgggt ttgatcttaa taaaggcatt      540
gaaggaaaga tacgtacgca tttgtcagag cattgtacaa atggatcaga agtacaaagt      600
ccatggatag aagcttctta tgggatatca gatgaaggaa gtttggaaac taaaattcag      660
gacatgaagt gtatatatta taactggcag tatttggtct gctcttggaa acctggcaag      720
acagtatatt ctgataccaa ctataccatg tttttctggt atgagggctt ggatcatgcc      780
ttacagtgtg ctgattacct ccagcatgat gaaaaaaatg ttggatgcaa actgtccaac      840
ttggactcat cagactataa agatttttt atctgtgtta atggatcttc aaagttggaa      900
cccatcagat ccagctatac agttttttcaa cttcaaaata tagttaaacc attgccacca      960
gaattccttc atattagtgt ggagaattcc attgatatta gaatgaaatg gagcacacct     1020
ggaggaccca ttccaccaag gtgttacact tatgaaattg tgatccgaga agacgatatt     1080
tcctgggagt ctgccacaga caaaaacgat atgaagttga agaggagagc aaatgaaagt     1140
gaagacctat gcttttttgt aagatgtaag gtcaatatat attgtgcaga tgatggaatt     1200
tggagcgaat ggagtgaaga ggaatgttgg gaaggttaca cagggccaga ctcaaagatt     1260
attttcatag taccagtttg tcttttcttt atattccttt tgttacttct ttgccttatt     1320
gtggagaagg aagaacctga acccacattg agcctccatg tggatctgaa caagaagtg     1380 tgtgcttatg aagatacccct ctgttaaacc accaatttct tgacatagag ccagccagca    1440
ggagtcatat taaactcaat ttctcttaaa atttcgaata catcttcttg aaaatccaaa    1500
aaaaaaaaaa aaaaaaaac tcgag                                           1525

<210> SEQ ID NO 96
<211> LENGTH: 1369
<212> TYPE: DNA
<213> ORGANISM: Canis familiaris

<400> SEQUENCE: 96
ggatccgcgc ggatgaaggc tatttgaagt cgccataacc tggtcagaag tgtgcctgtc       60
ggcggggaga gaggcaatat caaggtttta aatctcggag aaatggcttt cgtttgcttg     120
```

```
gctatcggat gcttatatac ctttctgata agcacaacat ttggctgtac ttcatcttca    180
gacaccgaga taaaagttaa ccctcctcag gattttgaga tagtggatcc cggatactta    240
ggttatctct atttgcaatg gcaacccca ctgtctctgg atcattttaa ggaatgcaca     300
gtggaatatg aactaaaata ccgaaacatt ggtagtgaaa catggaagac catcattact    360
aagaatctac attacaaaga tgggtttgat cttaacaagg cattgaagc gaagatacac     420 acgcttttac catggcaatg cacaaatgga tcagaagttc aaagttcctg gcagaaact    480 acttattgga tatcaccaca aggaattcca gaaactaaag ttcaggatat ggattgcgta    540
tattacaatt ggcaatattt actctgttct tggaaacctg gcataggtgt acttcttgat    600
accaattaca acttgtttta ctggtatgag ggcttggatc atgcattaca gtgtgttgat    660
tacatcaagg ctgatggaca aaatatagga tgcagatttc cctatttgga ggcatcagac    720
tataaagatt tctatatttg tgttaatgga tcatcagaga caagcctat cagatccagt    780 tatttcactt ttcagcttca aaatatagtt aaacctttgc cgccagtcta tcttactttt    840
actcgggaga gttcatgtga aattaagctg aaatggagca tacctttggg acctattcca    900
gcaaggtgtt ttgattatga aattgagatc agagaagatg atactacctt ggtgactgct    960
acagttgaaa atgaaacata caccttgaaa acaacaaatg aaacccgaca attatgcttt   1020
gtagtaagaa gcaaagtgaa tatttattgc tcagatgacg gaatttggag tgagtggagt   1080
gataaacaat gctgggaagg tgaagaccta tcgaagaaaa ctttgctacg tttctggcta   1140
ccatttggtt tcatcttaat attagttata tttgtaaccg gtctgctttt gcgtaagcca   1200
aacacctacc caaaaatgat tccagaattt ttctgtgata catgaagact ttccatatca   1260
agagacatgg tattgactca acagtttcca gtcatggcca aatgttcaat atgagtctca   1320
ataaactgaa tttttcttgc gaaaaaaaaa aaaaaaatc cgcggatcc                1369
```

<210> SEQ ID NO 97
<211> LENGTH: 1525
<212> TYPE: DNA
<213> ORGANISM: Canis familiaris

<400> SEQUENCE: 97

```
ctcgagtttt ttttttttt ttttttttgg attttcaaga agatgtattc gaaattttaa      60
gagaaattga gtttaatatg actcctgctg gctggctcta tgtcaagaaa ttggtggttt    120
aacagagggt atcttcataa gcacacactt ctttgttcag atccacatgg aggctcaatg    180
tgggttcagg ttcttccttc tccacaataa ggcaagaag taacaaaagg aatataaaga    240
aaagacaaac tggtactatg aaaataatct ttgagtctgg ccctgtgtaa ccttcccaac    300
attcctcttc actccattcg ctccaaattc catcatctgc acaatatata ttgaccttac    360
atcttacaaa aaagcatagg tcttcacttt catttgctct cctcttcaac ttcatatcgt    420
ttttgtctgt ggcagactcc caggaaatat cgtcttctcg gatcacaatt tcataagtgt    480
aacaccttgg tggaatgggt cctccaggtg tgctccattt cattctaata tcaatggaat    540
tctccacact aatatgaagg aattctggtg gcaatggttt aactatattt tgaagttgaa    600
aaactgtata gctggatctg atgggttcca actttgaaga tccattaaca cagataaaaa    660
aatctttata gtctgatgag tccaagttgg acagtttgca tccaacattt ttttcatcat    720
gctggaggta atcagcacac tgtaaggcat gatccaagcc ctcataccag aaaaacatgg    780
tatagttggt atcagaatat actgtcttgc caggtttcca agagcagacc aaatactgcc    840
```

```
agttataata tatacacttc atgtcctgaa ttttagtttc caaacttcct tcatctgata      900
tcccataaga agcttctatc catggacttt gtacttctga tccatttgta caatgctctg      960
acaaatgcgt acgtatcttt ccttcaatgc ctttattaag atcaaaccca tccttgtaaa     1020
ttagattcct agtaattata gtcttccagc tgtcgctatc aacatttcgg tattttaact     1080
catattctag tgtacagccc ttaaattttt ctataaccac aggaggtttc cattgcaaat     1140
agagataacc aagtaatcca ggatccaata tttcaaaatc ctgaggagga ttaacttttc     1200
tctccaaaga atagccagtt attgtacaaa gaagaatgaa acacaagcat ctgatatgca     1260
caaaagccat ttctccagga tttagtgtgc tgaaagctct actcaataat atggtttctc     1320
aagaaatgta ttatcacagg cagttatcac aagacctctt tgtcctcctt tccacattag     1380
acactaaatt gaatctctac tgttttcctt cctatacgt gaagagcaaa gcactgtctt      1440
gagagaggtc actgttcagg ggtagcaagc aatctttctc tctctctttc tatctttccc     1500
tcctcctctc cctcgtgccg aattc                                           1525

<210> SEQ ID NO 98
<211> LENGTH: 1369
<212> TYPE: DNA
<213> ORGANISM: Canis familiaris

<400> SEQUENCE: 98
ggatccgcgg attttttttt tttttttcg caagaaaaat tcagtttatt gagactcata       60
ttgaacattt ggccatgact ggaaactgtt gagtcaatac catgtctctt gatatggaaa      120
gtcttcatgt atcacagaaa aattctggaa tcatttttgg gtaggtgttt ggcttacgca      180
aaagcagacc ggttacaaat ataactaata ttaagatgaa accaaatggt agccagaaac      240
gtagcaaagt tttcttcgat aggtcttcac cttcccagca ttgtttatca ctccactcac      300
tccaaattcc gtcatctgag caataaatat tcactttgct tcttactaca aagcataatt      360
gtcgggtttc atttgttgtt ttcaaggtgt atgtttcatt ttcaactgta gcagtcacca      420
aggtagtatc atcttctctg atctcaattt cataatcaaa acaccttgct ggaataggtc      480
ccaaaggtat gctccatttc agcttaattt cacatgaact ctcccgagta aagtaagat      540 agactggcgg caaaggttta actatatttt gaagctgaaa agtgaaataa ctggatctga     600
taggcttgtt ctctgatgat ccattaacac aaatatagaa atctttatag tctgatgcct      660 ccaaatagg aaatctgcat cctatatttt gtccatcagc cttgatgtaa tcaacacact      720
gtaatgcatg atccaagccc tcataccagt aaaacaagtt gtaattggta tcaagaagta     780
cacctatgcc aggtttccaa gaacagagta aatattgcca attgtaatat acgcaatcca     840
tatcctgaac tttagtttct ggaattcctt gtggtgatat ccaataagta gtttctgccc     900
aggaactttg aacttctgat ccatttgtgc attgccatgg taaaagcgtg tgtatcttcg     960
cttcaatgcc cttgttaaga tcaaacccat cttgtaatg tagattctta gtaatgatgg     1020
tcttccatgt ttcactacca atgtttcggt attttagttc atattccact gtgcattcct     1080
taaaatgatc cagagacagt gggggttgcc attgcaaata gataaccct aagtatccgg     1140 gatccactat ctcaaaatcc tgaggagggt taactttat ctcggtgtct gaagatgaag     1200
tacagccaaa tgttgtgctt atcagaaagg tatataagca tccgatagcc aagcaaacga     1260
aagccatttc tccgagattt aaaaccttga tattgcctct ctccccgccg acaggcacac     1320
ttctgaccag gttatggcga cttcaaatag ccttcatccg cgcggatcc                 1369
```

```
<210> SEQ ID NO 99
<211> LENGTH: 27
<212> TYPE: DNA
<213> ORGANISM: Artificial sequence
<220> FEATURE:
<223> OTHER INFORMATION: Synthetic Primer

<400> SEQUENCE: 99
ctctactatt ggcacagcag cctggga                                            27

<210> SEQ ID NO 100
<211> LENGTH: 27
<212> TYPE: DNA
<213> ORGANISM: Artificial sequence
<220> FEATURE:
<223> OTHER INFORMATION: Synthetic Primer

<400> SEQUENCE: 100
agtcagagca aaggaacaac caatgtg                                            27

<210> SEQ ID NO 101
<211> LENGTH: 21
<212> TYPE: DNA
<213> ORGANISM: Artificial sequence
<220> FEATURE:
<223> OTHER INFORMATION: Synthetic Primer

<400> SEQUENCE: 101
cctcccgagg gagccagccc g                                                  21

<210> SEQ ID NO 102
<211> LENGTH: 21
<212> TYPE: DNA
<213> ORGANISM: Artificial sequence
<220> FEATURE:
<223> OTHER INFORMATION: Synthetic Primer

<400> SEQUENCE: 102
cgggctggct ccctcgggag g                                                  21

<210> SEQ ID NO 103
<211> LENGTH: 21
<212> TYPE: DNA
<213> ORGANISM: Artificial sequence
<220> FEATURE:
<223> OTHER INFORMATION: Synthetic Primer

<400> SEQUENCE: 103
catggtcccc ggcgttcttc c                                                  21

<210> SEQ ID NO 104
<211> LENGTH: 21
<212> TYPE: DNA
<213> ORGANISM: Artificial sequence
<220> FEATURE:
<223> OTHER INFORMATION: Synthetic Primer

<400> SEQUENCE: 104
ggtgagaata ccgaccccac g                                                  21
```

CANINE IL-13 RECEPTOR ALPHA-1 SUBUNIT NUCLEIC ACID MOLECULES

CROSS REFERENCE TO RELATED APPLICATIONS

This application is a divisional of U.S. patent application Ser. No. 09/828,995, filed Apr. 9, 2001, now U.S. Pat. No. 6,703,360 entitled "COMPOSITIONS AND METHODS RELATED TO CANINE IgG AND CANINE IL-13 RECEPTORS"; which claims priority to U.S. Provisional Application Ser. No. 60/195,874, filed Apr. 7, 2000, entitled "CANINE IMMUNOGLOBULIN G MOLECULES AND RELATED METHODS"; and U.S. Provisional Application Ser. No. 60/195,659, filed Apr. 7, 2000, entitled "CANINE IL-13 RECEPTORS, PROTEINS, NUCLEIC ACIDS AND USES THEREOF."

FIELD OF THE INVENTION

The present invention relates to novel canine proteins, and more particularly to canine IgG and canine interleuken-13 receptor proteins, fusion proteins, nucleic acid molecules encoding such proteins and methods of making and using the same.

BACKGROUND OF THE INVENTION

Regulation of immune and inflammatory responses in animals is important in disease management. Immune responses can be regulated by modifying the activity of immunoregulatory molecules and immune cells. Such immunoregulatory molecules include, for example, cytokines, chemokines as well as soluble and membrane-bound immunoglobulin molecules.

One type of immunoregulatory molecule is immunoglobulin, a class of which is immunoglobulin G (IgG). The DNA and amino acid sequences of IgG molecules from several species have been reported. Peptides derived from known IgG sequences have been used to generate antibodies which alter IgG function. In humans and mice, IgGs have been fairly well characterized. In general, IgGs have been characterized by function and not DNA similarity since DNA similarity is not a reliable indicator of function.

Another type of immunoregulatory molecule is interleuken-13 (IL-13). Interleukin-13 is a cytokine produced by activated type 2 helper cells (Th2 cells). IL-13 promotes growth and differentiation of B cells, and IL-13 inhibits the production of inflammatory cytokines such as interleukin-1 alpha, interleukin-1 beta, interleukin-6, interleukin-8, interleukin-10 and interleukin-12 (designated as IL-1α, IL-1β, IL-6, IL-8, IL-10 and IL-12, respectively), among others.

A cDNA encoding IL-13 was first isolated from the mouse in 1989 and the human homologue was isolated in 1993. The human IL-13 gene is located on chromosome 5 q 31 which is 12 kilobases (kb) upstream of the interleukin-4 (IL-4) gene. Given the close proximity of the two genes, it is not surprising that IL-13 and IL-4 proteins share 25% sequence identity in humans and 30% sequence identity in mice. IL-13 and IL-4 are often simultaneously produced (with other cytokines) by Th2 cells. Both IL-13 and IL-4 share functional characteristics, such as inhibiting the production of inflammatory cytokines, and up-regulating the MHC class II and CD23 expression on monocytes and/or macrophages in B cells. Furthermore, IL-4 and IL-13 induce the IgE class switch in human cells in vitro and trigger IgG and IgM synthesis.

Both IL-13 and IL-4 have long played a role in allergy and inflammation, but until recently it has been difficult to separate the roles of these cytokines. Th2 cells are important participants in allergic conditions; as Th2 cells differentiate they produce cytokines directly or signal other allergic effector cells which induce and maintain allergic inflammatory responses. It is proposed that an allergen stimulates Th2 cells to produce IL-13 and/or IL-4, which in turn binds to IL-4R and/or IL-13R, signaling induction of IgE synthesis on B cells. Allergen-specific IgE then binds to IgE receptors on mast cells and basophils activating these cells and causing release of mediators of allergic inflammation. Induction of allergen specific Th2 differentiation represents a hallmark of allergic disease because cytokines produced by these cells induce and maintain allergic inflammatory processes. Th2 cells selectively develop and expand in the presence of IL-4. In humans, IL-13 fails to induce Th2-cell differentiation due to the lack of functional IL-13 receptors on T cells. IL-13 and IL-4 both induce IgE synthesis on B cells though IL-13 appears to be less potent in humans.

IL-4 and IL-13 receptors (referred to as IL-4R and IL-13R, respectively) share structural homology, in that both receptor complexes contain the IL-4 receptor alpha (IL-4Rα) chain which is required for signal transduction. Binding of IL-13 or IL-4 to IL-4R and IL-13R results in comparable signaling pathways. For example, if monoclonal antibodies are directed against the IL-4Rα chain (part of both the IL-4 and IL-13R complexes) IL-4 and IL-13 activity would be inhibited. Inhibition of biological activity of either of these cytokines would cause downstream regulation changes suggesting the importance of IL-4R□ for signal transduction. IL-13R can also function as a second receptor for IL-4 in cases where the IL-4R complex is compromised.

IL-13R is expressed on many cell types such as B cells, monocytes, macrophages, basophils, eosinophils, mast cells, endothelial cells, keratinocytes and some types of tumor cells, but active receptors have not been found on human T cells or murine B cells. Generally IL-13R is present in high numbers and thought to bind IL-13 with high affinity. The human IL-13 receptor complex consists of the 140-kilodalton (kD) IL-4Rα chain, which binds IL-4 but not IL-13, and an IL-13 binding protein. cDNAs encoding two different IL-13Rα (designated as IL-13Rα1 and IL-13Rα2) proteins have been isolated from humans and mice. Human IL-13Rα1 consists of 427 amino acids and binds IL-13 with low affinity (kD~4 nanomoles/Liter) while human IL-13Rα2 is a 380 amino acid protein, which binds IL-13 with high affinity (kD~50 picomoles/Liter).

Differences in IL-13 and IL-13R have been observed between species. Functional IL-13R is found on B cells in humans, while no functional IL-13R is found on B cells in mice. As such, no IgE response can be elicited from mouse B cells, so the role of IL-13 in stimulating IgE synthesis in mice remains unclear. However, it has recently been shown that IL-4 deficient mice are able to produce IgE, presumably through an IL-13 and IL-4 independent pathway. Given the differences in IL-13 activity between human and mouse, there would be no way to predict the IL-13 activity in other species, including dogs. As such there remains a need for compounds and methods to regulate an immune response in dogs through manipulation of IL-13 and IL-13R activities. The present invention satisfies this need and provides related advantages.

SUMMARY OF THE INVENTION

The present invention relates to canine IgG and canine interleuken-13 receptor (IL-13R) proteins as well as fusion proteins containing regions from canine IgG, canine IL-13R proteins or both. Also included are nucleic acid molecules encoding such proteins as well as recombinant constructs and cells containing the nucleic acid molecules, antibodies to the isolated proteins of the present invention, therapeutic compositions useful for treating canine IgG (heavy and/or light chain) and/or canine IL-13R mediated responses including, for example, vaccines, inhibitors of the proteins and/or nucleic acid molecules, methods for treating canine IgG (heavy and/or light chain) and/or canine IL-13R mediated responses, methods for eliciting a canine IgG (heavy and/or light chain) and/or canine IL-13R mediated immune response, and kits containing the compositions of the present invention.

In one aspect the present invention relates to different canine IgG nucleic acid molecules and the corresponding encoded amino acid sequences. In particular, the present invention relates to isolated canine IgG nucleic acid molecules having one of the following nucleic acid sequences:
(a) a nucleic acid sequence which has at least 55% identity SEQ ID NO:1, SEQ ID NO:7, or SEQ ID NO:13, wherein said identity can be determined using a DNAsis computer program and default parameters;
(b) a nucleic acid sequence which has at least 95% identity to SEQ ID NO:4, SEQ ID NO:10, or SEQ ID NO:16, wherein said identity is determined using the DNAsis computer program and default parameters;
(c) a nucleic acid sequence which encodes a first amino acid sequence which has at least 40% identity to SEQ ID NO:2, or SEQ ID NO:14, wherein said identity is determined using the DNAsis computer program and default parameters;
(d) a nucleic acid sequence which encodes a second amino acid sequence which has at least 90% identity SEQ ID NO:5, SEQ ID NO:8, SEQ ID NO:11 or SEQ ID NO:17 wherein said identity is determined using the DNAsis computer program and default parameters;
(e) a nucleic acid sequence which is an allelic variant of SEQ ID NO:1, SEQ ID NO:4, SEQ ID NO:7, SEQ ID NO:10, SEQ ID NO:13, or SEQ ID NO:16; or
(f) a nucleic acid sequence complementary to any of the above nucleic acid sequences.

The isolated nucleic acid molecules can further include the following sequences:
(a) a nucleic acid sequence which has at least 70% identity to SEQ ID NO:1, SEQ ID NO:7, or SEQ ID NO:13, wherein said identity is determined using the DNAsis computer program and default parameters;
(b) a nucleic acid sequence which encodes a third amino acid sequence which has at least 70% identity to SEQ ID NO:2, or SEQ ID NO:14, wherein said identity is determined using the DNAsis computer program and default parameters;
(c) a nucleic acid sequence which is an allelic variant of SEQ ID NO:1, SEQ ID NO:7, or SEQ ID NO:13; or
(d) a nucleic acid sequence complementary to any of the nucleic acid sequences of (a), (b) or (c).

In yet a further embodiment, the isolated canine IgG nucleic acid molecule can have the following sequences:
(a) a nucleic acid sequence comprising at least 70 contiguous nucleotides of SEQ ID NO:1, SEQ ID NO:7 or SEQ ID NO:13;
(b) a nucleic acid sequence comprising at least 350 contiguous nucleotides of SEQ ID NO:4, SEQ ID NO:10, and SEQ ID NO:16;
(c) a nucleic acid sequence comprising at least 450 contiguous nucleotides of SEQ ID NO:19;
(d) a nucleic acid sequence which encodes a first amino acid sequence comprising at least 20 contiguous residues of the sequence shown in SEQ ID NO:2, and SEQ ID NO:14;
(e) a nucleic acid sequence which encodes a second amino acid sequence comprising at least 100 contiguous residues of the sequence shown in SEQ ID NO:5, SEQ ID NO:8, SEQ ID NO:11, or SEQ ID NO:17;
(f) a nucleic acid sequence which encodes a third amino acid sequence comprising at least 200 contiguous residues of the sequence shown in SEQ ID NO:20; and
(g) an nucleic acid sequence complementary to any of the above nucleic acid sequence.

In yet another embodiment, the isolated canine IgG nucleic acid molecules of the present invention can contain the following nucleic acid sequences:
(a) a nucleic acid sequence comprising at least 150 contiguous nucleotides of SEQ ID NO:1, SEQ ID NO:7 or SEQ ID NO:13;
(b) a nucleic acid sequence comprising at least 500 contiguous nucleotides of SEQ ID NO:4, SEQ ID NO:7, SEQ ID NO:10 or SEQ ID NO:16;
(c) a nucleic acid sequence comprising at least 700 contiguous nucleotides of the sequence shown in SEQ ID NO:19;
(d) a nucleic acid sequence which encodes a fourth amino acid sequence comprising at least 50 contiguous residues of the sequence shown in SEQ ID NO:2 or SEQ ID NO:14;
(e) a nucleic acid sequence which encodes a fifth amino acid sequence comprising at least 200 contiguous residues of SEQ ID NO:5, SEQ ID NO:8, SEQ ID NO:11 or SEQ ID NO:17;
(f) a nucleic acid sequence which encodes a sixth amino acid sequence comprising at least 300 contiguous residues of the sequence shown in SEQ ID NO:20; and
(g) a nucleic acid sequence complementary to the above nucleic acid sequences.

The isolated IgG nucleic acid molecules of the present invention can further contain the following nucleic acid sequences:
(a) a nucleic acid sequence which is selected from the group consisting of SEQ ID NO:1, SEQ ID NO:4, SEQ ID NO:7, SEQ ID NO:10, SEQ ID NO:13, SEQ ID NO:16, and SEQ ID NO:19;
(b) a nucleic acid sequence which is selected from the group consisting of SEQ ID NO:2, SEQ ID NO:5, SEQ ID NO:8, SEQ ID NO:11, SEQ ID NO:14, SEQ ID NO:17, and SEQ ID NO:20;
(c) a nucleic acid sequence complementary to any of the above nucleic acid sequences.

The present invention further provides canine IgG heavy chain proteins having an amino acid sequence encoded by any of the above-identified nucleic acid molecules or having an amino acid sequence selected from the following: SEQ ID NO:2, SEQ ID NO:5, SEQ ID NO:8, SEQ ID NO:11, SEQ ID NO:14, SEQ ID NO:17, or SEQ ID NO:19. The invention is also directed to fusion constructs containing at least one of the above-identified nucleic acid molecules, as well as to corresponding fusion proteins. The invention additionally provides recombinant vectors and recombinant cells containing at least one of the nucleic acid molecules or fusion constructs. Isolated antibodies selective for the canine IgG proteins of the present inventon are also provided.

Methods of detecting canine IgG nucleic acid molecules are also provided and can generally be accomplished by:

(a) contacting an isolated the isolated nucleic acid molecule of the present invention with a putative IgG nucleic acid-containing composition under conditions suitable for formation of a heavy chain of canine IgG nucleic acid molecule/IgG nucleic acid complex; and (b) detecting the presence of IgG nucleic acid by detecting the heavy chain of canine IgG nucleic acid molecule/IgG nucleic acid complex.

Also provided are kits containing any of the above isolated nucleic acid molecules, a protein encoded by the isolated nucleic acid molecules, an inhibitor of a nucleic acid molecule and/or an inhibitor of the protein encolded by the isolated nucleic acid molecules of the present invention.

The present invention also provides for canine interleukin-13 receptor (IL-13R) proteins, nucleic acid molecules encoding such proteins, antibodies raised against such proteins and/or inhibitors of such proteins or nucleic acid molecules. This aspect of the present invention particularly relates to canine interleukin-13 receptor alpha 1 (IL-13Rα1 or IL-13Rα1) and canine interleukin-13 receptor alpha 2 (IL-13Rα2 or IL-13Rα2) proteins, nucleic acid molecules, and antibodies and inhibitors of the IL-13R proteins and nucleic acids.

In one embodiment, the present invention provides the following isolated IL-13R nucleic acid molecules:

(a) a nucleic acid molecule comprising at least 75 contiguous nucleotides identical in sequence to an at least 75 contiguous nucleotide region of SEQ ID NO:48, SEQ ID NO:49, SEQ ID NO:51, SEQ ID NO:52 or SEQ ID NO:53;

(b) a nucleic acid molecule comprising a nucleic acid sequence that is at least 90 percent identical in sequence to SEQ ID NO:48, SEQ ID NO:49, SEQ ID NO:51, SEQ ID NO:52 or SEQ ID NO:53, and a fragment thereof, wherein said fragment is at least 80 nucleotides in length, and wherein said percent identity can be determined by a DNAsis™ computer program with a gap penalty set at 5, the number of top diagonals set at 5, a fixed gap penalty set at 10, a k-tuple set at 2, a window size set at 10 and a floating gap penalty set at 1;

(c) isolated nucleic acid molecule encoding a protein comprising amino acid sequence SEQ ID NO: 50;

(d) isolated nucleic acid molecule selected from the group consisting of:

(i) a first nucleic acid molecule having at least 40 contiguous nucleotides identical in sequence to at least 40 contiguous nucleotide region of SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 or SEQ ID NO:70; and (ii) a second nucleic acid molecule comprising a first nucleic acid sequence that is at least 80% identical in sequence to SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 or SEQ ID NO:70, and a fragment thereof, wherein said fragment is at least 50 nucleotides in length, and wherein said percent identity can be determined by a DNAsis™ computer program with a gap penalty set at 5, the number of top diagonals set at 5, a fixed gap penalty set at 10, a k-tuple set at 2, a window size set at 10 and a floating gap penalty set at 10.

(e) an isolated nucleic acid molecule encoding a protein comprising an amino acid sequence selected from the group consisting of SEQ ID NO:55, SEQ ID NO:58, SEQ ID NO:61, SEQ ID NO:66, and SEQ ID NO:69.

(f) an isolated nucleic acid molecule having a first nucleic acid sequence encoding a protein selected from the group consisting of:

(i) a protein that is at least 85 percent identical in sequence to SEQ ID NO:3, wherein said percent identity can be determined by the DNAsis™ computer program with a gap penalty set at 5, the number of top diagonals set at 5, a fixed gap penalty set at 10, a k-tuple set at 2, a window size set at 10 and a floating gap penalty set at 10; and (ii) a protein comprising a fragment of at least 45 contiguous amino acids identical in sequence to an at least 45 contiguous amino acid sequence of the second protein;

(g) an isolated nucleic acid molecule comprising a second nucleic acid sequence encoding a protein that comprises an at least 40 contiguous amino acid region identical in sequence to an at least 40 contiguous amino acid region of SEQ ID NO:3;

(h) an isolated nucleic acid molecule contains a nucleic acid sequence encoding an IL-13Rα1 protein of at least 45 contiguous amino acids in length, wherein the nucleic acid sequence comprises an at least 135 contiguous nucleotide sequence identical in sequence to at least 135 contiguous nucleotide region of SEQ ID NO:48, SEQ ID NO:49, SEQ ID NO:51, SEQ ID NO:52 or SEQ ID NO:53;

(i) an isolated nucleic acid molecule having a first nucleic acid sequence encoding a first protein selected from the group consisting of:

(i) a second protein comprising an amino acid sequence that is at least 70 percent identical in sequence to SEQ ID NO:55, SEQ ID NO:58, SEQ ID NO:61, SEQ ID NO:66, and SEQ ID NO:69, wherein percent identity is determined by a DNAsis™ computer program with a gap penalty set at 5, the number of top diagonals set at 5, a fixed gap penalty set at 10, a k-tuple set at 2, a window size set at 10 and a floating gap penalty set at 10;

(ii) a protein comprising a fragment of at least 40 contiguous amino acids identical in sequence to an at least 40 contiguous amino acids of the first protein;

j) an isolated nucleic acid molecule comprising a nucleic acid sequence encoding a protein that comprises an at least 30 contiguous amino acid region identical in sequence to an at least 30 contiguous amino acid region of SEQ ID NO:55, SEQ ID NO:58, SEQ ID NO:61, SEQ ID NO:66, and SEQ ID NO:69;

(k) an isolated nucleic acid molecule of (j), wherein the protein binds to canine IL-13, as measured by its ability to inhibit IL-13-stimulated TF-1 cell proliferation;

(l) an isolated nucleic acid molecule of (j), wherein the isolated nucleic acid molecule contains a nucleic acid sequence that encodes an IL-13Rα2 protein of at least 40 amino acids in length, wherein said nucleic acid sequence comprises an at least 120 contiguous nucleotide sequence identical in sequence to an at least 120 contiguous nucleotide region of SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 or SEQ ID NO:70, wherein said isolated nucleic acid molecule does not hybridize under conditions comprising hybridization at 65° C. in 0.1×SSC followed by washing at 65° C. in 0.1×SSC with the third nucleic acid sequence selected from the group consisting of SEQ ID NO:95, SEQ ID NO:96, SEQ ID NO:97 and SEQ ID NO:98; and (m) an isolated nucleic acid molecule complementary of any of the above isolated nucleic acid molecules.

In another embodiment of the invention, proteins encoded by the above nucleic acid molecules are also provided. Such proteins include the following:

(a) a protein comprising an at least 40 contiguous amino acid region identical in sequence to an at least 40 contiguous amino acid region of SEQ ID NO:50;

(b) a protein comprising an amino acid sequence that is at least 85 percent identical in sequence to amino acid sequence SEQ ID NO:50 and a fragment thereof, wherein said fragment is at least 45 amino acids in length, wherein percent identity can be determined by a DNAsis™ computer program;

(c) a protein encoded by a nucleic acid molecule comprising an at least 120 contiguous nucleotide region identical in sequence to an at least 120 contiguous nucleotide region of a nucleic acid sequence selected from the group consisting of SEQ ID NO:48, SEQ ID NO:49, and SEQ ID NO:52;

(d) a protein comprising a first amino acid sequence of at least 30 amino acids in length, wherein said first amino acid sequence has at least 30 contiguous amino acid region identical in sequence to at least 30 contiguous amino acid region of SEQ ID NO:55, SEQ ID NO:58, SEQ ID NO:61, SEQ ID NO:66, or SEQ ID NO:69;

(e) a protein comprising a third amino acid sequence that is at least 70 percent identical in sequence to SEQ ID NO:55, SEQ ID NO:58, SEQ ID NO:61, SEQ ID NO:66, or SEQ ID NO:69, and a fragment thereof, wherein said fragment is at least 40 amino acids in length, wherein percent identity is determined by a DNAsis™ computer program; and (f) a protein encoded by a nucleic acid molecule comprising an at least 90 contiguous nucleotide region identical in sequence to an at least 90 contiguous nucleotide region of SEQ ID NO:54, SEQ ID NO:57, SEQ ID NO:60, SEQ ID NO:63, SEQ ID NO:65 or SEQ ID NO:68.

The present invention also provides chimeric nucleic acid molecules encoding a fusion protein in which the chimeric nucleic acid molecules contain a nucleic acid molecule encoding a carrier protein domain and a nucleic acid molecule encoding a canine IL-13Rα protein domain. The fusion protein can also contain a linker sequence. The carrier protein domain can be an immunoglobulin Fc region, preferably a canine immunoglobulin Fc region, and more preferably a canine immunoglobulin IgG Fc region. The canine IL-13Rα protein domain can be IL-13Rα1 or IL-13Rα2 protein domains. The chimeric nucleic acid molecule can contain the following nucleic acid sequences: SEQ ID NO:71, SEQ ID NO:74, SEQ ID NO:77, SEQ ID NO:80 and SEQ ID NO:82, as well as SEQ ID NO:48, SEQ ID NO:49, SEQ ID NO:52, SEQ ID NO:54, SEQ ID NO:57, SEQ ID NO:60, SEQ ID NO:63, SEQ ID NO:65, and SEQ ID NO:68. Additionally, the chimeric nucleic acid molecules can have a nucleic acid molecule encoding the carrier protein domain on the 5' end and the nucleic acid molecule encoding the IL-13R protein domain on the 3' end. Alternatively, the domains can be reversed.

The present invention further provides fusion proteins containing a carrier protein domain and a canine IL-13Rα domain. Preferably, the fusion protein contains an amino acid sequence of SEQ ID NO:72, SEQ ID NO:75, SEQ ID NO:78, and SEQ ID NO:81, as well as SEQ ID NO:52, SEQ ID NO:55, SEQ ID NO:58, SEQ ID NO:61, SEQ ID NO:66, and SEQ ID NO:69.

Additional embodiments of the present invention include mimetopes and multimeric forms of any of the above proteins. Antibodies that selectively bind to any of the canine IL-13R proteins of the present invention are also provided, as well as recombinant vectors, fusion constructs, fusion sequences, and recombinant cells containing at least one nucleic acid molecules of the present invention.

The present invention also includes therapeutic compositions and kits containing such nucleic acid molecules, proteins, antibodies and/or inhibitors, as well as their use to evaluate and regulate an immune response of an animal, including naked nucleotide vaccines and recombinant cell vaccines.

Also provided are methods to produce a canine Il-13Rα proteins by culturing a recombinant cell capable of expressing the protein, as well as methods of identifying an inhibitor of canine Il-13Rα activity by contacting a canine Il-13Rα1 protein with a putative inhibitory compound and determining if Il-13Rα protein activity is inhibited.

DETAILED DESCRIPTION OF INVENTION

The present invention provides for isolated nucleic acid molecules which encode a canine IgG (heavy and/or light chain) protein, isolated proteins encoded by the nucleic acid molecules, recombinant constructs and cells comprising the nucleic acid molecules and/or proteins, antibodies to the isolated proteins, inhibitors of the proteins and nucleic acids, therapeutic compositions useful for treating canine IgG (heavy and/or light chain)-mediated responses (including e.g., vaccines), methods for treating canine IgG (heavy and/or light chain)-mediated responses, methods for eliciting a canine IgG (heavy and/or light chain)-mediated immune response, and kits comprising the materials provided. According to the present invention, an isolated, or biologically pure, nucleic acid molecule or protein, is a nucleic acid molecule or protein that has been removed from its natural milieu. As such, "isolated" and/or "biologically pure" do not necessarily reflect the extent to which the nucleic acid molecule or protein has been purified. "Proteins" means any compounds that comprise amino acids, including peptides, polypeptides, fusion proteins, etc. It is further to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (e.g., combinations) of two or more of the compounds.

The present invention also comprises expression vectors and recombinant cells comprising the present nucleic acid molecules. Also provided are fusion proteins comprising canine IgG heavy chain proteins as well as fusion protein constructs encoding such fusion proteins. "Fusion protein" means a protein (including polypeptides) which are a combination of two or more protein regions or whole proteins. For example, two proteins may be fused and both functional as present in nature, or fused such that their function is altered. They may be fused by linking internal to the protein sequence of one or the other, or fused with a linker sequence. The linker sequence can be of any length, and any amino acid composition; it may contain advantageous features such as a cleavage site, phosphorylation site, glycosylation site, etc. A fusion protein can be obtained through translation of a fusion sequence. "Fusion sequence" is meant to refer to any nucleic acid sequence that is not naturally-occurring and can include: a canine sequence; a murine sequence; a equine sequence; a feline sequence; and a human sequence; a non-canine receptor sequence; a non-canine immunoglobulin sequence; and a non-canine cytokine sequence. A fusion protein can be made up of canine IgG or a portion thereof, attached, fused, joined to proteins or portions thereof (e.g. variable region of other species immunoglobulins) to "caninize"; add to other molecules for stability, or as an adjuvant.

As used herein, a canid refers to any member of the canid family (i.e. the family Canidae), including, but not limited to, domestic dogs, and wild canids such as wolves, foxes, and coyotes. Similarly, the term canine refers to "of the family Canidae".

Canine IgG nucleic acid molecules can encode entire IgG (e.g. heavy and light chain, or portion thereof) at least Fcgamma, or fragment thereof and variable region or fragment thereof. "Fragment" is meant to refer to any subset of the referent nucleic acid molecule. Moreover, included is a light chain or a fragment thereof and may be a single chain antibody. "Antibody" as used herein includes both polyclonal and monoclonal antibodies as well as fragments thereof, such as Fv, Fab and F(ab)$_2$ fragments that are capable of binding antigen or hapten. Also included are heterospecies—e.g. Canine Fc and other species variable regions. Moreover, small, functional fragments are also included, such as, but not limited to: the hinge regions, other regions, such as regions which probide stability, complement activation, antigenic regions, or Fcgamma receptor binding regions. Each domain is included (gamma 1, gamma 2, and gamma 3), as are any uses thereof.

The present invention also provides for isolated canine interleukin-13 receptor (IL-13R), proteins, nucleic acid molecules encoding such proteins, antibodies raised against such proteins and/or inhibitors of such proteins or nucleic acid molecules. The present invention provides for isolated IL-13Rα proteins, such as canine interleukin-13 receptor alpha 1 (IL-13Rα1), canine interleukin-13 receptor alpha 2 (IL-13Rα 2), canine IL-13Rα:canine IgG fusion proteins and nucleic acid molecules, as well as antibodies raised against such proteins, and/or inhibitors of such proteins or nucleic acid molecules. Also included in the present invention is the use of these proteins, nucleic acid molecules, antibodies, and/or compounds derived therefrom as therapeutic compositions to regulate the immune response of an animal as well as in other applications, such as those disclosed below.

Also provided for in the present invention are isolated canine nucleic acid molecules that includes a canine IL-13R nucleic acid molecule. As used herein a canine IL-13R nucleic acid molecule refers to a nucleic acid molecule that includes a canine IL-13 receptor alpha chain (IL-13Rα) nucleic acid molecule that encodes a canine IL-13 receptor alpha chain protein and/or a complement thereof. Preferably, a canine IL-13Rα nucleic acid molecule of the present invention is a canine IL-13Rα1 or IL-13Rα2 nucleic acid molecule that encodes a canine IL-13Rα1 or IL-13Rα2 protein and/or a complement thereof. As used herein, a canine nucleic acid molecule of the present invention is a nucleic acid molecule that is isolated from a canid or is derived therefrom in that it is produced using recombinant DNA technology, or by chemical synthesis. As such, a canine nucleic acid molecule includes natural forms as well as any variants thereof, such as a canine nucleic acid molecule that has been altered in a manner known to those skilled in the art, such as those methods disclosed herein. As used herein, a canine nucleic acid molecule does not refer to a mouse or human nucleic acid molecule.

Nucleic acid molecules of the present invention of known length isolated from *Canis familiaris* are denoted as follows: IL-13Rα1 is denoted as nCaIL-13Rα1$_x$, wherein "x" refers to the number of nucleotides in that molecule for example, nCaIL-13Rα1$_{483}$ refers to a canine IL-13Rα1 nucleic acid molecule of 483 nucleotides; and in a similar fashion, a IL-13Rα2 nucleic acid molecule of length "x" is referred to as nCaIL-13Rα2$_x$. Similarly, *Canis familiaris* IL-13Rα1 and IL-13Rα2 proteins of the present invention of known length isolated from are denoted PCaIL-13Rα1$_x$, and/or PcaIL-13Rα2$_x$, respectively.

One embodiment of the present invention is an isolated protein that includes a canine IL-13 receptor (IL-13R) protein. As used herein a canine IL-13R protein refers to a protein, or protein complex, that includes a canine IL-13 receptor alpha chain (IL-13Rα) protein. Preferably, a canine IL-13Rα protein of the present invention is a IL-13Rα1 protein or IL-13Rα2 protein. As used herein, a canine protein of the present invention is a protein that is isolated from a canid or is derived therefrom in that it is produced using recombinant DNA technology, or by chemical synthesis. As such, a canine protein includes natural forms as well as any variants thereof, such as a canine protein that has been altered in a manner known to those skilled in the art, such as those methods disclosed herein. As used herein, a canine protein does not refer to a mouse or human protein.

Identification of the canine IL-13R nucleic acid molecules of the present invention and particularly of the canine IL-13Rα2 nucleic acid molecules of the present invention is unexpected because initial attempts to obtain canine IL-13Rα nucleic acid molecules using standard cDNA screening conditions were unsuccessful. While not being bound by theory, it is believed that canine mRNAs encoding IL-13Rα proteins are extremely rare (i.e. present in very low concentrations, at best, in a cell).

The following Table 1 summarizes the Sequence Listing for convenience:

TABLE 1

| SEQ ID NO | Molecule | Description of the Sequence | Approx. Closest Identity[1] |
|---|---|---|---|
| 1 | | DNA encoding hinge region of clone 3523 | 45% |
| 2 | | deduced amino acid sequenced encoded by SEQ ID NO 1 | 34% |

TABLE 1-continued

| SEQ ID NO | Molecule | Description of the Sequence | Approx. Closest Identity[1] |
|---|---|---|---|
| 3 | | deduced complement of SEQ ID NO 1 | |
| 4 | | DNA encoding clone 3523 | 88% |
| 5 | | deduced amino acid sequenced encoded by SEQ ID NO 4 | 86% |
| 6 | | deduced complement of SEQ ID NO 4 | |
| 7 | | DNA encoding hinge region of clone Bly 8 | 51% |
| 8 | | deduced amino acid sequenced encoded by SEQ ID NO 7 | 89% |
| 9 | | deduced complement of SEQ ID NO 7 | |
| 10 | | DNA encoding clone Bly 8 | 90% |
| 11 | | deduced amino acid sequenced encoded by SEQ ID NO 10 | 88% |
| 12 | | deduced complement of SEQ ID NO 10 | |
| 13 | | DNA encoding hinge region of clone Bly 9 | 41% |
| 14 | | deduced amino acid sequenced encoded by SEQ ID NO 13 | 16% |
| 15 | | deduced complement of SEQ ID NO 13 | |
| 16 | | DNA encoding clone Bly 9 | 89% |
| 17 | | deduced amino acid sequenced encoded by SEQ ID NO 16 | 82% |
| 18 | | deduced complement of SEQ ID NO 16 | |
| 19 | | DNA encoding clone 4325 | 98% |
| 20 | | deduced amino acid sequenced encoded by SEQ ID NO 19 | 98% |
| 21 | | deduced complement of SEQ ID NO 19 | |
| 22 | | DNA encoding hinge region of clone 4325 | |
| 23 | | deduced amino acid sequenced encoded by SEQ ID NO 22 | |
| 24 | | deduced complement of SEQ ID NO 2 | |
| 25 | | Lambda part | |
| 26 | | deduced amino acid sequenced encoded by SEQ ID NO 25 | |
| 27 | | deduced complement of SEQ ID NO 25 | |
| 28 | | 3523 part | |
| 29 | | deduced amino acid sequenced encoded by SEQ ID NO 28 | |
| 30 | | deduced complement of SEQ ID NO 28 | |
| 31 | | 4325 part | |
| 32 | | deduced amino acid sequenced encoded by SEQ ID NO 31 | |
| 33 | | deduced complement of SEQ ID NO 31 | |
| 34 | | Bly 8-5 part | |

TABLE 1-continued

| SEQ ID NO | Molecule | Description of the Sequence | Approx. Closest Identity[1] |
|---|---|---|---|
| 35 | | deduced amino acid sequenced encoded by SEQ ID NO 34 | |
| 36 | | deduced complement of SEQ ID NO 34 | |
| 37 | | Bly 8-3C part | |
| 38 | | deduced amino acid sequenced encoded by SEQ ID NO 37 | |
| 39 | | deduced complement of SEQ ID NO 37 | |
| 40 | | Primer C-IgG330-F | |
| 41 | | Primer IgG-FWD1 | |
| 42 | | Primer IgG-REV1 | |
| 43 | | Primer IgG-REV2 | |
| 44 | | Primer IgG-REV3 | |
| 45 | | Primer IgG-REV4 | |
| 46 | | Primer K9 IgG 5' (F) | |
| 47 | | Primer Bly 822F | |
| 48 | nCaIL-13Rα1483 | partial | |
| 49 | nCaIL-13Rα11547 | partial CDS? CDS 1-1215 | |
| 50 | PCaIL-13Rα1405 | translated sequence | |
| 51 | RC | | |
| 52 | nCaIL-13Rα11215 | coding for seq id no: 3 CDS 1-1215 | |
| 53 | RC | | |
| 54 | nCaIL-13Rα2620 | partial, 5' end CDS 184-620 | |
| 55 | PCaIL-13Rα2145 | translated sequence | |
| 56 | RC | | |
| 57 | nCaIL-13Rα2878 | partial, 3' end CDS 1-765 | |
| 58 | PCaIL-13Rα2255 | translated sequence | |
| 59 | RC | | |
| 60 | nCaIL-13Rα21454 | full length CDS 184-1341 | |
| 61 | P CaIL-13Rα2386 | full length protein + signal sequence | |
| 62 | reverse complement | | |
| 63 | nCaIL-13Rα21158 | coding for PCaIL-13R2386 CDS 1-1158 | |
| 64 | reverse complement | | |
| 65 | nCaIL-13Rα21095 | full length minus signal sequence CDS 1-1095 | |
| 66 | PCaIL-13Rα2365 | protein | |
| 67 | RC | | |

TABLE 1-continued

| SEQ ID NO | Molecule | Description of the Sequence | Approx. Closest Identity[1] |
|---|---|---|---|
| 68 | nCaIL-13Rα2954 | extracellular portion of molecule CDS 1-954 | |
| 69 | PCaIL-13Rα2318 | protein for extracellular portion | |
| 70 | reverse complement | | |
| 71 | nCaIL-13Rα2-Fc-3523 | chimera 1686 CDS 1-1683 | |
| 72 | PCaIL-13Rα2-Fc-3523 | 561 aa | |
| 73 | reverse complement | | |
| 74 | nCaIL-13Rα2-Fc-4325 | chimera 1698 CDS 1-1695 | |
| 75 | PCaIL-13Rα2-Fc-4325 | 565 aa | |
| 76 | reverse complement | | |
| 77 | nCaIL-13Rα2-Fc-B9 | chimera 1692 CDS 1-1689 | |
| 78 | PCaIL-13Rα2-Fc-B9 | 563 aa | |
| 79 | reverse complement | | |
| 80 | nCaIL-13Rα2-Fc-B8 | chimera 1686 CDS 1-1683 | |
| 81 | PCaIL-13Rα2-Fc-B8 | 561 aa | |
| 82 | reverse complement | | |
| 83 | primer 13R1F1 | | |
| 84 | primer I3R1R1 | | |
| 85 | primer 13R2F1D | GARATHAARGTNAAYCCNCCNCARGAYTTYG ARAT | |
| 86 | primer 13R2F2D | TAYAARGAYGGNTTCTGAYYTNAAYAARGGN ATHGA | |
| 87 | primer 13R2R1D | CCAYTCNSWCCADATNCCRTCRTCNGCRCART ADATRTTNACYTT | |
| 88 | primer 13R2R2D | GCRTGRTCNARNCCYTCRTACCA | |
| 89 | primer 13R2F5 | AGCGGATCCCTCTATGCTTTCAAATGCTGAGA TAAAAGTTAATCCTCCTGAGG | |
| 90 | primer 13R2F2 | TGGACATCACCACAAGGAAATCGGG | |
| 91 | primer 13R2FcF | | |
| 92 | primer 13R2FcR2 | | |
| 93 | primer cIgGFcF | | |
| 94 | primer cIgGFcR | | |
| 95 | murine IL-13R bc | No. 5,710,023 seq id no: 1 | |
| 96 | human IL-13R bc | No. 5,710,023 seq id no: 3 | |
| 97 | RC, murine IL-13R | rc of seq id no: 48 | |
| 98 | RC, human IL-13R | rc of seq id no: 49 | |
| 99 | primer 13R1F2 | CTC TAC TAT TGG CAC AGC CTG GGA | |
| 100 | primer 13R1R2 | AGT CAG AGC AAA GGA ACA ACC AAT GTG | |

TABLE 1-continued

| SEQ ID NO | Molecule | Description of the Sequence | Approx. Closest Identity[1] |
|---|---|---|---|
| 101 | primer 13R1F3 | CCT CCC GAG GGA GCC AGC CCG | |
| 102 | primer 13R1R3 | CGG GCT GGC TCC CTC GGG AGG | |
| 103 | primer 13R1F4 | CAT GGT CCC CGG CGT TCT TCC | |
| 104 | primer 13R1F5 | GGT GAG AAT ACC GAC CCC ACG | |

[1]These figures are the result of comparison of GenBank Accession Number E03345 with the sequences shown in the sequence listing.

Included within the scope of the present invention, with particular regard to the nucleic acid molecules of the present invention, are allelic variants, degenerate sequences and other homologues. An allelic variant of a nucleic acid molecule, including the particular SEQ ID NO's cited herein, is a gene that occurs at essentially the same locus (or loci) in the genome as the gene including the particular SEQ ID NO's cited herein, but which, due to natural variations caused by, for example, mutation or recombination, has a similar but not identical sequence. Also included in the term allelic variant are allelic variants of cDNAs derived from such genes. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given animal, and/or among a group of two or more animals, since the respective genomes are diploid, and sexual reproduction will result in the reassortment of alleles. The present invention also includes homologues due to laboratory manipulation, such as, but not limited to, variants produced during polymerase chain reaction amplification or site directed mutagenesis. It is also well known that there is a substantial amount of redundancy in the various codons which code for specific amino acids. Therefore, this invention is also directed to those nucleic acid sequences which contain alternative codons which code for the same amino acid. Also included within the scope of this invention are homologues either in the nucleic acid sequence or the translated protein which do not substantially alter the ultimate physical properties of the expressed protein. For example, substitution of valine for leucine, arginine for lysine, or asparagine for glutamine may not cause a change in functionality of the protein.

In particular, there are provided isolated nucleic acid molecules, wherein said nucleic acid molecules comprise a nucleic acid sequence selected from the group consisting of:

(a) a nucleic acid sequence which has at least 55% identity to a nucleic acid sequence which is selected from the group consisting of SEQ ID NO 1, SEQ ID NO 7, and SEQ ID NO 13, wherein said identity can be determined using the DNAsis computer program and default parameters, (b) a nucleic acid sequence which has at least 95% identity to a nucleic acid sequence which is selected from the group consisting of SEQ ID NO 4, SEQ ID NO 10, and SEQ ID NO 16, wherein said identity is determined using the DNAsis computer program and default parameters, (c) a nucleic acid sequence which encodes an amino acid sequence which has at least 40% identity to an amino acid sequence selected from the group consisting of SEQ ID NO 2, and SEQ ID NO 14, wherein said identity is determined using the DNAsis computer program and default parameters, (d) a nucleic acid sequence which encodes an amino acid sequence which has at least 90% identity to an amino acid sequence selected from the group consisting of SEQ ID NO 5, SEQ ID NO 8, SEQ ID NO 11 and SEQ ID NO 17 wherein said identity is determined using the DNAsis computer program and default parameters, (e) a nucleic acid sequence which is an allelic variant of a nucleic acid sequence selected from the group consisting of SEQ ID NO 1, SEQ ID NO 4, SEQ ID NO 7, SEQ ID NO 10, SEQ ID NO 13, or SEQ ID NO 16; and (f) a nucleic acid sequence fully complementary to a nucleic acid sequence selected from the group consisting of a nucleic acid sequence of (a), a nucleic acid sequence of (b), a nucleic acid sequence of (c), a nucleic acid sequence of (d), a nucleic acid sequence of (e), and a nucleic acid sequence of (f).

Also provided are isolated nucleic acid molecules, wherein said nucleic acid molecules comprise a nucleic acid sequence selected from the group consisting of (a) a nucleic acid sequence which has at least 70% identity to a nucleic acid sequence which is selected from the group consisting of SEQ ID NO 1, SEQ ID NO 7, and SEQ ID NO 13, wherein said identity is determined using the DNAsis computer program and default parameters, (b) a nucleic acid sequence which encodes an amino acid sequence which has at least 70% identity to an amino acid sequence selected from the group consisting of SEQ ID NO 2, and SEQ ID NO 14, wherein said identity is determined using the DNAsis computer program and default parameters, (c) a nucleic acid sequence which is an allelic variant of a nucleic acid sequence selected from the group consisting of SEQ ID NO 1, SEQ ID NO 7, and SEQ ID NO 13, and (d) a nucleic acid sequence fully complementary to a nucleic acid sequence selected from the group consisting of a nucleic acid sequence of (a), a nucleic acid sequence of (b), and a nucleic acid sequence of (c).

Clone 3523 that encodes a full length canine IgG represents 95% of IgG populations in the dog spleen cell cDNA library. Clone 4325 that encodes entire constant region (Cγ1, Cγ2 and Cγ3) of canine IgG and partial variable region ($V_H$) of the immunoglobulin consists of about 5% of IgG in the library. Two additional IgG clones, Bly8 and Bly9 that encode Cγ1, Cγ2 and Cγ3 domains of canine IgG, were identified from canine B-cell lymphoma samples and confirmed by PCR from the spleen cell cDNA library as well as cDNAs prepared from eleven dogs, although these two IgG sequences were not detected in screening the library with $^{32}$P-labeled canine IgG DNA probes. The homology study indicates that the similarity among these four canine IgGs is between 72% to 85%. Over all similarity between IgG subclasses from canine, human and mouse is around 52-53%. Within the group of canine IgG, the difference among these IgG sequences is mainly in the hinge region of the molecules, although small difference also detected in Cγ2 and Cγ3. Evaluation of more than 200 canine IgG sequences from eighteen B-cell lymphoma samples and cDNAs prepared from samples of canine T-cell lymphoma shows that amino acid sequences of hinge region is highly conserved within each canine IgG subclass in samples from different dogs. However, the hinge region is quite diverse among different canine IgG subclasses with similarity around 19-35%. These results indicate that the unique sequence in hinge region is the nature of each canine IgG subclass, and not due to the polymorphism of canine IgGs.

Identification and characterization of four DNA sequences encoding different canine IgG subclasses will have broad applications in canine immunology research as well as in canine health care practices. The applications include that: (a) the invention will enable the raising of subclass specific monoclonal antibodies; (b) the information regarding each canine subclass will help in investigating the immunological functions of the IgGs in dogs that have different immunological status; (c) the outcome of (a) and (b) may have significant impacts in clinical applications such as identifying certain diseases and monitoring immunological status of dogs during the course of immunotherapy; and (d) furthermore, the identification of DNA and amino acid sequences encoding different canine IgG subclasses will be important in engineering canine specific therapeutic agents, for example, caninization of specific antibodies or constructing immunoadhesins for certain diseases and immunological disorders.

Also provided for in the present invention are canine IL-13Rα1 nucleic acid molecules that includes one or more of the following nucleic acid sequences:
 (a) the nucleic acid sequence SEQ ID NO:1 and/or
 (b) SEQ ID NO:49, and/or
 (c) a complements of these nucleic acid sequences, i.e. SEQ ID NO:51 and/or SEQ ID NO:53, respectively.

These nucleic acid sequences are further described herein. For example, nucleic acid sequence SEQ ID NO:48 represents the deduced nucleic acid sequence of a coding strand that encodes a partial (i.e. non-full length) IL-13Rα1 protein. SEQ ID NO:49 represents the deduced sequence of the coding strand of a canine IL-13Rα1 nucleic acid molecule nCaIL-13Rα1$_{1547}$, the cloning of which is disclosed in the examples. The complement of SEQ ID NO:49, represented herein by SEQ ID NO:51, refers to the nucleic acid sequence of the strand that is fully complementary to the strand having SEQ ID NO:49, which can be easily be determined by those skilled in the art. Likewise, a nucleic acid sequence complement of any nucleic acid sequence of the present invention refers to the nucleic acid sequence of the nucleic acid strand that is fully complementary to, i.e. can form a complete double helix with, the strand for which the sequence is cited. It should be noted that since nucleic acid sequencing technology is not entirely error-free, SEQ ID NO:49, as well as other nucleic acid and protein sequences presented herein, represents an apparent nucleic acid sequence of the nucleic acid molecule encoding a IL-13Rα1 protein of the present invention.

The nucleic acid sequences of the coding strand and complementary strand of nCaIL-13Rα1$_{1547}$ are represented herein as SEQ ID NO:49 and SEQ ID NO:51, respectively. Translation of SEQ ID NO:49 suggests that nucleic acid molecule nCa IL-13Rα1$_{1547}$ encodes a non full-length PCaIL-13Rα1 protein of about 405 amino acids, denoted herein as PCa IL-13Rα1$_{405}$, the amino acid sequence of which is presented in SEQ ID NO:50, assuming an open reading frame having an initiation codon spanning from nucleotide 1 through nucleotide 3 of SEQ ID NO:49 and a stop codon spanning from nucleotide 1216 through nucleotide 1218 of SEQ ID NO:49. Translation of SEQ ID NO:49 yields SEQ ID NO:50 and a double-stranded nucleic acid molecule representing the region encoding PCa IL-13Rα1$_{405}$ is denoted herein as nCa IL-13Rα1$_{1215}$, represented by SEQ ID NO:52 (coding strand) and SEQ ID NO:53 (complementary strand).

Another embodiment of the present invention is a canine IL-13Rα2 nucleic acid molecule that includes one or more of the following nucleic acid sequences:
 (a) the nucleic acid sequence SEQ ID NO:54, SEQ ID NO:57, SEQ ID NO:60, SEQ ID NO:63 and/or SEQ ID NO:65, and/or
 (b) the respective complements of these nucleic acid sequences, i.e. SEQ ID NO:56, SEQ ID NO:59, SEQ ID NO:62, SEQ ID NO:64 and/or SEQ ID NO:67, respectively.

These nucleic acid sequences are further described herein. For example, nucleic acid sequence SEQ ID NO:54 and SEQ ID NO:57 encode partial length IL-13Rα2 proteins. SEQ ID NO:60 represents the deduced sequence of the coding strand of a canine cDNA, canine IL-13Rα2 nucleic acid molecule nCaIL-13Rα2$_{1454}$ the cloning of which is disclosed in the examples.

The nucleic acid sequences of the coding strand and complementary strand of nCaIL-13Rα2$_{1454}$ are represented herein as SEQ ID NO:60 and SEQ ID NO:62, respectively. Translation of SEQ ID NO:60 suggests that nucleic acid molecule nCaIL-13Rα2$_{1454}$ encodes a full-length PCaIL-13Rα2 protein of about 386 amino acids, denoted herein as PCa IL-13Rα2$_{386}$, the amino acid sequence of which is presented in SEQ ID NO:61, assuming an open reading frame having an initiation codon spanning from nucleotide 184 through nucleotide 186 of SEQ ID NO:60 and a stop codon spanning from nucleotide 1341 through nucleotide 1343 of SEQ ID NO:60. Translation of SEQ ID NO:60 yields SEQ ID NO:61, and a double-stranded nucleic acid molecule representing the region encoding PCa IL-13Rα2$_{386}$ is denoted herein as nCa IL-13Rα2$_{1158}$, represented by SEQ ID NO:63 (coding strand) and SEQ ID NO:64 (complementary strand). Translation of the putative extracellular domain extending from about residue 22 to about residue 338 of SEQ ID NO:60, represented herein by SEQ ID NO:68 yields SEQ ID NO:69 encoding PCa IL-13Rα2$_{318}$ the protein of the extracellular domain. It is to be noted that SEQ ID NO:68 actually contains an ATG prior to the nucleotides encoding the extracellular domain; as such SEQ ID NO:69 represents the amino acids of the extracellular domain plus an initiation methionine. The natural extra-cellular domain of IL-13Rα2 is actually a 317 amino acid protein with an amino acid sequence spanning 2-318 of SEQ ID NO:69.

Yet another embodiment of the present invention is an IL-13Rα1 nucleic acid molecule that can be an allelic variant that includes a similar but not identical sequence to SEQ ID NO:48, SEQ ID NO:49, SEQ ID NO:51, SEQ ID NO:52 and/or SEQ ID NO:53 and/or any other IL-13Rα1 nucleic acid sequence cited herein.

In another embodiment, an IL-13Rα2 nucleic acid molecule can be an allelic variant that includes a similar but not identical sequence to SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 and SEQ ID NO:70 and/or any other IL-13Rα2 nucleic acid sequence cited herein.

In one embodiment, an IL-13Rα1 proteins of the present invention is encoded by a nucleic acid molecule comprising an apparent full-length IL-13Rα1 coding regions, i.e., a nucleic acid molecule encoding an apparent full-length IL-13Rα1 protein. Another embodiment of a preferred IL-13Rα1 protein is a fragment thereof encoded by a nucleic acid molecule encoding a protein that includes the low affinity IL-13Rα1 binding site.

In another embodiment, a preferred IL-13Rα protein of the present invention is encoded by a nucleic acid molecule comprising an apparent full-length IL-13Rα2 coding region, i.e., a nucleic acid molecules encoding an apparent full-length IL-13Rα2 protein. Another embodiment of a preferred IL-13Rα2 protein is a fragment thereof encoded by a nucleic acid molecule encoding a protein that includes the high affinity IL-13 binding site.

One embodiment of the present invention is an isolated canine IL-13Rα nucleic acid molecule. Preferred is an isolated canine IL-13Rα1 nucleic acid molecule or an isolated canine IL-13Rα2 nucleic acid molecule. Such a nucleic acid molecule can be RNA, DNA, or a modification thereof. An IL-13Rα nucleic acid of the present invention can be a full-length nucleic acid molecule of a homologue thereof. An IL-13Rα nucleic acid molecule can be single stranded or double stranded. An IL-13Rα nucleic acid molecule of the present invention can e full-length gene, a full-length mRNA or cDNA (complementary DNA) or any portion thereof. A preferred nucleic acid molecule encodes an IL-13Rα protein of the present invention. Such a nucleic acid molecule can encode a full-length protein, mature protein, extracellular domain, or any portion thereof.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters. A nucleic acid sequence of the present invention may have at least 85%, preferably at least 90%, and more preferably at least 95%, or even more preferably 100% sequence identity with a nucleic acid molecule in the sequence listing.

Additional preferred canine IgG nucleic acid molecules comprising a nucleic acid sequence that is preferably at least about at least 45% identical, more preferably about at least 50% identical, more preferably at least 55% identical, more preferably about at least 60% identical, more preferably about at least 65% identical, more preferably about at least 70% identical, more preferably about at least 75% identical, more preferably about at least 80% identical, more preferably about at least 85% identical, more preferably about at least 90% identical and even more preferably about at least 95% identical to a nucleic acid sequence selected from the exemplified sequences (e.g. SEQ ID Nos 1, 4, 7, 10, 13, 16, 19, 22, 25, 28, 31, 34, 37). Hinge region sequences preferred are those exemplified (e.g. SEQ ID Nos 1, 7, 13, 22). Heavy chain IgG-encoding nucleic acid sequences are are preferred, with the exemplified sequences being most preferred (e.g. SEQ ID Nos 4, 10, 16, 19, 28, 31, 34 and 37). Light chain canine IgG sequences are also provided, particularly those exemplified (e.g. SEQ ID NO 25). Particularly preferred are nucleic acid molecules comprising the exemplified sequences. Also preferred are fragments of any of such nucleic acid molecules. Percent identity may be determined using the Compare function by maximum matching within the program DNAsis Version 2.1 using default parameters.

Stringent hybridization conditions are determined based on defined physical properties of the nucleic acid molecule to which the nucleic acid molecule to be compared is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about at least 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will dissociate, assuming 100% complementarity between the two strands: $T_m=81.5°$ C.$+16.6$ log M$+0.41$(% G+C)$-500/n-0.61$(% formamide). For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation: $T_d=4(G+C)+2(A+T)$. A temperature of 5° C. below $T_d$ is used to detect hybridization between perfectly matched molecules.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, e.g., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridized under stringent hybridization conditions with a canine nucleic acid molecule of about 150 bp in length, the following conditions could preferably be used. The average G+C content of canine genome is about 53%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 86.3° C.:

$$81.5° C.+16.6 \log(0.15M)+(0.41\times53)-(500/150)-(0.61\times0)=86.3° C.$$

The present invention also includes nucleic acid molecules that are oligonucleotides capable of hybridizing, under stringent hybridization conditions, with complementary regions of other, preferably longer, nucleic acid molecules of the present invention such as those comprising canine IgG (heavy and/or light chain) genes or other canine IgG (heavy and/or light chain) nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules. The present invention also includes the use of such oligonucleotides to protect animals from disease using one or more of such technologies. Appropriate oligonucleotide-containing therapeutic compositions can be administered to an animal using techniques known to those skilled in the art.

Also well known to those skilled in the art is how base-pair mismatch, e.g. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (e.g., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridized under conditions designed to allow a desired amount of base pair mismatch.

Thus, based on the equation given previously, to achieve hybridization with nucleic acid molecules having about 30% base-pair mismatch, hybridization washes would be carried out at a temperature of about 56.3° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 56.3° C.

In one embodiment of the present invention, a preferred canine IgG (heavy and/or light chain) nucleic acid molecule includes an isolated nucleic acid molecule which hybridizes under conditions which preferably allow about 50% or less base pair mismatch, more preferably under conditions which allow about 45% or less base pair mismatch, more preferably under conditions which allow about 40% or less base pair mismatch, more preferably under conditions which allow about 35% or less base pair mismatch, more preferably under conditions which allow about 30% or less base pair mismatch, more preferably under conditions which allow about 25% or less base pair mismatch, more preferably under conditions which allow about 20% or less base pair mismatch, more preferably under conditions which allow about 15% or less base pair mismatch, more preferably under conditions which allow about 10% or less base pair mismatch and even more preferably under conditions which allow about 5% or less base pair mismatch with a nucleic acid molecule selected from the exemplified compounds.

The present invention also provides isolated nucleic acid molecules, wherein said nucleic acid molecules comprise a nucleic acid sequence selected from the group consisting of:

(a) a nucleic acid sequence comprising at least 70 contiguous nucleotides of the sequence shown in the sequence selected from the group consisting of SEQ ID NO 1, SEQ ID NO 7 and SEQ ID NO 13.

(b) a nucleic acid sequence comprising at least 350 contiguous nucleotides of the sequence shown in the sequence selected from the group consisting of SEQ ID NO 4, SEQ ID NO 10, and SEQ ID NO 16

(c) a nucleic acid sequence comprising at least 450 contiguous nucleotides of the sequence shown in SEQ ID NO 19, (d) a nucleic acid sequence which encodes an amino acid comprising at least 20 contiguous residues of the sequence shown in SEQ ID NO 2, and SEQ ID NO 14, (d) a nucleic acid sequence which encodes an amino acid comprising at least 100 contiguous residues of the sequence selected from the sequences shown in SEQ ID NO 5, SEQ ID NO 8, SEQ ID NO 11, and SEQ ID NO 17, (e) a nucleic acid sequence which encodes an amino acid comprising at least 200 contiguous residues of the sequence shown in SEQ ID NO 20, (f) a nucleic acid sequence fully complementary to a nucleic acid sequence selected from the group consisting of a nucleic acid sequence of (a), a nucleic acid sequence of (b), a nucleic acid sequence of (c), a nucleic acid sequence of (d), a nucleic acid sequence of (e), and a nucleic acid sequence of (f).

Also provided are isolated nucleic acid molecules, wherein said nucleic acid molecules comprise a nucleic acid sequence selected from the group consisting of (a) a nucleic acid sequence comprising at least 150 contiguous nucleotides of the sequence shown in the sequence selected from the group consisting of SEQ ID NO 1, and SEQ ID NO 13.

(b) a nucleic acid sequence comprising at least 500 contiguous nucleotides of the sequence shown in the sequence selected from the group consisting of SEQ ID NO 4, SEQ ID NO 7, SEQ ID NO 10, and SEQ ID NO 16

(c) a nucleic acid sequence comprising at least 700 contiguous nucleotides of the sequence shown in SEQ ID NO 19, (d) a nucleic acid sequence which encodes an amino acid comprising at least 50 contiguous residues of the sequence shown in SEQ ID NO 2, and SEQ ID NO 14, (e) a nucleic acid sequence which encodes an amino acid comprising at least 200 contiguous residues of the sequence selected from the sequences shown in SEQ ID NO 5, SEQ ID NO 8, SEQ ID NO 11, and SEQ ID NO 17, (f) a nucleic acid sequence which encodes an amino acid comprising at least 300 contiguous residues of the sequence shown in SEQ ID NO 20, (g) a nucleic acid sequence fully complementary to a nucleic acid sequence selected from the group consisting of a nucleic acid sequence of (a), a nucleic acid sequence of (b), a nucleic acid sequence of (c), a nucleic acid sequence of (d), a nucleic acid sequence of (e), a nucleic acid sequence of (f), and a nucleic acid sequence of (g).

Also provided are isolated nucleic acid molecules, wherein said nucleic acid molecules comprise a nucleic acid sequence selected from the group consisting of (a) a nucleic acid sequence which is selected from the group consisting of SEQ ID NO 1, SEQ ID NO 4, SEQ ID NO 7, SEQ ID NO 10, SEQ ID NO 13, SEQ ID NO 16, and SEQ ID NO 19, (b) a nucleic acid sequence which is selected from the group consisting of SEQ ID NO 2, SEQ ID NO 5, SEQ ID NO 8, SEQ ID NO 111, SEQ ID NO 14, SEQ ID NO 17, and SEQ ID NO 20, (c) a nucleic acid sequence fully complementary to a nucleic acid sequence selected from the group consisting of a nucleic acid sequence of (a), and a nucleic acid sequence of (b).

Another embodiment of the present invention is a preferred canine IL-13Rα1 nucleic acid molecule that includes a isolated nucleic acid molecule of at least 75 nucleotides in length or (b) an isolated nucleic acid molecule that hybridizes under conditions which allow less than or equal to about 10% base pair mismatch, and even more preferably under conditions which allow less than or equal to about 5% base pair mismatch with a nucleic acid molecule selected from the group consisting of SEQ ID NO:48, SEQ ID NO:49, SEQ ID NO:51, SEQ ID NO:52 and/or SEQ ID NO:53, and/or a fragment thereof having at least 80 nucleotides.

Preferred canine IL-13Rα1 nucleic acid molecules of the present invention include nucleic acid molecules comprising a nucleic acid sequence that is preferably at least about 90%, more preferably at least about 92%, more preferably about 94%, more preferably about 96%, and even more preferably at least about 98% identical to a nucleic acid sequence selected from the group consisting of SEQ ID NO:48, SEQ ID NO:49, SEQ ID NO:51, SEQ ID NO:52 and/or SEQ ID NO:53. Also preferred are fragments of any of such nucleic acid molecules, particularly those that are at least about 80 nucleotides, at least about 85 nucleotides, at least about 90 nucleotides, at least about 95 nucleotides, at least about 100 nucleotides, at least about 120 nucleotides, at least about 140 nucleotides, at least about 160 nucleotides, at least about 180 nucleotides, at least about 200 nucleotides, at least about 250 nucleotides, at least about 300 nucleotides, at least about 350 nucleotides, or at least about 400 nucleotides at least about 500 nucleotides, at least about 600 nucleotides, at least about 700 nucleotides, at least about 800 nucleotides, at least about 900 nucleotides, at least about 1000 nucleotides, at least about 1100 nucleotides, at least about 1300 nucleotides, or at least about 1500 nucleotides. Percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10.

One embodiment of the present invention is a canine IL-13Rα1 nucleic acid molecule that includes an isolated nucleic acid molecule of at least 75 nucleotides that hybridizes under conditions which allow less than or equal to about 10% base pair mismatch, and even more preferably under conditions which allow less than or equal to about 5% base pair mismatch with a nucleic acid molecule selected from the group consisting of SEQ ID NO:48, SEQ ID NO:49, SEQ ID NO:51, SEQ ID NO:52 and/or SEQ ID NO:53, and/or a fragment thereof having at least 80 nucleotides. Also preferred are fragments of at least 85, at least 90, at least 95, at least 100, at least 110, at least 120, at least 140, at least 160, at least 180, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, or at least 1600 nucleotides in length.

Preferred canine IL-13Rα1 nucleic acid molecules of the present invention include nucleic acid molecules comprising a nucleic acid sequence that is preferably at least about 90%, more preferably at least about 92%, more preferably about 94%, more preferably about 96%, and even more preferably at least about 98% identical to a nucleic acid sequence selected from the group consisting of SEQ ID NO:48, SEQ ID NO:49, SEQ ID NO:51, SEQ ID NO:52 and/or SEQ ID NO:53. Also preferred are oligonucleotides of any of such nucleic acid molecules, particularly those that are at least about 80 nucleotides. Percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10.

Another embodiment of a canine IL-13Rα1 nucleic acid molecule of the present invention is
(a) an isolated nucleic acid molecule comprising a nucleic acid sequence encoding a protein selected from the group consisting of: (i) a protein that is at least 85, at least 90, at least 95, or at least 100 percent identical in sequence to amino acid sequence SEQ ID NO:50, wherein said percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10; and (ii) a protein comprising a fragment of at least 45 contiguous amino acids identical in sequence to an at least 45 contiguous amino acid sequence of a protein of (a);
(b) an isolated nucleic acid molecule comprising a nucleic acid sequence encoding a protein that comprises an at least 40 contiguous amino acid region identical in sequence to an at least 40 contiguous amino acid region of SEQ ID NO:50; and
(c) an isolated nucleic acid molecule fully complementary to any of the nucleic acid molecules of (a) or (b). Also preferred are fragments that are at least 50, at least 55, at least 60, at least 65, at least 70, at least 75, at least 80, at least 85, at least 90, at least 95, at least 100, at least 120, at least 140, at least 160, at least 180, at least 200, at least 250, at least 300, at least 350, at least 400, at least 450, at least 500, or at least 550 amino acids in length.

One embodiment of the present invention is an IL-13Rα2 nucleic acid molecule that includes at least one of the following: (a) an isolated nucleic acid molecule including at least 40 contiguous nucleotides identical in sequence to an at least 40 contiguous nucleotide region of at least one of the following nucleic acid sequences: SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 and SEQ ID NO:70; and (b) an isolated nucleic acid molecule including a nucleic acid sequence that is at least 80, at least 85, at least 90, at least 95, at least 100 percent identical in sequence to at least one of the following nucleic acid sequences: SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 and SEQ ID NO:70, and a fragment thereof, wherein the fragment is at least 50 nucleotides in length, and wherein percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10. In one embodiment, each of these nucleic acid molecule is a canine IL-13Rα2 nucleic acid molecule. In another embodiment, such nucleic acid molecules do not hybridize under conditions comprising hybridization at 65° C. in 0.1×SSC followed by washing at 65° C. in 0.1×SSC with a nucleic acid sequence selected from the group consisting of SEQ ID NO:95, SEQ ID NO:96, SEQ ID NO:97 and SEQ ID NO:98. In one embodiment, such nucleic acid molecules do not hybridize under conditions comprising hybridization at 52° C. in 5×SSC followed by washing at 52° C. in 2×SSC with a nucleic acid sequence selected from the group consisting of SEQ ID NO:95, SEQ ID NO:96, SEQ ID NO:97 and SEQ ID NO:98, unless detection of hybridization requires a long time to detect, for example, because the signal is so low as to resemble background. Also preferred are fragments that are at least 45, at least 55, at least 60, at least 65, at least 70, at least 75, at least 80, at least 85, at least 90, at least 95, at least 100, at least 120, at least 140, at least 160, at least 180, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, or at least 1600 nucleotides in length.

One embodiment of the present invention is a canine IL-13Rα2 nucleic acid molecule that hybridizes under conditions which allow less than or equal to about 20% base pair mismatch, preferably under conditions which allow less than or equal to about 15% base pair mismatch, more preferably under conditions which allow less than or equal to about 10% base pair mismatch, more preferably under conditions which allow less than or equal to about 5% base pair mismatch with a nucleic acid molecule selected from the group consisting of SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 and SEQ ID NO:70.

Another embodiment of the present invention is an isolated nucleic acid molecule selected from the group consisting of: (a) an isolated nucleic acid molecule comprising a nucleic acid sequence encoding a protein selected from the group consisting of: (i) a protein comprising an amino acid sequence that is at least 70, at least 75, at least 80, at least 85, at least 90, at least 95 or at least 100 percent identical in sequence to an amino acid sequence selected from the group consisting of SEQ ID NO:55, SEQ ID NO:58, SEQ ID NO:61, SEQ ID NO:66, and SEQ ID NO:69, wherein percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10, and ii) a protein comprising a fragment of at least 40 contiguous amino acids identical in sequence to an at least 40 contiguous amino acid sequence of a protein of (a)(i); (b) an isolated nucleic acid molecule comprising a nucleic acid sequence encoding a protein that comprises an at least 30 contiguous amino acid region identical in sequence to an at least 30 contiguous amino acid region of SEQ ID NO:55, SEQ ID NO:58, SEQ ID NO:61, SEQ ID NO:66, and SEQ ID NO:69; and (c) an isolated nucleic acid molecule fully complementary to any of the nucleic acid molecules of (a) or (b). In one embodiment, each of these nucleic acid molecule is a canine IL-13Rα2 nucleic acid molecule. In another embodiment, such nucleic acid molecules do not hybridize under conditions comprising hybridization at 65° C. in 0.1×SSC followed by washing at 65° C. in 0.1×SSC with a nucleic acid sequence selected from the group consisting of SEQ ID NO:95, SEQ ID NO:96, SEQ ID NO:97 and SEQ ID NO:98. In one embodiment, such nucleic acid molecules do not hybridize under conditions comprising hybridization at 52° C. in 5×SSC followed by washing at 52° C. in 2×SSC with a nucleic acid sequence selected from the group consisting of SEQ ID NO:95, SEQ ID NO:96, SEQ ID NO:97 and SEQ ID NO:98, unless detection of hybridization requires a long time to detect, for example, because the signal is so low as to resemble background. Also preferred are fragments that are at least 45, at least 50, at least 55, at least 60, at least 65, at least 70, at least 75, at least 80, at least 85, at least 90, at least 95, at least 100, at least 120, at least 140, at least 160, at least 180, at least 200, at least 250, at least 300, at least 350, at least 400, at least 450, at least 500, or at least 550 amino acids in length.

Another embodiment of the present invention, as discussed elsewhere herein, is a chimeric nucleic acid molecule that includes a nucleic acid molecule encoding a carrier protein domain and a nucleic acid molecule encoding a CaIL-13Rα protein domain. A nucleic acid molecule encoding a CaIL-13Rα protein domain can be any CaIL-13Rα protein-encoding nucleic acid molecule of the present invention, including any CaIL-13Rα1 protein-encoding nucleic acid molecule of the present invention or any CaIL-13Rα2 protein-encoding nucleic acid molecule of the present invention. The present invention also includes nucleic acid molecules fully complementary to the coding strands of such chimeric nucleic acid molecules.

One embodiment of the present invention is a nucleic acid molecule comprising all or part of nucleic acid molecules nCaIL-13Rα$1_{483}$, nCaIL-13Rα$1_{1547}$, nCaIL-13Rα$1_{1215}$, nCaIL-13Rα$2_{620}$, nCaIL-13Rα$2_{878}$, nCaIL-13Rα$2_{1454}$, nCaIL-13Rα$2_{1158}$, nCaIL-13Rα$2_{1098}$, nCaIL-13Rα$2_{954}$, nCaIL-13Rα2-Fc-3523, nCaIL-13Rα2-Fc-4325, nCaIL-13Rα2-Fc-B9, nCaIL-13Rα2-Fc-B8, or allelic variants of any of these nucleic acid molecules. As such, a preferred nucleic acid molecule of the present invention includes at least a portion of nucleic acid sequence SEQ ID NO:48, SEQ ID NO:49, SEQ ID NO:52, SEQ ID NO:54, SEQ ID NO:57, SEQ ID NO:60, SEQ ID NO:63, SEQ ID NO:65, SEQ ID NO:68, SEQ ID NO:71, SEQ ID NO:74, SEQ ID NO:77 and/or SEQ ID NO:80 as well as allelic variant of any of these listed nucleic acid molecules. Also included in the present invention are other homologs of nucleic acid molecules having these nucleic acid sequences; preferably such a homolog encodes or is complementary to a nucleic acid molecule that encodes at least one epitope that elicits an immune response against a protein having amino acid sequence SEQ ID NO:50, SEQ ID NO:55, SEQ ID NO:58, SEQ ID NO:61, SEQ ID NO:66, SEQ ID NO:69, SEQ ID NO:72, SEQ ID NO:75, SEQ ID NO:78 and/or SEQ ID NO:81. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound, such as a multivalent vaccine. The present invention also includes nucleic acid molecules that have been modified to accommodate codon usage properties of the cells in which such nucleic acid molecules are to be expressed.

In another embodiment, a preferred canine IL-13Rα1 nucleic acid molecule encodes a IL-13Rα1 protein at least about 45 amino acids, at least about 100 amino acids, at least about 120 amino acids, at least about 150 amino acids, at least about 170 amino acids, at least about 190 amino acids, at least about 210 amino acids in length, at least about 250 amino acids in length, at least about 350 amino acids in length, or about 405 amino acids in length.

In another embodiment, a preferred canine IL-13Rα2 nucleic acid molecule encodes a IL-13Rα2 protein at least about 40 amino acids, at least about 100 amino acids, at least about 120 amino acids, at least about 150 amino acids, at least about 170 amino acids, at least about 190 amino acids, at least about 210 amino acids in length, at least about 250 amino acids in length, at least about 350 amino acids in length, or about 386 amino acids in length.

A preferred canine nucleic acid molecule comprises a nucleic acid sequence that encodes at least a portion of a canine IL-13Rα2 protein that is capable of binding to IL-13Rα2 ligand(s) as disclosed herein. Preferably, such a nucleic acid molecule encodes a protein having SEQ ID NO:50, SEQ ID NO:55, SEQ ID NO:58, SEQ ID NO:61, SEQ ID NO:66, and/or SEQ ID NO:69, or allelic variants thereof.

The present invention also includes nucleic acid molecules that are oligonucleotides capable of hybridizing, under stringent hybridization conditions, with complementary regions of other, preferably longer, canine IL-13Rα nucleic acid molecules of the present invention. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention, typically from about 12 to 15 to about 17 to 18 nucleotides depending on the GC/AT content. A preferred oligonucleotide of the present invention has a maximum size of from about 100 to about 200 nucleotides. The present invention includes oligonucleotides that can be used as, for example, probes to identify nucleic acid molecules, primers to produce nucleic acid molecules, or therapeutic reagents to inhibit canine IL-13Rα protein production or activity, e.g., as antisense-, triplex formation-, ribozyme- and/or RNA drug-based reagents. The present invention also includes the use of such oligonucleotides to protect animals from disease using one or more of such technologies. Appropriate oligonucleotide-containing therapeutic compositions can be administered to an animal using techniques known to those skilled in the art.

Knowing the nucleic acid sequences of certain canine IgG (heavy and/or light chain) nucleic acid molecules and canine IL-13Rα nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), (c) obtain canine IgG (heavy and/or light chain) nucleic acid molecules and/or canine IL-13Rα nucleic acid molecules from other species, and (d) construct fusion nucleic acid molecules comprising canine IgG (heavy and/or light chain) and canine IL-13Rα nucleic acid sequences. Such nucleic acid molecules can be obtained in a variety of ways including screening appropriate expression libraries with antibodies of the present invention; traditional cloning techniques using oligonucleotide probes of the present invention to screen appropriate libraries of DNA; and PCR amplification of appropriate libraries or DNA using oligonucleotide primers of the present invention. Preferred libraries to screen or from which to amplify nucleic acid molecules include canine cDNA libraries as well as genomic DNA libraries. Similarly, preferred DNA sources to screen or from which to amplify nucleic acid molecules include canine adult cDNA and genomic DNA. Techniques to clone and amplify genes are disclosed, for example, in Sambrook et al., ibid.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of canine IgG (heavy and/or light chain) nucleic acid molecules and/or canine IL-13Rα nucleic acid molecules of the present invention.

One type of recombinant vector, referred to herein as a recombinant molecule, comprises a nucleic acid molecule of the present invention operatively linked to an expression vector. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (e.g., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, recombinant molecules of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with dogs.

Suitable and preferred nucleic acid molecules to include in recombinant vectors of the present invention are as disclosed herein. Preferred nucleic acid molecules to include in recombinant vectors include canine IgG, and fragments thereof, canine IL-13Rα as well as fusions of canine IgG and canine IL-13Rα nucleic acid sequences. Particularly preferred nucleic acid molecules to include in recombinant vectors, and particularly in recombinant molecules, include nCaIL-13Rα$1_{483}$, nCaIL-13Rα1547, nCaIL-13Rα1215, nCaIL-13Rα$2_{620}$, nCaIL-13Rα$2_{878}$, nCaIL-13Rα$2_{1454}$, nCaIL-13Rα$2_{1158}$, nCaIL-13Rα$2_{1098}$, nCaIL-13Rα$2_{954}$, nCaIL-13Rα2-Fc-3523, nCaIL-13Rα2-Fc-4325, n-CaIL-13Rα2-Fc-B9, and nCaIL-13Rα2-Fc-B8.

Recombinant molecules of the present invention may also (a) contain secretory signals (e.g., signal segment nucleic acid sequences) to enable an expressed canine IgG (heavy and/or light chain) protein and/or canine IL-13Rα proteins of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more nucleic acid molecules or recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed, i.e., recombinant, cell in such a manner that their ability to be expressed is retained.

Preferred nucleic acid molecules with which to transform a cell include canine IgG (heavy and/or light chain) nucleic acid molecules and/or canine IL-13Rα nucleic acid molecules and/or fusions of said nucleic acid molecules disclosed herein. Particularly preferred nucleic acid molecules with which to transform a cell include nCaIL-13Rα$1_{483}$, nCaIL-13Rα$1_{1547}$, nCaIL-13Rα$1_{1215}$, nCaIL-13Rα$2_{620}$, nCaIL-13Rα$2_{878}$, nCaIL-13Rα$2_{1454}$, nCaIL-13Rα$2_{1158}$, nCaIL-13Rα$2_{1098}$, nCaIL-13Rα$2_{954}$, nCaIL-13Rα2-Fc-3523, nCaIL-13Rα2-Fc-4325, nCaIL-13Rα2-Fc-B9, and nCaIL-13Rα2-Fc-B8.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Also provided by the present invention are recombinant cells transformed with a nucleic acid described herein. Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (e.g., naturally) capable of producing canine IgG (heavy and/or light chain) and/or canine IL-13Rα proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells. More preferred host cells include *Salmonella, Escherichia, Bacillus, Listeria, Saccharomyces, Spodoptera, Mycobacteria, Trichoplusia*, BHK (baby hamster kidney) cells, MDCK cells (normal dog kidney cell line for canine herpesvirus cultivation), CRFK cells (normal cat kidney cell line for canine herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1$_x$3987 and SR-11$_x$4072; *Spodoptera frugiperda; Trichoplusia ni*; BHK cells; MDCK cells; CRFK cells; CV-1 cells; COS cells; Vero cells; and non-tumorIgGnic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK[31] cells and/or HeLa cells. In one embodiment, the proteins may be expressed in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein.

Recombinant cells of the present invention can also be co-transformed with one or more recombinant molecules including canine IgG and/or canine IL-13Rα nucleic acid molecules encoding one or more proteins of the present invention and one or more other nucleic acid molecules encoding other compounds. Suitable and preferred nucleic acid molecules as well as suitable and preferred recombinant molecules with which to transform cells are disclosed herein.

Another embodiment of the present invention are isolated canine IgG proteins, wherein said proteins comprise an amino acid sequence selected from the group consisting of"
  (a) an amino acid sequence encoded by a nucleic acid sequence which has at least 70% identity to a nucleic acid sequence which is selected from the group consisting of SEQ ID NO 1, SEQ ID NO 7, and SEQ ID NO 13, wherein said identity is determined using the DNAsis computer program and default parameters,
  (b) an amino acid sequence which has at least 70% identity to an amino acid sequence selected from the group consisting of SEQ ID NO 2, and SEQ ID NO 14, wherein said identity is determined using the DNAsis computer program and default parameters, and
  (c) an amino acid sequence encoded by a nucleic acid sequence which is an allelic variant of a nucleic acid sequence selected from the group consisting of SEQ ID NO 1, SEQ ID NO 7, and SEQ ID NO 13.

Also provided are canine IgG proteins, wherein said proteins comprise an amino acid sequence selected from the group consisting of:
  (a) an amino acid sequence encoded by a nucleic acid sequence comprising at least 70 contiguous nucleotides of the sequence shown in the sequence selected from the group consisting of SEQ ID NO 1, and SEQ ID NO 13.
  (b) an amino acid sequence encoded by a nucleic acid sequence comprising at least 350 contiguous nucleotides of the sequence shown in the sequence selected from the group consisting of SEQ ID NO 4, SEQ ID NO 7, SEQ ID NO 10, and SEQ ID NO 16
  (c) an amino acid sequence encoded by a nucleic acid sequence comprising at least 450 contiguous nucleotides of the sequence shown in SEQ ID NO 19,
  (d) an amino acid sequence encoded by a nucleic acid sequence which is selected from the group consisting of SEQ ID NO 1, SEQ ID NO 4, SEQ ID NO 7, SEQ ID NO 10, SEQ ID NO 13, SEQ ID NO 16, and SEQ ID NO 19,
  (e) an amino acid comprising at least 20 contiguous residues of the sequence shown in SEQ ID NO 2, and SEQ ID NO 14,
  (f) an amino acid comprising at least 100 contiguous residues of the sequence selected from the sequences shown in SEQ ID NO 5, SEQ ID NO 8, SEQ ID NO 11, and SEQ ID NO 17, (g) an amino acid comprising at least 200 contiguous residues of the sequence shown in SEQ ID NO 20, (h) an amino acid sequence which is selected from the group consisting of SEQ ID NO 2, SEQ ID NO 5, SEQ ID NO 8, SEQ ID NO 11, SEQ ID NO 14, SEQ ID NO 17, and SEQ ID NO 19.

Moreover, there are provided isolated proteins, wherein said proteins comprise an amino acid sequence selected from the group consisting of:

(a) an amino acid sequence encoded by a nucleic acid sequence comprising at least 150 contiguous nucleotides of the sequence shown in the sequence selected from the group consisting of SEQ ID NO 1, and SEQ ID NO 13.

(b) an amino acid sequence encoded by a nucleic acid sequence comprising at least 500 contiguous nucleotides of the sequence shown in the sequence selected from the group consisting of SEQ ID NO 4, SEQ ID NO 7, SEQ ID NO 10, and SEQ ID NO 16

(c) an amino acid sequence encoded by a nucleic acid sequence comprising at least 700 contiguous nucleotides of the sequence shown in SEQ ID NO 19, (d) an amino acid sequence encoded by a nucleic acid sequence which is selected from the group consisting of SEQ ID NO 1, SEQ ID NO 4, SEQ ID NO 7, SEQ ID NO 10, SEQ ID NO 13, SEQ ID NO 16, and SEQ ID NO 19, (e) an amino acid comprising at least 50 contiguous residues of the sequence shown in SEQ ID NO 2, and SEQ ID NO 14, (f) an amino acid comprising at least 200 contiguous residues of the sequence selected from the sequences shown in SEQ ID NO 5, SEQ ID NO 8, SEQ ID NO 11, and SEQ ID NO 17, (g) an amino acid comprising at least 300 contiguous residues of the sequence shown in SEQ ID NO 20, (h) an amino acid sequence which is selected from the group consisting of SEQ ID NO 2, SEQ ID NO 5, SEQ ID NO 8, SEQ ID NO 11, SEQ ID NO 14, SEQ ID NO 17, and SEQ ID NO 19.

Proteins which would result from expression of the nucleic acid molecules herein disclosed are preferred, with the proteins which would result from expression of the exemplified nucleic acid molecules being most preferred (e.g. SEQ ID Nos 2, 5, 8, 11, 14, 17, 20, 23, 26, 29, 32, 35, and 38). Hinge region canine IgG proteins are provided, especially those exemplified (e.g. SEQ ID Nos 2, 8, 14, and 23). Heavy chain canine IgG proteins are also provided, especially those exemplified (e.g. SEQ ID Nos 5, 11, 17, 20, 29, 32, 35, and 38). Light chain sequences are also provided, especially those exemplified (e.g. SEQ ID NO 26). It is understood that proteins which result from expression of allelic variants of the exemplified sequences.

According to the present invention, a canine IgG (heavy and/or light chain) protein of the present invention refers to: a heavy or light chain of canine IgG protein; a heavy or light chain of canine IgG homolog; or a heavy or light chain of canine IgG peptide. Preferably, a heavy chain of canine IgG protein binds to the hinge regions, elicits immune (e.g. antibody) response, induces complement, binds to Fcgamma receptor, etc. In the present invention, a "protein" includes sequences, homologues, fragments (e.g. peptides).

A canine IgG heavy chain protein of the present invention, including a homolog, can be identified in a straight-forward manner by the protein's ability to bind to anti-canine IgG antibodies. Examples of canine IgG (heavy and/or light chain) protein homologs include canine IgG (heavy and/or light chain) proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog is capable of binding to anti-canine IgG antibodies.

In another embodiment, a preferred canine IgG (heavy and/or light chain) protein includes a protein encoded by a nucleic acid molecule that hybridizes under conditions which preferably allow about 35% or less base pair mismatch, more preferably under conditions which allow about 30% or less base pair mismatch, more preferably under conditions which allow about 25% or less base pair mismatch, more preferably under conditions which allow about 20% or less base pair mismatch, more preferably under conditions which allow about 15% or less base pair mismatch, more preferably under conditions which allow about 10% or less base pair mismatch, and even more preferably under conditions which allow about 5% or less base pair mismatch with a nucleic acid molecule selected from the exemplified nucleic acid molecules.

Another embodiment of the present invention includes a canine IgG (heavy and/or light chain) protein encoded by a nucleic acid molecule selected from the group consisting of: a nucleic acid molecule which hybridizes, in a solution comprising 1×SSC and 0% formamide, at a temperature of about 56° C., to a nucleic acid sequence selected from the exemplified nucleic acid sequences; and a nucleic acid molecule comprising a fragment of any of said nucleic acid molecules.

Yet another preferred canine IgG (heavy and/or light chain) protein of the present invention includes a protein encoded by a nucleic acid molecule which is preferably about at least 45% identical, more preferably about at least 50% identical, more preferably about at least 55% identical, more preferably about at least 60% identical, more preferably about at least 65% identical, more preferably about at least 70% identical, more preferably about at least 75% identical, more preferably about at least 80% identical, more preferably about at least 85% identical, more preferably about at least 90% identical and even more preferably about at least 95% identical, more preferably 100% identical to a presently-disclosed nucleic acid molecule, and/or fragments of such proteins. Percent identity as used herein is determined using the Compare function by maximum matching within the program DNAsis Version 2.1 using default parameters.

Preferred heavy chain canine IgG proteins of the present invention include proteins comprising amino acid sequences that are at least about 40%, particularly at least about 50%, preferably at least about 55%, more preferably at least about 60%, even more preferably at least about 65%, even more preferably at least about 70%, even more preferably at least about 75%, even more preferably at least about 80%, even more preferably at least about 85%, even more preferably at least about 90%, and even more preferably at least about 95%, identical to amino acid sequence exemplified herein.

The canine IgG (heavy and/or light chain) protein homologs can be the result of natural allelic variation or natural mutation. Canine IgG protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

The minimal size of an IgG protein homolog of the present invention is a size sufficient to be encoded by a nucleic acid molecule capable of forming a stable hybrid (e.g., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (e.g., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a heavy chain of canine IgG protein homolog of the present invention is from about 12 to about 18 nucleotides in length. Thus, the minimal size of a heavy chain of canine IgG protein homolog of the present invention is from about 4 to about 6 amino acids in length. There is no limit, other than a practical limit, on the maximal size of such a nucleic acid molecule in that the nucleic acid molecule can include gene, an entire gene, multiple genes, or portions thereof. The preferred size of a protein encoded by a nucleic acid molecule of the present invention depends on whether a full-length, fusion, multivalent, or functional portion of such a protein is desired.

The present invention also includes mimetopes of heavy chain of canine IgG proteins of the present invention. As used herein, a mimetope of a heavy chain of canine IgG protein of the present invention refers to any compound that is able to mimic the activity of such a heavy chain of canine IgG protein (e.g., ability to bind to anti-canine antibodies), often because the mimetope has a structure that mimics heavy chain of canine IgG protein. It is to be noted, however, that the mimetope need not have a structure similar to a heavy chain of canine IgG protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of heavy chain of canine IgG proteins of the present invention. Mimetopes can also be obtained by generating random samples of molecules, such as oligonucleotides, peptides or other organic molecules, and screening such samples by affinity chromatography techniques using the corresponding binding partner, (e.g., a canine Fcgamma-binding domain or anti-heavy chain of canine IgG antibody). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source.

Specific examples of heavy chain of canine IgG mimetopes include anti-idiotypic antibodies, oligonucleotides produced using Selex™ technology, peptides identified by random screening of peptide libraries and proteins identified by phage display technology. A preferred mimetope is a peptidomimetic compound that is structurally and/or functionally similar to a heavy chain of canine IgG protein of the present invention, particularly to the FcgammaR-binding domain of heavy chain of canine IgG protein.

As used herein, an isolated canine IL-13Rα protein can be a full-length protein or any homolog of such a protein. An isolated IL-13Rα protein of the present invention, including a homolog, can be identified in a straight-forward manner by the protein's ability to bind IL-13 or bind to an anti-IL-13Rα protein. Examples of protein homologs of the present invention include proteins of the present invention in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the protein homolog binds IL-13 or includes at least one epitope capable of eliciting an immune response against the parent protein or binding to an antibody directed against the parent protein, where the term parent refers to the longer and/or full-length protein that the homolog is derived from. Minimal size of epitope is about 4-6 amino acids. Minimal size of IL-13 binding domain can be determined by one skilled in the art.

Homologs of proteins of the present invention can be the result of natural allelic variation, including natural mutation. Protein homologs of the present invention can also be produced using techniques known in the art including, but not limited to, direct modifications to the protein and/or modifications to the gene encoding the protein using, for example, classic or recombinant DNA techniques to effect random or targeted mutagenesis.

One embodiment of the present invention is a canine IL-13Rα1 protein that includes amino acid sequence having SEQ ID NO:50. Preferred is a canine IL-13Rα1 protein that is encoded by nucleic acid sequences SEQ ID NO:48, SEQ ID NO:49 and/or SEQ ID NO:52.

In another embodiment of the present invention is a canine IL-13Rα 2 protein that includes at least one of the following amino acid sequences SEQ ID NO:55, SEQ ID NO:58, SEQ ID NO:61, SEQ ID NO:66, and SEQ ID NO:69. Preferred is a canine IL-13Rα2 protein encoded by one or more of the following nucleic acid sequences: the nucleic acid sequence SEQ ID NO:54, SEQ ID NO:57, SEQ ID NO:60, SEQ ID NO:63, SEQ ID NO:65 and/or SEQ ID NO:68.

In one embodiment of the present invention, isolated IL-13Rα proteins are encoded by nucleic acid molecules that hybridize under stringent hybridization conditions to the non-coding strand of nucleic acid molecules encoding canine IL-13Rα proteins. The minimal size of a IL-13R protein of the present invention (4-6 amino acids) is a size sufficient to be encoded by a nucleic acid molecule capable of forming a stable hybrid, i.e., hybridizing under stringent hybridization conditions, with the complementary sequence of a nucleic acid molecule encoding the corresponding natural protein. The size of a nucleic acid molecule (12-17/18 nucleotides) encoding such a protein is dependent on the nucleic acid composition and the percent homology between the IL-13Rα nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered, i.e. localized, in distinct regions on a given nucleic acid molecule.

A preferred canine IL-13Rα protein includes a protein encoded by a nucleic acid molecule selected from the group consisting of: (a) an isolated nucleic acid molecule comprising at least 75 contiguous nucleotides identical in sequence to an at least 75 contiguous nucleotide region of a nucleic acid sequence selected from the group consisting of SEQ ID NO:48, SEQ ID NO:49 and/or SEQ ID NO:52; and (b) an isolated nucleic acid molecule comprising a nucleic acid sequence that is at least 90% identical in sequence to a nucleic acid sequence to a nucleic acid sequence selected from the group consisting of SEQ ID NO:48, SEQ ID NO:49 and/or SEQ ID NO:52, wherein the percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10.

Another preferred canine protein of the present invention includes a protein encoded by an IL-13Rα1 nucleic acid molecule that is preferably at least 90% identical, more preferably at least 92%, more preferably at least 94%, more preferably at least 96%, and even more preferably at least 98% identical to a nucleic acid molecule having the nucleic acid sequence SEQ ID NO:48, and/or SEQ ID NO:49; wherein the percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10. Also preferred are fragments of such proteins encoded by nucleic acid molecules that are at least about 75 nucleotides, at least about 80 nucleotides, at least about 85 nucleotides, at least about 90 nucleotides, at least about 95 nucleotides, at least about 100 nucleotides, at least about 120 nucleotides, at least about 140 nucleotides, at least about 160 nucleotides, at least about 180 nucleotides, at least about 200 nucleotides, at least about 250 nucleotides, at least about 300 nucleotides, at least about 350 nucleotides, or at least about 400 nucleotides at least about 500 nucleotides, at least about 600 nucleotides, at least about 700 nucleotides, at least about 800 nucleotides, at least about 900 nucleotides, at least about 1000 nucleotides, at least about 1100 nucleotides, at least about 1300 nucleotides, or at least about 1500 nucleotides.

In one embodiment, a preferred protein of the present invention includes an IL-13Rα1 protein that is preferably at least about 85%, even more preferably at least about 90%, even more preferably at least about 95%, and even more preferably about 100% identical to PCaIL-13Rα1$_{405}$, with amino acid sequence SEQ ID NO:50. Additionally preferred are proteins encoded by allelic variants of a nucleic acid molecule encoding PCaIL-13Rα1$_{405}$. Also preferred are fragments thereof having at least about 45 amino acid residues as well as fragments thereof are at least 50 amino acids, at least 55 amino acids, at least 60 amino acids, at least 75 amino acids, at least 100 amino acids, at least 150 amino acids, at least 200 amino acids, at least 250 amino acids, at least 300 amino acids, at least 350 amino acids, or at least 400 amino acids in length.

A preferred canine IL-13Rα protein includes a protein encoded by a nucleic acid molecule consisting of an IL-13Rα2 nucleic acid molecule selected from the group consisting of: (a) an isolated nucleic acid molecule comprising at least 40 contiguous nucleotides identical in sequence to an at least 40 contiguous nucleotide region of a nucleic acid sequence selected from the group consisting of SEQ ID NO:54, SEQ ID NO:57, SEQ ID NO:60, SEQ ID NO:63, SEQ ID NO:65 and/or SEQ ID NO:68; and (b) an isolated nucleic acid molecule comprising a nucleic acid sequence that is at least 80% identical in sequence to a nucleic acid sequence selected from the group consisting of SEQ ID NO:54, SEQ ID NO:57, SEQ ID NO:60, SEQ ID NO:63, SEQ ID NO:65 and/or SEQ ID NO:68, wherein the percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10. In one embodiment, such a nucleic acid molecule does not hybridize under conditions comprising hybridization at 65° C. in 0.1×SSC followed by washing at 65° C. in 0.1×SSC with a nucleic acid sequence selected from the group consisting of SEQ ID NO:95, SEQ ID NO:96, SEQ ID NO:97 and SEQ ID NO:98. Also preferred are proteins encoded by portions of such nucleic acid molecules that are at least about 40 nucleotides, at least 50 nucleotides, at least 55 nucleotides, at least 60 nucleotides, at least 70 nucleotides, at least 80 nucleotides, at least 90 nucleotides, at least 100 nucleotides, at least 150 nucleotides, at least 200 nucleotides, at least 300 nucleotides, at least 400 nucleotides, at least 500 nucleotides, at least 600 nucleotides, or at least 700 nucleotides at least 800 nucleotides, at least 900 nucleotides, at least 1000 nucleotides, at least 1100 nucleotides, at least 1200 nucleotides, at least 1300 nucleotides, at least 1400 nucleotides in length.

Another preferred canine protein of the present invention includes a protein encoded by an IL-13Rα2 nucleic acid molecule that is preferably at least 80% identical, more preferably at least 85% identical, more preferably at least 90% identical, more preferably at least 95% identical to a nucleic acid molecule having the nucleic acid sequence SEQ ID NO:54, SEQ ID NO:57, SEQ ID NO:60, SEQ ID NO:63, SEQ ID NO:65 and/or SEQ ID NO:68; also preferred are fragments, i.e. portions, of such proteins encoded by nucleic acid molecules that are at least about 40 nucleotides, wherein the percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10. In one embodiment, such a nucleic acid molecule does not hybridize under conditions comprising hybridization at 65° C. in 0.1×SSC followed by washing at 65° C. in 0.1×SSC with a nucleic acid sequence selected from the group consisting of SEQ ID NO:95, SEQ ID NO:96, SEQ ID NO:97 and SEQ ID NO:98.

Another preferred protein of the present invention includes an IL-13Rα2 protein that is preferably at least 70% identical, more preferably at least 75% identical, more preferably at least 80% identical, more preferably at least 85%, more preferably at least 90%, more preferably at least 95%, and even more preferably about 100% identical to PCaIL-13Rα2$_{145}$, PCaIL-13Rα2$_{255}$, PCaIL-13Rα2$_{386}$, PCaIL-13Rα2$_{365}$, and/or PCaIL-13Rα2$_{318}$. Additionally preferred are proteins encoded by allelic variants of a nucleic acid molecule encoding proteins PCaIL-13Rα2$_{145}$, PCaIL-13Rα2$_{255}$, PCaIL-13Rα2$_{386}$, PCaIL-13Rα2$_{365}$, and/or PCaIL-13Rα2$_{318}$. Also preferred are fragments thereof having at least about 40, at least about 45, at least about 50, at least about 55, at least about 60, at least about 65, at least about 70, at least about 75, at least about 80, at least about 85, at least about 90, at least about 95, at least about 100, at least about 120, at least about 140, at least about 150, at least about 175, at least about 200, at least about 225, at least about 250, at least about 275, at least about 300, at least about 325 or at least about 350 amino acid residues.

In one embodiment of the present invention, canine IL-13Rα2 proteins comprise amino acid sequence SEQ ID NO:55, SEQ ID NO:58, SEQ ID NO:61, SEQ ID NO:66, SEQ ID NO:69, SEQ ID NO:72, SEQ ID NO:75, SEQ ID NO:78 and/or SEQ ID NO 81. Such proteins include, but are not limited to, the proteins consisting of the cited amino acid sequences, fusion proteins and multivalent proteins, and proteins encoded by allelic variants of nucleic acid molecules encoding proteins having amino acid sequence SEQ ID NO:55, SEQ ID NO:58, SEQ ID NO:61, SEQ ID NO:66, SEQ ID NO:69, SEQ ID NO:72, SEQ ID NO:75, SEQ ID NO:78 and/or SEQ ID NO 81.

One embodiment of a heavy chain of canine IgG protein of the present invention is a fusion protein that includes a heavy chain of canine IgG protein domain attached to one or more fusion segments. Suitable fusion segments for use with the present invention include, but are not limited to, segments that can: enhance a protein's stability; act as an immunopotentiator to enhance an immune response; act as an suppressor of immune response and/or assist purification of a heavy chain of canine IgG protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of heavy chain of canine IgG-containing domain of the protein and can be susceptible to cleavage in order to enable straight-forward recovery of a heavy chain of canine IgG protein. Fusion proteins are preferably produced by culturing a recombinant cell transformed with a fusion nucleic acid molecule that encodes a protein including the fusion segment attached to either the carboxyl and/or amino terminal end of a heavy chain of canine IgG-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); a "tag" domain (e.g., at least a portion of 13-galactosidase, a strep tag peptide, other domains that can be purified using compounds that bind to the domain, such as monoclonal antibodies); and/or a linker and enzyme domain (e.g., alkaline phosphatase domain connected to a heavy chain of canine IgG protein by a linker). More preferred fusion segments include metal binding domains, such as a poly-histidine segment; a maltose binding domain; a strep tag peptide, such as that available from Biometra in Tampa, Fla.; and a phage T7 S10 peptide.

In general, the present invention also comprises chimera of the following types: immunotoxins (the present proteins comprising a toxin, and directed to a particular target, either an IgG binding site, or a binding site of a variable region fused with an IgG protein herein), scavenger molecules (an IgG/variable region chimera designed so as to "clean up" unwanted compounds in the cellular milieu, by virtue of their ability to bind to them), drug delivery vehicles (IgG with a drug attached, and directed either to IgG binding site or to a site of choice), and molecules with increased half-life.

A heavy chain of canine IgG molecule of the present invention can also include chimeric molecules comprising canine IgG molecule and a second molecule that enables the chimeric molecule to be bound to a substrate. An example of a suitable second molecule includes an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

Chimeric immunoglobulin molecules are also included in the present invention. Specifically, a chimeric immunoglobulin molecule which contains a portion from a heavy chain of canine IgG and a portion that is not canine is contemplated. The non-canine portion is preferably the antigen binding site of the chimeric immunoglobulin. A chimeric molecule ideally contains only those portions of the non-canine variable region that bind to antigen, with the remainder of the immunoglobulin comprising canine sequence.

One embodiment of a canine IL-13Rα protein of the present invention is a fusion protein that includes a canine IL-13Rα2 protein-containing domain attached to one or more fusion segments. Suitable fusion segments for use with the present invention include, but are not limited to, segments that can: enhance a protein's stability; act as an immunopotentiator to enhance an immune response against canine IL-13Rα protein; and/or assist in purification of a canine IL-13Rα protein, e.g., by affinity chromatography. A suitable fusion segment can be a domain of any size that has the desired function, e.g., imparts increased stability, imparts increased immunogenicity to a protein, and/or simplifies purification of a protein. Fusion segments can be joined to amino and/or carboxyl termini of the IL-13Rα containing domain of the protein and can be susceptible to cleavage in order to enable straight-forward recovery of a IL-13Rα protein. Fusion proteins are preferably produced by culturing a recombinant cell transformed with a fusion, or chimeric nucleic acid molecule that encodes a protein including the fusion segment attached to either the carboxyl and/or amino terminal end of a IL-13Rα containing domain. Preferred fusion segments include an immunoglobulin domains, a metal binding domain, e.g., a poly-histidine segment; an immunoglobulin binding domain, e.g., Protein A, Protein G, T cell, B cell, Fc receptor or complement protein antibody-binding domains; a sugar binding domain, e.g., a maltose binding domain; and/or a tag domain, e.g., at least a portion of β-galactosidase, a strep tag peptide, a T7 tag peptide, a Flag™ peptide, or other domains that can be purified using compounds that bind to the domain, such as monoclonal antibodies. More preferred fusion segments include immunological domains such as Fcγ, Fcε, Fcα, Fcμ, or Fcδ domains; metal binding domains, such as a poly-histidine segment; a maltose binding domain; a strep tag peptide, such as that available from Biometra in Tampa, Fla.; and an S10 peptide. One embodiment of a fusion protein is a chimera of IL-13Rα domain with a functional moiety. This moiety can, for example, have the function of allowing oligomerization of the chimeric IL-13Rα proteins.

In one embodiment, a canine IL-13Rα protein of the present invention is a fusion protein that includes a carrier protein domain linked to an IL-13Rα domain such that either the carrier protein domain or the IL-13Rα domain can be the carboxyl terminal domain. Such a protein is preferably encoded by a chimeric nucleic acid molecule that includes a carrier protein encoding domain and an IL-13Rα encoding domain. A fusion protein of the present invention can also include a linker (i.e. a stretch of one or more additional amino acids) preferably located between the carrier protein domain and IL-13Rα domain. As used herein, a carrier protein domain has a meaning similar to a fusion segment. A preferred carrier protein domain is an immunoglobulin IgFc region, preferably a canine IFC region. In one embodiment, a canine IgE region, and preferably at least a portion of a canine gamma chain is preferred. Examples of canine gamma chains are disclosed herein. A fusion protein of the present invention can include any IL-13Rα protein of the present invention. Preferably the IL-13Rα domain binds IL-13. More preferred is a IL-13Rα2 protein of the present invention. Similarly, a chimeric nucleic acid molecule encoding a fusion protein of the present invention can include any IL-13Rα nucleic acid molecule of the present invention. Preferred is a IL-13Rα nucleic acid molecule that binds IL-13. More preferred is a IL-13Rα2 nucleic acid molecule of the present invention. A particularly preferred fusion protein of the present invention includes one or more of the following amino acid sequences: SEQ ID NO: 72, SEQ ID NO:75, SEQ ID NO:78 and/or SEQ ID NO:81. Production of such fusion proteins is described in the Examples. A preferred chimeric nucleic acid molecule of the present invention encodes one of such fusion proteins.

A particularly preferred chimera nucleic acid molecule of the present invention includes one or more of the following nucleic acid sequences: the nucleic acid sequence SEQ ID NO:71, SEQ ID NO:74, SEQ ID NO:77 and/or SEQ ID NO:80, and/or the respective complements of these nucleic acid sequences, i.e. SEQ ID NO:73, SEQ ID NO:76, SEQ ID NO:79 and/or SEQ ID NO:82, respectively. These nucleic acid sequences which contain canine IL-13Rα2 nucleic acid molecules linked to canine IgE-Fc nucleic acid molecules are further described herein. For example, SEQ ID NO:77 represents the deduced sequence of the coding strand of canine chimera nucleic acid molecule nCaIL-13Rα2-Fc-B9, the cloning of which is disclosed in the examples. The complement of SEQ ID NO:77, represented herein by SEQ ID NO:79, refers to the nucleic acid sequence of the strand complementary to the strand having SEQ ID NO:77, which can be easily be determined by those skilled in the art. The nucleic acid sequences of the coding strand and complementary strand of nCa IL-13Rα2-Fc-B9 are represented herein as SEQ ID NO:77 and SEQ ID NO:79, respectively. Translation of SEQ ID NO:77 indicates that nucleic acid molecule nCa IL-13Rα 2-Fc-B9 encodes a fusion protein of about 563 amino acids, denoted herein as PCa IL-13Rα 2-Fc-B9, the amino acid sequence of which is presented in SEQ ID NO:78, assuming an open reading frame having an initiation codon spanning from nucleotide 1 through nucleotide 3 of SEQ ID NO:77 and a stop codon spanning from nucleotide 1690 through nucleotide 1692 of SEQ ID NO:77. Other chimeric nucleic acid molecules are discussed in more detail in the examples.

A preferred fusion protein is encoded by a chimeric nucleic acid molecule that includes: (a) a nucleic acid sequence encoding a carrier protein domain; and (b) an nucleic acid molecule encoding an IL-13Rα2 protein domain selected from the group consisting of: (i) an isolated nucleic acid molecule comprising at least 40 contiguous nucleotides identical in sequence to an at least 40 contiguous nucleotide region of a nucleic acid sequence selected from the group consisting of SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 and SEQ ID NO:70; and (ii) an isolated nucleic acid molecule comprising a nucleic acid sequence that is at least 80% identical in sequence to a nucleic acid sequence selected from the group consisting of SEQ ID NO:54, SEQ ID NO:56, SEQ ID NO:57, SEQ ID NO:59, SEQ ID NO:60, SEQ ID NO:62, SEQ ID NO:63, SEQ ID NO:64, SEQ ID NO:65, SEQ ID NO:67, SEQ ID NO:68 and SEQ ID NO:70, wherein the percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10. In one embodiment, such a nucleic acid molecule does not hybridize under conditions comprising hybridization at 65° C. in 0.1×SSC followed by washing at 65° C. in 0.1×SSC with a nucleic acid sequence selected from the group consisting of SEQ ID NO:95, SEQ ID NO:96, SEQ ID NO:97 and SEQ ID NO:98.

Yet another preferred canine fusion protein of the present invention includes a protein that is encoded by chimeric nucleic acid molecule with an IL-13α2 encoding domain that is preferably at least 80% identical, more preferably at least 85% identical, more preferably at least 90% identical, more preferably at least 95% identical to a nucleic acid molecule having the nucleic acid sequence SEQ ID NO:54, SEQ ID NO:57, SEQ ID NO:60, SEQ ID NO:63, SEQ ID NO:65 and/or SEQ ID NO:68; also preferred are fragments, i.e. portions, of such proteins encoded by nucleic acid molecules that are at least about 40 nucleotides, wherein the percent identity is determined by the DNAsis™ computer program with the gap penalty set at 5, the number of top diagonals set at 5, the fixed gap penalty set at 10, the k-tuple set at 2, the window size set at 10 and the floating gap penalty set at 10. In one embodiment, such a nucleic acid molecule does not hybridize under conditions comprising hybridization at 65° C. in 0.1×SSC followed by washing at 65° C. in 0.1×SSC with a nucleic acid sequence selected from the group consisting of SEQ ID NO:95, SEQ ID NO:96, SEQ ID NO:97 and SEQ ID NO:98.

Another preferred protein of the present invention includes fusion protein comprising a carrier protein domain and a IL-13Rα2 protein domain that is preferably at least 70% identical, more preferably at least 75% identical, more preferably at least 80% identical, more preferably at least 85%, more preferably at least 90%, more preferably at least 95%, and even more preferably about 100% identical to PCaIL-13Rα2$_{145}$, PCaIL-3Rα2$_{255}$, PCaIL-13Rα2$_{386}$, PCaIL-13Rα2$_{365}$, and/or PCaIL-13Rα2$_{31\ 8}$. Additionally preferred are proteins encoded by allelic variants of a nucleic acid molecule encoding proteins PCaIL-13Rα2$_{145}$, PCaIL-13Rα2$_{255}$, PCaIL-13Rα2$_{386}$, PCaIL-13Rα2$_{365}$, and/or PCaIL-13Rα2$_{318}$. Also preferred are fragments thereof having at least about 40 amino acid residues.

One embodiment includes a canine IL-13Rα protein that is capable of binding IL-13. For a protein to be capable of binding to its ligand, in this case IL-13, the protein must have a functional binding domain. A functional binding domain is at least the smallest piece, or fragment, of the protein that is necessary to allow binding to a IL-13. For example, a functional binding domain also includes proteins that are larger than the smallest fragment necessary to allow binding to IL-13 or receptor. A preferred canine IL-13Rα protein comprises of an amino acid sequence selected from the group consisting of SEQ ID NO:50, SEQ ID NO:55, SEQ ID NO:58, SEQ ID NO:61, SEQ ID NO:66, SEQ ID NO:69, SEQ ID NO:72, SEQ ID NO:75, SEQ ID NO:78 and/or SEQ ID NO:81 and/or a fragment thereof, such that the fragment is capable of binding to canine IL-13; and a protein encoded by an allelic variant of a nucleic acid molecule which encodes any such protein. One skilled in the art can determine in a straight-forward manner whether an IL-13Rα protein binds IL-13. Examples of such methods include, determining the ability of an IL-13Rα protein to form a complex with IL-13 or determining the ability of an IL-13Rα protein to inhibit IL-13 stimulated Td-1 cell proliferation. Examples of such methods are disclosed herein.

One of skill in the art will understand that a DNA or protein fragment of the present invention is an example of a homolog that includes a portion of a larger nucleic acid molecule or protein, respectively, of the present invention. One of skill in the art will also understand that fragments including one or more of the functional domains of IL-13Rα can vary and extend beyond those particular nucleic acid or amino acid regions defined herein. Such active domains can vary in length by 1 amino acid to about 200 amino acids. Nucleic acids or amino acids essential to an active domain can be identified using standard protein or DNA binding assays known to those of skill in the art to determine the ability of an active domain to bind to its ligand(s), e.g. IL-13, or to its receptor(s), e.g. IL-13Rα.

Also provided in the present invention are recombinant cells comprising the fusion proteins describe herein.

A variety of procedures known in the art may be used to molecularly clone canine IgG (heavy and/or light chain) nucleic acid molecules and/or canine IL-13Rα nucleic acid molecules of the present invention. These methods include, but are not limited to, direct functional expression of a canine IgG (heavy and/or light chain) nucleic acid molecules and/or canine IL-13Rα nucleic acid molecules following construction of the heavy chain of a canine IgG-containing and/or canine IL-13Rα containing cDNA or genomic DNA library in an appropriate expression vector system. Another method is to screen a canine IgG (heavy and/or light chain)-containing and/or a canine IL-13Rα-containing cDNA or genomic DNA library constructed in a bacteriophage or plasmid shuttle vector with a labeled oligonucleotide probe designed from the amino acid sequence of a canine IgG (heavy and/or light chain) protein and/or a canine IL-13Rα protein of the present invention. An additional method consists of screening a canine IgG (heavy and/or light chain)-containing and/or a canine IL-13Rα-containing cDNA or genomic DNA library constructed in a bacteriophage or plasmid shuttle vector with a canine IgG nucleic acid molecule and/or canine IL-13Rα nucleic acid molecule of the present invention. Such a nucleic acid molecule can be is obtained by PCR amplification of canine IgG (heavy and/or light chain) nucleic acid molecule fragments and/or canine IL-13Rα nucleic acid molecule fragments through the design of degenerate oligonucleotide primers from the amino acid sequence of canine IgG (heavy and/or light chain) and/or canine IL-13Rα or of primers from canine IgG and/or canine IL-13Rα nucleic acid molecules.

The translation of the RNA into a protein will result in the production of at least a portion of canine IgG (heavy and/or light chain) and/or canine IL-13Rα protein, or fusions thereof, which can be identified, for example, by the activity of a canine IgG (heavy and/or light chain) and/or canine IL-13Rα protein or by immunological reactivity with an anti-canine IgG (heavy and/or light chain) and/or anti-canine IL-13R antibody. In this method, pools of mRNA isolated from canine IgG (heavy and/or light chain) and/or canine IL-13Rα protein-producing cells can be analyzed for the presence of an RNA which encodes at least a portion of a canine IgG (heavy and/or light chain) and/or canine IL-13Rα protein. Further fractionation of the RNA pool can be done to purify canine IgG (heavy and/or light chain) and/or canine IL-13Rα RNA from non-canine IgG (heavy and/or light chain) and/or canine IL-13Rα RNA. Protein produced by isolataion of RNA can be analyzed to provide amino acid sequences which in turn are used to provide primers for production of canine IgG (heavy and/or light chain) and/or canine IL-13Rα cDNA, or the RNA used for translation can be analyzed to provide nucleotide sequences encoding canine IgG (heavy and/or light chain) and/or canine IL-13Rα and produce probes for the production of canine IgG (heavy and/or light chain) and/or canine IL-13Rα cDNA. These methods are known in the art and can be found in, for example, Sambrook, J., Fritsch, E. F., Maniatis, T. in *Molecular Cloning: A Laboratory Manual, Second Edition*, Cold Spring Harbor Laboratory Press, Cold Spring Harbor, N.Y. 1989.

Other types of libraries, as well as libraries constructed from other cells or cell types, may be useful for isolating canine IgG (heavy and/or light chain) and/or canine IL-13Rα-encoding DNA. Other types of libraries include, but are not limited to, cDNA libraries derived from other canines or cell lines derived from other canines, and genomic DNA libraries. Preparation of cDNA libraries can be performed by standard techniques. Well known cDNA library construction techniques can be found in, for example, Sambrook, J., et al., ibid.

Nucleic acid molecules encoding canine IgGs and/or canine IL-13Rα proteins can also be isolated from a suitable genomic DNA library. Construction of genomic DNA libraries can be performed by standard techniques. Well known genomic DNA library construction techniques can be found in Sambrook, J., et al., ibid.

In order to clone a canine IgG (heavy and/or light chain) and/or canine IL-13Rα nucleic acid molecule by the above methods, knowledge of the amino acid sequence of said molecules may be necessary. One may either use the sequences herein exemplified or purify canine IgG (heavy and/or light chain) and/or canine IL-13Rα protein and sequence a portion of the protein by manual or automated sequencing. It is not necessary to determine the entire amino acid sequence, because the linear sequence of two regions of 6 to 8 amino acids from the protein can be determined and used to produce primers for PCR amplification of a canine IgG (heavy and/or light chain) and/or canine IL-13Rα nucleic acid molecule.

Once suitable amino acid sequences have been identified, DNA sequences capable of encoding such amino acid sequences are synthesized. Because the genetic code is degenerate, more than one codon may be used to encode a particular amino acid, and therefore, the amino acid sequence can be encoded by any of a set of similar DNA oligonucleotides. Only one member of the set will be identical to a canine IgG (heavy and/or light chain) and/or canine IL-13Rα sequence but will be capable of hybridizing to such nucleic acid molecules even in the presence of DNA oligonucleotides with mismatches under appropriate conditions.

Isolated canine IgG (heavy and/or light chain) proteins and canine Il-13Rα proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a canine IgG (heavy and/or light chain) and/or canine IL-13Rα protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit few impurities.

In addition, the recombinant canine IgG (heavy and/or light chain) and/or canine IL-13Rα proteins can be separated from other cellular proteins by use of an immunoaffinity column made using a substance that selectively binds to said proteins, such as a monoclonal or polyclonal antibodies that selectively bind the full length nascent canine IgG (heavy and/or light chain) and/or canine IL-13Rα proteins or polypeptide fragments of such proteins, an Fcgamma receptor protein, Protein A, etc.

Antibodies selective for a protein of the present invention, isolated cells cell comprising at least one protein of the present invention, and isolated fusion protein comprising at least one protein of the present invention are also within the scope of the present invention.

The present invention also includes isolated (e.g., removed from their natural milieu) antibodies that selectively bind to a the canine IgG (heavy and/or light chain) protein of the present invention or a mimetope thereof (e.g., anti-heavy chain antibodies). As used herein, the term "selectively binds to" a the canine IgG (heavy and/or light chain) protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti- the canine IgG (heavy and/or light chain) antibody preferably selectively binds to a the canine IgG (heavy and/or light chain) protein in such a way as to reduce the activity of that protein.

In particular, there are provided antibodies directed to the heavy chain of canine IgG. Preferred are antibodies selective for the hinge region of the heavy chain of canine IgG. In one preferred embodiment, there are provided antibodies selective for a protein selected from the group consisting of: the exemplified hinge region or heavy chain canine IgG proteins exemplified. These antibodies may be admixed or conjugated with additional materials, such as cytotic agents or other antibody fragments, including IgG fragments.

Isolated anti-canine IgG antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce anti-canine IgG antibodies of the present invention includes (a) administering to an animal an effective amount of a protein or mimetope thereof of the present invention to produce the antibodies and (b) recovering the antibodies. Anti-canine IgG antibodies of the present invention can also be produced recombinantly using techniques as heretofore disclosed to produce the heavy chain of canine IgG proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Anti-canine IgG antibodies of the present invention have a variety of potential uses that are within the scope of the present invention. For example, such antibodies can be used (a) as tools to detect total IgG and/or a specific IgG subclass, (b) to screen expression libraries, (c) to reduce IgG function, and/or (d) to recover desired proteins of the present invention from a mixture of proteins and other contaminants.

The present invention also includes isolated, i.e., removed from their natural milieu, antibodies that selectively bind to a canine IL-13Rα protein of the present invention or a mimetope thereof, e.g., anti-canine IL-13Rα antibodies. As used herein, the term selectively binds to an IL-13Rα protein refers to the ability of antibodies of the present invention to preferentially bind to specified proteins and mimetopes thereof of the present invention. Binding can be measured using a variety of methods standard in the art including enzyme immunoassays, e.g., ELISA, immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated herein by reference in its entirety. An anti-IL-13Rα antibody of the present invention preferably selectively binds to a canine IL-13Rα protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope of the present invention to produce the antibodies and (b) recovering the antibodies. In another method, antibodies of the present invention are produced recombinantly using techniques as heretofore disclosed to produce IL-13Rα proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) to evaluate the immune status in canids with diseases such as allergy, cancer and pathogen infections. Furthermore, antibodies of the present invention can be used to target cytotoxic agents to canine IL-13Rα and cells containing canine IL-13Rα on the cell surface. Targeting can be accomplished by conjugating, i.e., stably joining, such antibodies to the cytotoxic agents using techniques known to those skilled in the art. Suitable cytotoxic agents are known to those skilled in the art. Furthermore, antibodies of the present invention can be used to detect IL-13Rα in a putative IL-13Rα containing biological sample, by contacting the putative IL-13Rα containing biological sample with anti-IL-13Rα antibodies under conditions suitable for formation of a IL-13Rα-antibody complex, and then detecting said complex. Methods to detect said method are known to those skilled in the art and are contained herein.

In general, the present invention provides methods to detect any of the following: canine IgG, cDNA encoding IgG (especially for research purposes), mRNA encoding IgG (for research as well as diagnostic detection purposes), etc. Means for detection may include: antibodies directed to canine IgG protein, including polyclonal or monoclonal antibodies directed to specific regions or specific subclasses, probes identified as hybridizable to the cDNA or mRNA, primers useful for amplifying canine IgG nucleic acid. The following patents describe such procedures, and are hereby incorporated by reference in this patent application: General characteristics of diagnostic reagents and methods to produce and use such diagnostic reagents are disclosed, for example, in U.S. Pat. No. 5,958,880, issued Sep. 28, 1999, by Frank et al.; PCT International Publication No. WO 99/54349, published Oct. 28, 1999, by McCall et al.; PCT Application Ser. No. PCT/US99/21428, filed Sep. 18, 1999, by Jensen; U.S. patent application Ser. No. 09/479,614, entitled "FELINE IMMUNOGLOBULIN E MOLECULES AND RELATED METHODS", filed Jan. 7, 2000, by McCall et al.; U.S. Provisional Patent Application Ser. No. 60/195,659, entitled CANINE IL-13 RECEPTORS, PROTEINS, NUCLEIC ACIDS AND USES THEREOF", filed Apr. 7, 2000, by Tang; each of these references is incorporated by reference herein in its entirety; furthermore, the disclosed reagents and methods are incorporated by reference herein in their entireties. It is to be noted that although the reagents and methods disclosed in each of the citations do not relate to the canine IgG proteins, nucleic acid molecules, antibodies and inhibitors of the present invention per se, the disclosed reagents and methods are applicable by those skilled in the art to diagnostic reagents, kits and detection methods of the present invention. General characteristics of therapeutic compositions and methods to produce and use such therapeutic compositions are disclosed, for example, in U.S. Pat. No. 5,958,880, issued Sep. 28, 1999, by Frank et al., and PCT International Publication No. WO 99/54349, published Oct. 28, 1999, by McCall et al., both of which are incorporated by reference herein in their entirety. It is to be noted that although the compositions and methods disclosed in each of the citations do not relate to the canine IgG proteins, nucleic acid molecules, antibodies and inhibitors of the present invention per se, they are applicable by those skilled in the art to therapeutic compositions and methods of the present invention.

In other embodiments, there are provided methods to detect IgG nucleic acid comprising (a) contacting an isolated the canine IgG (heavy and/or light chain) nucleic acid molecule of the present invention with a putative IgG nucleic acid-containing composition under conditions suitable for formation of a canine IgG nucleic acid molecule IgG nucleic acid complex, and (b) detecting the presence of IgG nucleic acid by detecting the canine IgG nucleic acid molecule IgG nucleic acid complex.

As used herein, the term "contacting" refers to combining or mixing ingredients, as all of those terms are known in the art. "Formation of a complex" refers to the ability of the molecules to form a stable complex that can be measured (e.g., detected). Binding is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., ibid.

In one embodiment, a test compound of the present method includes a biological sample from an animal. A suitable biological sample includes, but is not limited to, a bodily fluid composition or a cellular composition. A bodily fluid refers to any fluid that can be collected (e.g., obtained) from an animal, examples of which include, but are not limited to, blood, serum, plasma, urine, tears, aqueous humor, cerebrospinal fluid (CSF), saliva, lymph, nasal secretions, traceobronchial aspirations, intestinal secretions, colostrum, milk and feces. Such a composition of the present method can, but need not be, pretreated to remove at least some of the non-IgG isotypes of immunoglobulin and/or other proteins, such as albumin, present in the fluid. Such removal can include, but is not limited to, contacting the bodily fluid with a material, such as Protein G, to remove IgG antibodies and/or affinity purifying IgG antibodies from other components of the body fluid by exposing the fluid to, for example, Concanavalin A. In another embodiment, a composition includes collected bodily fluid that is pretreated to concentrate immunoglobulin contained in the fluid. For example, immunoglobulin contained in a bodily fluid can be precipitated from other proteins using appropriate concentrations of ammonium sulfate. A preferred composition of the present method is serum.

For protein and peptides, complex can be detected in a variety of ways including, but not limited to use of one or more of the following assays: an enzyme-linked immunoassay, a radioimmunoassay, a fluorescence immunoassay, a luminescence assay (e.g. a chemiluminescent assay or a bioluminescent assay), a lateral flow assay, an agglutination assay, a flow-through assay, a particulate-based assay (e.g., using particulates such as, but not limited to, magnetic particles or plastic polymers, such as latex or polystyrene beads), an immunoprecipitation assay, an electonic sensory assay, a BioCore™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. Examples of detectable markers include, but are not limited to, a metal-binding label, a physical label, and electronic labela radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin available from Pierce, Rockford, Ill.). According to the present invention, a detectable marker can be connected to a the heavy chain of canine IgG molecule using, for example, chemical conjugation or recombinant DNA technology (e.g., connection of a fusion segment such as that described herein for a metal binding domain; an immunoglobulin binding; a sugar binding domain; and a "tag" domain). Preferably a carbohydrate group of the heavy chain of canine IgG molecule is chemically conjugated to biotin.

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect the heavy chain of canine IgG molecules of the present invention is an immunosorbent assay. An immunoabsorbent assay of the present invention comprises a capture molecule and an indicator molecule. A capture molecule of the present invention binds to an IgG in such a manner that the IgG is immobilized to a substrate. As such, a capture molecule is preferably immobilized to a substrate of the present invention prior to exposure of the capture molecule to a putative IgG-containing composition. An indicator molecule of the present invention detects the presence of an IgG bound to a capture molecule. As such, an indicator molecule preferably is not immobilized to the same substrate as a capture molecule prior to exposure of the capture molecule to a putative IgG-containing composition.

Both a capture molecule and an indicator molecule of the present invention are capable of binding to an IgG. Preferably, a capture molecule binds to a different region of an IgG than an indicator molecule, thereby allowing a capture molecule to be bound to an IgG at the same time as an indicator molecule. The use of a reagent as a capture molecule or an indicator molecule depends upon whether the molecule is immobilized to a substrate when the molecule is exposed to an IgG. For example, a heavy chain of canine IgG molecule of the present invention is used as a capture molecule when the heavy chain of canine IgG molecule is bound on a substrate. Alternatively the heavy chain of canine IgG molecule is used as an indicator molecule when the heavy chain of canine IgG molecule is not bound on a substrate. Suitable molecules for use as capture molecules or indicator molecules include, but are not limited to, a heavy chain of canine IgG molecule of the present invention, an antigen reagent or an anti-IgG antibody reagent of the present invention.

An immunoabsorbent assay of the present invention can further comprise one or more layers and/or types of secondary molecules or other binding molecules capable of detecting the presence of an indicator molecule. For example, an untagged (e.g., not conjugated to a detectable marker) secondary antibody that selectively binds to an indicator molecule can be bound to a tagged (e.g., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include an antigen, an anti-IgG idiotypic antibody and an anti-IgG isotypic antibody. Preferred tertiary molecules can be selected by a skilled artisan based upon the characteristics of the secondary molecule. The same strategy is applied for subsequent layers.

In one embodiment, the heavy chain of canine IgG molecule is used as a capture molecule by being immobilized on a substrate, such as a microtiter dish well or a dipstick. A biological sample collected from an animal is applied to the substrate and incubated under conditions suitable to allow for the heavy chain of canine IgG inolecule: test compound complex formation bound to the substrate. Excess non-bound material, if any, is removed from the substrate under conditions that retain the heavy chain of canine IgG molecule:test compound complex binding to the substrate. An indicator molecule that can selectively bind to a test compound bound to the heavy chain of canine IgG molecule is added to the substrate and incubated to allow formation of a complex between the indicator molecule and the heavy chain of canine IgG molecule: test compound complex. Preferably, the indicator molecule is conjugated to a detectable marker (preferably to an enzyme label, to a colorimetric label, to a fluorescent label, to a radioisotope, or to a ligand such as of the biotin or avidin family). Excess indicator molecule is removed, a developing agent is added if required, and the substrate is submitted to a detection device for analysis. Preferred test compounds to detect are antigens or anti-IgG antibodies.

In one embodiment, an immunosorbent assay of the present invention does not utilize a capture molecule. In this embodiment, a test sample is applied to a substrate, such as a microtiter dish well or a dipstick, and incubated under conditions suitable to allow for the test compound binding to the substrate. Any test compound is immobilized on the substrate. Excess non-bound material, if any, is removed from the substrate under conditions that retain test compound binding to the substrate. A the heavy chain of canine IgG molecule is added to the substrate and incubated to allow formation of a complex between the heavy chain of canine IgG molecule and the test compound. Preferably, the heavy chain of canine IgG molecule is conjugated to a detectable marker (preferably to biotin, an enzyme label or a fluorescent label). Excess the heavy chain of canine IgG molecule is removed, a developing agent is added if required, and the substrate is submitted to a detection device for analysis. Preferred test compounds to detect are antigens or anti-IgG antibodies.

Another preferred method to detect a test compound is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a heavy chain of canine IgG, the labeling reagent being impregnated within the support structure in a labeling zone; and (c) a capture reagent comprising an anti-heavy chain of canine IgG antibody. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (e.g., anionic or cationic) material. Examples of such a material include, but are not limited to, nitrocellulose (NC), PVDF, carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the heavy chain of canine IgG. A preferred labeling reagent is the heavy chain of canine IgG conjugated, either directly or through a linker, to a plastic bead substrate, such as to a latex bead. The substrate also includes a detectable marker, preferably a calorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case an anti-the heavy chain of canine IgG antibody, as disclosed above, that immobilizes the IgG complexed to the anti-IgG in the capture zone. The capture reagent is preferably fixed to the support structure by drying or lyophilizing. The labeling reagent accumulates in the capture zone and the accumulation is assessed visually or by an optical detection device.

Yet another embodiment of the present invention is a therapeutic composition that, when administered to a canid in an effective manner, is capable of protecting that animal from a disease mediated by canine IgE, such as, for example, allergy or inflammation. Therapeutic compositions of the present invention include therapeutic (protective or regulatory) compounds that are capable of regulating IL-13 amounts and/or activity. A therapeutic compound of the present invention is capable of regulating IL-13 activity and availability. Examples of regulatory compounds related to IL-13Rα proteins of the present invention include an isolated antibody that selectively binds to a canine IL-13Rα protein or other inhibitors or activators of IL-13Rα protein activity or amount. As such, these regulatory compounds may include antibodies, peptides, substrate analogs, and other large or small molecules which can be organic or inorganic. As used herein, a protective compound refers to a compound, that when administered to an animal in an effective manner, is able to treat, ameliorate, and/or prevent a disease mediated by IgE.

The efficacy of a therapeutic composition of the present invention to protect an animal from a disease mediated by IL-13 can be tested in a variety of ways including, but not limited to, detection of protective antibodies (using, for example, proteins or mimetopes of the present invention), detection of the amount of IL-13, or detection of cellular immunity within the treated animal. In one embodiment, therapeutic compositions can be tested in animal models such as mice. Such techniques are known to those skilled in the art.

One embodiment of the present invention is a therapeutic composition that, when administered to a canid, reduces allergy or inflammation present in said canid, said therapeutic composition comprising an excipient and a therapeutic compound selected from the group consisting of:
  (a) an isolated protein selected from the group consisting of: (i) a protein comprising an at least 40 contiguous amino acid region identical in sequence to an at least 40 contiguous amino acid region selected from the group consisting of SEQ ID NO:50, SEQ ID NO:55, SEQ ID NO:58, SEQ ID NO:61, SEQ ID NO:66, and/or SEQ ID NO:69; and (ii) a protein comprising an amino acid sequence that is at least 70 percent identical a sequence selected from the group consisting of SEQ ID NO:50, SEQ ID NO:55, SEQ ID NO:58, SEQ ID NO:61, SEQ ID NO:66, and/or SEQ ID NO:69; (iii) a fusion protein comprising: (a) a carrier protein; and ((b)) a protein selected from the group consisting of: ((i)) a protein comprising an at least 30 contiguous amino acid region identical in sequence to an at least 30 contiguous amino acid region selected from the group consisting of SEQ ID NO:50, SEQ ID NO:55, SEQ ID NO:58, SEQ ID NO:61, SEQ ID NO:66, and/or SEQ ID NO:69; and ((ii)) a protein comprising an amino acid sequence that is at least 80 percent identical a sequence selected from the group consisting of SEQ ID NO:50, SEQ ID NO:55, SEQ ID NO:58, SEQ ID NO:61, SEQ ID NO:66, and/or SEQ ID NO:69; and (iv) any other IL-13Rα protein (including a fusion protein) of the present invention;
  (b) a mimetope of any of the proteins;
  (c) a multimeric form of any of the proteins; (d) an isolated nucleic acid molecule comprising an IL-13Rα nucleic acid molecule, including an IL-13Rα2 chimeric nucleic acid molecule of the present invention; (e) an antibody that selectively binds any of the proteins of the present invention; and (f) an inhibitor identified by its ability to inhibit the activity of any of the proteins of the present invention.

The present invention also includes a therapeutic composition comprising at least one therapeutic compound of the present invention in combination with at least one additional compound protective against allergy or inflammation. Examples of such protective compounds include anti-inflammatory steroids, antihistamines, and anti-IgE antibodies.

In one embodiment, a therapeutic composition of the present invention can be used to protect an animal from a disease mediated by IL-13 by administering a IL-13Rα therapeutic composition to a canid in order to prevent undesirable IgE levels. Such administration can include, but is not limited to, oral, intravenous, intramuscular, intra ocular, mucosal, intranasal, subcutaneous, or transdermal application. A preferred route of administration is subcutaneous. In order to protect an animal from a disease mediated by IgE, a therapeutic composition of the present invention is administered to the animal in an effective manner such that the composition is capable of protecting that animal from a disease mediated by IgE. Therapeutic compositions of the present invention can be administered to animals prior to disease in order to prevent disease and/or can be administered to animals after disease occurs. The exact dose, administration regimen, and administration route of therapeutic compositions of the present invention can be determined by one skilled in the art.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable, i.e., bioerodible.

Naked nucleic acid molecules of the present invention can be administered by a variety of methods. Suitable delivery methods include, for example, intramuscular injection, subcutaneous injection, intradermal injection, intradermal scarification, particle bombardment, oral application, and nasal application, with intramuscular injection, intradermal injection, intradermal scarification and particle bombardment being preferred. A preferred single dose of a naked DNA molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked DNA molecules of the present invention can be contained in an aqueous excipient (e.g., phosphate buffered saline) and/or with a carrier (e.g., lipid-based vehicles), or it can be bound to microparticles (e.g., gold particles).

According to one embodiment, a nucleic acid molecule of the present invention can be administered to an animal in a fashion to enable expression of that nucleic acid molecule into a protective protein or protective RNA, e.g., antisense RNA, ribozyme, triple helix forms or RNA drug, in the animal. Nucleic acid molecules can be delivered to an animal in a variety of methods including, but not limited to, (a) administering a naked, i.e., not packaged in a viral coat or cellular membrane, nucleic acid as a genetic vaccine, e.g., as naked DNA or RNA molecules, such as is taught, for example in Wolff et al., 1990, *Science* 247, 1465-1468, or (b) administering a nucleic acid molecule packaged as a recombinant virus vaccine or as a recombinant cell vaccine, i.e., the nucleic acid molecule is delivered by a viral or cellular vehicle.

Administration of soluble receptor protein of the present invention, more preferably the extracellular portion of the receptor, to an animal will result in a decrease of circulating IL-13, the IL-13 receptor acts as a sponge to remove IL-13 from the circulation.

A genetic, i.e., naked nucleic acid, vaccine of the present invention includes a nucleic acid molecule of the present invention and preferably includes a recombinant molecule of the present invention. A genetic vaccine of the present invention can comprise one or more nucleic acid molecules of the present invention operatively linked to a transcriptional control sequence. In one embodiment, genetic vaccines include at least a portion of a viral genome, i.e., a viral vector. Any suitable transcription control sequence can be used, including those disclosed as suitable for protein production. Particularly preferred transcription control sequences include cytomegalovirus immediate early, preferably in conjunction with Intron-A, Rous sarcoma virus long terminal repeat, and tissue-specific transcription control sequences, as well as transcription control sequences endogenous to viral vectors if viral vectors are used. The incorporation of a "strong" polyadenylation signal is also preferred. Preferred viral vectors include those based on alphaviruses, poxviruses, adenoviruses, herpesviruses, picornaviruses, and retroviruses.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 μg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient, e.g., phosphate buffered saline, alone or in a carrier, e.g., lipid-based vehicles.

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses, such as Sindbis virus, raccoon poxviruses, species-specific herpesviruses and species-specific poxviruses. An example of methods to produce and use alphavirus recombinant virus vaccines are disclosed in U.S. Pat. No. 5,766,602, Xiong et al., issued Jun. 16, 1998; U.S. Pat. No. 5,753,235, Haanes et al., issued May 19, 1998; and U.S. Pat. No. 5,804,197, Haanes et al., issued Sep. 8, 1998, all of which are incorporated by reference herein in their entirety.

When administered to an animal, a recombinant virus vaccine of the present invention infects cells within the immunized animal and directs the production of a protective protein or RNA nucleic acid molecule that is capable of protecting the animal from a disease. For example, a recombinant virus vaccine comprising a canine IL-13R nucleic acid molecule of the present invention is administered according to a protocol that results in the animal producing a sufficient immune response to protect itself from a disease mediated by IL-13. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS, e.g., COS-7, Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

A IL-13Rα inhibitor of the present invention is identified by its ability to bind to, modify, or otherwise interact with, a IL-13Rα protein, thereby inhibiting the activity of IL-13Rα. Suitable inhibitors of IL-13Rα activity are compounds that inhibit IL-13Rα protein activity in at least one of a variety of ways: (1) by binding to or otherwise interacting with or otherwise modifying the IL-13Rα binding, i.e. ligand binding, site, (2) by interacting with other regions of the IL-13Rα protein to inhibit IL-13Rα activity, for example, by allosteric interaction, and (3) by binding to or otherwise interacting with or otherwise modifying a IL-13Rα receptor binding site such that IL-13 is less likely to bind to the IL-13Rα receptor binding site. Inhibitors of IL-13Rα are preferably relatively small compounds.

Canine IL-13Rα proteins of the present invention can be used to develop regulatory compounds including inhibitors and activators that, when administered to a canid in an effective manner, are capable of protecting that canid from disease mediated by IL-13Rα or IL-13. Preferred regulatory compounds derived from the present invention include inhibitors and activators. In accordance with the present invention, the ability of a regulatory compound, including an inhibitor or activator, of the present invention to protect a canid from disease mediated by IL-13Rα or IL-13 refers to the ability of that protein to, for example, treat, ameliorate or prevent a disease mediated by IL-13Rα in that canid.

In one embodiment of the present invention a compound that inhibits the activity of a IL-13Rα protein is identified by a) contacting an isolated canine IL-13Rα protein with a putative inhibitory compound under conditions in which, in the absence of a compound, IL-13Rα protein has IL-13 binding activity; and (b) determining if a inhibitory compound inhibits IL-13 binding activity. Preferably such a method is also conducted in the presence of IL-13.

A variety of methods are known to one skilled in the art to detect binding of IL-13 to an IL-13Rα protein. Such methods include, but are not limited to an assay in which IL-13 and a IL-13Rα binding partner can interact and/or bind to each other, using, for example, the yeast two-hybrid system, see for example, Luban, et al. 1995, *Curr. Opin. Biotechnol.*, 6, 59-64; and identifying those proteins that specifically bind to the canine IL-13Rα protein binding domain. Additional methods to identify protein-protein interactions include Biacore® screening, confocal immunofluorescent microscopy, UV cross-linking, and immunoprecipitations. An example of a IL-13Rα protein binding domain is an IL-13Rα2-binding domain, and a protein that would bind to a IL-13Rα2-binding domain would be IL-13. Additional teachings of general characteristics of reagents for use in the detection of binding between two moieties (e.g., between IL-13 and its receptor) as well as methods to produce and use such reagents are disclosed, for example, in U.S. Pat. No. 5,958,880, issued Sep. 28, 1999, by Frank et al.; and PCT International Publication No. WO 99/54349, published Oct. 28, 1999, by McCall et al.; each of these references is incorporated by reference herein in its entirety; furthermore, the disclosed reagents and methods are incorporated by reference herein in their entireties. It is to be noted that although the reagents and methods disclosed in each of the citations do not relate to the proteins, nucleic acid molecules, antibodies and inhibitors of the present invention per se, the disclosed reagents and methods are applicable by those skilled in the art to reagents, kits and detection methods of the present invention.

One embodiment of the present invention includes an assay kit to identify the presence of an inhibitor of a canine IL-13Rα protein in a canid, comprising an isolated IL-13Rα protein, and a means for determining the inhibition of activity of IL-13Rα, wherein said means enables the detection of inhibition, wherein detection of inhibition identifies an inhibitor of the ability of canine IL-13Rα protein to bind IL-13. Such a kit preferably also includes IL-13, preferably canine IL-13.

The present invention also includes a method and kit to detect IL-13, preferably canine IL-13. Higher than normal levels of IL-13 indicate the presence of allergy or inflammation in a canid. Such methods and kits use a canine IL-13Rα protein, preferably a canine IL-13Rα2 protein, of the present invention and involve the formation and detection of a complex between any IL-13 in a sample and that IL-13Rα protein. General characteristics of methods and reagents to detect IL-13 are disclosed herein, e.g., in U.S. Pat. No. 5,958,880, ibid.

Also provided are kits comprising a container comprising at least one composition selected from the group consisting of
 (a) a nucleic acid molecule of the present invention,
 (b) a protein encoded by a nucleic acid of the present invention,
 (c) a chimera of the present invention
 (d) a fusion protein of the present invention
 (e) a fusion sequence of the present invention.

In broad terms, a kit may contain canine IgG DNA or antibodies to the heavy chain of canine IgG. A kit may be used to detect DNA which hybridizes to canine IgG nucleic acid molecule of the present invention or amplified (PCR) using a nucleic acid molecule of the present invention, or to detect the presence of the heavy chain of canine IgG protein or peptide fragments in a sample. Such characterization is useful for a variety of purposes including but not limited to forensic analyses and epidemiological studies. Alternatively, a kit may contain DNA molecules, RNA molecules, recombinant protein and antibodies of the present invention for the purpose of screening and measuring levels of the heavy chain of canine IgG DNA, the heavy chain of canine IgG RNA or the heavy chain of canine IgG protein. The recombinant proteins, DNA molecules, RNA molecules and antibodies lend themselves to the formulation of kits suitable for the detection and typing of the heavy chain of canine IgG. All of these kits would comprise a compartmentalized carrier suitable to hold in close confinement at least one container. The carrier may also further comprise reagents such as recombinant the heavy chain of canine IgG protein or anti-the heavy chain of canine IgG antibodies suitable for detecting the heavy chain of canine IgG. The carrier may also contain a means for detection such as labeled antigen or enzyme substrates or the like. A preferred kit of the present invention further comprises a detection means including one or more antigens disclosed herein, an antibody capable of selectively binding to an IgG disclosed herein and/or a compound capable of binding to a detectable marker conjugated to a the heavy chain of canine IgG protein (e.g., avidin, streptavidin and ImmunoPure® NeutrAvidin when the detectable marker is biotin). Such antigens preferably induce IgG antibody production in animals including canines, canines and/or equines.

In particular, kits useful in vaccination, therapy, diagnosis, detection of IgG, detection of specific IgG subclasses, identification of diseases by subclass, and monitoring of immune response are provided.

The following examples illustrate the present invention without, however, limiting it. It is to be noted that the Examples include a number of molecular biology, microbiology, immunology and biochemistry techniques considered to be known to those skilled in the art. Disclosure of such techniques can be found, for example, in Sambrook et al., ibid., and related references.

EXAMPLE 1

Cloning the Heavy Chain of Canine IgG

Canine IgG Probe Preparation:

Degenerate primer C-IgG330-F (designated as SEQ ID NO: 40) was designed based on the conserved regions of IgGs from human, mouse, pig and bovine.

A ~750 bp DNA fragment was amplified with C-IgG330-F and M13 Forward primers from canine spleen cell cDNA library in a "touch-down" PCR reaction. The reaction condition was 94° C. for 8 min, 3 cycles of 94 C for 30 Sec, 58 C for 45 Sec and 72 C for 1.2 min, then annealing temperature changed from 58 C to 56, 54, 52, 50, 48 and 46 C step-wise. The reaction was carried out for 3 cycles for each annealing temperature and 25 cycles at 44 C. The amplified DNA fragment was inserted into TA vector (Invitrogen). Plasmids that carry PCR amplified DNA were purified for sequencing. Blast search of the sequencing data indicated that the DNA fragment was coding for canine IgG.

cIg-13. DNA (designated as SEQ ID NO: 28; the reverse and complement of this sequence is SEQ ID NO: 30). The cDNA fragment was found to contain DNA sequence (578 bp) encoding for CH3 and part of CH2 domains of canine IgG, and 3' UTR cIg-13.AMI (designated SEQ ID NO:29) is the decoded amino acid sequence (AA 141) for cIg-13.DNA;

Screening Canine IgG from a Canine Spleen Cell cDNA Library:

PCR fragments encoding canine IgG were used as probes in southern blots for screening canine IgG clones from a canine spleen cell cDNA library. Two distinct IgG heavy chains and a light chain DNA sequences were identified in the screening. One of the two heavy chains was a full length canine IgG (clone 3523), and the other a partial canine IgG DNA sequence (4325-P) that encodes CH3, CH2, CH1 and part of variable region of the IgG.

3523.DNA (1654 bp; designated SEQ ID NO:4; the reverse and complement of SEQ ID NO:4 is SEQ ID NO: 6)

3523.AMI (AA: 468; designated SEQ ID NO: 5) is the coding region of 3523.DNA.

TABLE 2

| Clone 3523 | VH | $C_H1$ | Hinge | $C_H2$ | $C_H3$ |
|---|---|---|---|---|---|
| DNA (bp) | 70-480 | 481-774 | 775-825 | 826-1143 | 1144-1473 |
| Amino acid | 1-137 | 138-235 | 236-252 | 253-358 | 359-468 |

Estimated molecular mass of canine IgG-3523 is about 51.7 kDa with pI about 6.55.

4325-P.DNA (1364 bp) is designated SEQ ID NO: 31; the reverse and complement of SEQ ID NO: 31 is SEQ ID NO: 33.

4325-P.AMI (AA: 392; designated SEQ ID NO: 32) is the coding region of 4325-P.DNA)

TABLE 3

| Clone 4325-P | VH | C$_H$1 | Hinge | C$_H$2 | C$_H$3 |
|---|---|---|---|---|---|
| DNA (bp) | 1-179 | 180-473 | 474-539 | 540-857 | 858-1187 |
| Amino acid | 1-57 | 58-155 | 156-177 | 178-283 | 284-392 |

Light chain DNA (Lambda chain, 938 bp) is designated SEQ ID NO: 25 (the reverse and complement of SEQ ID NO: 25 is SEQ ID NO: 27).

Light chain (AA: 235; designated SEQ ID NO: 26) represents the coding region of Lambda chain from 49 to 756 bp). Estimated molecular mass of canine IgG Lambda light chain is about 24.7 kDa with pI about 4.97.

Specific canine IgG primers in the conserved regions of IgG heavy chains were designed based on canine IgG sequences:

```
IgG-FWD1:  5'GCCCTCCAGCAGGTGGCCCAGCGAGACC3';  (SEQ ID NO: 41)

IgG-REV1:  5'GGGGATGGCGGCAGGACATACAC3';  (SEQ ID NO: 42)

IgG-REV2:  5'TTTACCCGGAGAATGGGAGAGGG3';  (SEQ ID NO: 43)

IgG-REV3:  5'GGTCTGCGTGGGCCACCTGCTGGAGGGC3';  (SEQ ID NO: 44)

IgG-REV4:  5'GGGTGGGGGGCTTGCTGGGTGCCGGGCG3'.  (SEQ ID NO: 45)
```

The primers were used in PCRs for amplification of other canine IgG heavy chain subclasses.

PCR amplification of IgGs from canine B-cell and T-cell lymphoma samples: First strand cDNAs prepared from 18 different canine B cell lymphoma samples were used as the templates in PCR reactions with IgG-FWD1 and IgG-REV2 primer set. The reaction condition is 94 C for 5 min; then 32 cycles on 94 C for 45 Sec, 54 C for 45 Sec and 72 C for 45 Sec. The amplified DNA fragments from the PCR will contain hinge region, CH2 and CH3 domains of canine IgG heavy chain. In addition to the DNA sequences of IgGs identified from the canine spleen cell cDNA library, two new IgG with different DNA sequences on hinge region were identified from the B cell lymphoma samples.

DNA and Encoded Amino Acid Sequences of Hinge Region of Canine IgG Heavy Chains:

The DNA sequence of 3523-hinge region is designated SEQ ID NO: 1; the reverse complement of SEQ ID NO:1 is SEQ ID NO:3.

The amino acid sequence of 3523-hinge region is designated SEQ ID NO:2

The DNA sequence of 4325-hinge region is designated SEQ ID NO: 22; the reverse complement of SEQ ID NO:22 is SEQ ID NO:24.

The amino acid sequence of 4325-hinge region is designated SEQ ID NO: 23.

The DNA sequence of Bly8-hinge region is designated SEQ ID NO: 7; the reverse complement of SEQ ID NO: 7 is SEQ ID NO:9.

The amino acid sequence of Bly8-hinge region is designated SEQ ID NO:8.

The DNA sequence of Bly9-hinge region is designated SEQ ID NO: 13; the reverse complement of SEQ ID NO:13 is SEQ ID NO: 15.

The amino acid sequence of Bly9-hinge region is designated SEQ ID NO:14.

PCR reactions were carried out using 5' end of canine IgG forward primer K9IgG5' (designated SEQ ID NO: 46) and canine IgG reverse primer IgG-REV4 and IgG-REV2, respectively. The reaction condition was carried out for 1 cycle of 94 C for 5 min, 3 cycles of 94 C for 35 Sec, 58/56/54/52 C for 45 Sec and 72 C for 1.5 min, then 22 cycles of 94 C for 35 Sec, 50 C for 45 Sec and 72 C for 1.5 min.

4325.DNA (1453 bp; designated SEQ ID NO: 19) is a cDNA fragment of the PCR using K9IgG5' and IgG-REV4 primers. (The reverse complement of SEQ ID NO:19 is SEQ ID NO: 21)

4325.AMI (AA: 473; designated SEQ ID NO: 20) is the deduced amino acid sequence encoded by SEQ ID NO;19.

TABLE 4

| Clone 4325 | V$_H$ | C$_H$1 | Hinge | C$_H$2 | C$_H$3 |
|---|---|---|---|---|---|
| DNA (bp) | 32-445 | 446-739 | 740-805 | 806-1123 | 1124-1450 |
| Amino acid | 1-138 | 139-236 | 237-258 | 259-364 | 365-473 |

Estimated molecular mass of canine IgG-4325 is about 52 kDa with pI about 8.17.

Clone Bly-8 was the product of two PCR fragments, Bly8-5C and Bly8-3C. Bly8-5C was a PCR fragment amplified from B-cell lymphoma sample using K9IgG5 and IgG-REV2 primers.

Bly8-5C.DNA (1168 bp) is designated as SEQ ID NO: 34; the reverse complement of SEQ ID NO:34 is SEQ ID NO: 36.

Bly8-5C.AMI (AA: 373; designated as SEQ ID NO:35) is the deduced amino acid sequence encoded by SEQ ID NO:34.

Based on DNA sequence of Bly8-5C variable region, a specific primer, Bly822F, (designated SEQ ID NO: 47) was designed.

Bly8-3C was amplified by PCR from the same B-cell lymphoma sample using Bly822F and IgG-REV2 primers.

Bly-8-3C.DNA (1059 bp) is designated as SEQ ID NO: 37; the reverse complement of SEQ ID NO: 37 is SEQ ID NO:39.

Bly8-3C.AMI (AA: 350; designated SEQ ID NO: 38) is the ddeduced amino acid sequence encoded by the SEQ ID NO:37.

Overlapping of the identical region of DNA fragments of Bly8-5C and Bly8-3C, a consensus DNA sequence was generated (Bly8).

Bly8.DNA (1460 bp) is designated as SEQ ID NO: 10; the reverse complement of SEQ ID NO:10 is SEQ ID NO:12.

Bly8.AMI (AA: 470) is designated as SEQ ID NO: 11) is the deduced amino acid sequence encoded by SEQ ID NO:10.

TABLE 5

| Clone Bly8 | VH | $C_H1$ | Hinge | $C_H2$ | $C_H3$ |
| --- | --- | --- | --- | --- | --- |
| DNA (bp) | 48-464 | 465-758 | 759-809 | 810-1127 | 1128-1457 |
| Amino acid | 1-139 | 140-237 | 238-254 | 255-360 | 361-470 |

Estimated molecular mass of canine IgG-Bly8 is about 51.2 kDa with pI about 6.24.

Bly9.DNA (1456 bp; designated SEQ ID NO:16) is a cDNA fragment of the PCR using K9IgG5' and IgG-REV4 primers); the reverse complement of SEQ ID NO:16 is SEQ ID NO:18.

Bly9.AMI (AA: 474; designated SEQ ID NO:17) is the deduced amino acid sequence encoded by SEQ ID NO:16.

TABLE 6

| Clone Bly9 | VH | $C_H1$ | Hinge | $C_H2$ | $C_H3$ |
| --- | --- | --- | --- | --- | --- |
| DNA (bp) | 32-454 | 455-748 | 749-808 | 809-1126 | 1127-1453 |
| Amino acid | 1-141 | 142-239 | 240-259 | 260-365 | 366-474 |

Estimated molecular mass of canine IgG-Bly9 is about 51.8 kDa with pI about 6.15.

EXAMPLE 2

This example describes the isolation and sequencing of nucleic acid molecules encoding canine IL-13 receptor α1 (i.e. nCaIL-13Rα1) nucleic acid molecules of the present invention.

A cDNA library was prepared from a canine PBMC cDNA library. The library was a *C. familiaris* mitogen activated PBMC cDNA library that was constructed in the Uni-Zap® XR Vector (available from Stratagene Cloning Systems, La Jolla, Calif.) using Stratagene's ZAP-cDNA® Synthesis Kit and the manufacturer's protocol. Two degenerate synthetic oligonucleotide primers were designed from the conserved regions of bovine, mouse and human IL-13 receptors (IL-13R): Primer 13R1F1, a sense primer corresponding to amino acid residues from 48 through 59 of human IL-13 receptor α1 denoted herein as SEQ ID NO:50 as found in U.S. Pat. No. 5,710,023, ibid has the sequence 5' ATHTGGACNTGGAAYCCNCCNGARGGNGC 3', denoted herein as SEQ ID NO:36; Primer 13R1R1, a anti-sense primer corresponding to amino acid residues from 202 through 213 of the same human IL-13 receptor α1 has the sequence 5' ATYTTNCCNGCRTTRTCYTTNACCAT-DATYTGNAC 3', denoted herein as SEQ ID NO:84, where D represents A, T OR G, H represents A or C or T, N represents A or C or G or T, R represents A or G and Y represents C or T. PCR amplification of fragments from the PBMC cDNA library was conducted using touch-down PCR amplification conditions, which consist of 1 cycle at 94° C. for 8 min; 3 cycles of 94° C. for 30 seconds, 58° C. for 45 seconds and 72° C. for 1 min; then annealing temperature changed from 58° C. to 56° C., 54° C., 52° C., 50° C., 48° C., 46° C. and 44° C. step-wise. The reaction was carried out for 3 cycles for each annealing temperature and 25 cycles at 44° C. A PCR amplification product of about 500 base pairs (bp) was generated and is denoted herein as nCaIL-13Rα1$_{483}$.

The amplified DNA fragment was purified with Qiagen gel purification kit, available from Qiagen, La Jolla, Calif.) and PCR products were cloned into the TA cloning vector (available from Invitrogen Corporation, Carlsbad, Calif.), and the resulting clones were sequenced using an ABI Prism Model 377 Automatic DNA Sequencer (available from Perkin-Elmer Applied Biosystems Inc., Foster City, Calif.). DNA sequencing reactions were performed using Prism™ dRhodamine Terminator Cycle Sequencing Ready Reaction kits (available from PE Applied Biosystems Inc.).

The sequencing results indicated that nCaIL-13Rα1$_{483}$ contained 483 nucleotides and coded for a portion of canine IL-13Rα1. The coding strand of nCaIL-13Rα1$_{483}$ was shown to have a nucleic acid sequence referred to herein as SEQ ID NO:48.

To identify a cDNA encoding a full-length canine IL-13Rα1 protein, nCaIL-13Rα1$_{483}$ was labeled with $^{32}P$ and used as a probe to screen the canine PBMC cDNA library described above. Hybridization was done at about 6×SSC, 5× Denhardt's solution, 0.5% SDS, 100 μg/ml of ssDNA at about 68° C., for about 36 hr. (the compositions of SSC, Denhardt's and ssDNA are described in Sambrook et al., ibid.). The filters were washed 3 times, for about 30 minutes per wash, at about 55° C. in about 2×SSC, 0.2% SDS, followed by a final wash of about 30 minutes in the same buffer except using about 1×SSC. Ninety six positive clones were selected in the first screen. Sixty of 96 clones scored as positive by PCR when 13R1F1 and 13R1R1 primers were used in the reaction. Two positive clones (clone #44 and #48) from this screening were picked for excision using ExAssis™/SOLR™ system (available from Stratagene, La Jolla, Calif.); DNA was isolated from each clone, purified by mini-prep and submitted for sequencing. The cDNA insert of clone # 44 was sequenced for both strands using vector flanking primers and gene-specific internal primers. Sequence analysis was performed using the GAP program of GCG (available from the University of Wisconsin) using the alignment settings of: gap weight set at 50, length weight set at 3, and average match set at 10 for nucleic acid sequence comparisons; and gap weight set at 12, length weight set at 4, and average match set at 2.912 for amino acid sequence comparisons. The cDNA insert, determined to be 1547 bp in length, is referred to herein as nCaIL-13Rα1$_{1547}$, the coding strand of which was shown to have a nucleic acid sequence denoted herein as SEQ ID NO:49. The complement of SEQ ID NO:49 is represented herein by SEQ ID NO:51. Translation of SEQ ID NO:2 suggests that nucleic acid molecule nCaIL-13Rα1$_{1547}$ encodes a full-length IL-13Rα1 protein of about 405 amino acids, denoted herein as PcaIL-13Rα1$_{405}$, the amino acid sequence of which is presented in SEQ ID NO:50, assuming an open reading frame spannning from nucleotide 1 to nucleotide 3 of SEQ ID NO:49 and a stop codon spanning from nucleotide 1216 through nucleotide 1218 of SEQ ID NO:49. The coding region encoding PcaIL-13Rα1$_{405}$ is presented herein as nCaIL-13Rα1$_{1215}$, which has the nucleotide sequence SEQ ID NO:52 (the coding strand) and SEQ ID NO:53 (the complementary strand).

EXAMPLE 3

This example describes the isolation and sequencing of nucleic acid molecules encoding a canine IL-13 receptor α2 (i.e., nCaIL-13Rα2) nucleic acids molecules of the present invention.

The same PBMC cDNA library described in Example 1 and a canine mast cell cDNA library were used as templates for the amplification of nCaIL-13Rα2 nucleic acid molecules. The canine mast cell cDNA library was prepared as follows. Total RNA was extracted from approximately 7×10$^8$ freshly harvested canine mast cells using an acid-guanidinium-phenol-chloroform method similar to that described by Chomzynski et al., 1987, *Anal. Biochem* 162, 156-159. Poly A$^+$ selected RNA was separated from the total RNA preparation by oligo-dT cellulose chromatography using the mRNA Purification Kit (available from Pharmacia, Newark, N.J.) according to the method recommended by the manufacturer. The canine mast cell cDNA library was constructed in lambda-Uni-ZAP® Synthesis Kit protocol (available from Stratagene, La Jolla, Calif.), using Stratagene's ZAP-cDNA Synthesis Kit protocol. Approximately 5 micrograms (μg) of mast cell Poly A$^+$ RNA was used to produce the mast cell cDNA library. Four degenerate synthetic oligonucleotide primers were designed from the conserved region of IL-13 receptor α2 chains from mouse and human: Primer 13R2F1D, a sense primer corresponding to amino acid residues from 28 through 40 of human IL-13 receptor chain denoted herein as SEQ ID NO:50 as found in U.S. Pat. No. 5,710,023, ibid has the sequence 5'GARATHAARGT-NAAYCCNCCNCARGAYTTYGARAT 3', denoted herein as SEQ ID NO:85. Primer 13R2F2D, a sense primer corresponding to amino acid residues from 91 through 100 of the same human IL-13 receptor α2 has the sequence 5' TAYAARGAYGGNTTCTGAYYT-NAAYAARGGNATHGA 3', denoted herein as SEQ ID NO:86. Primer 13R2R1D, a anti-sense primer corresponding to amino acid residues from 317 through 326 of the same human IL-13 receptor α2 has the sequence 5' CCAYTCN-SWCCADATNCCRTCRTCNGCRCARTA-DATRTTNACYTT 3', denoted herein as SEQ ID NO:87, and primer 13R2R2D, another anti-sense primer corresponding to amino acid residues from 174 through 181 of the same human IL-13 receptor α2 has the sequence 5'GCRT-GRTCNARNCCYTCRTACCA 3', also known as SEQ ID NO:88, where D represents A, T OR G, H represents A or C or T, N represents A or C or G or T, R represents A or G and Y represents C or T. PCR amplifications of DNA fragments from the cDNA libraries were conducted using the touchdown PCR amplification conditions as described in Example 1 with an M13 reverse primer (available from Stratagene Cloning Systems, La Jolla, Calif.) and the 13R2R1D primer. The reaction mix from the first PCR was used as the template in the second PCR with a T3 primer (available from Stratagene Cloning Systems, La Jolla, Calif.) and the 13R2R2D primer to amplify a DNA fragment of about 750 bp denoted herein as nCaIL-13Rα2$_{620}$.

The amplified DNA fragment was purified with the Qiagen gel purification kit, PCR products were cloned into the TA cloning vector and the resulting clones were sequenced as described in Example 1.

The sequencing results indicated that nCaIL-13Rα2$_{620}$ the cDNA contained 620 nucleotides and coded for the amino-terminal portion of a canine IL-13Rα2 protein. The coding strand of nCaIL-13Rα2$_{620}$ was shown to have a nucleic acid sequence referred to herein as nCaIL-13Rα2$_{620}$, also denoted as SEQ ID NO:54. Translation of SEQ ID NO:54 shows that the nucleic acid nCaIL-13Rα2$_{620}$ encodes a partial protein of 145 amino acids, denoted herein as PcaIL-13Rα2$_{145}$, the amino acid sequence of which is presented in SEQ ID NO:55, assuming an open reading frame having an initiation codon spanning from nucleotide 184 through nucleotide 186 of SEQ ID NO:54 and continuing through nucleotide 620 of SEQ ID NO:54. The complement of SEQ ID NO$_{54}$ is represented herein by SEQ ID NO:56.

A similar PCR cloning approach was used to isolate a cDNA encoding the carbonyl terminal region of a canine IL-13Rα2 protein. The canine mast cell library was used as the template. Two primer sets, 13R2F1D/T7 and 13R2F2D/KS, were used in the PCR. The reaction mix from the first PCR was used in the second PCR with 13R2F2D/13R2R1D and 13R2F2/13R2R1D primer sets, respectively. DNA fragments of predicted size were purified and submitted for sequencing. The sequencing result showed that the DNA fragments coded for canine IL-13-Rα2 proteins.

Specific IL-13-Rα2 primers were designed based on the obtained canine IL-13-Rα2 DNA sequence. 13R2F5 with the DNA sequence of 5'AGCGGATCCCTCTAT-GCTTTCAAATGCTGAGATAAAAGT-TAATCCTCCTCAG G 3', denoted herein as SEQ ID NO:89 and 13R2F2 with the sequence of 5'TGGACATCACCA-CAAGGAAATCGGG 3', denoted herein as SEQ ID NO:90. A PCR reaction mixture generated using 13R2F5/M13 forward primers was used as the template in a second PCR with 13R2F2 and T7 primers in a manner as described in Example 1. An approximately 900 bp DNA fragment was detected in the reaction. This DNA fragment, denoted herein as nCaIL-13Rα2$_{878}$ was purified and subcloned into TA vector. The positive clones were purified and submitted for sequencing as described in Example 1. The sequencing results indicated that the nCaIL-13Rα2$_{878}$ molecule contained 878 nucleotides and coded for the carboxyl portion of canine IL-13Rα2 and also includes the untranslated terminal region (UTR). The coding strand of nCaIL-13Rα2$_{878}$ was shown to have a nucleic acid sequence referred to herein as SEQ ID NO:57. Translation of SEQ ID NO:57 shows that the nucleic acid nCaIL-13Rα2$_{878}$ encodes a protein of 255 amino acids, denoted herein as PCaIL-13Rα2$_{255}$, the amino acid sequence of which is presented in SEQ ID NO:58, assuming an open reading frame spanning from nucleotide 1 to nucleotide 3 of SEQ ID NO:57 and a stop codon spanning from nucleotide 766 through nucleotide 768 of SEQ ID NO:57. The complement of SEQ ID NO:57 is represented herein by SEQ ID NO:59.

A cDNA encoding a full-length canine IL-13Rα2 protein was constructed by lining up nCaIL-13Rα2$_{620}$ and nCaIL-13Rα2$_{878}$ to form a consensus nucleic acid molecule sequence, referred to herein as nCaIL-13Rα2$_{1454}$, the coding strand of which has a nucleic acid sequence denoted herein as SEQ ID NO:60 and the complementary strand which has a nucleic acid sequence represented herein by SEQ ID NO:62. Translation of SEQ ID NO:60 suggests that nucleic acid molecule nCaIL-13Rα2$_{1454}$ encodes a full-length IL-13Rα2 protein of 386 amino acids, denoted herein as PcaIL-13Rα2$_{386}$, the amino acid sequence of which is presented in SEQ ID NO:61, assuming an open reading frame having an initiation codon spanning from nucleotide 184 through nucleotide 186 of SEQ ID NO:60 and a stop codon spanning from nucleotide 1342 through nucleotide 1345 of SEQ ID NO:60. The coding region encoding PcaIL-13Rα2$_{386}$ is presented herein as nCaIL-13Rα2$_{1158}$, which has the nucleotide sequence SEQ ID NO:63 (the coding strand) and SEQ ID NO:64 (the complementary strand). A putative signal sequence coding region extends from nucleotide 184 through nucleotide 246 of SEQ ID NO:60. The proposed mature protein (i.e., canine IL-13Rα2 protein from which the signal sequence has been cleaved), denoted herein as PCAIL-13Rα2$_{365}$, contains about 365 amino acids, extending from residue 22 through residue 386 of SEQ ID NO:61; amino acid sequence of PCaIL-13Rα2$_{365}$ is represented herein as SEQ ID NO:66. The nucleic acid molecule encoding PCaIL-13Rα2$_{365}$ is denoted herein as nCaIL-13Rα2$_{1095}$, extending from nucleotide 247 through nucleotide 1345 of SEQ ID NO:60. nCaIL-13Rα2$_{1095}$ has a coding sequence denoted SEQ ID NO:65 and a complementary sequence denoted SEQ ID NO:67. PCaIL-13Rα2$_{386}$ has an apparent extracellular domain, extending from residue S-22 to T-338 of SEQ ID NO:61, denoted herein as PCaIL-13Rα2$_{318}$, represented herein by SEQ ID NO:69. The nucleic acid molecule encoding PCaIL-13Rα2$_{318}$ is denoted herein as nCaIL-13Rα2$_{954}$, extending from nucleotide 247 through nucleotide 1197 of SEQ ID NO:60. nCaIL-13Rα2$_{954}$ has a coding sequence denoted SEQ ID NO:68 and a complementary sequence represented herein by SEQ ID NO:70. PCaIL-13Rα2$_{318}$, represented herein by SEQ ID NO:69. The nucleic acid molecule nCaIL-13Rα2$_{954}$, herein denoted SEQ ID NO:69, when expressed in *Escherichia coli* is processed with an additional methionine (ATG) start sequence on the amino terminal end of the nucleic acid sequence. Translation of nCaIL-13Rα2$_{954}$ results in a protein PCaIL-13Rα2$_{318}$ which also contains the additional methionine at the amino terminal end.

EXAMPLE 4

This example describes the preparation of canine IL-13Rα2-Fc chimeric nucleic acid molecules, recombinant molecules and recombinant cells as well as expression and biological activity of respective fusion proteins of the present invention. A. Construction of canine IL-13Rα2 chimeric nucleic acid molecules, recombinant molecule sequences and recombinant cells.

In order to create a canine chimeric nCaIL-13-Rα2-Fc nucleic acid molecules, four specific primers were designed based on nCaIL-13-Rα2$_{954}$ and canine IgE-Fc nucleic acid sequences. Canine IgE-Fc nucleic acid and amino acid sequences are disclosed in U.S.C.A. entitled "CANINE IMMUNOGLOBULIN G MOLECULES AND RELATED METHODS", filed Apr. 7, 2000 by Tang referred to The following primers were constructed: primer 13R2FcF (forward primer containing an NdeI site), with the sequence 5'GCACATATGTCTATGCTTTCAAATGCT-GAATAAAAGTTAATCCTCCTCAGG3', denoted SEQ ID NO:91; primer 13R2FcR2 (reverse primer containing a BamHI site), with the sequence 5'AAAGGATCCGGTTTC-CTTCCAGATATCATTTCCAGC3', represented herein as SEQ ID NO:92; primer CIgGFcF (forward primer containing a BamHI site), having the sequence 5'CCGGGATC-CAACACTAAAGTAGACAAGCGTG 3', represented herein as SEQ ID NO:93; and primer cIgGFcR (reverse primer containing a XhoI site), having the sequence 5' GCGCTCGAGTCATTTACCCGGAGAATGGGAGGG 3', represented herein as SEQ ID NO:94.

A nCaIL-13-Rα2$_{954}$ nucleic acid molecule (with coding strand of SEQ ID NO:68) that encodes an extracellular portion of canine IL-13Rα2 DNA (from S$^{22}$ to T$^{338}$) was PCR amplified from the mast cell cDNA library described in Example 2 using the above primers to introduce restriction sites NdeI and BamHI, the resulting product was digested with NdeI and BamHI; restriction enzymes (available from New England Biolabs, Inc., Beverly, Mass.). NdeI/BamHI digested nucleic acid molecule nCaIL-13-Rα2$_{954}$ was fractionated on a 1% agarose gel, purified with Qiagen gel purification kit (available from Qiagen, La Jolla, Calif.) and subcloned into similarly cleaved plasmid λPRcro/T2ori/RSET-B, produced as described in PCT Patent Publication No. WO; 98/12563, published Mar. 26, 1998 by Grieve, et al. After confirmation of the correct ligation of NdeI/BamHI digested canine nCaIL-13-Rα2$_{954}$ into the λPRcro/T2ori/RSET-B plasmid by DNA sequencing, λPRcro/T2ori/RSET-B vector containing nCaIL-13-Rα2$_{954}$ referred to herein as recombinant molecule pλp$_R$-nCaIL-13-Rα2$_{954}$ was digested with BamHI and XhoI restriction enzymes. Nucleic acid molecules encoding four canine IgG-Fc partial-length proteins were constructed by combining a nCa IL-13Rα2$_{954}$ fragment of the BamHI/XhoI digest with a IgG-Fc fragment, produced by methods of which are described herein, as follows:

Nucleic acid molecule nCaIL-13Rα2-Fc-3523$_{1683}$ includes nucleic acid molecule nCaIL-13Rα2$_{954}$ linked to a canine Ig gamma chain nucleic acid molecule the coding strand of which includes nucleotides 748 through 1473 of SEQ ID NO:51. Fusion protein PCaIL-13Rα2-Fc-3523 includes PCaIL-13Rα2$_{318}$ linked to a canine Ig gamma chain protein that includes amino acids 227 through 468 of SEQ ID NO:52.

Chimeric nCaIL-13Rα2-Fc-3523$_{1683}$, in which NdeI/BamHI digested nCaIL-13Rα2$_{954}$ is ligated to nCaFcγ3523$_{1473}$, has a coding strand the nucleic acid sequence of which is represented by SEQ ID NO:71 and a complementary strand the nucleic acid sequence of which is represented by SEQ ID NO:73.

Translation of SEQ ID NO:71 shows that the nucleic acid molecule nCaIL-13Rα2-Fc-3523$_{1683}$ encodes a fusion protein of 561 amino acids, denoted herein as PcaIL-13Rα2-Fc-3523$_{561}$.

The chimeric nucleic acid molecule was ligated into λPRcro/T2ori/RSET-B to form recombinant molecule nCaIL-13Rα2-Fc-3523$_{1683}$, which was transformed into *E. coli* to form recombinant cell nCaIL-13Rα2-Fc-3523$_{1683}$.

Nucleic acid molecule nCaIL-13Rα2-Fc-4325$_{1695}$ includes nucleic acid molecule nCaIL-13Rα2$_{954}$ linked to a canine Ig gamma chain nucleic acid molecule the coding strand of which includes nucleotides 713 through 1450 of SEQ ID NO:66.

Fusion protein PCaIL-13Rα2-Fc-4325 includes PCaIL-13Rα2$_{318}$ linked to a canine Ig gamma chain protein that includes amino acids 228 through 473 of SEQ ID NO:67.

Chimeric nCaIL-13Rα2-Fc-4325$_{1695}$, in which NdeI/BamHI digested nCaIL-13Rα2$_{954}$ is ligated to nCaFcγ4325$_{1450}$, has a coding strand the nucleic acid sequence of which is represented by SEQ ID NO:74 and a complementary strand the nucleic acid sequence of which is represented by SEQ ID NO:76.

Translation of SEQ ID NO:74 shows that the nucleic acid molecule nCaIL-13Rα2-Fc-4325$_{1695}$ encodes a fusion protein of 565 amino acids, denoted herein as PCaIL-13Rα2-Fc-4325$_{565}$.

The chimeric nucleic acid molecule was ligated into ?PRcro/T2ori/RSET-B to form recombinant molecule nCaIL-13Rα2-Fc-4325$_{1695}$, which was transformed into *E. coli* to form recombinant cell nCaIL-13Rα2-Fc-4325$_{1695}$.

Nucleic acid molecule nCaIL-13Rα2-Fc-B9$_{1689}$ includes nucleic acid molecule nCaIL-13Rα2$_{954}$ linked to a canine Ig gamma chain nucleic acid molecule the coding strand of which includes nucleotides 725 through 1453 of SEQ ID NO:63.

Fusion protein PCaIL-13Rα2-Fc-B9$_{563}$ includes PCaIL-13Rα2$_{318}$ linked to a canine Ig gamma chain protein that includes amino acids 232 through 474 of SEQ ID NO:64.

Chimeric nCaIL-13Rα2-Fc-B9$_{1689}$, in which NdeI/BamHI digested nCaIL-13Rα2$_{954}$ is ligated to nCaFcγ B9$_{474}$, has a coding strand the nucleic acid sequence of which is represented by SEQ ID NO:77 and a complementary strand the nucleic acid sequence of which is represented by SEQ ID NO:79.

Translation of SEQ ID NO:77 shows that the nucleic acid molecule nCaIL-13Rα2-Fc-B9$_{1689}$ encodes a fusion protein of 563 amino acids, denoted herein as PCaIL-13Rα2-Fc-B9$_{563}$.

The chimeric nucleic acid molecule was ligated into λPRcro/T2ori/RSET-B to form recombinant molecule nCaIL-13Rα2-Fc-B9$_{1689}$, which was transformed into *E. coli* to form recombinant cell nCaIL-13Rα2-Fc-B9$_{1689}$.

Nucleic acid molecule nCaIL-13Rα2-Fc-B8$_{1683}$ includes nucleic acid molecule nCaIL-13Rα2$_{954}$ linked to a canine Ig gamma chain nucleic acid molecule the coding strand of which includes nucleotides 732 through 1457 of SEQ ID NO:57.

Fusion protein PCaIL-13Rα2-Fc-B8$_{561}$ includes PCaIL-13Rα2$_{318}$ linked to a canine Ig gamma chain protein that includes amino acids 229 through 470 of SEQ ID NO:58.

Chimeric nCaIL-13Rα2-Fc-B8$_{1683}$, in which NdeI/BamHI digested nCaIL-13Rα2$_{954}$ is ligated to nCaFcγ B9$_{474}$, has a coding strand the nucleic acid sequence of which is represented by SEQ ID NO:80 and a complementary strand the nucleic acid sequence of which is represented by SEQ ID NO:82.

Translation of SEQ ID NO:80 shows that the nucleic acid molecule nCaIL-13Rα2-Fc-B8$_{1683}$ encodes a fusion protein of 561 amino acids, denoted herein as PcaIL-13Rα2-Fc-B8$_{561}$.

The chimeric nucleic acid molecule was ligated into λPRcro/T2ori/RSET-B to form recombinant molecule nCaIL-13Rα2-Fc-B8$_{1683}$, which was transformed into *E. coli* to form recombinant cell nCaIL-13Rα2-Fc-B8$_{1683}$.

B Expression, refolding and biological activity of IL-13Rα2-Fc fusion proteins.

Recombinant cells nCaIL-13Rα2-Fc-3523$_{1683}$, nCaIL-13Rα2-Fc-4325$_{1695}$, nCaIL-13Rα2-Fc-B9$_{1689}$, and nCaIL-13Rα2-Fc-B81683 produced as described in Example 3A were each cultured at 30° C. for 5 hours until the culture reached an OD of expression of 1.2 the fusion protein was induced by changing the culture temperature to 42° C. for 3 hours. Cell pellets were then collected by centrifugation at 3000×g. Each of the four recombinant cells expressed its respective fusion protein as determined by appearance of the correct molecular weight band on an SDS-polyacrylamide gel using standard conditions and protein markers.

Fusion protein PCaIL-13Rα2-Fc-B9$_{563}$ (SEQ ID NO:78) was solubilized by the following method: the cell pellet was resuspended in cracking buffer (25 mM Tris-HCl pH 7.5, available from Sigma, St. Louis, Mo.) at 100 mg/ml (milligrams per milliliter) and homogenized with a polytron (available from Brinkman Instrument, Westbury, N.Y.). The cells were broken using a microfluidizer (available from Microfluidics, Newton, Mass.) at 120 psi by recirculating 20 ml batches of resuspended cells for 30 pulses. The broken cell suspension was centrifuged at 30,000 times gravity (xg) for 30 minutes. The cell pellet from this centrifugation was resuspended (same volume as above) in a buffer containing 25 mM Tris-HCl pH 7.5, 1% deoxycholate, and 1% Triton X-100 (all available from Sigma), and rocked for 30 minutes at 4° C., centrifuged at 30,000×g for 30 minutes, the pellet was resuspended in cracking buffer (above), and recentrifuged at 1000×g for 5 minutes. The supernatant from the low-speed centrifugation (1000×g) was then recentrifuged at 30,000×g for 30 minutes. The pellet was resuspended (same volume as above) in 25 mM Tris-HCl pH 9.5, 8 M urea, and 50 mM beta-mercaptoethanol (all available from Sigma).

The resuspended inclusion bodies were incubated at 4° C. for 30 minutes, recentrifuged at 30,000×g for 30 minutes, yielding a supernatant that contains solubilized IL-13Rα2-Fc fusion protein. The protein concentration of the supernatant containing the fusion protein as determined by absorbance at 280 nanometers (nm), was approximately 1 mg/ml.

Using solubilized chimera PCaIL-13Rα2-Fc-B9$_{563}$, a number of different refolding conditions were tried. To 10 mls of resolubilized PCaIL-13Rα2-Fc-B9$_{563}$, 1.1 ml of a buffer in Column A of Table 7 was added to the solubilized IL-13Rα2-Fc-B9$_{563}$ such that final concentrations as noted in Table 7 were achieved. The resulting mixture was incubated at 30° C. for 2 hours, then 120 ml of a buffer from Column B of Table 7 was added, to give final concentrations as noted in Table 7. This mixture was incubated overnight at 4° C. The resulting material was then placed into 12,000 MWCO dialysis membranes (available from Spectrum, Gardena, Calif.), and dialyzed overnight at 4° C. against phosphate buffered saline (PBS pH 7.5), with three changes of 4 liters each. The dialyzed protein was centrifuged at 10,000×g for 30 minutes, and the supernatant was collected.

The ability of PCaIL-13-Rα2-Fc fusion protein refolded under each set of conditions to inhibit the biological activity of recombinant canine IL-13 was determined by TF-1 cell proliferation. TF-1 cells (available from R&D Systems, Minneapolis, Minn.), a human erthyroleukemia cell line, were maintained in RPMI-1640 media (available from Sigma Chemical Corp) supplemented with 2 mM L-glutamine (available from Life Technologies, Gaithersburg, Md.), 5 microgram (μg)/ml gentamycin (available from Sigma Chemical Corp), 5% fetal bovine serum (available from Summit, Fort Collins, Colo.), and 2 nanogram/ml recombinant human GM-CSF (rhuGM-CSF, available from R&D systems), referred to as Complete Culture Medium. Cells were cultured in a humidified incubator, maintained at 37° C. with a mix of 5% $CO_2$ and 95% ambient air. PCaIL-13-Rα2-Fc fusion protein supernatants, produced as described above and canine IL-13 (prepared as described in U.S. Ser. No. 09/322,409, filed May 28, 1999) were each diluted to the appropriate concentration in Complete Culture Medium (see above), without rhuGM-CSF, and filter sterilized. The diluted IL-13 and fusion protein solutions were then mixed at an initial cytokine to receptor molar ratio of either 1:25 (6.6 ug/ml for IL-13α2-Fc, and 50 ng/ml IL-13) or 1:125 cytokine to receptor (6.6 ug/ml for IL-13α2-Fc, and 10 ng/ml IL-13) and incubated overnight at 4° C. in a sterile, 96-well flat bottom tissue culture plate (available from Beckton Dickson Labware, Franklin Lakes, N.J.). Cultured TF-1 cells were then extensively washed to remove rhuGM-CSF and added at $1 \times 10^4$ cells per well. Cells were incubated with the recombinant canine IL-13/IL-13Rα2-Fc fusion protein mixture as described above (except in the absence of rhuGM-CSF) for 48 hours, then pulsed with 1 microcurie per well tritiated thymidine (available from ICN Pharmaceuticals, Irvine, Calif.) and incubation continued for another 18 hours. Contents of the wells were harvested onto glass fiber filters (available from Wallac, Inc., Gaithersburg, Md.), and counted in a Wallac Trilux 1450 scintillation counter (available from Wallac Inc).

TABLE 7

Refolding conditions and resultant activity for PCaIL-13Rα2-Fc-B9$_{563}$.

| Condition | Buffer A | Buffer B | Percent inhibition of IL-13 stimulated TF-1 cell proliferation; IL-13 at 50 ng/ml | Percent inhibition of IL-13 stimulated TF-1 cell proliferation; IL-13 at 10 ng/ml |
|---|---|---|---|---|
| 1A | 25 mM GSH, 6 mM DTT 0.05% Tween 80, 1 mM EDTA | 50 mM Tris pH 10, 12.5 mM cysteine, 2 mM EDTA | 29.4 | 30.9 |
| 1B | 25 mM GSH, 6 mM DTT 0.05% Tween 80, 1 mM EDTA | 50 mM Tris pH 8, 12.5 mM cysteine, 2 mM EDTA | 34.6 | 43.7 |
| 1C | 25 mM GSH, 6 mM DTT 0.05% Tween 80, 1 mM EDTA | 50 mM Tris pH 10, 2.7 mM GSSG, 0.8 mM EDTA | 92.3 | 100 |
| 1D | 25 mM GSH, 6 mM DTT 0.05% Tween 80, 1 mM EDTA | 50 mM Tris pH 8, 2.7 mM GSSG, 0.8 mM EDTA | 31.7 | 99.8 |
| 2A | 25 mM GSSG, 6 mM DTT, 0.05% Tween-80, 1 mM EDTA | 50 mM Tris pH 10, 12.5 mM cysteine, 2 mM EDTA | 19.7 | 35.1 |
| 2B | 25 mM GSSG, 6 mM DTT, 0.05% Tween-80, 1 mM EDTA | 50 mM Tris pH 8, 12.5 mM cysteine, 2 mM EDTA | 24 | 18 |
| 2C | 25 mM GSSG, 6 mM DTT, 0.05% Tween-80, 1 mM EDTA | 50 mM Tris pH 10, 2.7 mM GSSG, 0.8 mM EDTA | 11.9 | 16 |
| 2D | 25 mM GSSG, 6 mM DTT, 0.05% Tween-80, 1 mM EDTA | 50 mM Tris pH 8, 2.7 mM GSSG, 0.8 mM EDTA | 28.8 | 7.5 |
| 3A | 6 mM DTT, 0.05% Tween-80, 1 mM EDTA | 50 mM Tris pH 10, 12.5 mM cysteine, 2 mM EDTA | 44.7 | 81.3 |
| 3B | 6 mM DTT, 0.05% Tween-80, 1 mM EDTA | 50 mM Tris pH 8, 12.5 mM cysteine, 2 mM EDTA | 92.5 | 96.3 |
| 3C | 6 mM DTT, 0.05% Tween-80, 1 mM EDTA | 50 mM Tris pH 10, 2.7 mM GSSG, 0.8 mM EDTA | 95.4 | 98.9 |
| 3D | 6 mM DTT, 0.05% Tween-80, 1 mM EDTA | 50 mM Tris pH 8, 2.7 mM GSSG, 0.8 mM EDTA | 32.7 | 49.9 |

Results from Table 7 indicated that refolding conditions 1C, 3B, and 3C (see above table) yielded IL-13Rα2-Fc-B9$_{563}$ fusion protein preparations with roughly equivalent activities, as measured in the TF-1 assay. Condition 3C was chosen as the standard condition with which to produce IL-13Rα2-Fc-B9$_{563}$ fusion protein for the subsequent experiments.

C. Competition Assay, IL-13RαR2-Fc-B9 v. IL-13.

In the following experiment, the ability of IL-13Rα2-Fc-B9 fusion protein to inhibit the biological activity of canine IL-13 was determined by the TF-1 cell proliferation assay as described in Example 3B. IL-13 and IL-13RαR2-Fc-B9 were described in Example 3B such that the concentration of IL-13 in the mixture was 50 ng/ml and that of Il-13Rα2-Fc-B9 was as indicated in Table 8.

TABLE 8

Competition assay, IL-13Rα2-Fc-B9 v. IL-13.

| Sample Number | μg/ml IL-13Rα2-Fc-B9 | Percent inhibition of IL-13 stimulated TF-1 proliferation |
|---|---|---|
| 1 | 13.2 | 100 |
| 2 | 6.6 | 99 |
| 3 | 3.3 | 98 |
| 4 | 1.6 | 92 |
| 5 | 0.8 | 38 |
| 6 | 0.4 | 0 |
| 7 | 0.2 | 0 |
| 8 | 0.1 | 0 |
| 9 | media | 0 |
| 10 | no cells | 0 |

Results indicate that IL-13Rα2-Fc-B9 inhibited the biological activity of canine IL-13 in a dose dependent manner as measured by TF-1 cell proliferation. IL-13Rα2-Fc-B9 at 3.3 and 6.6 µg/ml inhibited over 95% of canine IL-13 activity in the bioassay, and at 1.6 µg/ml inhibited 92% of canine IL-13 activity in the bioassay, indicating the ability of IL-13Rα2-Fc-B9 to bind canine IL-13.

EXAMPLE 5

This example describes the ability of IL-13-Rα2-Fc-B9 to inhibit IL-13 stimulation of canine peripheral blood mononuclear cells to produce antigen-specific antibody.

A. Preparation of canine PBMC cultures.

Canine peripheral blood mononuclear cells (PBMCs) from flea saliva-sensitized dogs were prepared as described in U.S. Pat. No. 5,646,115, issued Jul. 8, 1997, entitled "NOVEL ECTOPARASITE SALIVA PROTEINS AND APPARATUS TO COLLECT SUCH PROTEINS" by Frank et al. incorporated in its entirety herein by reference.

B. Inhibition Assay

PBMCs were cultured for 2 weeks in RPMI media containing 5% normal dog serum (available from Gemini, Calabasas, Calif.), 200 mM L-glutamine, 50 µg/ml gentamicin, 1X non-essential amino acids, 1X amino acids, 1× sodium pyruvate, and approximately 5.5 X10-5 M beta-mercaptoethanol. (All these components available from Sigma Chemical Co).

The following sample reactions were set up: (1) medium only plus cells (2) flea saliva product 1 µg/ml (prepared as described in Example 4A); (3) flea saliva product (obtained as described in Example 4A) plus IL-13Rα2-B9 at 6.6 µg/ml; (4) IL-13 (as described in Example 3B) at 50 ng/ml; (5) IL-13 (50 ng/ml) plus IL-13Rα2-B9(6.6 µg/ml), preincubated together before addition to the assay overnight at 4° C.; and (6) medium alone, no cells.

The results are set forth in Table 9, below. Flea saliva product (prepared as described in U.S. Pat. No. 5,646,115.) was diluted in 100 PI CBC buffer (50 mM sodium carbonate, 50 nM sodium bicarbonate, pH 9.6) and coated at a concentration of 100 nanograms per well onto Immulon II microtiter plates (available from Dynex Technologies, Chantilly, Va.). The coated plates were covered and incubated overnight coated at 4° C. Excess fluid was removed and wells were blocked with 200 µl Assay Buffer for one hour at room temperature. Assay buffer contains 4% fetal calf serum (available from Summit Laboratories, Fort Collins, Colo.) in phosphate buffered saline (PBS, recipe in Sambrook, ibid.), plus 0.05% Tween-20 (available from Sigma, St. Louis, Mo.). Plates were then washed for 4 cycles on an automatic plate washer (Ultrawash, available from Dynatech Laboratories) using PBS with 0.05% Tween-20.

Samples as described in above, were diluted 1.6 fold with assay buffer and 100 µl/well was applied to duplicate wells for an 18 hour incubation at 4° C. Positive control wells received 100 µl of a pool of flea allergic dog sera (FAD Pool #9) titered 1:10 to 1:320 by two-fold dilution in the IgE assay and 1:50 to 1:1600 by two fold dilution in the IgG assay (not shown). Control wells, cells from sample (6) were treated identically except that no serum was added. Plates were then washed as described above.

To determine IgE production in the samples, biotinylated human IgE receptor alpha chain ($Fc_{\epsilon\alpha}R1\alpha$-biotin) (100 µl of 13 ng/ml) prepared as described in U.S. Pat. No. 5,945,294, ibid., was added and incubated for one hour at room temperature. After this incubation, plates were washed as described above. Streptavidin-horseradish peroxidase conjugate (0.5 mg/ml, available from KPL Labs, Gaithersburg, Md.) was added at a 1:5000 dilution (100 ng/ml) in Assay Buffer for one hour at room temperature, after which plates were washed as described above.

To determine IgG production in the samples, 100 ng of horseradish peroxidase-labeled goat anti-dog IgG (KPL Labs) was added to each well and incubated for a one hour at room temperature. TMB peroxidase substrate system, (2 part system available from KPL Labs, #0-76-00), added at 100 µl per well, was used according to the manufacturer's directions. The color reaction was allowed to proceed until good color development was reached (about 10-15 min); then the reaction was stopped with 100 µl per well of 1 M phosphoric acid.

Bound IgE or IgG was determined by measuring absorbance (Optical Density, or OD) at 450 nm (nanometers) using an ELISA plate reader (such as Spectramax", Molecular Devices, Sunnyvale, Calif.). Background OD readings in the control wells were subtracted from all numbers. Results are reported in Table 9 as OD multiplied by 1000, and are the mean of duplicate wells. OD numbers greater than 100 are considered to be positive for a reaction with IgE or IgG.

TABLE 9

Effect of IL-13Rα2-Fc-B9 on Flea-allergic canine PBMC cultures, antigen-specific and IgE and IgG production.

| Sample | Sample Treatment | OD, IgE | OD, IgG |
|---|---|---|---|
| 1 | Medium plus cells | 102 | 1095 |
| 2 | Flea saliva, 1 µg/ml | 42 | 1397 |
| 3 | FS + PCaIL13-Rα2-Fc-B9 | 43 | 950 |
| 4 | IL-13 alone | 879 | 1589 |
| 5 | IL-13 + PCaIL13-Rα2-Fc-B9 | 86 | 775 |
| 6 | background (3 wells) | 70 | 881 |

Results in Table 9 indicate that while IL-13 stimulates antigen-specific IgE production from PBMC, the IL-13Rα2-Fc-B9 chimera prevents the IL-13 stimulation, demonstrating that IL-13Rα2-Fc-B9 chimera binds to IL-13. In samples 2 and 3, the PBMCs were cultured with flea saliva antigen or with flea saliva antigen plus IL-13Rα2-Fc-B9 chimera. However, no effect was seen on the IgE production of the PBMCs in response to incubation with flea saliva.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule comprising a nucleic acid sequence selected from the group consisting of:
   (a) a nucleic acid sequence encoding a protein comprising an amino acid sequence at least 95% identical to SEQ ID NO:50; wherein said protein binds canine IL-13;
   (b) a nucleic acid sequence encoding a protein comprising at least 100 contiguous amino acids identical in sequence to 100 contiguous amino acids from SEQ ID NO:50; wherein said protein binds canine IL-13; and
   (c) a nucleic acid sequence fully complementary to the nucleic acid sequence of (a) or (b).

2. The isolated nucleic acid molecule of claim 1, wherein said nucleic acid sequence encodes a protein comprising SEQ ID NO:50.

3. The isolated nucleic acid molecule of claim 1, wherein said nucleic acid sequence is selected from the group consisting of SEQ ID NO:48, SEQ ID NO:49, SEQ ID NO:51, SEQ ID NO:52 and SEQ ID NO:53.

4. A recombinant molecule comprising the nucleic acid molecule of claim 1 operatively linked to a transcription control sequence.

5. A recombinant virus comprising the isolated nucleic acid molecule of claim 1.

6. A recombinant cell comprising the isolated nucleic acid molecule of claim 1.

7. An isolated nucleic acid molecule comprising a nucleic acid sequence selected from the group consisting of:
   (a) a nucleic acid sequence comprising at least 300 contiguous nucleotides identical in sequence to 300 contiguous nucleotides from SEQ ID NO:49 or SEQ ID NO:52, wherein said nucleic acid sequence encodes a protein that binds canine IL-13;
   (b) a nucleic acid sequence at least 95% identical to SEQ ID NO:49 or SEQ ID NO:52, wherein said nucleic acid sequence encodes a protein that binds canine IL-13; and,
   (c) a nucleic acid sequence fully complementary to the nucleic acid sequence of (a) or (b).

8. The isolated nucleic acid molecule of claim 7, wherein said nucleic acid sequence is selected from the group consisting of SEQ ID NO:48, SEQ ID NO:49, SEQ ID NO:51, SEQ ID NO:52 and SEQ ID NO:53.

9. A recombinant molecule comprising the nucleic acid molecule of claim 7 operatively linked to a transcription control sequence.

10. A recombinant virus comprising the isolated nucleic acid molecule of claim 7.

11. A recombinant cell comprising the isolated nucleic acid molecule of claim 7.

12. An isolated nucleic acid molecule encoding a fusion protein comprising a carrier protein domain fused to a second protein domain selected from the group consisting of:
   (a) a protein domain comprising an amino acid sequence at least 95% identical in sequence to SEQ ID NO:50, wherein said protein binds canine IL-13; and
   (b) a protein domain comprising at least 100 contiguous amino acids identical in sequence to at least 100 contiguous amino acids from SEQ ID NO:50, wherein said protein binds canine IL-13.

13. The isolated nucleic acid molecule of claim 12, wherein said encoded carrier protein domain is an immunoglobulin Fc region.

14. The isolated nucleic acid molecule of claim 12, wherein said encoded carrier protein domain is a canine immunoglobulin IgG Fc region.

15. The isolated nucleic acid molecule of claim 12, wherein said second protein domain comprises SEQ ID NO:50.

16. A fusion protein comprising a carrier protein domain fused to a second protein domain selected from the group consisting of:
   (a) a protein domain comprising an amino acid sequence at least 95% identical in sequence to SEQ ID NO:50, wherein said protein binds canine IL-13; and
   (b) a protein domain comprising at least 100 contiguous amino acids identical in sequence to at least 100 contiguous amino acids from SEQ ID NO:50, wherein said protein binds canine IL-13.

17. The fusion protein of claim 16, wherein said second protein domain comprises SEQ ID NO:50.

18. An isolated nucleic acid molecule, wherein said isolated nucleic acid molecule consists of at least 100 contiguous nucleotides from a nucleic acid sequence selected from the group consisting of (a) a nucleic acid sequence that encodes SEQ ID NO:50, and (b) a nucleic acid sequence fully complementary to the nucleic acid sequence of (a).

19. The isolated nucleic acid molecule of claim 18, wherein said nucleic acid molecule consists of a nucleic acid sequence selected from the group consisting of (a) a nucleic acid sequence encoding SEQ ID NO:50, and (b) a nucleic acid sequence fully complementary to the nucleic acid sequence of (a).

20. The isolated nucleic acid molecule of claim 18, wherein said nucleic acid molecule consists of a nucleic acid sequence selected from the group consisting of SEQ ID NO:48, SEQ ID NO:49, SEQ ID NO:51, SEQ ID NO:52 and SEQ ID NO:53.

* * * * *